United States Patent
Koizumi et al.

(10) Patent No.: US 7,651,999 B2
(45) Date of Patent: Jan. 26, 2010

(54) 2', 5'-OLIGOADENYLATE ANALOGS

(75) Inventors: Makoto Koizumi, Kanagawa (JP); Koji Morita, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 780 days.

(21) Appl. No.: 11/131,412

(22) Filed: May 16, 2005

(65) Prior Publication Data
US 2005/0261235 A1  Nov. 24, 2005

Related U.S. Application Data

(63) Continuation-in-part of application No. PCT/JP03/014748, filed on Nov. 19, 2003.

(30) Foreign Application Priority Data
Nov. 19, 2002  (JP) ............................. 2002-334731

(51) Int. Cl.
*A61K 31/70*  (2006.01)
*C07H 21/02*  (2006.01)
(52) U.S. Cl. .................... 514/44; 536/24.5; 536/25.2
(58) Field of Classification Search .................... None
See application file for complete search history.

(56) References Cited

FOREIGN PATENT DOCUMENTS

| EP | 1 013 661 A1 | 6/2000 |
|---|---|---|
| EP | 1 152 009 A1 | 11/2001 |
| JP | 10-195098 A | 7/1998 |
| JP | 10-304889 A | 11/1998 |
| JP | 2000-297097 A | 10/2000 |
| JP | 3420984 B2 | 10/2000 |
| JP | 2002-249497 A | 9/2002 |
| WO | WO 89/12380 A2 | 12/1989 |
| WO | WO 01/22970 A1 | 4/2001 |

OTHER PUBLICATIONS

Mark R. Player et al., "The 2-5A System: Modulation of Viral and Cellular Processes Through Acceleration of RNA Degradation," *Pharmacol. Ther.*, vol. 78, No. 2, pp. 55-113, (1998).
Lorraine Rusch, "Caspase-Dependent Apoptosis by 2', 5'-Oligoadenylate Activation of RNase L is Enhanced by IFN-β," *J. Interferon Cytokine Res.*, 20, pp. 1091-1100, (2000).
Robert W. Sobol et al., "Inhibition of HIV-1 Replication and Activation of RNase L by Phosphorothioate/Phosphodiester 2', 5'-Oligoadenylate Derivatives," *J. Biol. Chem.*, vol. 270, No. 11, pp. 5963-5978, (1995).
Susan M. Freier et al., "The ups and downs of nucleic acid duplex stability: structure-stability studies on chemically-modified DNA:RNA duplexes," *Nucleic Acids Research*, vol. 25, No. 22, pp. 4429-4443, (1997).
J. Carpten et al., "Germline mutations in the ribonuclease L gene in families showing linkage with HPC1," *Nat. Genetics*, vol. 30, No. 2, pp. 181-184, (2002).

Steven A. Adah et al., "Chemistry and Biochemistry of 2', 5'-Oligoadenylate-Based Antisense Strategy," *Curr. Med. Chem.*, 8, pp. 1189-1212, (2001).
Masamitu Shimazu et al., "Regio- and stereocontrolled synthesis of 2'-5' linked phosphorothioate oligoadenylates by uranyl ion catalyst in aqueous solution," *J. Chem. Soc. Perkin Trans.*, No. 15, pp. 1778-1785, (2002).
Sharon Naik et al., "RNase L dimerization in a mammalian two-hybrid system in response to 2', 5' -oligoadenylates," *Nucl. Acid Res.*, vol. 26, No. 6, pp. 1522-1527, (1998).
Wei Xiao et al., "Synthesis of a 5'-Thiophosphate Analogue of 2-5A, A Phosphatase Resistant Activator of the 2-5A-Dependent Ribonuclease," *Bioorg. Med. Chem. Let.*, vol. 4, No. 21, pp. 2609-2614, (1994).
D. Watling et al., "Analogue inhibitor of 2-5A action: effect on the interferon- mediated inhbition of encephalomyocarditis virus replication," *The EMBO. J.*, vol. 4, No. 2, pp. 431-436, (1985).

(Continued)

*Primary Examiner*—Lawrence E Crane
(74) *Attorney, Agent, or Firm*—Frishauf, Holtz, Goodman & Chick, P.C.

(57) ABSTRACT

A 2-5A analog represented by the formula (1):

$$R^1-\overset{O}{\underset{R^2}{\overset{\|}{P}}}-E^1-\overset{O}{\underset{R^3}{\overset{\|}{P}}}-E^2-\overset{O}{\underset{R^4}{\overset{\|}{P}}}-E^3-\left(\overset{O}{\underset{R^5}{\overset{\|}{P}}}-E^4\right)_m\left(\overset{O}{\underset{R^6}{\overset{\|}{P}}}-R^7\right)_n-R^8$$

wherein m is 0 or 1; n is 0 to 2; $R^1$ represents an alkoxy group having from 1 to 6 carbon atoms which may be substituted, an unprotected mercapto group, a mercapto group protected by a nucleic acid synthesis protecting group, or an alkylthio group having from 1 to 4 carbon atoms which may be substituted; $R^2$, $R^3$, $R^4$, $R^5$ and $R^6$ represent an unprotected hydroxyl group, a hydroxyl group protected by a nucleic acid synthesis protecting group, an alkoxy group having from 1 to 6 carbon atoms which may be substituted, an unprotected mercapto group, a mercapto group protected by a nucleic acid synthesis protecting group, or an alkylthio group having from 1 to 4 carbon atoms which may be substituted; $R^7$ represents an oxygen atom, or a —O(CH$_2$CH$_2$O)q- group, wherein q is 2 to 6; $R^8$ represents a hydrogen atom, an alkyl group having from 1 to 6 carbon atoms which may be substituted, or a 5'-phosphorylated oligonucleotide analog which has one hydroxyl group removed from the 5'-phosphoric acid group; $E^1$, $E^2$, $E^3$ and $E^4$ represent a naturally occurring or modified nucleic acid unit, or a pharmacologically acceptable salt thereof.

18 Claims, 1 Drawing Sheet

OTHER PUBLICATIONS

Paul F. Torrence et al., "Oligonucleotide Structural Parameters That Influence Binding of 5'-O-Triphosphoadenylyl-(2'-5')-adenylyl-(2'-5')-adenosine to the 5'-O- Triphosphoadenylyl-(2'-5')-adenylyl-(2'-5')-adenosine Dependent Endoribonuclease: Chain Length, Phosphorylation State, and Heterocyclic Base," *J. Med. Chem.*, vol. 27, pp. 726-733, (1984).

Margaret Haugh et al., "Analogues and Analogue Inhibitors of ppp $(A2'p)_n A$ Their Stability and Biological Activity,", *Eur. J. Biochem.*, vol. 132, No. 1, pp. 77-84, (1983).

Simon S. Jones et al., "Chemical Synthesis of 5'-O-Triphosphoryladenylyl-(2'-5')-adenylyl-(2'-5')-adenosine (2-5A)," *J. Ame. Chem. Soc.*, vol. 24, pp. 7399-7401, (1979).

Ying Xiang et al., "Effects of RNase L Mutations Associated with Prostate Cancer on Apoptosis Induced by 2',5'-Oligoadenylates,", *Cancer Res.*, vol. 63, No. 20, pp. 6795-6801, (2003).

Yoshihito Ueno et al., "Synthesis of the antisense oligonucleotides carrying the modified 2-5A molecules at their 5'-termini and their properties," *Nucl. Acid Res., Suppl.* No. 2, pp. 45-46, (2002).

English-language International Preliminary Examination Report dated May 12, 2005 of International application PCT/JP2003/014748 filed Nov. 19, 2003 Applicant: Sankyo Company, Ltd.

2', 5'-OLIGOADENYLATE ANALOGS

CROSS-REFERENCE TO RELATED APPLICATION

This application is a continuation-in-part application of International application PCT/JP2003/014748 filed Nov. 19, 2003, the entire contents of which are hereby incorporated by reference herein.

BACKGROUND OF THE INVENTION

1. Field of the Invention

The present invention relates to analogs of 2',5'-oligoadenylate (2-5A) that are stable and have superior activity (particularly antitumor activity).

2. Background Art 2-5A, which is known as a biological substance that has antiviral activity (Pharmacol. Ther. Vol. 78, No. 2, pp. 55-113, 1998), is a short-chain oligonucleotide composed of three or more adenosine units in which two adenosine 2' and 5' hydroxyl groups are linked with phosphate 2',5'-phosphodiester bonds, and in which a triphosphate group is bonded to the 5' end. When cells infected by a virus are subjected to extracellular interferon stimulation, 2-5A synthetase is induced in the presence of viral dsRNA, and 2-5A is produced from ATP. 2-5A is a substance that converts the inactive form of the RNA degrading enzyme, RNase L, into the active form within host cells. This activated RNase L inhibits viral growth in cells by degrading viral RNA. Moreover, when ovarian cancer cells Hey1B are transfected with 2-5A, sequence-specific cleavage of 18S rRNA is known to occur, that results in demonstration of antitumor activity as a result of apoptosis through release of cytochrome c and activation of caspase (J. Interferon Cytokine Res., 20, 1091-1100 (2000)). Thus, 2-5A is expected to act as a virus growth inhibitor, and, more specifically, as an antivirus drug or antitumor drug.

In an in vitro experiment, an oligonucleotide composed of three or more adenosine units having a monophosphate group on the 5' end and linked with 2'-5' phosphodiester bonds is known to activate RNase L (Pharmacol. Ther. Vol. 78, No. 2, pp. 55-113, 1998; J. Biol. Chem. Vol. 270, No. 11, pp. 5963-5978 (1995)). However, 2-5A itself is easily degraded to AMP and ATP by 2'-phosphodiesterase and nuclease. Moreover, the 5'-phosphate group or 5'-triphosphate group ends up being dephosphorylated by phosphatases in the living body and losing activity. Thus, in the case of using 2-5A as a virus growth inhibitor or antitumor drug, a 2-5A analog is desirable that has similar activity, but has high stability, making it more resistant to degradation and metabolism in the living body.

In order to overcome these shortcomings, various methods have been attempted as examples of modifying the phosphate groups. Examples of known methods include a method in which the non-bridging oxygen atom bonded to the phosphorus atom of the phosphodiester bond of the oligonucleotide is substituted with a sulfur atom (phosphorothioate modification), a method in which said oxygen atom is substituted with a methyl group, a method in which said oxygen atom is substituted with a boron atom, and a method in which the sugar portion or nucleobase portion of the oligonucleotide is chemically modified (Freier, S. M.; Altmann, K. H., Nucleic Acids Res., 25, 4429 (1997)). A known example of such a 2-5A analog is the adenosine tetramer which has undergone the phosphorothioate modification shown below (Carpten, J. et al. Nature Genetics, 30, 181 (2002)).

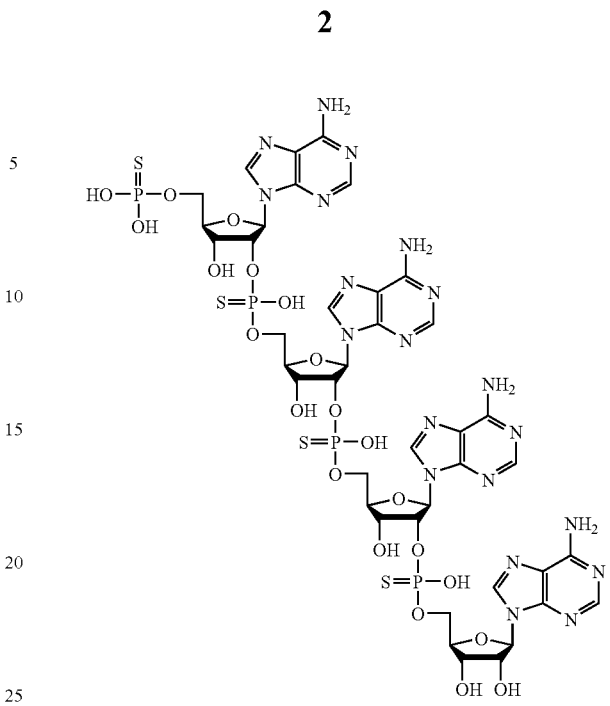

Moreover, analogs having a chemical structure like that shown below, in which the sugar portion of adenosine has been modified, are described in Japanese Patent Application (Kokai) No. Hei 10-195098 and Japanese Patent No. 3420984 as adenosine units of 2-5A analogs.

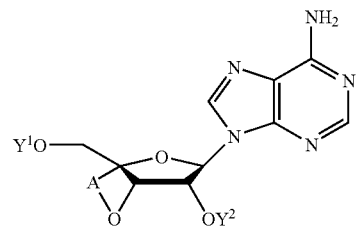

In the above formula, $Y^1$ and $Y^2$ represent a hydrogen atom or a protecting group for a hydroxy group, and A represents an alkylene group having from 1 to 3 carbon atoms.

In addition, a 2-5A molecule bonded by means of a linker with an antisense molecule in the form of an oligonucleotide having a sequence complementary to mRNA involved in diseases has been used as a 2-5A antisense oligonucleotide that inhibits the function of mRNA (S. A. Adah, et al., Current Medicinal Chemistry (2001), 8, 1189-1212). A highly stable 2-5A analog that is resistant to degradation and metabolism in the living body serves as a portion of a superior 2-5A antisense oligonucleotide, and is expected to be a useful drug. In particular, oligonucleotides containing a bridged nucleoside in which an oxygen atom at the 2' position and a carbon atom at the 4' position of the sugar portion are bonded with an alkylene group are known to be useful as antisense molecules (Japanese Patent Application (Kokai) No. Hei 10-304889, Japanese Patent Application (Kokai) No. 2000-297097).

SUMMARY OF THE INVENTION

The inventors of the present invention conducted extensive research over the course of many years on non-natural type 2-5A analogs that have antivirus activity, antitumor activity or superior antisense activity, are stable in the living body, and are associated with the occurrence of few adverse side effects. As a result, they were found to be useful as stable and superior antivirus drugs, antitumor drugs and antisense drugs, thereby leading to completion of the present invention.

The 2-5A analog of the present invention relates to a 2',5'-oligoadenylate analog represented by the general formula (1):

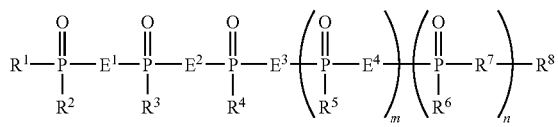

[wherein m represents an integer of 0 or 1; n represents an integer of 0 to 2; $R^1$ represents an alkoxy group having from 1 to 6 carbon atoms which may be substituted, a mercapto group, a mercapto group protected by a nucleic acid synthesis protecting group, an alkylthio group having from 1 to 4 carbon atoms which may be substituted, an amino group, an amino group protected by a nucleic acid synthesis protecting group, an amino group substituted by alkyl group(s), having from 1 to 6 carbon atoms which may be substituted, an alkyl group having from 1 to 6 carbon atoms which may be substituted, an aryloxy group which may be substituted, or an arylthio group which may be substituted, or a group of formula: $X_1—X_2—X_3—S—$; $R^2$, $R^3$, $R^4$, $R^5$ and $R^6$ represent a hydroxyl group, a hydroxyl group protected by a nucleic acid synthesis protecting group, an alkoxy group having from 1 to 6 carbon atoms which may be substituted, a mercapto group, a mercapto group protected by a nucleic acid synthesis protecting group, an alkylthio group having from 1 to 4 carbon atoms which may be substituted, an amino group, an amino group protected by a nucleic acid synthesis protecting group, an amino group substituted by alkyl group(s) having from 1 to 6 carbon atoms which may be substituted, or an alkyl group having from 1 to 6 carbon atoms which may be substituted; $R^7$ represents an oxygen atom, a sulfur atom, —NH—, a —O(CH$_2$CH$_2$O)q- group (q represents an integer of 2 to 6), an oxyalkyleneoxy group having from 1 to 6 carbon atoms, or a group of formula: $X_1—X_2—X_3—S—$; $R^8$ represents a hydrogen atom, an alkyl group having from 1 to 6 carbon atoms which may be substituted, an aralkyl group which may be substituted, an aryl group which may be substituted, or a 5'-phosphorylated oligonucleotide analog which has one hydroxyl group removed from the 5'-phosphoric acid group; $E^1$, $E^2$, $E^3$ and $E^4$ are the same or different and represent $K^1$, $K^2$, $K^3$ or $K^4$ ($K^1$, $K^2$, $K^3$ and $K^4$ represent

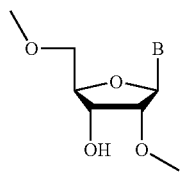

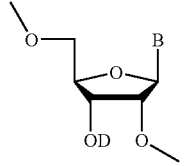

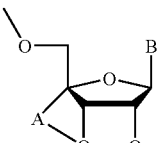

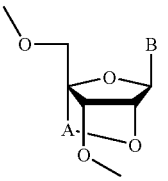

respectively, wherein, B represents a purin-9-yl group or a substituted purin-9-yl group having substituent(s) selected from the following Group α, A represents an alkylene group having from 1 to 4 carbon atoms, D represents an alkyl group having from 1 to 6 carbon atoms which may be substituted, or an alkenyl group having from 2 to 6 carbon atoms which may be substituted); $X_1$ represents an alkyl group having from 1 to 24 carbon atoms which may be substituted, or an aryl group which may be substituted, or an aralkyl group which may be substituted; $X_2$ represents a —C(=O)O—, OC(=O)—, —C(=O)NH—, —NHC(=O)—, —C(=O)S—, —SC(=O)—, —OC(=O)NH—, —NHC(=O)O—, —NHC(=O)NH—, —OC(=S)—, or a —C(=S)O—, —NHC(=S)—, —C(=S)NH— group; and $X_3$ represents an alkylene group having from 1 to 6 carbon atoms which may be substituted] (provided that compounds in which m is 0, n is 1, $R^2$, $R^3$, $R^4$ and $R^6$ are a hydroxyl group, $R^7$ is an oxygen atom, and $R^8$ is a 2-hydroxyethyl group, and the compound in which m is 1, n is 0, $R^1$, $R^3$, $R^9$ and $R^5$ are a mercapto group, $R^2$ is a hydroxyl group, $R^8$ is a hydrogen atom, and all of $E^1$, $E^2$, $E^3$ and $E^4$ are $K^1$ are excluded), or a pharmacologically acceptable salt thereof.

(Group α)
 a hydroxyl group,
 a hydroxyl group protected by a nucleic acid synthesis protecting group,
 an alkoxy group having from 1 to 6 carbon atoms which may be substituted,
 a mercapto group,
 a mercapto group protected by a nucleic acid synthesis protecting group,
 an alkylthio group having from 1 to 4 carbon atoms which may be substituted,
 an amino group,
 an amino group protected by a nucleic acid synthesis protecting group,
 an amino group substituted by alkyl group(s) having from 1 to 4 carbon atoms which may be substituted,
 an alkyl group having from 1 to 6 carbon atoms which may be substituted, and
 a halogen atom.

The above 2',5'-oligoadenylate analog or pharmacologically acceptable salt thereof is preferably (1) a 2',5'-oligoadenylate analog or pharmacologically acceptable salt thereof, in which $R^1$ is an alkoxy group having from 1 to 4 carbon atoms which may be substituted, a mercapto group, a mercapto group protected by a nucleic acid synthesis protecting group, or an alkylthio group having from 1 to 4 carbon atoms which may be substituted, or a group of formula: $X_1-X_2-X_3-S-$; $R^2, R^3, R^4, R^5$ and $R^6$ represent a hydroxyl group, a hydroxyl group protected by a nucleic acid synthesis protecting group, an alkoxy group having from 1 to 4 carbon atoms which may be substituted, a mercapto group, a mercapto group protected by a nucleic acid synthesis protecting group, an alkylthio group having from 1 to 4 carbon atoms which may be substituted, or a group of formula: $X_1-X_2-X_3-S-$; $X_1$ is an alkyl group having from 10 to 24 carbon atoms which may be substituted; $X_2$ is a $-C(=O)O-$, $-C(=O)NH-$, $-C(=O)S-$, $-NHC(=O)O-$, or $-C(=S)NH-$ group; and $X_3$ is an alkylene group having from 1 to 4 carbon atoms which may be substituted;

(2) a 2',5'-oligoadenylate analog or pharmacologically acceptable salt thereof, in which $R^7$ represents an oxygen atom, a $-O(CH_2CH_2O)q-$ group (q represents an integer of 2 to 6), or an oxyalkyleneoxy group having from 1 to 6 carbon atoms; and $R^8$ is a hydrogen atom; an alkyl group having from 1 to 6 carbon atoms which may be substituted, or a 5'-phosphorylated oligonucleotide analog which has one hydroxyl group removed from the 5'-phosphoric acid group;

(3) a 2',5'-oligoadenylate analog or pharmacologically acceptable salt thereof, wherein $E^2$ is $K^1$;

(4) a 2',5'-oligoadenylate analog or pharmacologically acceptable salt thereof, wherein $E^1$ is $K^2$, and D is a methyl group or a 2-propenyl group;

(5) a 2',5'-oligoadenylate analog or pharmacologically acceptable salt thereof, wherein $E^3$ is $K^3$ or $K^4$, and A is a methylene, ethylene, or propylene group;

(6) a 2',5'-oligoadenylate analog or pharmacologically acceptable salt thereof, wherein B is a 6-aminopurin-9-yl (that is, adeninyl), 6-amino-8-bromopurin-9-yl, 6-amino-8-chloropurin-9-yl, 6-amino-8-fluoropurin-9-yl, 6-amino-8-methoxypurin-9-yl, 6-amino-8-ethoxypurin-9-yl, 6-amino-8-t-butoxypurin-9-yl, 6-amino-2-bromopurin-9-yl, 6-amino-2-chloropurin-9-yl, 6-amino-2-fluoropurin-9-yl, 6-amino-2-methoxypurin-9-yl, 6-amino-2-ethoxypurin-9-yl, 6-amino-2-t-butoxypurin-9-yl, or 2,6-diaminopurin-9-yl group; or (7) a 2',5'-oligoadenylate analog or pharmacologically acceptable salt thereof, wherein B is 6-aminopurin-9-yl (that is, adeninyl) or 6-amino-8-bromopurin-9-yl.

DETAILED DESCRIPTION OF THE INVENTION

Figure 1:
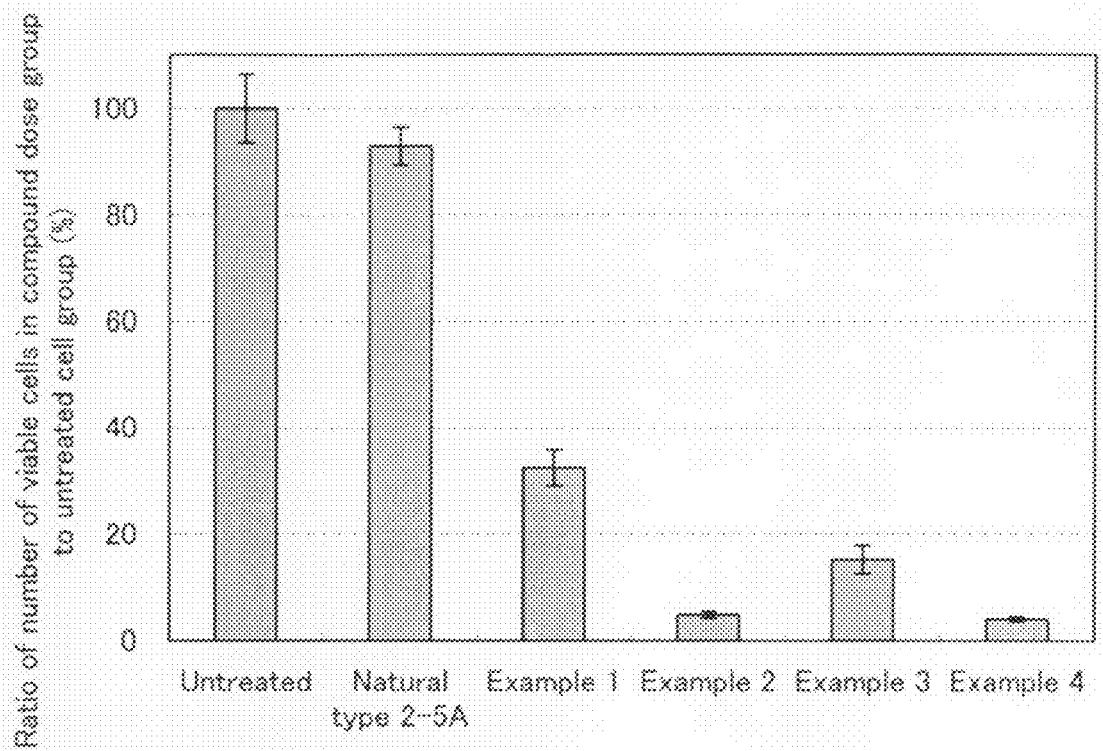
FIG. 1 is a graph showing the cytotoxic activity on A549 cells as a result of the addition of compounds, namely, natural type 2-5A, the compound of Example 1 (Exemplary Compound No. 4), the compound of Example 2 (Exemplary Compound No. 1), the compound of Example 3 (Exemplary Compound No. 5) and the compound of Example 4 (Exemplary Compound No. 8).

In the above general formula, the "alkylene group having from 1 to 4 carbon atoms" of A can be, for example, a methylene, ethylene, trimethylene or tetramethylene group, and is preferably an ethylene or trimethylene group.

In the above general formula (1), the protecting group of the "hydroxyl group protected by a nucleic acid synthesis protecting group" of $R^2$, $R^3$, $R^4$, $R^5$ and $R^6$ or the Group α is not particularly limited so long as it can stably protect a hydroxyl group during nucleic acid synthesis, and specifically means a protecting group stable under acidic or neutral conditions, and cleavable by a chemical method such as hydrogenolysis, hydrolysis, electrolysis or photolysis. Such a protecting group can be, for example, an "aliphatic acyl group" such as an alkylcarbonyl group, e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl; a carboxylated alkylcarbonyl group, e.g., succinoyl, glutaroyl and adipoyl; a halogeno lower alkylcarbonyl group, e.g., chloroacetyl, dichloroacetyl, trichloroacetyl and trifluoroacetyl; a lower alkoxy lower alkylcarbonyl group, e.g., methoxyacetyl; or an unsaturated alkylcarbonyl group, e.g., (E)-2-methyl-2-butenoyl;

a "lower alkyl group" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl;

a "lower alkenyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl;

an "aromatic acyl group" such as an arylcarbonyl group, e.g., benzoyl, α-naphthoyl and β-naphthoyl; a halogeno arylcarbonyl group, e.g., 2-bromobenzoyl and 4-chlorobenzoyl; a lower alkylated arylcarbonyl group, e.g., 2,4,6-trimethylbenzoyl and 4-toluoyl; a lower alkoxylated arylcarbonyl group, e.g., 4-anisoyl; a carboxylated arylcarbonyl group, e.g., 2-carboxybenzoyl, 3-carboxybenzoyl and 4-carboxybenzoyl; a nitrated arylcarbonyl group, e.g., 4-nitrobenzoyl and 2-nitrobenzoyl; a lower alkoxycarbonylated arylcarbonyl group, e.g., 2-(methoxycarbonyl)benzoyl; or an arylated arylcarbonyl group, e.g., 4-phenylbenzoyl;

a "tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl;

a "tetrahydrofuranyl or tetrahydrothiofuranyl group" such as tetrahydrofuran-2-yl and tetrahydrothiofuran-2-yl;

a "silyl group" such as a tri-lower alkylsilyl group, e.g., trimethylsilyl, triethylsilyl, isopropyldimethylsilyl, t-butyldimethylsilyl, methyldiisopropylsilyl, methyldi-t-butylsilyl and triisopropylsilyl; or a tri-lower alkylsilyl group substituted by 1 or 2 aryl groups, e.g., diphenylmethylsilyl, diphenylbutylsilyl, diphenylisopropylsilyl and phenyldiisopropylsilyl;

a "lower alkoxymethyl group" such as methoxymethyl, 1,1-dimethyl-1-methoxymethyl, ethoxymethyl, propoxymethyl, isopropoxymethyl, butoxymethyl and t-butoxymethyl;

a "lower alkoxylated lower alkoxymethyl group" such as 2-methoxyethoxymethyl;

a "halogeno lower alkoxymethyl" such as 2,2,2-trichloroethoxymethyl and bis(2-chloroethoxy)methyl;

a "lower alkoxylated ethyl group" such as 1-ethoxyethyl and 1-(isopropoxy)ethyl;

a "halogenated ethyl group" such as 2,2,2-trichloroethyl;

a "methyl group substituted by from 1 to 3 aryl groups" such as benzyl, α-naphthylmethyl, β-naphthylmethyl, diphenylmethyl, triphenylmethyl, α-naphthyldiphenylmethyl and 9-anthrylmethyl;

a "methyl group substituted by from 1 to 3 aryl groups whose aryl ring is substituted by lower alkyl, lower alkoxy, halogen or cyano group(s)" such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl and 4-cyanobenzyl;

a "lower alkoxycarbonyl group" such as methoxycarbonyl, ethoxycarbonyl, t-butoxycarbonyl and isobutoxycarbonyl;

an "aryl group substituted by halogen atom(s), lower alkoxy group(s) or nitro group(s)" such as 4-chlorophenyl, 2-chlorophenyl, 4-methoxyphenyl, 4-nitrophenyl and 2,4-dinitrophenyl;

a "lower alkoxycarbonyl group substituted by halogen or tri-lower alkylsilyl group(s)" such as 2,2,2-trichloroethoxycarbonyl and 2-trimethylsilylethoxycarbonyl;

an "alkenyloxycarbonyl group" such as vinyloxycarbonyl and allyloxycarbonyl;

an "aralkyloxycarbonyl group whose aryl ring may be substituted by 1 or 2 lower alkoxy or nitro groups" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl;

an "aliphatic acyloxymethyl group" such as an alkylcarbonyloxymethyl group, e.g., acetyloxymethyl, propionyloxymethyl, butyryloxymethyl, isobutyryloxymethyl, pentanoyloxymethyl, pivaloyloxymethyl, valeryloxymethyl, isovaleryloxymethyl, octanoyloxymethyl, nonanoyloxymethyl, decanoyloxymethyl, 3-methylnonanoyloxymethyl, 8-methylnonanoyloxymethyl, 3-ethyloctanoyloxymethyl, 3,7-dimethyloctanoyloxymethyl, undecanoyloxymethyl, dodecanoyloxymethyl, tridecanoyloxymethyl, tetradecanoyloxymethyl, pentadecanoyloxymethyl, hexadecanoyloxymethyl, 1-methylpentadecanoyloxymethyl, 14-methylpentadecanoyloxymethyl, 13,13-dimethyltetradecanoyloxymethyl, heptadecanoyloxymethyl, 15-methylhexadecanoyloxymethyl, octadecanoyloxymethyl, 1-methylheptadecanoyloxymethyl, nonadecanoyloxymethyl, eicosanoyloxymethyl and heneicosanoyloxymethyl; a carboxylated alkylcarbonyloxymethyl group, e.g., succinoyloxymethyl, glutaroyloxymethyl and adipoyloxymethyl; a halogeno lower alkylcarbonyloxymethyl group, e.g., chloroacetyloxymethyl, dichloroacetyloxymethyl, trichloroacetyloxymethyl and trifluoroacetyloxymethyl; a lower alkoxy lower alkylcarbonyloxymethyl group, e.g., methoxyacetyloxymethyl; or an unsaturated alkylcarbonyloxymethyl group, e.g., (E)-2-methyl-2-butenoyl;

an "aliphatic acylthioethyl group" such as an alkylcarbonylthioethyl group, e.g., acetylthioethyl, propionylthioethyl, butyrylthioethyl, isobutyrylthioethyl, pentanoylthioethyl, pivaloylthioethyl, valerylthioethyl, isovalerylthioethyl, octanoylthioethyl, nonanoylthioethyl, decanoylthioethyl, 3-methylnonanoylthioethyl, 8-methylnonanoylthioethyl, 3-ethyloctanoylthioethyl, 3,7-dimethyloctanoylthioethyl, undecanoylthioethyl, dodecanoylthioethyl, tridecanoylthioethyl, tetradecanoylthioethyl, pentadecanoylthioethyl, hexadecanoylthioethyl, 1-methylpentadecanoylthioethyl, 14-methylpentadecanoylthioethyl, 13,13-dimethyltetradecanoylthioethyl, heptadecanoylthioethyl, 15-methylhexadecanoylthioethyl, octadecanoylthioethyl, 1-methylheptadecanoylthioethyl, nonadecanoylthioethyl, eicosanoylthioethyl and heneicosanoylthioethyl; a carboxylated alkylcarbonylthioethyl group, e.g., succinoylthioethyl, glutaroylthioethyl and adipoylthioethyl; a halogeno lower alkylcarbonylthioethyl group, e.g., chloroacetylthioethyl, dichloroacetylthioethyl, trichloroacetylthioethyl and trifluoroacetylthioethyl; a lower alkoxy lower alkylcarbonylthioethyl group, e.g., methoxyacetylthioethyl; or an unsaturated alkylcarbonylthioethyl group, e.g., (E)-2-methyl-2-butenoyl.

The protecting group of the "hydroxyl group protected by a nucleic acid synthesis protecting group" of $R^2$, $R^3$, $R^4$, $R^5$ and $R^6$ or the Group α is preferably a "methyl group substituted by from 1 to 3 aryl groups", an "aryl group substituted by halogen atom(s), lower alkoxy group(s) or nitro group(s)", a "lower alkyl group", a "lower alkenyl group", an "aliphatic acyloxymethyl group", or an "aliphatic acylthioethyl group", more preferably a benzyl group, a 2-chlorophenyl group, a 4-chlorophenyl group, a 2-propenyl group, a pivaloyloxymethyl group, an acetylthioethyl group, or a pivaloylthioethyl group.

In the above general formula (1), the "alkoxy group having from 1 to 6 carbon atoms which may be substituted" of $R^1$, $R^2$, $R^3$, $R^4$, $R^5$, $R^6$ or the Group α can be, for example, a "lower alkyloxy group" such as methoxy, ethoxy, n-propoxy, isopropoxy, n-butoxy, isobutoxy, s-butoxy, n-pentyloxy, isopentyloxy, 2-methylbutoxy, neopentyloxy, 1-ethylpropoxy, n-hexyloxy, isohexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy;

a "lower alkyloxy group substituted by hydroxyl group(s)" such as 1-hydroxymethyloxy, 2-hydroxyethyloxy, 3-hydroxypropyloxy, 4-hydroxybutyloxy, 2-hydroxypropyloxy, 1-methyl-2-hydroxyethyloxy, 1-methyl-1-hydroxyethyloxy, 1,1-dimethyl-2-hydroxyethyloxy, 2-hydroxybutyloxy, 3-hydroxybutyloxy, 1-methyl-3-hydroxypropyloxy and 2-methyl-3-hydroxypropyloxy;

a "lower alkyloxy group substituted by amino group(s)" such as 1-aminomethyloxy, 2-aminoethyloxy, 3-aminopropyloxy, 4-aminobutyloxy, 2-aminopropyloxy, 1-methyl-2-aminoethyloxy, 1-methyl-1-aminoethyloxy, 1,1-dimethyl-1-aminoethyloxy, 2-aminobutyloxy, 3-aminobutyloxy, 1-methyl-3-aminopropyloxy and 2-methyl-3-aminopropyloxy;

a "lower alkyloxy group substituted by alkoxy group(s)" such as 1-methoxymethyloxy, 2-methoxyethyloxy, 3-methoxypropyloxy, 4-methoxybutyloxy, 2-methoxypropyloxy, 1-methyl-2-methoxyethyloxy, 1-methyl-1-methoxyethyloxy, 1,1-dimethyl-2-methoxyethyloxy, 2-methoxybutyloxy, 3-methoxybutyloxy, 1-methyl-3-methoxypropyloxy, 2-methyl-3-methoxypropyloxy, 1-ethoxymethyloxy, 2-ethoxyethyloxy, 3-ethoxypropyloxy, 4-ethoxybutyloxy, 2-ethoxypropyloxy, 1-methyl-2-ethoxyethyloxy, 1-methyl-1- ethoxyethyloxy, 1,1-dimethyl-2-ethoxyethyloxy, 2-ethoxybutyloxy, 3-ethoxybutyloxy, 1-methyl-3-ethoxypropyloxy and 2-methyl-3-ethoxypropyloxy; or a "cycloalkyloxy group" such as cyclopropoxy, cyclobutyloxy, cyclopentyloxy, cyclohexyloxy, cycloheptyloxy, norbornyloxy and adamantyloxy; and is preferably a 2-hydroxyethoxy group.

In the above general formula (1), the "oxyalkyleneoxy group having from 1 to 6 carbon atoms" of $R^7$ can be, for example, an oxymethyleneoxy, oxyethyleneoxy, oxytrimethyleneoxy, oxytetramethyleneoxy, oxypentamethyleneoxy, or oxyhexamethyleneoxy group, and is preferably an oxytetramethyleneoxy or oxypentamethyleneoxy group.

In the above general formula (1), the protecting group of the "mercapto group protected by a nucleic acid synthesis protecting group" of $R^1, R^2, R^3, R^4, R^5$ and $R^6$ or the Group α is not particularly limited so long as it can stably protect a mercapto group during nucleic acid synthesis, and specifically means a protecting group stable under acidic or neutral conditions, and cleavable by a chemical method such as hydrogenolysis, hydrolysis, electrolysis or photolysis. Such a protecting group can be, for example, a "group which can form a disulfide" such as an alkylthio group, e.g., methylthio, ethylthio and tert-butylthio, or an arylthio group, e.g. benzylthio, in addition to the groups listed as a protecting group of a hydroxyl group, and is preferably an "aliphatic acyl group", an "aromatic acyl group", an "aliphatic acyloxymethyl group", or an "aliphatic acylthioethyl group", more preferably a pivaloyloxymethyl group, an acetylthioethyl group, or a pivaloylthioethyl group.

In the above general formula (1), the "alkylthio group having from 1 to 4 carbon atoms which may be substituted" of $R^1, R^2, R^3, R^4, R^5$ and $R^6$ or the Group α can be, for example, methylthio, ethylthio, propylthio, isopropylthio, butylthio, isobutylthio, s-butylthio, or tert-butylthio, and is preferably a methylthio or ethylthio group.

In the above general formula (1), the protecting group of the "amino group protected by a nucleic acid synthesis protecting group" of $R^1 R^2, R^3, R^4, R^5$ and $R^6$ or the Group α is not particularly limited so long as it can stably protect an amino group during nucleic acid synthesis, and specifically means a protecting group stable under acidic or neutral conditions and cleavable by a chemical method such as hydrogenolysis, hydrolysis, electrolysis or photolysis. Such a protecting group can be, for example, an "aliphatic acyl group" such as an alkylcarbonyl group, e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl; a carboxylated alkylcarbonyl group, e.g., succinoyl, glutaroyl and adipoyl; a halogeno lower alkylcarbonyl group, e.g., chloroacetyl, dichloroacetyl, trichloroacetyl and trifluoroacetyl; a lower alkoxy lower alkylcarbonyl group, e.g., methoxyacetyl; or an unsaturated alkylcarbonyl group, e.g., (E)-2-methyl-2-butenoyl;

an "aromatic acyl group" such as an arylcarbonyl group, e.g., benzoyl, α-naphthoyl and β-naphthoyl; a halogeno arylcarbonyl group, e.g., 2-bromobenzoyl and 4-chlorobenzoyl; a lower alkylated arylcarbonyl group, e.g., 2,4,6-trimethylbenzoyl and 4-toluoyl; a lower alkoxylated arylcarbonyl group, e.g., 4-anisoyl; a carboxylated arylcarbonyl group, e.g., 2-carboxybenzoyl, 3-carboxybenzoyl and 4-carboxybenzoyl; a nitrated arylcarbonyl group, e.g., 4-nitrobenzoyl and 2-nitrobenzoyl; a lower alkoxycarbonylated arylcarbonyl group, e.g., 2-(methoxycarbonyl)benzoyl; or an arylated arylcarbonyl group, e.g., 4-phenylbenzoyl;

a "lower alkoxycarbonyl group" such as methoxycarbonyl, ethoxycarbonyl, t-butoxycarbonyl and isobutoxycarbonyl;

a "lower alkoxycarbonyl group substituted by halogen or tri-lower alkylsilyl group(s)" such as 2,2,2-trichloroethoxycarbonyl and 2-trimethylsilylethoxycarbonyl;

an "alkenyloxycarbonyl group" such as vinyloxycarbonyl and allyloxycarbonyl; or an "aralkyloxycarbonyl group whose aryl ring may be substituted by 1 or 2 lower alkoxy or nitro groups" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl; and is preferably an "aliphatic acyl group" or an "aromatic acyl group", more preferably a benzoyl group.

In the above general formula (1), the "amino group substituted by alkyl group(s) having from 1 to 4 carbon atoms which may be substituted" of $R^1, R^2, R^3, R^4, R^5$ and $R^6$ or the Group α can be, for example, a "lower alkylamino group" such as methylamino, ethylamino, propylamino, isopropylamino, butylamino, isobutylamino, s-butylamino, tert-butylamino, dimethylamino, diethylamino, dipropylamino, diisopropylamino, dibutylamino, diisobutylamino, di(s-butyl)amino and di(tert-butyl)amino;

a "lower alkylamino group substituted by hydroxyl group(s), lower alkoxy group(s) or halogen atom(s)" such as 1-hydroxyethylamino, 2-hydroxyethylamino, 1-methoxyethylamino, 2-methoxyethylamino, 1-bromoethylamino, 2-methoxyethylamino, 1-chloroethylamino and 2-chloroethylamino; or a "lower alkoxycarbonylamino group" such as 1-methoxycarbonylethylamino, 2-methoxycarbonylethylamino, 1-ethoxycarbonylethylamino, 2-ethoxycarbonylethylamino, 1-propoxycarbonylethylamino and 1-propoxycarbonylethylamino; and is preferably a 1-hydroxyethylamino, 2-hydroxyethylamino, methylamino, ethylamino, dimethylamino, diethylamino, diisopropylamino, 1-methoxycarbonylethylamino or 1-ethoxycarbonylethylamino group.

In the above general formula (1), the "alkyl group having from 1 to 6 carbon atoms which may be substituted" of D, $R^1, R^2, R^3, R^4, R^5, R^6, R^8$ or the Group α can be, for example, a "lower alkyl group" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl;

a "lower alkyl group substituted by hydroxyl group(s)" such as 1-hydroxymethyl, 2-hydroxyethyl, 3-hydroxypropyl, 4-hydroxybutyl, 2-hydroxypropyl, 1-methyl-2-hydroxyethyl, 1-methyl-1-hydroxyethyl, 1,1-dimethyl-2-hydroxyethyl, 2-hydroxybutyl, 3-hydroxybutyl, 1-methyl-3-hydroxypropyl and 2-methyl-3-hydroxypropyl;

a "lower alkyl group substituted by amino group(s)" such as 1-aminomethyl, 2-aminoethyl, 3-aminopropyl, 4-aminobutyl, 2-aminopropyl, 1-methyl-2-aminoethyl, 1-methyl-1- aminoethyl, 1,1-dimethyl-2-aminoethyl, 2-aminobutyl, 3-aminobutyl, 1-methyl-3-aminopropyl and 2-methyl-3-aminopropyl;

a "lower alkyl group substituted by alkoxy group(s)" such as 1-methoxymethyl, 2-methoxyethyl, 3-methoxypropyl, 4-methoxybutyl, 2-methoxypropyl, 1-methyl-2-methoxyethyl, 1-methyl-1-methoxyethyl, 1,1-dimethyl-2-methoxyethyl, 2-methoxybutyl, 3-methoxybutyl, 1-methyl-3-methoxypropyl, 2-methyl-3-methoxypropyl, 1-ethoxymethyl, 2-ethoxyethyl, 3-ethoxypropyl, 4-ethoxybutyl, 2-ethoxypropyl, 1-methyl-2-ethoxyethyl, 1-methyl-1-ethoxyethyl, 1,1-dimethyl-2-ethoxyethyl, 2-ethoxybutyl, 3-ethoxybutyl, 1-methyl-3-ethoxypropyl and 2-methyl-3-ethoxypropyl; or a "cycloalkyl group" such as cyclopropyl, cyclobutyl, cyclopentyl, cyclohexyl, cycloheptyl, norbornyl and adamantyl;

and is preferably a 2-methoxyethyl group or a 2-hydroxyethyl group.

In the above general formula (1), the "alkyl group having from 1 to 24 carbon atoms which may be substituted" of $X_1$ can be, for example, stearyl, 2,2-dimethylstearyl, heptadecyl, 2,2-dimethylheptadecyl, hexadecyl, 2,2-dimethylhexadecyl, pentadecyl, 2,2-dimethylpentadecyl, tetradecyl, 2,2-dimethyltetradecyl, tridecyl, 2,2-dimethyltridecyl, dodecyl, 2,2-dimethyldodecyl, undecyl, 2,2-dimethylundecyl, decyl, 2,2-dimethyldecyl, nonyl, 2,2-dimethylnonyl, octyl, 2,2-dimethyloctyl, heptyl, 2,2-dimethylheptyl, hexyl, 2,2-dimethylhexyl, pentyl, 2,2-dimethylpentyl, butyl, 2,2-dimethylbutyl, propyl, 2,2-tert-butyl, ethyl, or methyl, and is preferably stearyl or 2,2-dimethylstearyl.

In the above general formula (1), the "alkylene group having from 1 to 6 carbon atoms which may be substituted" of $X_3$ can be, for example, methylene, ethylene, propylene, butylene, 2,2-dimethylethylene, 2,2-dimethylpropylene, or 2,2-dimethylbutylene, and is preferably methylene or ethylene.

In the above general formula (1), the "aryloxy group which may be substituted" of $R^1$ can be, for example, an "aryloxy group substituted by lower alkyl group(s), halogen atom(s) or nitro group(s)" such as 2-methylphenoxy, 3-methylphenoxy, 4-methylphenoxy, 2,6-dimethylphenoxy, 2-chlorophenoxy, 4-chlorophenoxy, 2,4-dichlorophenoxy, 2,5-dichlorophenoxy, 2-bromophenoxy, 4-nitrophenoxy and 4-chloro-2-nitrophenoxy.

In the above general formula (1), the "aryl group which may be substituted" of $R^8$ or $X_1$ can be, for example, an "aryl group substituted by lower alkyl group(s), halogen atom(s) or nitro group(s)" such as 2-methylphenyl, 3-methylphenyl, 4-methylphenyl, 2,6-dimethylphenyl, 2-chlorophenyl, 4-chlorophenyl, 2,4-dichlorophenyl, 2,5-dichlorophenyl, 2-bromophenyl, 4-nitrophenyl and 4-chloro-2-nitrophenyl.

In the above general formula (1), the "arylthio group which may be substituted" of $R^1$ can be, for example, an "arylthio group substituted by lower alkyl group(s), halogen atom(s) or nitro group(s)" such as 2-methylphenylthio, 3-methylphenylthio, 4-methylphenylthio, 2,6-dimethylphenylthio, 2-chlorophenylthio, 4-chlorophenylthio, 2,4-dichlorophenylthio, 2,5-dichlorophenylthio, 2-bromophenylthio, 4-nitrophenylthio and 4-chloro-2-nitrophenylthio.

In the above general formula (1), the "alkenyl group having from 2 to 6 carbon atoms which may be substituted" of D can be, for example, ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, or 5-hexenyl.

In the above general formula (1), the "aralkyl group which may be substituted" of $R^8$ or $X_1$ can be, for example, an "aralkyl group" such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl; or an "aralkyl group whose aryl ring is substituted by nitro group(s) or halogen atom(s)" such as 4-chlorobenzyl, 2-(4-nitrophenyl)ethyl, o-nitrobenzyl, 4-nitrobenzyl, 2,4-dinitrobenzyl and 4-chloro-2-nitrobenzyl.

In the above general formula (1), of all of the "purin-9-yl group" and the "substituted purin-9-yl group" of B, the preferred groups are 6-amino-purin-9-yl (that is, adeninyl), 6-amino-purin-9-yl in which the amino group is protected by a nucleic acid synthesis protecting group, 6-amino-8-bromopurin-9-yl, 6-amino-8-bromopurin-9-yl in which the amino group is protected by a nucleic acid synthesis protecting group, 6-amino-8-chloropurin-9-yl, 6-amino-8-chloropurin-9-yl in which the amino group is protected by a nucleic acid synthesis protecting group, 6-amino-8-fluoropurin-9-yl, 6-amino-8-fluoropurin-9-yl in which the amino group is protected by a nucleic acid synthesis protecting group, 6-amino-8-methoxypurin-9-yl, 6-amino-8-methoxypurin-9-yl in which the amino group is protected by a nucleic acid synthesis protecting group, 6-amino-8-ethoxypurin-9-yl, 6-amino-8-ethoxypurin-9-yl in which the amino group is protected by a nucleic acid synthesis protecting group, 6-amino-8-t-butoxypurin-9-yl, 6-amino-8-t-butoxypurin-9-yl in which the amino group is protected by a nucleic acid synthesis protecting group, 2,6-diaminopurin-9-yl, 2-amino-6-chloropurin-9-yl, 2-amino-6-chloropurin-9-yl in which the amino group is protected by a nucleic acid synthesis protecting group, 2-amino-6-fluoropurin-9-yl, 2-amino-6-fluoropurin-9-yl in which the amino group is protected by a nucleic acid synthesis protecting group, 2-amino-6-bromopurin-9-yl, 2-amino-6-bromopurin-9-yl in which the amino group is protected by a nucleic acid synthesis protecting group, 2-amino-6-hydroxypurin-9-yl (that is, guaninyl), 2-amino-6-hydroxypurin-9-yl in which the amino group is protected by a nucleic acid synthesis protecting group, 6-amino-2-methoxypurin-9-yl, 6-amino-2-methoxypurin-9-yl in which the amino group is protected by a nucleic acid synthesis protecting group, 6-amino-2-chloropurin-9-yl, 6-amino-2-chloropurin-9-yl in which the amino group is protected by a nucleic acid synthesis protecting group, 6-amino-2-fluoropurin-9-yl, 6-amino-2-fluoropurin-9-yl in which the amino group is protected by a nucleic acid synthesis protecting group, 2,6-dimethoxypurin-9-yl, 2,6-dichloropurin-9-yl, and 6-mercaptopurin-9-yl group, and the more preferred groups are 6-benzoylaminopurin-9-yl or adeninyl.

There is no particular limitation on the functional group represented by "$X_1-X_2-X_3-S$", provided that it is a combination comprising $X_1$, $X_2$, $X_3$ and S mentioned above, and it can be, for example, an acyloxyalkylthio group such as 2-(stearoyloxy)ethylthio, 2-(myristoyloxy)ethylthio, 2-(decanoyloxy)ethylthio, 2-(benzoyloxy)ethylthio, 2-(pivaloyloxy)ethylthio, 2-(2,2-dimethyloctadecanoyloxy)ethylthio, 3-(stearoyloxy)propylthio, 3-(myristoyloxy)propylthio, 3-(decanoyloxy)propylthio, 3-(benzoyloxy)propylthio, 3-(pivaloyloxy)propylthio, 3-(2,2-dimethyloctadecanoyloxy)propylthio, 4-(stearoyloxy)butylthio, 4-(myristoyloxy)butylthio, 4-(decanoyloxy)butylthio, 4-(benzoyloxy)butylthio, 4-(pivaloyloxy)butylthio and 4-(2,2-dimethyloctadecanoyloxy)butylthio, or an alkylcarbamoyloxyalkylthio group such as 2-(stearylcarbamoyloxy)ethylthio, or the following compounds:

In the above general formula (1), the "halogen atom" of the Group α can be, for example, a fluorine atom, a chlorine atom, a bromine atom or an iodine atom, and is preferably a bromine atom or a chlorine atom.

The "2',5'-oligoadenylate analog (2-5A analog)" means a non-natural type derivative of "2',5'-oligoadenylate", in which the 2' position and 5' position of the 3 or 4 "nucleosides", being the same or different, are bonded by a phosphodiester bond linkage or a modified phosphodiester linkage, and a phosphoryl derivative is bonded to the 5'-terminal, or a phosphoryl derivative is optionally bonded to the 2'-terminal, or a 5'-phosphorylated oligonucleotide analog is optionally bonded to the 2'-terminal through an alkylene linker. Such an analog can preferably be a sugar derivative wherein the sugar portion is modified; a thioate derivative wherein the phosphodiester bonding portion is thioated; a

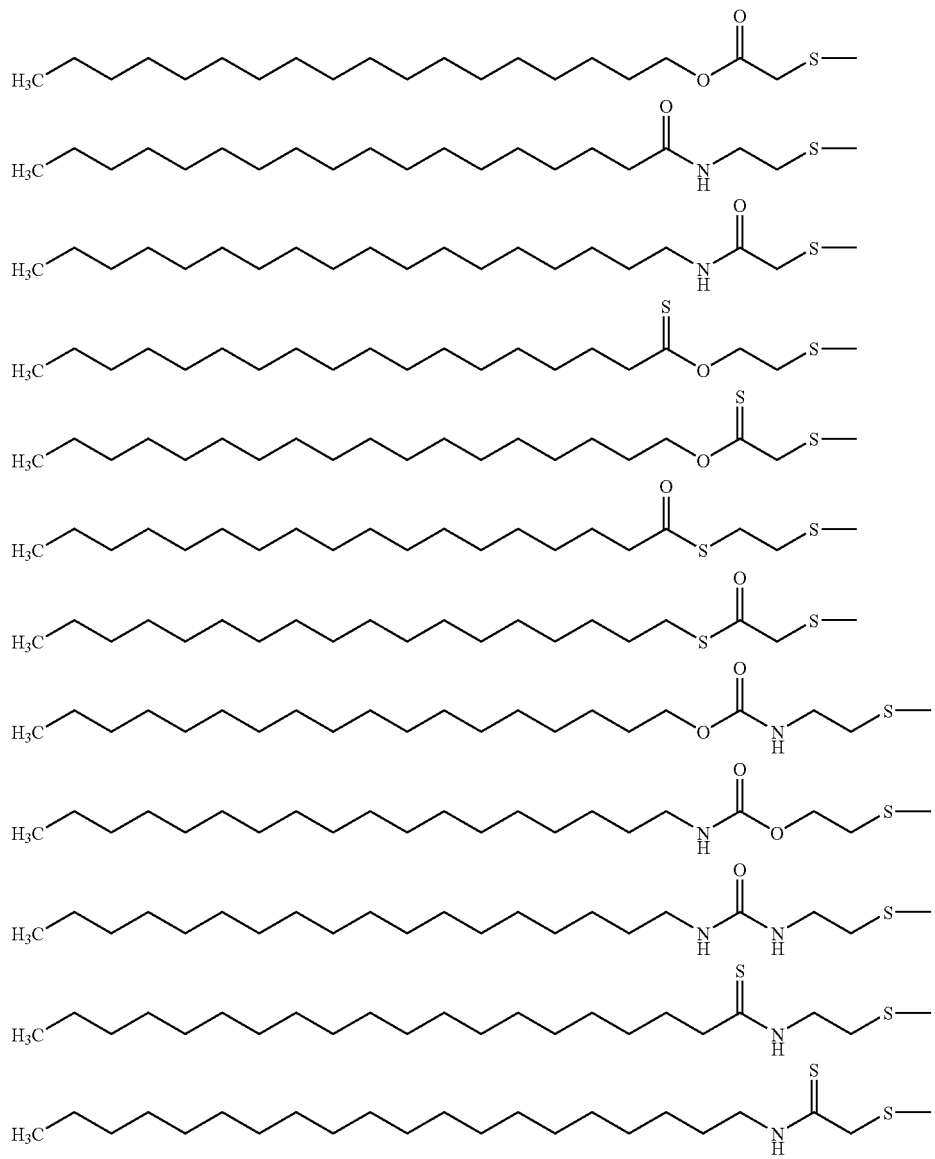

and is preferably a 2-stearoyloxyethylthio or 2-(2,2-dimethyloctadecanoyloxy)ethylthio group.

phosphoryl derivative wherein the phosphoric acid portion at the terminal is substituted; or a purine derivative wherein the purine base is substituted; and is more preferably a phosphoryl derivative wherein the phosphoric acid portion at the terminal is substituted, a sugar derivative wherein the sugar portion is modified, or a thioate derivative wherein the phosphodiester bonding portion is thioated.

The "5'-phosphorylated oligonucleotide analog which has one hydroxyl group removed from the 5'-phosphoric acid group" means a non-natural type derivative of "oligonucleotide" in which 2 to 50 "nucleosides" being the same or different, are bonded by phosphodiester bond linkages, and means a derivative having the following residual group:

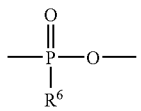

(wherein $R^6$ has the same meaning as defined above) instead of the hydroxyl group at the 5' end of the oligonucleotide.

Such an analog can preferably be a sugar derivative wherein the sugar portion is modified; a thioate derivative wherein the phosphodiester bonding portion is thioated; an ester wherein the phosphoric acid portion at the terminal is esterified; or an amide wherein the amino group on the purine base is amidated; and is more preferably a sugar derivative wherein the sugar portion is modified, or a thioate derivative wherein the phosphodiester bonding portion is thioated.

"Salt thereof" means a salt of the compound (1) of the present invention, since the compound can be converted to a salt. Such a salt can preferably be a metal salt such as an alkali metal salt, e.g., a sodium salt, a potassium salt and a lithium salt; an alkaline earth metal salt, e.g., a calcium salt and a magnesium salt; an aluminum salt, an iron salt, a zinc salt, a copper salt, a nickel salt or a cobalt salt; an amine salt such as inorganic salt, e.g., an ammonium salt; or an organic salt, e.g., a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt and a tris(hydroxymethyl)aminomethane salt; an inorganic acid salt such as a hydrogen halide salt, e.g., hydrofluoride, hydrochloride, hydrobromide and hydroiodide; nitrate, perchlorate, sulfate or phosphate; or an organic acid salt such as a lower alkanesulfonate, e.g., methanesulfonate, trifluoromethanesulfonate and ethanesulfonate; an arylsulfonate, e.g., benzenesulfonate and p-toluenesulfonate; acetate, malate, fumarate, succinate, citrate, tartrate, oxalate or maleate; or an amino acid salt such as a glycine salt, a lysine salt, an arginine salt, an ornithine salt, a glutamate, or an aspartate.

A "pharmacologically acceptable salt thereof" means a salt of the 2-5A analog of the present invention, since it can be converted into a salt. Such a salt can preferably be a metal salt such as an alkali metal salt, e.g., a sodium salt, a potassium salt and a lithium salt; an alkaline earth metal salt, e.g., a calcium salt and a magnesium salt; an aluminum salt, an iron salt, a zinc salt, a copper salt, a nickel salt or a cobalt salt; an amine salt such as an inorganic salt, e.g., an ammonium salt; or an organic salt; e.g., a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt and a tris(hydroxymethyl)aminomethane salt; an inorganic acid salt such as a hydrogen halide salt, e.g., hydrofluoride, hydrochloride, hydrobromide and hydroiodide; nitrate, perchlorate, sulfate or phosphate; or an organic acid salt such as a lower alkanesulfonate, e.g., methanesulfonate, trifluoromethanesulfonate and ethanesulfonate; an arylsulfonate, e.g., benzenesulfonate and p-toluenesulfonate; acetate, malate, fumarate, succinate, citrate, tartrate, oxalate or maleate; or an amino acid salt such as a glycine salt, a lysine salt, an arginine salt, an ornithine salt, a glutamate, or an aspartate.

Specific compounds included in the compound of the above formula (1) of the present invention are illustrated in Table 1. However, the compounds of the present invention are not limited to these.

TABLE 1

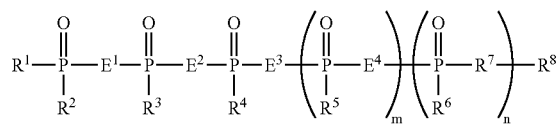

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1 | $K^{2-1}$ | $K^{1-1}$ | $K^{3-1}$ | — | OH | SH | OH | OH | — | — | — | H | 0 | 0 |
| 2 | $K^{2-1}$ | $K^{1-1}$ | $K^{3-1}$ | — | $OC_2H_4OH$ | OH | OH | OH | — | — | — | H | 0 | 0 |
| 3 | $K^{2-1}$ | $K^{1-1}$ | $K^{3-1}$ | — | $OC_2H_4OH$ | SH | OH | OH | — | — | — | H | 0 | 0 |
| 4 | $K^{1-1}$ | $K^{1-1}$ | $K^{1-1}$ | — | $OC_2H_4OH$ | OH | SH | SH | — | — | — | H | 0 | 0 |
| 5 | $K^{1-1}$ | $K^{1-1}$ | $K^{1-1}$ | — | $OC_2H_4OH$ | SH | SH | SH | — | — | — | H | 0 | 0 |
| 6 | $K^{1-1}$ | $K^{1-1}$ | $K^{1-1}$ | $K^{1-1}$ | $OC_2H_4OH$ | OH | SH | SH | SH | — | — | H | 1 | 0 |
| 7 | $K^{1-1}$ | $K^{1-1}$ | $K^{1-1}$ | $K^{1-1}$ | $OC_2H_4OH$ | SH | SH | SH | SH | — | — | H | 1 | 0 |
| 8 | $K^{1-1}$ | $K^{1-1}$ | $K^{1-1}$ | — | OH | SH | SH | SH | — | — | — | H | 0 | 0 |
| 9 | $K^{2-2}$ | $K^{1-1}$ | $K^{3-1}$ | — | OH | SH | OH | OH | — | — | — | H | 0 | 0 |
| 10 | $K^{2-3}$ | $K^{1-1}$ | $K^{3-1}$ | — | OH | SH | OH | OH | — | — | — | H | 0 | 0 |
| 11 | $K^{2-4}$ | $K^{1-1}$ | $K^{3-1}$ | — | OH | SH | OH | OH | — | — | — | H | 0 | 0 |
| 12 | $K^{2-1}$ | $K^{1-2}$ | $K^{3-1}$ | — | OH | SH | OH | OH | — | — | — | H | 0 | 0 |
| 13 | $K^{2-1}$ | $K^{1-1}$ | $K^{3-2}$ | — | OH | SH | OH | OH | — | — | — | H | 0 | 0 |
| 14 | $K^{2-1}$ | $K^{1-1}$ | $K^{3-3}$ | — | OH | SH | OH | OH | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 15 | $K^{2-1}$ | $K^{1-1}$ | $K^{3-4}$ | — | OH | SH | OH | OH | — | — | — | H | 0 | 0 |
| 16 | $K^{2-1}$ | $K^{1-1}$ | $K^{3-5}$ | — | OH | SH | OH | OH | — | — | — | H | 0 | 0 |
| 17 | $K^{2-2}$ | $K^{1-1}$ | $K^{3-2}$ | — | OH | SH | OH | OH | — | — | — | H | 0 | 0 |
| 18 | $K^{2-2}$ | $K^{1-2}$ | $K^{3-2}$ | — | $OC_2H_4OH$ | SH | OH | OH | — | — | — | H | 0 | 0 |
| 19 | $K^{2-3}$ | $K^{1-1}$ | $K^{3-1}$ | — | $OC_2H_4OH$ | SH | OH | OH | — | — | — | H | 0 | 0 |
| 20 | $K^{2-4}$ | $K^{1-1}$ | $K^{3-1}$ | — | $OC_2H_4OH$ | SH | OH | OH | — | — | — | H | 0 | 0 |
| 21 | $K^{2-1}$ | $K^{1-2}$ | $K^{3-1}$ | — | $OC_2H_4OH$ | SH | OH | OH | — | — | — | H | 0 | 0 |
| 22 | $K^{2-1}$ | $K^{1-1}$ | $K^{3-2}$ | — | $OC_2H_4OH$ | SH | OH | OH | — | — | — | H | 0 | 0 |
| 23 | $K^{2-1}$ | $K^{1-1}$ | $K^{3-3}$ | — | $OC_2H_4OH$ | SH | OH | OH | — | — | — | H | 0 | 0 |
| 24 | $K^{2-1}$ | $K^{1-1}$ | $K^{3-4}$ | — | $OC_2H_4OH$ | SH | OH | OH | — | — | — | H | 0 | 0 |
| 25 | $K^{2-1}$ | $K^{1-1}$ | $K^{3-5}$ | — | $OC_2H_4OH$ | SH | OH | OH | — | — | — | H | 0 | 0 |
| 26 | $K^{2-2}$ | $K^{1-2}$ | $K^{3-2}$ | — | $OC_2H_4OH$ | SH | OH | OH | — | — | — | H | 0 | 0 |
| 27 | $K^{1-1}$ | $K^{1-1}$ | $K^{1-2}$ | — | $OC_2H_4OH$ | OH | SH | SH | — | — | — | H | 0 | 0 |
| 28 | $K^{1-1}$ | $K^{1-1}$ | $K^{1-2}$ | — | $OC_2H_4OH$ | SH | SH | SH | — | — | — | H | 0 | 0 |
| 29 | $K^{1-1}$ | $K^{1-1}$ | $K^{1-2}$ | $K^{1-1}$ | $OC_2H_4OH$ | OH | SH | SH | SH | — | — | H | 1 | 0 |
| 30 | $K^{1-1}$ | $K^{1-1}$ | $K^{1-2}$ | $K^{1-1}$ | $OC_2H_4OH$ | SH | SH | SH | SH | — | — | H | 1 | 0 |
| 31 | $K^{1-1}$ | $K^{1-1}$ | $K^{1-2}$ | — | OH | SH | SH | SH | — | — | — | H | 0 | 0 |
| 32 | $K^{2-1}$ | $K^{1-1}$ | $K^{3-1}$ | — | OH | SH | OH | OH | — | $O(CH_2)_3OH$ | O | H | 0 | 1 |
| 33 | $K^{2-1}$ | $K^{1-1}$ | $K^{3-1}$ | — | $OC_2H_4OH$ | OH | OH | OH | — | $O(CH_2)_3OH$ | O | H | 0 | 1 |
| 34 | $K^{2-1}$ | $K^{1-1}$ | $K^{3-1}$ | — | $OC_2H_4OH$ | SH | OH | OH | — | $O(CH_2)_3OH$ | O | H | 0 | 1 |
| 35 | $K^{1-1}$ | $K^{1-1}$ | $K^{1-1}$ | — | $OC_2H_4OH$ | OH | OH | OH | — | $O(CH_2)_3OH$ | O | H | 0 | 1 |
| 36 | $K^{1-1}$ | $K^{1-1}$ | $K^{1-1}$ | — | $OC_2H_4OH$ | SH | SH | SH | — | $O(CH_2)_3OH$ | O | H | 0 | 1 |
| 37 | $K^{1-1}$ | $K^{1-1}$ | $K^{1-1}$ | $K^{1-1}$ | $OC_2H_4OH$ | OH | SH | SH | SH | $O(CH_2)_3OH$ | O | H | 1 | 1 |
| 38 | $K^{1-1}$ | $K^{1-1}$ | $K^{1-1}$ | — | $OC_2H_4OH$ | OH | OH | OH | — | $O(CH_2)_3OH$ | O | H | 0 | 1 |
| 39 | $K^{1-1}$ | $K^{1-1}$ | $K^{1-1}$ | — | OH | SH | SH | SH | — | $O(CH_2)_3OH$ | O | H | 0 | 1 |
| 40 | $K^{1-1}$ | $K^{1-1}$ | $K^{3-2}$ | — | OH | SH | OH | OH | — | $O(CH_2)_3OH$ | O | H | 0 | 1 |
| 41 | $K^{1-1}$ | $K^{1-1}$ | $K^{1-2}$ | — | $OC_2H_4OH$ | OH | SH | SH | — | $O(CH_2)_3OH$ | O | H | 0 | 1 |
| 42 | $K^{1-1}$ | $K^{1-1}$ | $K^{1-2}$ | — | $OC_2H_4OH$ | SH | SH | SH | — | $O(CH_2)_3OH$ | O | H | 0 | 1 |
| 43 | $K^{2-1}$ | $K^{1-1}$ | $K^{3-1}$ | — | OH | OH | OH | OH | — | $O(CH_2)_4OH$ | O | H | 0 | 1 |
| 44 | $K^{2-1}$ | $K^{1-1}$ | $K^{3-1}$ | — | $OC_2H_4OH$ | OH | OH | OH | — | $O(CH_2)_4OH$ | O | H | 0 | 1 |
| 45 | $K^{2-1}$ | $K^{1-1}$ | $K^{3-1}$ | — | $OC_2H_4OH$ | SH | OH | OH | — | $O(CH_2)_4OH$ | O | H | 0 | 1 |
| 46 | $K^{1-1}$ | $K^{1-1}$ | $K^{1-1}$ | — | $OC_2H_4OH$ | OH | OH | OH | — | $O(CH_2)_4OH$ | O | H | 0 | 1 |
| 47 | $K^{1-1}$ | $K^{1-1}$ | $K^{1-1}$ | — | $OC_2H_4OH$ | SH | SH | SH | — | $O(CH_2)_4OH$ | O | H | 0 | 1 |
| 48 | $K^{1-1}$ | $K^{1-1}$ | $K^{1-1}$ | $K^{1-1}$ | $OC_2H_4OH$ | OH | SH | SH | SH | $O(CH_2)_4OH$ | O | H | 1 | 1 |
| 49 | $K^{1-1}$ | $K^{1-1}$ | $K^{1-1}$ | — | $OC_2H_4OH$ | OH | OH | OH | — | $O(CH_2)_4OH$ | O | H | 0 | 1 |
| 50 | $K^{1-1}$ | $K^{1-1}$ | $K^{1-1}$ | — | OH | SH | SH | SH | — | $O(CH_2)_4OH$ | O | H | 0 | 1 |
| 51 | $K^{2-1}$ | $K^{1-1}$ | $K^{3-2}$ | — | OH | SH | OH | OH | — | $O(CH_2)_4OH$ | O | H | 0 | 1 |
| 52 | $K^{1-1}$ | $K^{1-1}$ | $K^{1-2}$ | — | $OC_2H_4OH$ | OH | SH | SH | — | $O(CH_2)_4OH$ | O | H | 0 | 1 |
| 53 | $K^{1-1}$ | $K^{1-1}$ | $K^{1-2}$ | — | $OC_2H_4OH$ | SH | 5H | SH | — | $O(CH_2)_4OH$ | O | H | 0 | 1 |
| 54 | $K^{2-1}$ | $K^{1-1}$ | $K^{3-1}$ | — | OH | SH | OH | OH | — | $O(CH_2)_2OH$ | O | H | 0 | 2 |
| 55 | $K^{2-1}$ | $K^{1-1}$ | $K^{3-1}$ | — | $OC_2H_4OH$ | OH | OH | OH | — | $O(CH_2)_2OH$ | O | H | 0 | 2 |
| 56 | $K^{2-1}$ | $K^{1-1}$ | $K^{3-1}$ | — | $OC_2H_4OH$ | SH | OH | OH | — | $O(CH_2)_2OH$ | O | H | 0 | 2 |
| 57 | $K^{1-1}$ | $K^{1-1}$ | $K^{1-1}$ | — | $OC_2H_4OH$ | OH | OH | OH | — | $O(CH_2)_2OH$ | O | H | 0 | 2 |
| 58 | $K^{1-1}$ | $K^{1-1}$ | $K^{1-1}$ | — | $OC_2H_4OH$ | SH | SH | SH | — | $O(CH_2)_2OH$ | O | H | 0 | 2 |
| 59 | $K^{1-1}$ | $K^{1-1}$ | $K^{1-1}$ | $K^{1-1}$ | $OC_2H_4OH$ | OH | SH | SH | SH | $O(CH_2)_2OH$ | O | H | 1 | 2 |
| 60 | $K^{1-1}$ | $K^{1-1}$ | $K^{1-1}$ | — | $OC_2H_4OH$ | OH | OH | OH | — | $O(CH_2)_2OH$ | O | H | 0 | 2 |
| 61 | $K^{1-1}$ | $K^{1-1}$ | $K^{1-1}$ | — | OH | SH | SH | SH | — | $O(CH_2)_2OH$ | O | H | 0 | 2 |
| 62 | $K^{1-1}$ | $K^{1-1}$ | $K^{3-2}$ | — | OH | OH | OH | OH | — | $O(CH_2)_2OH$ | O | H | 0 | 2 |
| 63 | $K^{1-1}$ | $K^{1-1}$ | $K^{1-2}$ | — | $OC_2H_4OH$ | OH | SH | SH | — | $O(CH_2)_2OH$ | O | H | 0 | 2 |
| 64 | $K^{1-1}$ | $K^{1-1}$ | $K^{1-2}$ | — | $OC_2H_4OH$ | SH | SH | SH | — | $O(CH_2)_2OH$ | O | H | 0 | 2 |
| 65 | $K^{2-1}$ | $K^{1-1}$ | $K^{3-1}$ | — | $O(CH_2)_3OH$ | OH | OH | OH | — | — | — | H | 0 | 0 |
| 66 | $K^{2-1}$ | $K^{1-1}$ | $K^{3-1}$ | — | $O(CH_2)_4OH$ | OH | OH | OH | — | — | — | H | 0 | 0 |
| 67 | $K^{2-1}$ | $K^{1-1}$ | $K^{3-1}$ | — | $O(CH_2)_6OH$ | OH | OH | OH | — | — | — | H | 0 | 0 |
| 68 | $K^{2-1}$ | $K^{1-1}$ | $K^{3-1}$ | — | $O(CH_2)_8OH$ | OH | OH | OH | — | — | — | H | 0 | 0 |
| 69 | $K^{2-1}$ | $K^{1-1}$ | $K^{3-1}$ | — | $O(CH_2)_3NH_2$ | OH | OH | OH | — | — | — | H | 0 | 0 |
| 70 | $K^{2-1}$ | $K^{1-1}$ | $K^{3-1}$ | — | $O(CH_2)_6NH_2$ | OH | OH | OH | — | — | — | H | 0 | 0 |
| 71 | $K^{2-1}$ | $K^{1-1}$ | $K^{3-1}$ | — | OPh | OH | OH | OH | — | — | — | H | 0 | 0 |
| 72 | $K^{2-1}$ | $K^{1-1}$ | $K^{3-1}$ | — | OBn | OH | OH | OH | — | — | — | H | 0 | 0 |
| 73 | $K^{2-1}$ | $K^{1-1}$ | $K^{3-1}$ | — | OMe | OH | OH | OH | — | — | — | H | 0 | 0 |
| 74 | $K^{2-1}$ | $K^{1-1}$ | $K^{3-1}$ | — | OEt | OH | OH | OH | — | — | — | H | 0 | 0 |
| 75 | $K^{2-1}$ | $K^{1-1}$ | $K^{3-1}$ | — | OPr | OH | OH | OH | — | — | — | H | 0 | 0 |
| 76 | $K^{2-1}$ | $K^{1-1}$ | $K^{3-1}$ | — | Gly | OH | OH | OH | — | — | — | H | 0 | 0 |
| 77 | $K^{2-1}$ | $K^{1-1}$ | $K^{3-1}$ | — | Me | OH | OH | OH | — | — | — | H | 0 | 0 |
| 78 | $K^{2-1}$ | $K^{1-1}$ | $K^{3-1}$ | — | Et | OH | OH | OH | — | — | — | H | 0 | 0 |
| 79 | $K^{2-1}$ | $K^{1-1}$ | $K^{3-1}$ | — | $CH_2OH$ | OH | OH | OH | — | — | — | H | 0 | 0 |
| 80 | $K^{2-1}$ | $K^{1-1}$ | $K^{3-1}$ | — | $C_2H_4OH$ | OH | OH | OH | — | — | — | H | 0 | 0 |
| 81 | $K^{2-1}$ | $K^{1-1}$ | $K^{3-1}$ | — | Ph | OH | OH | OH | — | — | — | H | 0 | 0 |
| 82 | $K^{2-1}$ | $K^{1-1}$ | $K^{3-1}$ | — | $CH_2Ph$ | OH | OH | OH | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | E¹ | E² | E³ | E⁴ | R¹ | R² | R³ | R⁴ | R⁵ | R⁶ | R⁷ | R⁸ | m | n |
|---|---|---|---|---|---|---|---|---|---|---|---|---|---|---|
| 83 | K²⁻¹ | K¹⁻¹ | K³⁻¹ | — | NH₂ | OH | OH | OH | — | — | — | H | 0 | 0 |
| 84 | K²⁻¹ | K¹⁻¹ | K³⁻¹ | — | NHPh | OH | OH | OH | — | — | — | H | 0 | 0 |
| 85 | K²⁻¹ | K¹⁻¹ | K³⁻¹ | — | N(Me)₂ | OH | OH | OH | — | — | — | H | 0 | 0 |
| 86 | K²⁻¹ | K¹⁻¹ | K³⁻¹ | — | N(Et)₂ | OH | OH | OH | — | — | — | H | 0 | 0 |
| 87 | K²⁻¹ | K¹⁻¹ | K³⁻¹ | — | SMe | OH | OH | OH | — | — | — | H | 0 | 0 |
| 88 | K²⁻¹ | K¹⁻¹ | K³⁻¹ | — | SEt | OH | OH | OH | — | — | — | H | 0 | 0 |
| 89 | K²⁻¹ | K¹⁻¹ | K³⁻¹ | — | SPh | OH | OH | OH | — | — | — | H | 0 | 0 |
| 90 | K²⁻¹ | K¹⁻¹ | K³⁻¹ | — | O(CH₂)₃OH | SH | OH | OH | — | — | — | H | 0 | 0 |
| 91 | K²⁻¹ | K¹⁻¹ | K³⁻¹ | — | O(CH₂)₄OH | SH | OH | OH | — | — | — | H | 0 | 0 |
| 92 | K²⁻¹ | K¹⁻¹ | K³⁻¹ | — | O(CH₂)₆OH | SH | OH | OH | — | — | — | H | 0 | 0 |
| 93 | K²⁻¹ | K¹⁻¹ | K³⁻¹ | — | O(CH₂)₈OH | SH | OH | OH | — | — | — | H | 0 | 0 |
| 94 | K²⁻¹ | K¹⁻¹ | K³⁻¹ | — | O(CH₂)₃NH₂ | SH | OH | OH | — | — | — | H | 0 | 0 |
| 95 | K²⁻¹ | K¹⁻¹ | K³⁻¹ | — | O(CH₂)₆NH₂ | SH | OH | OH | — | — | — | H | 0 | 0 |
| 96 | K²⁻¹ | K¹⁻¹ | K³⁻¹ | — | OPh | SH | OH | OH | — | — | — | H | 0 | 0 |
| 97 | K²⁻¹ | K¹⁻¹ | K³⁻¹ | — | OBn | SH | OH | OH | — | — | — | H | 0 | 0 |
| 98 | K²⁻¹ | K¹⁻¹ | K³⁻¹ | — | OMe | SH | OH | OH | — | — | — | H | 0 | 0 |
| 99 | K²⁻¹ | K¹⁻¹ | K³⁻¹ | — | OEt | SH | OH | OH | — | — | — | H | 0 | 0 |
| 100 | K²⁻¹ | K¹⁻¹ | K³⁻¹ | — | OPr | SH | OH | OH | — | — | — | H | 0 | 0 |
| 101 | K²⁻¹ | K¹⁻¹ | K³⁻¹ | — | Gly | SH | OH | OH | — | — | — | H | 0 | 0 |
| 102 | K²⁻¹ | K¹⁻¹ | K³⁻¹ | — | Me | SH | OH | OH | — | — | — | H | 0 | 0 |
| 103 | K²⁻¹ | K¹⁻¹ | K³⁻¹ | — | Et | SH | OH | OH | — | — | — | H | 0 | 0 |
| 104 | K²⁻¹ | K¹⁻¹ | K³⁻¹ | — | CH₂OH | SH | OH | OH | — | — | — | H | 0 | 0 |
| 105 | K²⁻¹ | K¹⁻¹ | K³⁻¹ | — | C₂H₄OH | SH | OH | OH | — | — | — | H | 0 | 0 |
| 106 | K²⁻¹ | K¹⁻¹ | K³⁻¹ | — | Ph | SH | OH | OH | — | — | — | H | 0 | 0 |
| 107 | K²⁻¹ | K¹⁻¹ | K³⁻¹ | — | CH₂Ph | SH | OH | OH | — | — | — | H | 0 | 0 |
| 108 | K²⁻¹ | K¹⁻¹ | K³⁻¹ | — | NH₂ | SH | OH | OH | — | — | — | H | 0 | 0 |
| 109 | K²⁻¹ | K¹⁻¹ | K³⁻¹ | — | NHPh | SH | OH | OH | — | — | — | H | 0 | 0 |
| 110 | K²⁻¹ | K¹⁻¹ | K³⁻¹ | — | N(Me)₂ | SH | OH | OH | — | — | — | H | 0 | 0 |
| 111 | K²⁻¹ | K¹⁻¹ | K³⁻¹ | — | N(Et)₂ | SH | OH | OH | — | — | — | H | 0 | 0 |
| 112 | K²⁻¹ | K¹⁻¹ | K³⁻¹ | — | SMe | SH | OH | OH | — | — | — | H | 0 | 0 |
| 113 | K²⁻¹ | K¹⁻¹ | K³⁻¹ | — | SEt | SH | OH | OH | — | — | — | H | 0 | 0 |
| 114 | K²⁻¹ | K¹⁻¹ | K³⁻¹ | — | SPh | SH | OH | OH | — | — | — | H | 0 | 0 |
| 115 | K²⁻¹ | K¹⁻¹ | K³⁻¹ | — | O(CH₂)₃OH | NH₂ | OH | OH | — | — | — | H | 0 | 0 |
| 116 | K²⁻¹ | K¹⁻¹ | K³⁻¹ | — | O(CH₂)₄OH | NH₂ | OH | OH | — | — | — | H | 0 | 0 |
| 117 | K²⁻¹ | K¹⁻¹ | K³⁻¹ | — | O(CH₂)₆OH | NH₂ | OH | OH | — | — | — | H | 0 | 0 |
| 118 | K²⁻¹ | K¹⁻¹ | K³⁻¹ | — | O(CH₂)₈OH | NH₂ | OH | OH | — | — | — | H | 0 | 0 |
| 119 | K²⁻¹ | K¹⁻¹ | K³⁻¹ | — | O(CH₂)₃NH₂ | NH₂ | OH | OH | — | — | — | H | 0 | 0 |
| 120 | K²⁻¹ | K¹⁻¹ | K³⁻¹ | — | O(OH₂)₆NH₂ | NH₂ | OH | OH | — | — | — | H | 0 | 0 |
| 121 | K²⁻¹ | K¹⁻¹ | K³⁻¹ | — | OPh | NH₂ | OH | OH | — | — | — | H | 0 | 0 |
| 122 | K²⁻¹ | K¹⁻¹ | K³⁻¹ | — | OBn | NH₂ | OH | OH | — | — | — | H | 0 | 0 |
| 123 | K²⁻¹ | K¹⁻¹ | K³⁻¹ | — | OMe | NH₂ | OH | OH | — | — | — | H | 0 | 0 |
| 124 | K²⁻¹ | K¹⁻¹ | K³⁻¹ | — | OEt | NH₂ | OH | OH | — | — | — | H | 0 | 0 |
| 125 | K²⁻¹ | K¹⁻¹ | K³⁻¹ | — | OPr | NH₂ | OH | OH | — | — | — | H | 0 | 0 |
| 126 | K²⁻¹ | K¹⁻¹ | K³⁻¹ | — | Gly | NH₂ | OH | OH | — | — | — | H | 0 | 0 |
| 127 | K²⁻¹ | K¹⁻¹ | K³⁻¹ | — | Me | NH₂ | OH | OH | — | — | — | H | 0 | 0 |
| 128 | K²⁻¹ | K¹⁻¹ | K³⁻¹ | — | Et | NH₂ | OH | OH | — | — | — | H | 0 | 0 |
| 129 | K²⁻¹ | K¹⁻¹ | K³⁻¹ | — | CH₂OH | NH₂ | OH | OH | — | — | — | H | 0 | 0 |
| 130 | K²⁻¹ | K¹⁻¹ | K³⁻¹ | — | C₂H₄OH | NH₂ | OH | OH | — | — | — | H | 0 | 0 |
| 131 | K²⁻¹ | K¹⁻¹ | K³⁻¹ | — | Ph | NH₂ | OH | OH | — | — | — | H | 0 | 0 |
| 132 | K²⁻¹ | K¹⁻¹ | K³⁻¹ | — | CH₂Ph | NH₂ | OH | OH | — | — | — | H | 0 | 0 |
| 133 | K²⁻¹ | K¹⁻¹ | K³⁻¹ | — | NH₂ | NH₂ | OH | OH | — | — | — | H | 0 | 0 |
| 134 | K²⁻¹ | K¹⁻¹ | K³⁻¹ | — | NHPh | NH₂ | OH | OH | — | — | — | H | 0 | 0 |
| 135 | K²⁻¹ | K¹⁻¹ | K³⁻¹ | — | N(Me)₂ | NH₂ | OH | OH | — | — | — | H | 0 | 0 |
| 136 | K²⁻¹ | K¹⁻¹ | K³⁻¹ | — | N(Et)₂ | NH₂ | OH | OH | — | — | — | H | 0 | 0 |
| 137 | K²⁻¹ | K¹⁻¹ | K³⁻¹ | — | SMe | NH₂ | OH | OH | — | — | — | H | 0 | 0 |
| 138 | K²⁻¹ | K¹⁻¹ | K³⁻¹ | — | SEt | NH₂ | OH | OH | — | — | — | H | 0 | 0 |
| 139 | K²⁻¹ | K¹⁻¹ | K³⁻¹ | — | SPh | NH₂ | OH | OH | — | — | — | H | 0 | 0 |
| 140 | K¹⁻¹ | K¹⁻¹ | K¹⁻¹ | — | O(CH₂)₂OH | OH | SH | SH | — | — | — | H | 0 | 0 |
| 141 | K¹⁻¹ | K¹⁻¹ | K¹⁻¹ | — | O(CH₂)₄OH | OH | SH | SH | — | — | — | H | 0 | 0 |
| 142 | K¹⁻¹ | K¹⁻¹ | K¹⁻¹ | — | O(CH₂)₆OH | OH | SH | SH | — | — | — | H | 0 | 0 |
| 143 | K¹⁻¹ | K¹⁻¹ | K¹⁻¹ | — | O(CH₂)₈OH | OH | SH | SH | — | — | — | H | 0 | 0 |
| 144 | K¹⁻¹ | K¹⁻¹ | K¹⁻¹ | — | O(CH₂)₃NH₂ | OH | SH | SH | — | — | — | H | 0 | 0 |
| 145 | K¹⁻¹ | K¹⁻¹ | K¹⁻¹ | — | O(CH₂)₆NH₂ | OH | SH | SH | — | — | — | H | 0 | 0 |
| 146 | K¹⁻¹ | K¹⁻¹ | K¹⁻¹ | — | OPh | OH | SH | SH | — | — | — | H | 0 | 0 |
| 147 | K¹⁻¹ | K¹⁻¹ | K¹⁻¹ | — | OBn | OH | SH | SH | — | — | — | H | 0 | 0 |
| 148 | K¹⁻¹ | K¹⁻¹ | K¹⁻¹ | — | OMe | OH | SH | SH | — | — | — | H | 0 | 0 |
| 149 | K¹⁻¹ | K¹⁻¹ | K¹⁻¹ | — | OEt | OH | SH | SH | — | — | — | H | 0 | 0 |
| 150 | K¹⁻¹ | K¹⁻¹ | K¹⁻¹ | — | OPr | OH | SH | SH | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n R^8$$

| Exemplified Compound No. | E¹ | E² | E³ | E⁴ | R¹ | R² | R³ | R⁴ | R⁵ | R⁶ | R⁷ | R⁸ | m | n |
|---|---|---|---|---|---|---|---|---|---|---|---|---|---|---|
| 151 | K¹⁻¹ | K¹⁻¹ | K¹⁻¹ | — | Gly | OH | SH | SH | — | — | — | H | 0 | 0 |
| 152 | K¹⁻¹ | K¹⁻¹ | K¹⁻¹ | — | Me | OH | SH | SH | — | — | — | H | 0 | 0 |
| 153 | K¹⁻¹ | K¹⁻¹ | K¹⁻¹ | — | Et | OH | SH | SH | — | — | — | H | 0 | 0 |
| 154 | K¹⁻¹ | K¹⁻¹ | K¹⁻¹ | — | CH₂OH | OH | SH | SH | — | — | — | H | 0 | 0 |
| 155 | K¹⁻¹ | K¹⁻¹ | K¹⁻¹ | — | C₂H₄OH | OH | SH | SH | — | — | — | H | 0 | 0 |
| 156 | K¹⁻¹ | K¹⁻¹ | K¹⁻¹ | — | Ph | OH | SH | SH | — | — | — | H | 0 | 0 |
| 157 | K¹⁻¹ | K¹⁻¹ | K¹⁻¹ | — | CH₂Ph | OH | SH | SH | — | — | — | H | 0 | 0 |
| 158 | K¹⁻¹ | K¹⁻¹ | K¹⁻¹ | — | NH₂ | OH | SH | SH | — | — | — | H | 0 | 0 |
| 159 | K¹⁻¹ | K¹⁻¹ | K¹⁻¹ | — | NHPh | OH | SH | SH | — | — | — | H | 0 | 0 |
| 160 | K¹⁻¹ | K¹⁻¹ | K¹⁻¹ | — | N(Me)₂ | OH | SH | SH | — | — | — | H | 0 | 0 |
| 161 | K¹⁻¹ | K¹⁻¹ | K¹⁻¹ | — | N(Et)₂ | OH | SH | SH | — | — | — | H | 0 | 0 |
| 162 | K¹⁻¹ | K¹⁻¹ | K¹⁻¹ | — | SMe | OH | SH | SH | — | — | — | H | 0 | 0 |
| 163 | K¹⁻¹ | K¹⁻¹ | K¹⁻¹ | — | SEt | OH | SH | SH | — | — | — | H | 0 | 0 |
| 164 | K¹⁻¹ | K¹⁻¹ | K¹⁻¹ | — | SPh | OH | SH | SH | — | — | — | H | 0 | 0 |
| 165 | K¹⁻¹ | K¹⁻¹ | K¹⁻¹ | — | O(CH₂)₃OH | SH | SH | SH | — | — | — | H | 0 | 0 |
| 166 | K¹⁻¹ | K¹⁻¹ | K¹⁻¹ | — | O(CH₂)₄OH | SH | SH | SH | — | — | — | H | 0 | 0 |
| 167 | K¹⁻¹ | K¹⁻¹ | K¹⁻¹ | — | O(CH₂)₆OH | SH | SH | SH | — | — | — | H | 0 | 0 |
| 168 | K¹⁻¹ | K¹⁻¹ | K¹⁻¹ | — | O(CH₂)₈OH | SH | SH | SH | — | — | — | H | 0 | 0 |
| 169 | K¹⁻¹ | K¹⁻¹ | K¹⁻¹ | — | O(CH₂)₃NH₂ | SH | SH | SH | — | — | — | H | 0 | 0 |
| 170 | K¹⁻¹ | K¹⁻¹ | K¹⁻¹ | — | O(CH₂)₆NH₂ | SH | SH | SH | — | — | — | H | 0 | 0 |
| 171 | K¹⁻¹ | K¹⁻¹ | K¹⁻¹ | — | OPh | SH | SH | SH | — | — | — | H | 0 | 0 |
| 172 | K¹⁻¹ | K¹⁻¹ | K¹⁻¹ | — | OBn | SH | SH | SH | — | — | — | H | 0 | 0 |
| 173 | K¹⁻¹ | K¹⁻¹ | K¹⁻¹ | — | OMe | SH | SH | SH | — | — | — | H | 0 | 0 |
| 174 | K¹⁻¹ | K¹⁻¹ | K¹⁻¹ | — | OEt | SH | SH | SH | — | — | — | H | 0 | 0 |
| 175 | K¹⁻¹ | K¹⁻¹ | K¹⁻¹ | — | OPr | SH | SH | SH | — | — | — | H | 0 | 0 |
| 176 | K¹⁻¹ | K¹⁻¹ | K¹⁻¹ | — | Gly | SH | SH | SH | — | — | — | H | 0 | 0 |
| 177 | K¹⁻¹ | K¹⁻¹ | K¹⁻¹ | — | Me | SH | SH | SH | — | — | — | H | 0 | 0 |
| 178 | K¹⁻¹ | K¹⁻¹ | K¹⁻¹ | — | Et | SH | SH | SH | — | — | — | H | 0 | 0 |
| 179 | K¹⁻¹ | K¹⁻¹ | K¹⁻¹ | — | CH₂OH | SH | SH | SH | — | — | — | H | 0 | 0 |
| 180 | K¹⁻¹ | K¹⁻¹ | K¹⁻¹ | — | C₂H₄OH | SH | SH | SH | — | — | — | H | 0 | 0 |
| 181 | K¹⁻¹ | K¹⁻¹ | K¹⁻¹ | — | Ph | SH | SH | SH | — | — | — | H | 0 | 0 |
| 182 | K¹⁻¹ | K¹⁻¹ | K¹⁻¹ | — | CH₂Ph | SH | SH | SH | — | — | — | H | 0 | 0 |
| 183 | K¹⁻¹ | K¹⁻¹ | K¹⁻¹ | — | NH₂ | SH | SH | SH | — | — | — | H | 0 | 0 |
| 184 | K¹⁻¹ | K¹⁻¹ | K¹⁻¹ | — | NHPh | SH | SH | SH | — | — | — | H | 0 | 0 |
| 185 | K¹⁻¹ | K¹⁻¹ | K¹⁻¹ | — | N(Me)₂ | SH | SH | SH | — | — | — | H | 0 | 0 |
| 186 | K¹⁻¹ | K¹⁻¹ | K¹⁻¹ | — | N(Et)₂ | SH | SH | SH | — | — | — | H | 0 | 0 |
| 187 | K¹⁻¹ | K¹⁻¹ | K¹⁻¹ | — | SMe | SH | SH | SH | — | — | — | H | 0 | 0 |
| 188 | K¹⁻¹ | K¹⁻¹ | K¹⁻¹ | — | SEt | SH | SH | SH | — | — | — | H | 0 | 0 |
| 189 | K¹⁻¹ | K¹⁻¹ | K¹⁻¹ | — | SPh | SH | SH | SH | — | — | — | H | 0 | 0 |
| 190 | K¹⁻¹ | K¹⁻¹ | K¹⁻¹ | — | O(CH₂)₃OH | NH₂ | SH | SH | — | — | — | H | 0 | 0 |
| 191 | K¹⁻¹ | K¹⁻¹ | K¹⁻¹ | — | O(CH₂)₄OH | NH₂ | SH | SH | — | — | — | H | 0 | 0 |
| 192 | K¹⁻¹ | K¹⁻¹ | K¹⁻¹ | — | O(CH₂)₆OH | NH₂ | SH | SH | — | — | — | H | 0 | 0 |
| 193 | K¹⁻¹ | K¹⁻¹ | K¹⁻¹ | — | O(CH₂)₈OH | NH₂ | SH | SH | — | — | — | H | 0 | 0 |
| 194 | K¹⁻¹ | K¹⁻¹ | K¹⁻¹ | — | O(CH₂)₃NN₂ | NH₂ | SH | SH | — | — | — | H | 0 | 0 |
| 195 | K¹⁻¹ | K¹⁻¹ | K¹⁻¹ | — | O(CH₂)₆NH₂ | NH₂ | SH | SH | — | — | — | H | 0 | 0 |
| 196 | K¹⁻¹ | K¹⁻¹ | K¹⁻¹ | — | OPh | NH₂ | SH | SH | — | — | — | H | 0 | 0 |
| 197 | K¹⁻¹ | K¹⁻¹ | K¹⁻¹ | — | OBn | NH₂ | SH | SH | — | — | — | H | 0 | 0 |
| 198 | K¹⁻¹ | K¹⁻¹ | K¹⁻¹ | — | OMe | NH₂ | SH | SH | — | — | — | H | 0 | 0 |
| 199 | K¹⁻¹ | K¹⁻¹ | K¹⁻¹ | — | OEt | NH₂ | SH | SH | — | — | — | H | 0 | 0 |
| 200 | K¹⁻¹ | K¹⁻¹ | K¹⁻¹ | — | OPt | NH₂ | SH | SH | — | — | — | H | 0 | 0 |
| 201 | K¹⁻¹ | K¹⁻¹ | K¹⁻¹ | — | Gly | NH₂ | SH | SH | — | — | — | H | 0 | 0 |
| 202 | K¹⁻¹ | K¹⁻¹ | K¹⁻¹ | — | Me | NH₂ | SH | SH | — | — | — | H | 0 | 0 |
| 203 | K¹⁻¹ | K¹⁻¹ | K¹⁻¹ | — | Et | NH₂ | SH | SH | — | — | — | H | 0 | 0 |
| 204 | K¹⁻¹ | K¹⁻¹ | K¹⁻¹ | — | CH₂OH | NH₂ | SH | SH | — | — | — | H | 0 | 0 |
| 205 | K¹⁻¹ | K¹⁻¹ | K¹⁻¹ | — | C₂H₄OH | NH₂ | SH | SH | — | — | — | H | 0 | 0 |
| 206 | K¹⁻¹ | K¹⁻¹ | K¹⁻¹ | — | Ph | NH₂ | SH | SH | — | — | — | H | 0 | 0 |
| 207 | K¹⁻¹ | K¹⁻¹ | K¹⁻¹ | — | CH₂Ph | NH₂ | SH | SH | — | — | — | H | 0 | 0 |
| 208 | K¹⁻¹ | K¹⁻¹ | K¹⁻¹ | — | NH₂ | NH₂ | SH | SH | — | — | — | H | 0 | 0 |
| 209 | K¹⁻¹ | K¹⁻¹ | K¹⁻¹ | — | NHPh | NH₂ | SH | SH | — | — | — | H | 0 | 0 |
| 210 | K¹⁻¹ | K¹⁻¹ | K¹⁻¹ | — | N(Me)₂ | NH₂ | SH | SH | — | — | — | H | 0 | 0 |
| 211 | K¹⁻¹ | K¹⁻¹ | K¹⁻¹ | — | N(Et)₂ | NH₂ | SH | SH | — | — | — | H | 0 | 0 |
| 212 | K¹⁻¹ | K¹⁻¹ | K¹⁻¹ | — | SMe | NH₂ | SH | SH | — | — | — | H | 0 | 0 |
| 213 | K¹⁻¹ | K¹⁻¹ | K¹⁻¹ | — | SEt | NH₂ | SH | SH | — | — | — | H | 0 | 0 |
| 214 | K¹⁻¹ | K¹⁻¹ | K¹⁻² | — | SPh | NH₂ | SH | SH | — | — | — | H | 0 | 0 |
| 215 | K¹⁻¹ | K¹⁻¹ | K¹⁻² | — | O(CH₂)₃OH | OH | SH | SH | — | — | — | H | 0 | 0 |
| 216 | K¹⁻¹ | K¹⁻¹ | K¹⁻² | — | O(CH₂)₄OH | OH | SH | SH | — | — | — | H | 0 | 0 |
| 217 | K¹⁻¹ | K¹⁻¹ | K¹⁻² | — | O(CH₂)₆OH | OH | SH | SH | — | — | — | H | 0 | 0 |
| 218 | K¹⁻¹ | K¹⁻¹ | K¹⁻² | — | O(CH₂)₈OH | OH | SH | SH | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n R^8$$

| Exemplified Compound No. | E$^1$ | E$^2$ | E$^3$ | E$^4$ | R$^1$ | R$^2$ | R$^3$ | R$^4$ | R$^5$ | R$^6$ | R$^7$ | R$^8$ | m | n |
|---|---|---|---|---|---|---|---|---|---|---|---|---|---|---|
| 219 | K$^{1-1}$ | K$^{1-1}$ | K$^{1-2}$ | — | O(CH$_2$)$_3$NH$_2$ | OH | SH | SH | — | — | — | H | 0 | 0 |
| 220 | K$^{1-1}$ | K$^{1-1}$ | K$^{1-2}$ | — | O(CH$_2$)$_6$NH$_2$ | OH | SH | SH | — | — | — | H | 0 | 0 |
| 221 | K$^{1-1}$ | K$^{1-1}$ | K$^{1-2}$ | — | OPh | OH | SH | SH | — | — | — | H | 0 | 0 |
| 222 | K$^{1-1}$ | K$^{1-1}$ | K$^{1-2}$ | — | OBn | OH | SH | SH | — | — | — | H | 0 | 0 |
| 223 | K$^{1-1}$ | K$^{1-1}$ | K$^{1-2}$ | — | OMe | OH | SH | SH | — | — | — | H | 0 | 0 |
| 224 | K$^{1-1}$ | K$^{1-1}$ | K$^{1-2}$ | — | OEt | OH | SH | SH | — | — | — | H | 0 | 0 |
| 225 | K$^{1-1}$ | K$^{1-1}$ | K$^{1-2}$ | — | OPr | OH | SH | SH | — | — | — | H | 0 | 0 |
| 226 | K$^{1-1}$ | K$^{1-1}$ | K$^{1-2}$ | — | Gly | OH | SH | SH | — | — | — | H | 0 | 0 |
| 227 | K$^{1-1}$ | K$^{1-1}$ | K$^{1-2}$ | — | Me | OH | SH | SH | — | — | — | H | 0 | 0 |
| 228 | K$^{1-1}$ | K$^{1-1}$ | K$^{1-2}$ | — | Et | OH | SH | SH | — | — | — | H | 0 | 0 |
| 229 | K$^{1-1}$ | K$^{1-1}$ | K$^{1-2}$ | — | CH$_2$OH | OH | SH | SH | — | — | — | H | 0 | 0 |
| 230 | K$^{1-1}$ | K$^{1-1}$ | K$^{1-2}$ | — | C$_2$H$_4$OH | OH | SH | SH | — | — | — | H | 0 | 0 |
| 231 | K$^{1-1}$ | K$^{1-1}$ | K$^{1-2}$ | — | Ph | OH | SH | SH | — | — | — | H | 0 | 0 |
| 232 | K$^{1-1}$ | K$^{1-1}$ | K$^{1-2}$ | — | CH$_2$Ph | OH | SH | SH | — | — | — | H | 0 | 0 |
| 233 | K$^{1-1}$ | K$^{1-1}$ | K$^{1-2}$ | — | NH$_2$ | OH | SH | SH | — | — | — | H | 0 | 0 |
| 234 | K$^{1-1}$ | K$^{1-1}$ | K$^{1-2}$ | — | NHPh | OH | SH | SH | — | — | — | H | 0 | 0 |
| 235 | K$^{1-1}$ | K$^{1-1}$ | K$^{1-2}$ | — | N(Me)$_2$ | OH | SH | SH | — | — | — | H | 0 | 0 |
| 236 | K$^{1-1}$ | K$^{1-1}$ | K$^{1-2}$ | — | N(Et)$_2$ | OH | SH | SH | — | — | — | H | 0 | 0 |
| 237 | K$^{1-1}$ | K$^{1-1}$ | K$^{1-2}$ | — | SMe | OH | SH | SH | — | — | — | H | 0 | 0 |
| 238 | K$^{1-1}$ | K$^{1-1}$ | K$^{1-2}$ | — | SEt | OH | SH | SH | — | — | — | H | 0 | 0 |
| 239 | K$^{1-1}$ | K$^{1-1}$ | K$^{1-2}$ | — | SPh | OH | SH | SH | — | — | — | H | 0 | 0 |
| 240 | K$^{1-1}$ | K$^{1-1}$ | K$^{1-2}$ | — | O(CH$_2$)$_3$OH | SH | SH | SH | — | — | — | H | 0 | 0 |
| 241 | K$^{1-1}$ | K$^{1-1}$ | K$^{1-2}$ | — | O(CH$_2$)$_4$OH | SH | SH | SH | — | — | — | H | 0 | 0 |
| 242 | K$^{1-1}$ | K$^{1-1}$ | K$^{1-2}$ | — | O(CH$_2$)$_6$OH | SH | SH | SH | — | — | — | H | 0 | 0 |
| 243 | K$^{1-1}$ | K$^{1-1}$ | K$^{1-2}$ | — | O(OH$_2$)$_8$OH | SH | SH | SH | — | — | — | H | 0 | 0 |
| 244 | K$^{1-1}$ | K$^{1-1}$ | K$^{1-2}$ | — | O(CH$_2$)$_3$NH$_2$ | SH | SH | SH | — | — | — | H | 0 | 0 |
| 245 | K$^{1-1}$ | K$^{1-1}$ | K$^{1-2}$ | — | O(CH$_2$)$_6$NH$_2$ | SH | SH | SH | — | — | — | H | 0 | 0 |
| 246 | K$^{1-1}$ | K$^{1-1}$ | K$^{1-2}$ | — | OPh | SH | SH | SH | — | — | — | H | 0 | 0 |
| 247 | K$^{1-1}$ | K$^{1-1}$ | K$^{1-2}$ | — | OBn | SH | SH | SH | — | — | — | H | 0 | 0 |
| 248 | K$^{1-1}$ | K$^{1-1}$ | K$^{1-2}$ | — | OMe | SH | SH | SH | — | — | — | H | 0 | 0 |
| 249 | K$^{1-1}$ | K$^{1-1}$ | K$^{1-2}$ | — | OEt | SH | SH | SH | — | — | — | H | 0 | 0 |
| 250 | K$^{1-1}$ | K$^{1-1}$ | K$^{1-2}$ | — | OPr | SH | SH | SH | — | — | — | H | 0 | 0 |
| 251 | K$^{1-1}$ | K$^{1-1}$ | K$^{1-2}$ | — | Gly | SH | SH | SH | — | — | — | H | 0 | 0 |
| 252 | K$^{1-1}$ | K$^{1-1}$ | K$^{1-2}$ | — | Me | SH | SH | SH | — | — | — | H | 0 | 0 |
| 253 | K$^{1-1}$ | K$^{1-1}$ | K$^{1-2}$ | — | Et | SH | SH | SH | — | — | — | H | 0 | 0 |
| 254 | K$^{1-1}$ | K$^{1-1}$ | K$^{1-2}$ | — | CH$_2$OH | SH | SH | SH | — | — | — | H | 0 | 0 |
| 255 | K$^{1-1}$ | K$^{1-1}$ | K$^{1-2}$ | — | C$_2$H$_4$OH | SH | SH | SH | — | — | — | H | 0 | 0 |
| 256 | K$^{1-1}$ | K$^{1-1}$ | K$^{1-2}$ | — | Ph | SH | SH | SH | — | — | — | H | 0 | 0 |
| 257 | K$^{1-1}$ | K$^{1-1}$ | K$^{1-2}$ | — | CH$_2$Ph | SH | SH | SH | — | — | — | H | 0 | 0 |
| 258 | K$^{1-1}$ | K$^{1-1}$ | K$^{1-2}$ | — | NH$_2$ | SH | SH | SH | — | — | — | H | 0 | 0 |
| 259 | K$^{1-1}$ | K$^{1-1}$ | K$^{1-2}$ | — | NHPh | SH | SH | SH | — | — | — | H | 0 | 0 |
| 260 | K$^{1-1}$ | K$^{1-1}$ | K$^{1-2}$ | — | N(Me)$_2$ | SH | SH | SH | — | — | — | H | 0 | 0 |
| 261 | K$^{1-1}$ | K$^{1-1}$ | K$^{1-2}$ | — | N(Et)$_2$ | SH | SH | SH | — | — | — | H | 0 | 0 |
| 262 | K$^{1-1}$ | K$^{1-1}$ | K$^{1-2}$ | — | SMe | SH | SH | SH | — | — | — | H | 0 | 0 |
| 263 | K$^{1-1}$ | K$^{1-1}$ | K$^{1-2}$ | — | SEt | SH | SH | SH | — | — | — | H | 0 | 0 |
| 264 | K$^{1-1}$ | K$^{1-1}$ | K$^{1-2}$ | — | SPh | SH | SH | SH | — | — | — | H | 0 | 0 |
| 265 | K$^{1-1}$ | K$^{1-1}$ | K$^{1-2}$ | — | O(CH$_2$)$_3$OH | NH$_2$ | SH | SH | — | — | — | H | 0 | 0 |
| 266 | K$^{1-1}$ | K$^{1-1}$ | K$^{1-2}$ | — | O(CH$_2$)$_4$OH | NH$_2$ | SH | SH | — | — | — | H | 0 | 0 |
| 267 | K$^{1-1}$ | K$^{1-1}$ | K$^{1-2}$ | — | O(CH$_2$)$_6$OH | NH$_2$ | SH | SH | — | — | — | H | 0 | 0 |
| 268 | K$^{1-1}$ | K$^{1-1}$ | K$^{1-2}$ | — | O(CH$_2$)$_8$OH | NH$_2$ | SH | SH | — | — | — | H | 0 | 0 |
| 269 | K$^{1-1}$ | K$^{1-1}$ | K$^{1-2}$ | — | O(CH$_2$)$_3$NH$_2$ | NH$_2$ | SH | SH | — | — | — | H | 0 | 0 |
| 270 | K$^{1-1}$ | K$^{1-1}$ | K$^{1-2}$ | — | O(CH$_2$)$_6$NH$_2$ | NH$_2$ | SH | SH | — | — | — | H | 0 | 0 |
| 271 | K$^{1-1}$ | K$^{1-1}$ | K$^{1-2}$ | — | OPh | NH$_2$ | SH | SH | — | — | — | H | 0 | 0 |
| 272 | K$^{1-1}$ | K$^{1-1}$ | K$^{1-2}$ | — | OBn | NH$_2$ | SH | SH | — | — | — | H | 0 | 0 |
| 273 | K$^{1-1}$ | K$^{1-1}$ | K$^{1-2}$ | — | OMe | NH$_2$ | SH | SH | — | — | — | H | 0 | 0 |
| 274 | K$^{1-1}$ | K$^{1-1}$ | K$^{1-2}$ | — | OEt | NH$_2$ | SH | SH | — | — | — | H | 0 | 0 |
| 275 | K$^{1-1}$ | K$^{1-1}$ | K$^{1-2}$ | — | OPr | NH$_2$ | SH | SH | — | — | — | H | 0 | 0 |
| 276 | K$^{1-1}$ | K$^{1-1}$ | K$^{1-2}$ | — | Gly | NH$_2$ | SH | SH | — | — | — | H | 0 | 0 |
| 277 | K$^{1-1}$ | K$^{1-1}$ | K$^{1-2}$ | — | Me | NH$_2$ | SH | SH | — | — | — | H | 0 | 0 |
| 278 | K$^{1-1}$ | K$^{1-1}$ | K$^{1-2}$ | — | Et | NH$_2$ | SH | SH | — | — | — | H | 0 | 0 |
| 279 | K$^{1-1}$ | K$^{1-1}$ | K$^{1-2}$ | — | CH$_2$OH | NH$_2$ | SH | SH | — | — | — | H | 0 | 0 |
| 280 | K$^{1-1}$ | K$^{1-1}$ | K$^{1-2}$ | — | C$_2$H$_4$OH | NH$_2$ | SH | SH | — | — | — | H | 0 | 0 |
| 281 | K$^{1-1}$ | K$^{1-1}$ | K$^{1-2}$ | — | Ph | NH$_2$ | SH | SH | — | — | — | H | 0 | 0 |
| 282 | K$^{1-1}$ | K$^{1-1}$ | K$^{1-2}$ | — | CH$_2$Ph | NH$_2$ | SH | SH | — | — | — | H | 0 | 0 |
| 283 | K$^{1-1}$ | K$^{1-1}$ | K$^{1-2}$ | — | NH$_2$ | NH$_2$ | SH | SH | — | — | — | H | 0 | 0 |
| 284 | K$^{1-1}$ | K$^{1-1}$ | K$^{1-2}$ | — | NHPh | NH$_2$ | SH | SH | — | — | — | H | 0 | 0 |
| 285 | K$^{1-1}$ | K$^{1-1}$ | K$^{1-2}$ | — | N(Me)$_2$ | NH$_2$ | SH | SH | — | — | — | H | 0 | 0 |
| 286 | K$^{1-1}$ | K$^{1-1}$ | K$^{1-2}$ | — | N(Et)$_2$ | NH$_2$ | SH | SH | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 287 | $K^{1-1}$ | $K^{1-1}$ | $K^{1-2}$ | — | SMe | $NH_2$ | SH | SH | — | — | — | H | 0 | 0 |
| 288 | $K^{1-1}$ | $K^{1-1}$ | $K^{1-2}$ | — | SEt | $NH_2$ | SH | SH | — | — | — | H | 0 | 0 |
| 289 | $K^{1-1}$ | $K^{1-1}$ | $K^{1-2}$ | — | SPh | $NH_2$ | SH | SH | — | — | — | H | 0 | 0 |
| 290 | $K^{2-1}$ | $K^{1-1}$ | $K^{3-1}$ | — | OH | POMS | OH | OH | — | — | — | H | 0 | 0 |
| 291 | $K^{2-1}$ | $K^{1-1}$ | $K^{3-1}$ | — | OH | POMO | OH | OH | — | — | — | H | 0 | 0 |
| 292 | $K^{2-1}$ | $K^{1-1}$ | $K^{3-1}$ | — | OH | POMS | POMS | POMS | — | — | — | H | 0 | 0 |
| 293 | $K^{2-1}$ | $K^{1-1}$ | $K^{3-1}$ | — | $OC_2H_4OH$ | POMS | OH | OH | — | — | — | H | 0 | 0 |
| 294 | $K^{2-1}$ | $K^{1-1}$ | $K^{3-1}$ | — | $OC_2H_4OH$ | POMO | POMO | POMO | — | — | — | H | 0 | 0 |
| 295 | $K^{2-1}$ | $K^{1-1}$ | $K^{3-1}$ | — | $OC_2H_4OH$ | POMS | POMO | POMO | — | — | — | H | 0 | 0 |
| 296 | $K^{2-1}$ | $K^{1-1}$ | $K^{3-1}$ | — | $OC_2H_4OH$ | POMS | POMS | POMS | — | — | — | H | 0 | 0 |
| 297 | $K^{2-1}$ | $K^{1-1}$ | $K^{3-2}$ | — | OH | POMS | OH | OH | — | — | — | H | 0 | 0 |
| 298 | $K^{2-1}$ | $K^{1-1}$ | $K^{3-2}$ | — | OH | POMO | OH | OH | — | — | — | H | 0 | 0 |
| 299 | $K^{2-1}$ | $K^{1-1}$ | $K^{3-2}$ | — | OH | POMS | POMS | POMS | — | — | — | H | 0 | 0 |
| 300 | $K^{2-1}$ | $K^{1-1}$ | $K^{3-2}$ | — | $OC_2H_4OH$ | POMS | OH | OH | — | — | — | H | 0 | 0 |
| 301 | $K^{2-1}$ | $K^{1-1}$ | $K^{3-2}$ | — | $OC_2H_4OH$ | POMO | POMO | POMO | — | — | — | H | 0 | 0 |
| 302 | $K^{2-1}$ | $K^{1-1}$ | $K^{3-2}$ | — | $OC_2H_4OH$ | POMS | POMO | POMO | — | — | — | H | 0 | 0 |
| 303 | $K^{2-1}$ | $K^{1-1}$ | $K^{3-2}$ | — | $OC_2H_4OH$ | POMS | POMS | POMS | — | — | — | H | 0 | 0 |
| 304 | $K^{1-1}$ | $K^{1-1}$ | $K^{1-1}$ | — | POMO | POMO | POMO | POMO | — | — | — | H | 0 | 0 |
| 305 | $K^{1-1}$ | $K^{1-1}$ | $K^{1-1}$ | — | OH | POMO | POMO | POMO | — | — | — | H | 0 | 0 |
| 306 | $K^{1-1}$ | $K^{1-1}$ | $K^{1-1}$ | — | POMO | POMS | POMS | POMS | — | — | — | H | 0 | 0 |
| 307 | $K^{1-1}$ | $K^{1-1}$ | $K^{1-1}$ | — | OH | POMS | POMS | POMS | — | — | — | H | 0 | 0 |
| 308 | $K^{1-1}$ | $K^{1-1}$ | $K^{1-1}$ | — | POMO | POMS | POMO | POMO | — | — | — | H | 0 | 0 |
| 309 | $K^{1-1}$ | $K^{1-1}$ | $K^{1-1}$ | — | OH | POMS | POMO | POMO | — | — | — | H | 0 | 0 |
| 310 | $K^{1-1}$ | $K^{1-1}$ | $K^{1-1}$ | — | POMO | POMO | SH | SH | — | — | — | H | 0 | 0 |
| 311 | $K^{1-1}$ | $K^{1-1}$ | $K^{1-1}$ | — | OH | POMO | SH | SH | — | — | — | H | 0 | 0 |
| 312 | $K^{1-1}$ | $K^{1-1}$ | $K^{1-1}$ | — | POMO | POMS | SH | SH | — | — | — | H | 0 | 0 |
| 313 | $K^{1-1}$ | $K^{1-1}$ | $K^{1-1}$ | — | OH | POMS | SH | SH | — | — | — | H | 0 | 0 |
| 314 | $K^{1-1}$ | $K^{1-1}$ | $K^{1-1}$ | — | OH | SH | POMO | POMO | — | — | — | H | 0 | 0 |
| 315 | $K^{1-1}$ | $K^{1-1}$ | $K^{1-1}$ | — | OH | SH | POMO | POMO | — | — | — | H | 0 | 0 |
| 316 | $K^{1-1}$ | $K^{1-1}$ | $K^{1-1}$ | — | $OC_2H_4OH$ | POMO | POMO | POMO | — | — | — | H | 0 | 0 |
| 317 | $K^{1-1}$ | $K^{1-1}$ | $K^{1-1}$ | — | $OC_2H_4OH$ | POMS | POMO | POMO | — | — | — | H | 0 | 0 |
| 318 | $K^{1-1}$ | $K^{1-1}$ | $K^{1-1}$ | — | $OC_2H_4OH$ | POMO | POMS | POMS | — | — | — | H | 0 | 0 |
| 319 | $K^{1-1}$ | $K^{1-1}$ | $K^{1-1}$ | — | $OC_2H_4OH$ | POMS | POMS | POMS | — | — | — | H | 0 | 0 |
| 320 | $K^{1-1}$ | $K^{1-1}$ | $K^{1-1}$ | — | $OC_2H_4OH$ | OH | POMS | POMS | — | — | — | H | 0 | 0 |
| 321 | $K^{2-1}$ | $K^{1-1}$ | $K^{3-1}$ | — | OH | ATEO | OH | OH | — | — | — | H | 0 | 0 |
| 322 | $K^{2-1}$ | $K^{1-1}$ | $K^{3-1}$ | — | OH | SH | ATEO | OH | — | — | — | H | 0 | 0 |
| 323 | $K^{2-1}$ | $K^{1-1}$ | $K^{3-1}$ | — | OH | SH | OH | ATEO | — | — | — | H | 0 | 0 |
| 324 | $K^{2-1}$ | $K^{1-1}$ | $K^{3-1}$ | — | OH | SH | ATEO | ATEO | — | — | — | H | 0 | 0 |
| 325 | $K^{2-1}$ | $K^{1-1}$ | $K^{3-1}$ | — | OH | ATEO | ATEO | ATEO | — | — | — | H | 0 | 0 |
| 326 | $K^{2-1}$ | $K^{1-1}$ | $K^{3-1}$ | — | $OC_2H_4OH$ | ATEO | OH | OH | — | — | — | H | 0 | 0 |
| 327 | $K^{2-1}$ | $K^{1-1}$ | $K^{3-1}$ | — | $OC_2H_4OH$ | SH | ATEO | OH | — | — | — | H | 0 | 0 |
| 328 | $K^{2-1}$ | $K^{1-1}$ | $K^{3-1}$ | — | $OC_2H_4OH$ | SH | OH | ATEO | — | — | — | H | 0 | 0 |
| 329 | $K^{2-1}$ | $K^{1-1}$ | $K^{3-1}$ | — | $OC_2H_4OH$ | SH | ATEO | ATEO | — | — | — | H | 0 | 0 |
| 330 | $K^{2-1}$ | $K^{1-1}$ | $K^{3-1}$ | — | $OC_2H_4OH$ | ATEO | ATEO | ATEO | — | — | — | H | 0 | 0 |
| 331 | $K^{2-1}$ | $K^{1-1}$ | $K^{3-1}$ | — | $OC_2H_4OH$ | OH | ATEO | OH | — | — | — | H | 0 | 0 |
| 332 | $K^{2-1}$ | $K^{1-1}$ | $K^{3-1}$ | — | $OC_2H_4OH$ | OH | OH | ATEO | — | — | — | H | 0 | 0 |
| 333 | $K^{2-1}$ | $K^{1-1}$ | $K^{3-1}$ | — | $OC_2H_4OH$ | OH | ATEO | ATEO | — | — | — | H | 0 | 0 |
| 334 | $K^{2-1}$ | $K^{1-1}$ | $K^{3-1}$ | — | OH | ATES | OH | OH | — | — | — | H | 0 | 0 |
| 335 | $K^{2-1}$ | $K^{1-1}$ | $K^{3-1}$ | — | OH | SH | ATES | OH | — | — | — | H | 0 | 0 |
| 336 | $K^{2-1}$ | $K^{1-1}$ | $K^{3-1}$ | — | OH | SH | OH | ATES | — | — | — | H | 0 | 0 |
| 337 | $K^{2-1}$ | $K^{1-1}$ | $K^{3-1}$ | — | OH | SH | ATES | ATES | — | — | — | H | 0 | 0 |
| 338 | $K^{2-1}$ | $K^{1-1}$ | $K^{3-1}$ | — | OH | ATES | ATES | ATES | — | — | — | H | 0 | 0 |
| 339 | $K^{2-1}$ | $K^{1-1}$ | $K^{3-1}$ | — | $OC_2H_4OH$ | ATES | OH | OH | — | — | — | H | 0 | 0 |
| 340 | $K^{2-1}$ | $K^{1-1}$ | $K^{3-1}$ | — | $OC_2H_4OH$ | SH | ATES | OH | — | — | — | H | 0 | 0 |
| 341 | $K^{2-1}$ | $K^{1-1}$ | $K^{3-1}$ | — | $OC_2H_4OH$ | SH | OH | ATES | — | — | — | H | 0 | 0 |
| 342 | $K^{2-1}$ | $K^{1-1}$ | $K^{3-1}$ | — | $OC_2H_4OH$ | SH | ATES | ATES | — | — | — | H | 0 | 0 |
| 343 | $K^{2-1}$ | $K^{1-1}$ | $K^{3-1}$ | — | $OC_2H_4OH$ | ATES | ATES | ATES | — | — | — | H | 0 | 0 |
| 344 | $K^{2-1}$ | $K^{1-1}$ | $K^{3-1}$ | — | $OC_2H_4OH$ | OH | ATES | OH | — | — | — | H | 0 | 0 |
| 345 | $K^{2-1}$ | $K^{1-1}$ | $K^{3-1}$ | — | $OC_2H_4OH$ | OH | OH | ATES | — | — | — | H | 0 | 0 |
| 346 | $K^{2-1}$ | $K^{1-1}$ | $K^{3-1}$ | — | $OC_2H_4OH$ | OH | ATES | ATES | — | — | — | H | 0 | 0 |
| 347 | $K^{1-1}$ | $K^{1-1}$ | $K^{1-1}$ | — | OH | ATEO | SH | SH | — | — | — | H | 0 | 0 |
| 348 | $K^{1-1}$ | $K^{1-1}$ | $K^{1-1}$ | — | OH | SH | ATEO | SH | — | — | — | H | 0 | 0 |
| 349 | $K^{1-1}$ | $K^{1-1}$ | $K^{1-1}$ | — | OH | SH | SH | ATEO | — | — | — | H | 0 | 0 |
| 350 | $K^{1-1}$ | $K^{1-1}$ | $K^{1-1}$ | — | OH | SH | ATEO | ATEO | — | — | — | H | 0 | 0 |
| 351 | $K^{1-1}$ | $K^{1-1}$ | $K^{1-1}$ | — | OH | ATEO | ATEO | ATEO | — | — | — | H | 0 | 0 |
| 352 | $K^{1-1}$ | $K^{1-1}$ | $K^{1-1}$ | — | $OC_2H_4OH$ | ATEO | SH | SH | — | — | — | H | 0 | 0 |
| 353 | $K^{1-1}$ | $K^{1-1}$ | $K^{1-1}$ | — | $OC_2H_4OH$ | SH | ATEO | SH | — | — | — | H | 0 | 0 |
| 354 | $K^{1-1}$ | $K^{1-1}$ | $K^{1-1}$ | — | $OC_2H_4OH$ | SH | SH | ATEO | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | E¹ | E² | E³ | E⁴ | R¹ | R² | R³ | R⁴ | R⁵ | R⁶ | R⁷ | R⁸ | m | n |
|---|---|---|---|---|---|---|---|---|---|---|---|---|---|---|
| 355 | K¹⁻¹ | K¹⁻¹ | K¹⁻¹ | — | OC₂H₄OH | SH | ATEO | ATEO | — | — | — | H | 0 | 0 |
| 356 | K¹⁻¹ | K¹⁻¹ | K¹⁻¹ | — | OC₂H₄OH | ATEO | ATEO | ATEO | — | — | — | H | 0 | 0 |
| 357 | K¹⁻¹ | K¹⁻¹ | K¹⁻¹ | — | OC₂H₄OH | OH | ATEO | SH | — | — | — | H | 0 | 0 |
| 358 | K¹⁻¹ | K¹⁻¹ | K¹⁻¹ | — | OC₂H₄OH | OH | SH | ATEO | — | — | — | H | 0 | 0 |
| 359 | K¹⁻¹ | K¹⁻¹ | K¹⁻¹ | — | OC₂H₄OH | OH | ATEO | ATEO | — | — | — | H | 0 | 0 |
| 360 | K¹⁻¹ | K¹⁻¹ | K¹⁻¹ | — | OH | ATES | SH | SH | — | — | — | H | 0 | 0 |
| 361 | K¹⁻¹ | K¹⁻¹ | K¹⁻¹ | — | OH | SH | ATES | SH | — | — | — | H | 0 | 0 |
| 362 | K¹⁻¹ | K¹⁻¹ | K¹⁻¹ | — | OH | SH | SH | ATES | — | — | — | H | 0 | 0 |
| 363 | K¹⁻¹ | K¹⁻¹ | K¹⁻¹ | — | OH | SH | ATES | ATES | — | — | — | H | 0 | 0 |
| 364 | K¹⁻¹ | K¹⁻¹ | K¹⁻¹ | — | OH | ATES | ATES | ATES | — | — | — | H | 0 | 0 |
| 365 | K¹⁻¹ | K¹⁻¹ | K¹⁻¹ | — | OC₂H₄OH | ATES | SH | SH | — | — | — | H | 0 | 0 |
| 366 | K¹⁻¹ | K¹⁻¹ | K¹⁻¹ | — | OC₂H₄OH | SH | ATES | SH | — | — | — | H | 0 | 0 |
| 367 | K¹⁻¹ | K¹⁻¹ | K¹⁻¹ | — | OC₂H₄OH | SH | SH | ATES | — | — | — | H | 0 | 0 |
| 368 | K¹⁻¹ | K¹⁻¹ | K¹⁻¹ | — | OC₂H₄OH | SH | ATES | ATES | — | — | — | H | 0 | 0 |
| 369 | K¹⁻¹ | K¹⁻¹ | K¹⁻¹ | — | OC₂H₄OH | ATES | ATES | ATES | — | — | — | H | 0 | 0 |
| 370 | K¹⁻¹ | K¹⁻¹ | K¹⁻¹ | — | OC₂H₄OH | OH | ATES | SH | — | — | — | H | 0 | 0 |
| 371 | K¹⁻¹ | K¹⁻¹ | K¹⁻¹ | — | OC₂H₄OH | OH | SH | ATES | — | — | — | H | 0 | 0 |
| 372 | K¹⁻¹ | K¹⁻¹ | K¹⁻¹ | — | OC₂H₄OH | OH | ATES | ATES | — | — | — | H | 0 | 0 |
| 373 | K²⁻¹ | K¹⁻¹ | K³⁻¹ | — | OH | PTEO | OH | OH | — | — | — | H | 0 | 0 |
| 374 | K²⁻¹ | K¹⁻¹ | K³⁻¹ | — | OH | SH | PTEO | OH | — | — | — | H | 0 | 0 |
| 375 | K²⁻¹ | K¹⁻¹ | K³⁻¹ | — | OH | SH | OH | PTEO | — | — | — | H | 0 | 0 |
| 376 | K²⁻¹ | K¹⁻¹ | K³⁻¹ | — | OH | SH | PTEO | PTEO | — | — | — | H | 0 | 0 |
| 377 | K²⁻¹ | K¹⁻¹ | K³⁻¹ | — | OH | PTEO | PTEO | PTEO | — | — | — | H | 0 | 0 |
| 378 | K²⁻¹ | K¹⁻¹ | K³⁻¹ | — | OC₂H₄OH | PTEO | OH | OH | — | — | — | H | 0 | 0 |
| 379 | K²⁻¹ | K¹⁻¹ | K³⁻¹ | — | OC₂H₄OH | SH | PTEO | OH | — | — | — | H | 0 | 0 |
| 380 | K²⁻¹ | K¹⁻¹ | K³⁻¹ | — | OC₂H₄OH | SH | OH | PTEO | — | — | — | H | 0 | 0 |
| 381 | K²⁻¹ | K¹⁻¹ | K³⁻¹ | — | OC₂H₄OH | SH | PTEO | PTEO | — | — | — | H | 0 | 0 |
| 382 | K²⁻¹ | K¹⁻¹ | K³⁻¹ | — | OC₂H₄OH | PTEO | PTEO | PTEO | — | — | — | H | 0 | 0 |
| 383 | K²⁻¹ | K¹⁻¹ | K³⁻¹ | — | OC₂H₄OH | OH | PTEO | OH | — | — | — | H | 0 | 0 |
| 384 | K²⁻¹ | K¹⁻¹ | K³⁻¹ | — | OC₂H₄OH | OH | OH | PTEO | — | — | — | H | 0 | 0 |
| 385 | K²⁻¹ | K¹⁻¹ | K³⁻¹ | — | OC₂H₄OH | OH | PTEO | PTEO | — | — | — | H | 0 | 0 |
| 386 | K²⁻¹ | K¹⁻¹ | K³⁻¹ | — | OH | PTES | OH | OH | — | — | — | H | 0 | 0 |
| 387 | K²⁻¹ | K¹⁻¹ | K³⁻¹ | — | OH | SH | PTES | OH | — | — | — | H | 0 | 0 |
| 388 | K²⁻¹ | K¹⁻¹ | K³⁻¹ | — | OH | SH | OH | PTES | — | — | — | H | 0 | 0 |
| 389 | K²⁻¹ | K¹⁻¹ | K³⁻¹ | — | OH | SH | PTES | PTES | — | — | — | H | 0 | 0 |
| 390 | K²⁻¹ | K¹⁻¹ | K³⁻¹ | — | OH | PTES | PTES | PTES | — | — | — | H | 0 | 0 |
| 391 | K²⁻¹ | K¹⁻¹ | K³⁻¹ | — | OC₂H₄OH | PTES | OH | OH | — | — | — | H | 0 | 0 |
| 392 | K²⁻¹ | K¹⁻¹ | K³⁻¹ | — | OC₂H₄OH | SH | PTES | OH | — | — | — | H | 0 | 0 |
| 393 | K²⁻¹ | K¹⁻¹ | K³⁻¹ | — | OC₂H₄OH | SH | OH | PTES | — | — | — | H | 0 | 0 |
| 394 | K²⁻¹ | K¹⁻¹ | K³⁻¹ | — | OC₂H₄OH | SH | PTES | PTES | — | — | — | H | 0 | 0 |
| 395 | K²⁻¹ | K¹⁻¹ | K³⁻¹ | — | OC₂H₄OH | PTES | PTES | PTES | — | — | — | H | 0 | 0 |
| 396 | K²⁻¹ | K¹⁻¹ | K³⁻¹ | — | OC₂H₄OH | OH | PTES | OH | — | — | — | H | 0 | 0 |
| 397 | K²⁻¹ | K¹⁻¹ | K³⁻¹ | — | OC₂H₄OH | OH | OH | PTES | — | — | — | H | 0 | 0 |
| 398 | K²⁻¹ | K¹⁻¹ | K³⁻¹ | — | OC₂H₄OH | OH | PTES | PTES | — | — | — | H | 0 | 0 |
| 399 | K¹⁻¹ | K¹⁻¹ | K¹⁻¹ | — | OH | PTEO | SH | SH | — | — | — | H | 0 | 0 |
| 400 | K¹⁻¹ | K¹⁻¹ | K¹⁻¹ | — | OH | SH | PTEO | SH | — | — | — | H | 0 | 0 |
| 401 | K¹⁻¹ | K¹⁻¹ | K¹⁻¹ | — | OH | SH | SH | PTEO | — | — | — | H | 0 | 0 |
| 402 | K¹⁻¹ | K¹⁻¹ | K¹⁻¹ | — | OH | SH | PTEO | PTEO | — | — | — | H | 0 | 0 |
| 403 | K¹⁻¹ | K¹⁻¹ | K¹⁻¹ | — | OH | PTEO | PTEO | PTEO | — | — | — | H | 0 | 0 |
| 404 | K¹⁻¹ | K¹⁻¹ | K¹⁻¹ | — | OC₂H₄OH | PTEO | SH | SH | — | — | — | H | 0 | 0 |
| 405 | K¹⁻¹ | K¹⁻¹ | K¹⁻¹ | — | OC₂H₄OH | SH | PTEO | SH | — | — | — | H | 0 | 0 |
| 406 | K¹⁻¹ | K¹⁻¹ | K¹⁻¹ | — | OC₂H₄OH | SH | SH | PTEO | — | — | — | H | 0 | 0 |
| 407 | K¹⁻¹ | K¹⁻¹ | K¹⁻¹ | — | OC₂H₄OH | SH | PTEO | PTEO | — | — | — | H | 0 | 0 |
| 408 | K¹⁻¹ | K¹⁻¹ | K¹⁻¹ | — | OC₂H₄OH | PTEO | PTEO | PTEO | — | — | — | H | 0 | 0 |
| 409 | K¹⁻¹ | K¹⁻¹ | K¹⁻¹ | — | OC₂H₄OH | OH | PTEO | SH | — | — | — | H | 0 | 0 |
| 410 | K¹⁻¹ | K¹⁻¹ | K¹⁻¹ | — | OC₂H₄OH | OH | SH | PTEO | — | — | — | H | 0 | 0 |
| 411 | K¹⁻¹ | K¹⁻¹ | K¹⁻¹ | — | OC₂H₄OH | OH | PTEO | PTEO | — | — | — | H | 0 | 0 |
| 412 | K¹⁻¹ | K¹⁻¹ | K¹⁻¹ | — | OH | PTES | SH | SH | — | — | — | H | 0 | 0 |
| 413 | K¹⁻¹ | K¹⁻¹ | K¹⁻¹ | — | OH | SH | PTES | SH | — | — | — | H | 0 | 0 |
| 414 | K¹⁻¹ | K¹⁻¹ | K¹⁻¹ | — | OH | SH | SH | PTES | — | — | — | H | 0 | 0 |
| 415 | K¹⁻¹ | K¹⁻¹ | K¹⁻¹ | — | OH | SH | PTES | PTES | — | — | — | H | 0 | 0 |
| 416 | K¹⁻¹ | K¹⁻¹ | K¹⁻¹ | — | OH | PTES | PTES | PTES | — | — | — | H | 0 | 0 |
| 417 | K¹⁻¹ | K¹⁻¹ | K¹⁻¹ | — | OC₂H₄OH | PTES | SH | SH | — | — | — | H | 0 | 0 |
| 418 | K¹⁻¹ | K¹⁻¹ | K¹⁻¹ | — | OC₂H₄OH | SH | PTES | SH | — | — | — | H | 0 | 0 |
| 419 | K¹⁻¹ | K¹⁻¹ | K¹⁻¹ | — | OC₂H₄OH | SH | SH | PTES | — | — | — | H | 0 | 0 |
| 420 | K¹⁻¹ | K¹⁻¹ | K¹⁻¹ | — | OC₂H₄OH | SH | PTES | PTES | — | — | — | H | 0 | 0 |
| 421 | K¹⁻¹ | K¹⁻¹ | K¹⁻¹ | — | OC₂H₄OH | PTES | PTES | PTES | — | — | — | H | 0 | 0 |
| 422 | K¹⁻¹ | K¹⁻¹ | K¹⁻¹ | — | OC₂H₄OH | OH | PTES | SH | — | — | — | H | 0 | 0 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 423 | $K^{1-1}$ | $K^{1-1}$ | $K^{1-1}$ | — | $OC_2H_4OH$ | OH | SH | PTES | — | — | — | H | 0 | 0 |
| 424 | $K^{1-1}$ | $K^{1-1}$ | $K^{1-1}$ | — | $OC_2H_4OH$ | OH | PTES | PTES | — | — | — | H | 0 | 0 |
| 425 | $K^{2-1}$ | $K^{1-1}$ | $K^{3-1}$ | — | OPh | ALM | OH | OH | — | — | — | H | 0 | 0 |
| 426 | $K^{2-1}$ | $K^{1-1}$ | $K^{3-1}$ | — | OPh | ALM | ALM | OH | — | — | — | H | 0 | 0 |
| 427 | $K^{2-1}$ | $K^{1-1}$ | $K^{3-1}$ | — | OPh | ALM | OH | ALM | — | — | — | H | 0 | 0 |
| 428 | $K^{2-1}$ | $K^{1-1}$ | $K^{3-1}$ | — | OPh | ALM | ALM | ALM | — | — | — | H | 0 | 0 |
| 429 | $K^{2-1}$ | $K^{1-1}$ | $K^{3-1}$ | — | OH | SH | ALM | ALM | — | — | — | H | 0 | 0 |
| 430 | $K^{2-1}$ | $K^{1-1}$ | $K^{3-1}$ | — | OH | SH | OH | ALM | — | — | — | H | 0 | 0 |
| 431 | $K^{2-1}$ | $K^{1-1}$ | $K^{3-1}$ | — | OH | SH | ALM | OH | — | — | — | H | 0 | 0 |
| 432 | $K^{2-1}$ | $K^{1-1}$ | $K^{3-1}$ | — | $OC_2H_4OH$ | OH | ALM | ALM | — | — | — | H | 0 | 0 |
| 433 | $K^{2-1}$ | $K^{1-1}$ | $K^{3-1}$ | — | $OC_2H_4OH$ | OH | OH | ALM | — | — | — | H | 0 | 0 |
| 434 | $K^{2-1}$ | $K^{1-1}$ | $K^{3-1}$ | — | $OC_2H_4OH$ | OH | ALM | OH | — | — | — | H | 0 | 0 |
| 435 | $K^{2-1}$ | $K^{1-1}$ | $K^{3-1}$ | — | $OC_2H_4OH$ | SH | OH | ALM | — | — | — | H | 0 | 0 |
| 436 | $K^{2-1}$ | $K^{1-1}$ | $K^{3-1}$ | — | $OC_2H_4OH$ | SH | OH | ALM | — | — | — | H | 0 | 0 |
| 437 | $K^{2-1}$ | $K^{1-1}$ | $K^{3-1}$ | — | $OC_2H_4OH$ | SH | ALM | OH | — | — | — | H | 0 | 0 |
| 438 | $K^{1-1}$ | $K^{1-1}$ | $K^{1-1}$ | — | OPh | ALM | SH | SH | — | — | — | H | 0 | 0 |
| 439 | $K^{1-1}$ | $K^{1-1}$ | $K^{1-1}$ | — | OPh | ALM | ALM | SH | — | — | — | H | 0 | 0 |
| 440 | $K^{1-1}$ | $K^{1-1}$ | $K^{1-1}$ | — | OPh | ALM | SH | ALM | — | — | — | H | 0 | 0 |
| 441 | $K^{1-1}$ | $K^{1-1}$ | $K^{1-1}$ | — | OPh | ALM | ALM | ALM | — | — | — | H | 0 | 0 |
| 442 | $K^{1-1}$ | $K^{1-1}$ | $K^{1-1}$ | — | OH | SH | ALM | ALM | — | — | — | H | 0 | 0 |
| 443 | $K^{1-1}$ | $K^{1-1}$ | $K^{1-1}$ | — | OH | SH | SH | ALM | — | — | — | H | 0 | 0 |
| 444 | $K^{1-1}$ | $K^{1-1}$ | $K^{1-1}$ | — | OH | SH | ALM | SH | — | — | — | H | 0 | 0 |
| 445 | $K^{1-1}$ | $K^{1-1}$ | $K^{1-1}$ | — | $OC_2H_4OH$ | OH | ALM | ALM | — | — | — | H | 0 | 0 |
| 446 | $K^{1-1}$ | $K^{1-1}$ | $K^{1-1}$ | — | $OC_2H_4OH$ | OH | SH | ALM | — | — | — | H | 0 | 0 |
| 447 | $K^{1-1}$ | $K^{1-1}$ | $K^{1-1}$ | — | $OC_2H_4OH$ | OH | ALM | SH | — | — | — | H | 0 | 0 |
| 448 | $K^{1-1}$ | $K^{1-1}$ | $K^{1-1}$ | — | $OC_2H_4OH$ | SH | ALM | ALM | — | — | — | H | 0 | 0 |
| 449 | $K^{1-1}$ | $K^{1-1}$ | $K^{1-1}$ | — | $OC_2H_4OH$ | SH | SH | ALM | — | — | — | H | 0 | 0 |
| 450 | $K^{1-1}$ | $K^{1-1}$ | $K^{1-1}$ | — | $OC_2H_4OH$ | SH | ALM | SH | — | — | — | H | 0 | 0 |
| 451 | $K^{2-1}$ | $K^{1-1}$ | $K^{3-1}$ | — | $OC_2H_4OH$ | OH | OH | OH | — | OH | $L^1$ | $ON^{1-1}$ | 0 | 2 |
| 452 | $K^{1-1}$ | $K^{1-1}$ | $K^{1-1}$ | — | $OC_2H_4OH$ | OH | SH | SH | — | OH | $L^1$ | $ON^{1-1}$ | 0 | 2 |
| 453 | $K^{1-1}$ | $K^{1-1}$ | $K^{1-1}$ | — | $OC_2H_4OH$ | SH | SH | SH | — | OH | $L^1$ | $ON^{1-1}$ | 0 | 2 |
| 454 | $K^{1-1}$ | $K^{1-1}$ | $K^{1-1}$ | $K^{1-1}$ | $OC_2H_4OH$ | OH | SH | SH | SH | OH | $L^1$ | $ON^{1-1}$ | 1 | 2 |
| 455 | $K^{1-1}$ | $K^{1-1}$ | $K^{1-1}$ | — | OH | SH | SH | SH | — | OH | $L^1$ | $ON^{1-1}$ | 0 | 2 |
| 456 | $K^{2-1}$ | $K^{1-1}$ | $K^{3-1}$ | — | $OC_2H_4OH$ | OH | OH | OH | — | OH | $L^2$ | $ON^{1-1}$ | 0 | 1 |
| 457 | $K^{1-1}$ | $K^{1-1}$ | $K^{1-1}$ | — | $OC_2H_4OH$ | OH | SH | SH | — | OH | $L^2$ | $ON^{1-1}$ | 0 | 1 |
| 458 | $K^{1-1}$ | $K^{1-1}$ | $K^{1-1}$ | — | $OC_2H_4OH$ | SH | SH | SH | — | OH | $L^2$ | $ON^{1-1}$ | 0 | 1 |
| 459 | $K^{1-1}$ | $K^{1-1}$ | $K^{1-1}$ | $K^{1-1}$ | $OC_2H_4OH$ | OH | SH | SH | SH | OH | $L^2$ | $ON^{1-1}$ | 1 | 1 |
| 460 | $K^{1-1}$ | $K^{1-1}$ | $K^{1-1}$ | — | OH | SH | SH | SH | — | OH | $L^2$ | $ON^{1-1}$ | 0 | 1 |
| 461 | $K^{2-1}$ | $K^{1-1}$ | $K^{3-1}$ | — | $OC_2H_4OH$ | OH | OH | OH | — | OH | $L^1$ | $ON^{1-2}$ | 0 | 2 |
| 462 | $K^{1-1}$ | $K^{1-1}$ | $K^{1-1}$ | — | $OC_2H_4OH$ | OH | SH | SH | — | OH | $L^1$ | $ON^{1-2}$ | 0 | 2 |
| 463 | $K^{1-1}$ | $K^{1-1}$ | $K^{1-1}$ | — | $OC_2H_4OH$ | SH | SH | SH | — | OH | $L^1$ | $ON^{1-2}$ | 0 | 2 |
| 464 | $K^{1-1}$ | $K^{1-1}$ | $K^{1-1}$ | $K^{1-1}$ | $OC_2H_4OH$ | OH | SH | SH | SH | OH | $L^1$ | $ON^{1-2}$ | 1 | 2 |
| 465 | $K^{1-1}$ | $K^{1-1}$ | $K^{1-1}$ | — | OH | SH | SH | SH | — | OH | $L^1$ | $ON^{1-2}$ | 0 | 2 |
| 466 | $K^{2-1}$ | $K^{1-1}$ | $K^{3-1}$ | — | $OC_2H_4OH$ | OH | OH | OH | — | OH | $L^2$ | $ON^{1-2}$ | 0 | 1 |
| 467 | $K^{1-1}$ | $K^{1-1}$ | $K^{1-1}$ | — | $OC_2H_4OH$ | OH | SH | SH | — | OH | $L^2$ | $ON^{1-2}$ | 0 | 1 |
| 468 | $K^{1-1}$ | $K^{1-1}$ | $K^{1-1}$ | — | $OC_2H_4OH$ | SH | SH | SH | — | OH | $L^2$ | $ON^{1-2}$ | 0 | 1 |
| 469 | $K^{1-1}$ | $K^{1-1}$ | $K^{1-1}$ | $K^{1-1}$ | $OC_2H_4OH$ | OH | SH | SH | SH | OH | $L^2$ | $ON^{1-2}$ | 1 | 1 |
| 470 | $K^{1-1}$ | $K^{1-1}$ | $K^{1-1}$ | — | OH | SH | SH | SH | — | OH | $L^2$ | $ON^{1-2}$ | 0 | 1 |
| 471 | $K^{2-1}$ | $K^{1-1}$ | $K^{3-1}$ | — | $OC_2H_4OH$ | OH | OH | OH | — | OH | $L^1$ | $ON^{1-3}$ | 0 | 2 |
| 472 | $K^{1-1}$ | $K^{1-1}$ | $K^{1-1}$ | — | $OC_2H_4OH$ | OH | SH | SH | — | OH | $L^1$ | $ON^{1-3}$ | 0 | 2 |
| 473 | $K^{1-1}$ | $K^{1-1}$ | $K^{1-1}$ | — | $OC_2H_4OH$ | SH | SH | SH | — | OH | $L^1$ | $ON^{1-3}$ | 0 | 2 |
| 474 | $K^{1-1}$ | $K^{1-1}$ | $K^{1-1}$ | $K^{1-1}$ | $OC_2H_4OH$ | OH | SH | SH | SH | OH | $L^1$ | $ON^{1-3}$ | 1 | 2 |
| 475 | $K^{1-1}$ | $K^{1-1}$ | $K^{1-1}$ | — | OH | SH | SH | SH | — | OH | $L^1$ | $ON^{1-3}$ | 0 | 2 |
| 476 | $K^{2-1}$ | $K^{1-1}$ | $K^{3-1}$ | — | $OC_2H_4OH$ | OH | OH | OH | — | OH | $L^2$ | $ON^{1-3}$ | 0 | 1 |
| 477 | $K^{1-1}$ | $K^{1-1}$ | $K^{1-1}$ | — | $OC_2H_4OH$ | OH | SH | SH | — | OH | $L^2$ | $ON^{1-3}$ | 0 | 1 |
| 478 | $K^{1-1}$ | $K^{1-1}$ | $K^{1-1}$ | — | $OC_2H_4OH$ | SH | PTES | SH | — | OH | $L^2$ | $ON^{1-3}$ | 0 | 1 |
| 479 | $K^{1-1}$ | $K^{1-1}$ | $K^{1-1}$ | $K^{1-1}$ | $OC_2H_4OH$ | OH | SH | SH | SH | OH | $L^2$ | $ON^{1-3}$ | 1 | 1 |
| 480 | $K^{1-1}$ | $K^{1-1}$ | $K^{1-1}$ | — | OH | SH | SH | SH | — | OH | $L^2$ | $ON^{1-3}$ | 0 | 1 |
| 481 | $K^{2-1}$ | $K^{1-1}$ | $K^{3-1}$ | — | $OC_2H_4OH$ | OH | OH | OH | — | OH | $L^1$ | $ON^{1-4}$ | 0 | 2 |
| 482 | $K^{1-1}$ | $K^{1-1}$ | $K^{1-1}$ | — | $OC_2H_4OH$ | OH | SH | SH | — | OH | $L^1$ | $ON^{1-4}$ | 0 | 2 |
| 483 | $K^{1-1}$ | $K^{1-1}$ | $K^{1-1}$ | — | $OC_2H_4OH$ | SH | SH | SH | — | OH | $L^1$ | $ON^{1-4}$ | 0 | 2 |
| 484 | $K^{1-1}$ | $K^{1-1}$ | $K^{1-1}$ | $K^{1-1}$ | $OC_2H_4OH$ | OH | SH | SH | SH | OH | $L^1$ | $ON^{1-4}$ | 1 | 2 |
| 485 | $K^{1-1}$ | $K^{1-1}$ | $K^{1-1}$ | — | OH | SH | SH | SH | — | OH | $L^1$ | $ON^{1-4}$ | 0 | 2 |
| 486 | $K^{2-1}$ | $K^{1-1}$ | $K^{3-1}$ | — | $OC_2H_4OH$ | OH | OH | OH | — | OH | $L^2$ | $ON^{1-4}$ | 0 | 1 |
| 487 | $K^{1-1}$ | $K^{1-1}$ | $K^{1-1}$ | — | $OC_2H_4OH$ | OH | SH | SH | — | OH | $L^2$ | $ON^{1-4}$ | 0 | 1 |
| 488 | $K^{1-1}$ | $K^{1-1}$ | $K^{1-1}$ | — | $OC_2H_4OH$ | SH | SH | SH | — | OH | $L^2$ | $ON^{1-4}$ | 0 | 1 |
| 489 | $K^{1-1}$ | $K^{1-1}$ | $K^{1-1}$ | $K^{1-1}$ | $OC_2H_4OH$ | OH | SH | SH | SH | OH | $L^2$ | $ON^{1-4}$ | 1 | 1 |
| 490 | $K^{1-1}$ | $K^{1-1}$ | $K^{1-1}$ | — | OH | SH | SH | SH | — | OH | $L^2$ | $ON^{1-4}$ | 0 | 1 |

TABLE 1-continued

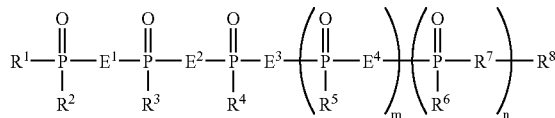

| Exemplified Compound No. | E¹ | E² | E³ | E⁴ | R¹ | R² | R³ | R⁴ | R⁵ | R⁶ | R⁷ | R⁸ | m | n |
|---|---|---|---|---|---|---|---|---|---|---|---|---|---|---|
| 491 | $K^{2-1}$ | $K^{1-1}$ | $K^{3-1}$ | — | $OC_2H_4OH$ | OH | OH | OH | — | OH | $L^1$ | $ON^{1-5}$ | 0 | 2 |
| 492 | $K^{1-1}$ | $K^{1-1}$ | $K^{1-1}$ | — | $OC_2H_4OH$ | OH | SH | SH | — | OH | $L^1$ | $ON^{1-5}$ | 0 | 2 |
| 493 | $K^{1-1}$ | $K^{1-1}$ | $K^{1-1}$ | — | $OC_2H_4OH$ | SH | SH | SH | — | OH | $L^1$ | $ON^{1-5}$ | 0 | 2 |
| 494 | $K^{1-1}$ | $K^{1-1}$ | $K^{1-1}$ | $K^{1-1}$ | $OC_2H_4OH$ | OH | SH | SH | SH | OH | $L^1$ | $ON^{1-5}$ | 1 | 2 |
| 495 | $K^{1-1}$ | $K^{1-1}$ | $K^{1-1}$ | — | OH | SH | SH | SH | — | OH | $L^1$ | $ON^{1-5}$ | 0 | 2 |
| 496 | $K^{2-1}$ | $K^{1-1}$ | $K^{3-1}$ | — | $OC_2H_4OH$ | OH | OH | OH | — | OH | $L^2$ | $ON^{1-5}$ | 0 | 1 |
| 497 | $K^{1-1}$ | $K^{1-1}$ | $K^{1-1}$ | — | $OC_2H_4OH$ | OH | SH | SH | — | OH | $L^2$ | $ON^{1-5}$ | 0 | 1 |
| 498 | $K^{1-1}$ | $K^{1-1}$ | $K^{1-1}$ | — | $OC_2H_4OH$ | SH | SH | SH | — | OH | $L^2$ | $ON^{1-5}$ | 0 | 1 |
| 499 | $K^{1-1}$ | $K^{1-1}$ | $K^{1-1}$ | $K^{1-1}$ | $OC_2H_4OH$ | OH | SH | SH | SH | OH | $L^2$ | $ON^{1-5}$ | 1 | 1 |
| 500 | $K^{1-1}$ | $K^{1-1}$ | $K^{1-1}$ | — | OH | SH | SH | SH | — | OH | $L^2$ | $ON^{1-5}$ | 0 | 1 |
| 501 | $K^{2-1}$ | $K^{1-1}$ | $K^{3-1}$ | — | $OC_2H_4OH$ | OH | OH | OH | — | OH | $L^1$ | $ON^{2-1}$ | 0 | 2 |
| 502 | $K^{1-1}$ | $K^{1-1}$ | $K^{1-1}$ | — | $OC_2H_4OH$ | OH | SH | SH | — | OH | $L^1$ | $ON^{2-1}$ | 0 | 2 |
| 503 | $K^{1-1}$ | $K^{1-1}$ | $K^{1-1}$ | — | $OC_2H_4OH$ | SH | SH | SH | — | OH | $L^1$ | $ON^{2-1}$ | 0 | 2 |
| 504 | $K^{1-1}$ | $K^{1-1}$ | $K^{1-1}$ | $K^{1-1}$ | $OC_2H_4OH$ | OH | SH | SH | SH | OH | $L^1$ | $ON^{2-1}$ | 1 | 2 |
| 505 | $K^{1-1}$ | $K^{1-1}$ | $K^{1-1}$ | — | OH | SH | SH | SH | — | OH | $L^1$ | $ON^{2-1}$ | 0 | 2 |
| 506 | $K^{2-1}$ | $K^{1-1}$ | $K^{3-1}$ | — | $OC_2H_4OH$ | OH | OH | OH | — | OH | $L^2$ | $ON^{2-1}$ | 0 | 1 |
| 507 | $K^{1-1}$ | $K^{1-1}$ | $K^{1-1}$ | — | $OC_2H_4OH$ | OH | SH | SH | — | OH | $L^2$ | $ON^{2-1}$ | 0 | 1 |
| 508 | $K^{1-1}$ | $K^{1-1}$ | $K^{1-1}$ | — | $OC_2H_4OH$ | SH | SH | SH | — | OH | $L^2$ | $ON^{2-1}$ | 0 | 1 |
| 509 | $K^{1-1}$ | $K^{1-1}$ | $K^{1-1}$ | $K^{1-1}$ | $OC_2H_4OH$ | OH | SH | SH | SH | OH | $L^2$ | $ON^{2-1}$ | 1 | 1 |
| 510 | $K^{1-1}$ | $K^{1-1}$ | $K^{1-1}$ | — | OH | SH | SH | SH | — | OH | $L^2$ | $ON^{2-1}$ | 0 | 1 |
| 511 | $K^{2-1}$ | $K^{1-1}$ | $K^{3-1}$ | — | $OC_2H_4OH$ | OH | OH | OH | — | OH | $L^1$ | $ON^{2-2}$ | 0 | 2 |
| 512 | $K^{1-1}$ | $K^{1-1}$ | $K^{1-1}$ | — | $OC_2H_4OH$ | OH | SH | SH | — | OH | $L^1$ | $ON^{2-2}$ | 0 | 2 |
| 513 | $K^{1-1}$ | $K^{1-1}$ | $K^{1-1}$ | — | $OC_2H_4OH$ | SH | SH | SH | — | OH | $L^1$ | $ON^{2-2}$ | 0 | 2 |
| 514 | $K^{1-1}$ | $K^{1-1}$ | $K^{1-1}$ | $K^{1-1}$ | $OC_2H_4OH$ | OH | SH | SH | SH | OH | $L^1$ | $ON^{2-2}$ | 1 | 2 |
| 515 | $K^{1-1}$ | $K^{1-1}$ | $K^{1-1}$ | — | OH | SH | SH | SH | — | OH | $L^1$ | $ON^{2-2}$ | 0 | 2 |
| 516 | $K^{2-1}$ | $K^{1-1}$ | $K^{3-1}$ | — | $OC_2H_4OH$ | OH | OH | OH | — | OH | $L^2$ | $ON^{2-2}$ | 0 | 1 |
| 517 | $K^{1-1}$ | $K^{1-1}$ | $K^{1-1}$ | — | $OC_2H_4OH$ | OH | SH | SH | — | OH | $L^2$ | $ON^{2-2}$ | 0 | 1 |
| 518 | $K^{1-1}$ | $K^{1-1}$ | $K^{1-1}$ | — | $OC_2H_4OH$ | SH | SH | SH | — | OH | $L^2$ | $ON^{2-2}$ | 0 | 1 |
| 519 | $K^{1-1}$ | $K^{1-1}$ | $K^{1-1}$ | $K^{1-1}$ | $OC_2H_4OH$ | OH | SH | SH | SH | OH | $L^2$ | $ON^{2-2}$ | 1 | 1 |
| 520 | $K^{1-1}$ | $K^{1-1}$ | $K^{1-1}$ | — | OH | SH | SH | SH | — | OH | $L^2$ | $ON^{2-2}$ | 0 | 1 |
| 521 | $K^{2-1}$ | $K^{1-1}$ | $K^{3-1}$ | — | $OC_2H_4OH$ | OH | OH | OH | — | OH | $L^1$ | $ON^{2-3}$ | 0 | 2 |
| 522 | $K^{1-1}$ | $K^{1-1}$ | $K^{1-1}$ | — | $OC_2H_4OH$ | OH | SH | SH | — | OH | $L^1$ | $ON^{2-3}$ | 0 | 2 |
| 523 | $K^{1-1}$ | $K^{1-1}$ | $K^{1-1}$ | — | $OC_2H_4OH$ | SH | SH | SH | — | OH | $L^1$ | $ON^{2-3}$ | 0 | 2 |
| 524 | $K^{1-1}$ | $K^{1-1}$ | $K^{1-1}$ | $K^{1-1}$ | $OC_2H_4OH$ | OH | SH | SH | SH | OH | $L^1$ | $ON^{2-3}$ | 1 | 2 |
| 525 | $K^{1-1}$ | $K^{1-1}$ | $K^{1-1}$ | — | OH | SH | SH | SH | — | OH | $L^1$ | $ON^{2-3}$ | 0 | 2 |
| 526 | $K^{2-1}$ | $K^{1-1}$ | $K^{3-1}$ | — | $OC_2H_4OH$ | OH | OH | OH | — | OH | $L^2$ | $ON^{2-3}$ | 0 | 1 |
| 527 | $K^{1-1}$ | $K^{1-1}$ | $K^{1-1}$ | — | $OC_2H_4OH$ | OH | SH | SH | — | OH | $L^2$ | $ON^{2-3}$ | 0 | 1 |
| 528 | $K^{1-1}$ | $K^{1-1}$ | $K^{1-1}$ | — | $OC_2H_4OH$ | SH | SH | SH | — | OH | $L^2$ | $ON^{2-3}$ | 0 | 1 |
| 529 | $K^{1-1}$ | $K^{1-1}$ | $K^{1-1}$ | $K^{1-1}$ | $OC_2H_4OH$ | OH | SH | SH | SH | OH | $L^2$ | $ON^{2-3}$ | 1 | 1 |
| 530 | $K^{1-1}$ | $K^{1-1}$ | $K^{1-1}$ | — | OH | SH | SH | SH | — | OH | $L^2$ | $ON^{2-3}$ | 0 | 1 |
| 531 | $K^{2-1}$ | $K^{1-1}$ | $K^{3-1}$ | — | $OC_2H_4OH$ | OH | OH | OH | — | OH | $L^1$ | $ON^{2-4}$ | 0 | 2 |
| 532 | $K^{1-1}$ | $K^{1-1}$ | $K^{1-1}$ | — | $OC_2H_4OH$ | OH | SH | SH | — | OH | $L^1$ | $ON^{2-4}$ | 0 | 2 |
| 533 | $K^{1-1}$ | $K^{1-1}$ | $K^{1-1}$ | — | $OC_2H_4OH$ | SH | SH | SH | — | OH | $L^1$ | $ON^{2-4}$ | 0 | 2 |
| 534 | $K^{1-1}$ | $K^{1-1}$ | $K^{1-1}$ | $K^{1-1}$ | $OC_2H_4OH$ | OH | SH | SH | SH | OH | $L^1$ | $ON^{2-4}$ | 1 | 2 |
| 535 | $K^{1-1}$ | $K^{1-1}$ | $K^{1-1}$ | — | OH | SH | SH | SH | — | OH | $L^1$ | $ON^{2-4}$ | 0 | 2 |
| 536 | $K^{2-1}$ | $K^{1-1}$ | $K^{3-1}$ | — | $OC_2H_4OH$ | OH | OH | OH | — | OH | $L^2$ | $ON^{2-4}$ | 0 | 1 |
| 537 | $K^{1-1}$ | $K^{1-1}$ | $K^{1-1}$ | — | $OC_2H_4OH$ | OH | SH | SH | — | OH | $L^2$ | $ON^{2-4}$ | 0 | 1 |
| 538 | $K^{1-1}$ | $K^{1-1}$ | $K^{1-1}$ | — | $OC_2H_4OH$ | SH | SH | SH | — | OH | $L^2$ | $ON^{2-4}$ | 0 | 1 |
| 539 | $K^{1-1}$ | $K^{1-1}$ | $K^{1-1}$ | $K^{1-1}$ | $OC_2H_4OH$ | OH | SH | SH | SH | OH | $L^2$ | $ON^{2-4}$ | 1 | 1 |
| 540 | $K^{1-1}$ | $K^{1-1}$ | $K^{1-1}$ | — | OH | SH | SH | SH | — | OH | $L^2$ | $ON^{2-4}$ | 0 | 1 |
| 541 | $K^{2-1}$ | $K^{1-1}$ | $K^{3-1}$ | — | $OC_2H_4OH$ | OH | OH | OH | — | OH | $L^1$ | $ON^{2-5}$ | 0 | 2 |
| 542 | $K^{1-1}$ | $K^{1-1}$ | $K^{1-1}$ | — | $OC_2H_4OH$ | OH | SH | SH | — | OH | $L^1$ | $ON^{2-5}$ | 0 | 2 |
| 543 | $K^{1-1}$ | $K^{1-1}$ | $K^{1-1}$ | — | $OC_2H_4OH$ | SH | SH | SH | — | OH | $L^1$ | $ON^{2-5}$ | 0 | 2 |
| 544 | $K^{1-1}$ | $K^{1-1}$ | $K^{1-1}$ | $K^{1-1}$ | $OC_2H_4OH$ | OH | SH | SH | SH | OH | $L^1$ | $ON^{2-5}$ | 1 | 2 |
| 545 | $K^{1-1}$ | $K^{1-1}$ | $K^{1-1}$ | — | OH | SH | SH | SH | — | OH | $L^1$ | $ON^{2-5}$ | 0 | 2 |
| 546 | $K^{2-1}$ | $K^{1-1}$ | $K^{3-1}$ | — | $OC_2H_4OH$ | OH | OH | OH | — | OH | $L^2$ | $ON^{2-5}$ | 0 | 1 |
| 547 | $K^{1-1}$ | $K^{1-1}$ | $K^{1-1}$ | — | $OC_2H_4OH$ | OH | SH | SH | — | OH | $L^2$ | $ON^{2-5}$ | 0 | 1 |
| 548 | $K^{1-1}$ | $K^{1-1}$ | $K^{1-1}$ | — | $OC_2H_4OH$ | SH | SH | SH | — | OH | $L^2$ | $ON^{2-5}$ | 0 | 1 |
| 549 | $K^{1-1}$ | $K^{1-1}$ | $K^{1-1}$ | $K^{1-1}$ | $OC_2H_4OH$ | OH | SH | SH | SH | OH | $L^2$ | $ON^{2-5}$ | 1 | 1 |
| 550 | $K^{1-1}$ | $K^{1-1}$ | $K^{1-1}$ | — | OH | SH | SH | SH | — | OH | $L^2$ | $ON^{2-5}$ | 0 | 1 |
| 551 | $K^{2-1}$ | $K^{1-1}$ | $K^{3-1}$ | — | $OC_2H_4OH$ | OH | OH | OH | — | OH | $L^1$ | $ON^{3-1}$ | 0 | 2 |
| 552 | $K^{1-1}$ | $K^{1-1}$ | $K^{1-1}$ | — | $OC_2H_4OH$ | OH | SH | SH | — | OH | $L^1$ | $ON^{3-1}$ | 0 | 2 |
| 553 | $K^{1-1}$ | $K^{1-1}$ | $K^{1-1}$ | — | $OC_2H_4OH$ | SH | SH | SH | — | OH | $L^1$ | $ON^{3-1}$ | 0 | 2 |
| 554 | $K^{1-1}$ | $K^{1-1}$ | $K^{1-1}$ | $K^{1-1}$ | $OC_2H_4OH$ | OH | SH | SH | SH | OH | $L^1$ | $ON^{3-1}$ | 1 | 2 |
| 555 | $K^{1-1}$ | $K^{1-1}$ | $K^{1-1}$ | — | OH | SH | SH | SH | — | OH | $L^1$ | $ON^{3-1}$ | 0 | 2 |
| 556 | $K^{2-1}$ | $K^{1-1}$ | $K^{3-1}$ | — | $OC_2H_4OH$ | OH | OH | OH | — | OH | $L^2$ | $ON^{3-1}$ | 0 | 1 |
| 557 | $K^{1-1}$ | $K^{1-1}$ | $K^{1-1}$ | — | $OC_2H_4OH$ | OH | SH | SH | — | OH | $L^2$ | $ON^{3-1}$ | 0 | 1 |
| 558 | $K^{1-1}$ | $K^{1-1}$ | $K^{1-1}$ | — | $OC_2H_4OH$ | SH | SH | SH | — | OH | $L^2$ | $ON^{3-1}$ | 0 | 1 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 559 | $K^{1-1}$ | $K^{1-1}$ | $K^{1-1}$ | $K^{1-1}$ | $OC_2H_4OH$ | OH | SH | SH | SH | OH | $L^2$ | $ON^{3-1}$ | 1 | 1 |
| 560 | $K^{1-1}$ | $K^{1-1}$ | $K^{1-1}$ | — | OH | SH | SH | SH | — | OH | $L^2$ | $ON^{3-1}$ | 0 | 1 |
| 561 | $K^{2-1}$ | $K^{1-1}$ | $K^{3-1}$ | — | $OC_2H_4OH$ | OH | OH | OH | — | OH | $L^1$ | $ON^{3-2}$ | 0 | 2 |
| 562 | $K^{1-1}$ | $K^{1-1}$ | $K^{1-1}$ | — | $OC_2H_4OH$ | OH | SH | SH | — | OH | $L^1$ | $ON^{3-2}$ | 0 | 2 |
| 563 | $K^{1-1}$ | $K^{1-1}$ | $K^{1-1}$ | — | $OC_2H_4OH$ | SH | SH | SH | — | OH | $L^1$ | $ON^{3-2}$ | 0 | 2 |
| 564 | $K^{1-1}$ | $K^{1-1}$ | $K^{1-1}$ | $K^{1-1}$ | $OC_2H_4OH$ | OH | SH | SH | SH | OH | $L^1$ | $ON^{3-2}$ | 1 | 2 |
| 565 | $K^{1-1}$ | $K^{1-1}$ | $K^{1-1}$ | — | OH | SH | SH | SH | — | OH | $L^1$ | $ON^{3-2}$ | 0 | 2 |
| 566 | $K^{2-1}$ | $K^{1-1}$ | $K^{3-1}$ | — | $OC_2H_4OH$ | OH | OH | OH | — | OH | $L^2$ | $ON^{3-2}$ | 0 | 1 |
| 567 | $K^{1-1}$ | $K^{1-1}$ | $K^{1-1}$ | — | $OC_2H_4OH$ | OH | SH | SH | — | OH | $L^2$ | $ON^{3-2}$ | 0 | 1 |
| 568 | $K^{1-1}$ | $K^{1-1}$ | $K^{1-1}$ | — | $OC_2H_4OH$ | SH | SH | SH | — | OH | $L^2$ | $ON^{3-2}$ | 0 | 1 |
| 569 | $K^{1-1}$ | $K^{1-1}$ | $K^{1-1}$ | $K^{1-1}$ | $OC_2H_4OH$ | OH | SH | SH | SH | OH | $L^2$ | $ON^{3-2}$ | 1 | 1 |
| 570 | $K^{1-1}$ | $K^{1-1}$ | $K^{1-1}$ | — | OH | SH | SH | SH | — | OH | $L^2$ | $ON^{3-2}$ | 0 | 1 |
| 571 | $K^{2-1}$ | $K^{1-1}$ | $K^{3-1}$ | — | $OC_2H_4OH$ | OH | OH | OH | — | OH | $L^1$ | $ON^{3-3}$ | 0 | 2 |
| 572 | $K^{1-1}$ | $K^{1-1}$ | $K^{1-1}$ | — | $OC_2H_4OH$ | OH | SH | SH | — | OH | $L^1$ | $ON^{3-3}$ | 0 | 2 |
| 573 | $K^{1-1}$ | $K^{1-1}$ | $K^{1-1}$ | — | $OC_2H_4OH$ | SH | SH | SH | — | OH | $L^1$ | $ON^{3-3}$ | 0 | 2 |
| 574 | $K^{1-1}$ | $K^{1-1}$ | $K^{1-1}$ | $K^{1-1}$ | $OC_2H_4OH$ | OH | SH | SH | SH | OH | $L^1$ | $ON^{3-3}$ | 1 | 2 |
| 575 | $K^{1-1}$ | $K^{1-1}$ | $K^{1-1}$ | — | OH | SH | SH | SH | — | OH | $L^1$ | $ON^{3-3}$ | 0 | 2 |
| 576 | $K^{2-1}$ | $K^{1-1}$ | $K^{3-1}$ | — | $OC_2H_4OH$ | OH | OH | OH | — | OH | $L^2$ | $ON^{3-3}$ | 0 | 1 |
| 577 | $K^{1-1}$ | $K^{1-1}$ | $K^{1-1}$ | — | $OC_2H_4OH$ | OH | SH | SH | — | OH | $L^2$ | $ON^{3-3}$ | 0 | 1 |
| 578 | $K^{1-1}$ | $K^{1-1}$ | $K^{1-1}$ | — | $OC_2H_4OH$ | SH | SH | SH | — | OH | $L^2$ | $ON^{3-3}$ | 0 | 1 |
| 579 | $K^{1-1}$ | $K^{1-1}$ | $K^{1-1}$ | $K^{1-1}$ | $OC_2H_4OH$ | OH | SH | SH | SH | OH | $L^2$ | $ON^{3-3}$ | 1 | 1 |
| 580 | $K^{1-1}$ | $K^{1-1}$ | $K^{1-1}$ | — | OH | SH | SH | SH | — | OH | $L^2$ | $ON^{3-3}$ | 0 | 1 |
| 581 | $K^{2-1}$ | $K^{1-1}$ | $K^{3-1}$ | — | $OC_2H_4OH$ | OH | OH | OH | — | OH | $L^1$ | $ON^{3-4}$ | 0 | 2 |
| 582 | $K^{1-1}$ | $K^{1-1}$ | $K^{1-1}$ | — | $OC_2H_4OH$ | OH | SH | SH | — | OH | $L^1$ | $ON^{3-4}$ | 0 | 2 |
| 583 | $K^{1-1}$ | $K^{1-1}$ | $K^{1-1}$ | — | $OC_2H_4OH$ | SH | SH | SH | — | OH | $L^1$ | $ON^{3-4}$ | 0 | 2 |
| 584 | $K^{1-1}$ | $K^{1-1}$ | $K^{1-1}$ | — | $OC_2H_4OH$ | OH | SH | SH | SH | OH | $L^1$ | $ON^{3-4}$ | 1 | 2 |
| 585 | $K^{1-1}$ | $K^{1-1}$ | $K^{1-1}$ | — | OH | SH | SH | SH | — | OH | $L^1$ | $ON^{3-4}$ | 0 | 2 |
| 586 | $K^{1-1}$ | $K^{1-1}$ | $K^{1-1}$ | — | $OH_2H_4OH$ | OH | OH | OH | — | OH | $L^1$ | $ON^{3-4}$ | 0 | 1 |
| 587 | $K^{1-1}$ | $K^{1-1}$ | $K^{1-1}$ | — | $OC_2H_4OH$ | OH | SH | SH | — | OH | $L^1$ | $ON^{3-4}$ | 0 | 1 |
| 588 | $K^{1-1}$ | $K^{1-1}$ | $K^{1-1}$ | — | $OC_2H_4OH$ | SH | SH | SH | — | OH | $L^1$ | $ON^{3-4}$ | 0 | 1 |
| 589 | $K^{1-1}$ | $K^{1-1}$ | $K^{1-1}$ | — | $OC_2H_4OH$ | OH | SH | SH | SH | OH | $L^1$ | $ON^{3-4}$ | 1 | 1 |
| 590 | $K^{1-1}$ | $K^{1-1}$ | $K^{1-1}$ | — | OH | SH | SH | SH | — | OH | $L^1$ | $ON^{3-4}$ | 0 | 1 |
| 591 | $K^{1-1}$ | $K^{1-1}$ | $K^{1-1}$ | — | $OC_2H_4OH$ | OH | OH | OH | — | OH | $L^1$ | $ON^{3-5}$ | 0 | 2 |
| 592 | $K^{1-1}$ | $K^{1-1}$ | $K^{1-1}$ | — | $OC_2H_4OH$ | OH | SH | SH | — | OH | $L^1$ | $ON^{3-5}$ | 0 | 2 |
| 593 | $K^{1-1}$ | $K^{1-1}$ | $K^{1-1}$ | — | $OC_2H_4OH$ | SH | SH | SH | — | OH | $L^1$ | $ON^{3-5}$ | 0 | 2 |
| 594 | $K^{1-1}$ | $K^{1-1}$ | $K^{1-1}$ | — | $OC_2H_4OH$ | OH | SH | SH | SH | OH | $L^1$ | $ON^{3-5}$ | 1 | 2 |
| 595 | $K^{1-1}$ | $K^{1-1}$ | $K^{1-1}$ | — | OH | SH | SH | SH | — | OH | $L^1$ | $ON^{3-5}$ | 0 | 2 |
| 596 | $K^{1-1}$ | $K^{1-1}$ | $K^{1-1}$ | — | $OC_2H_4OH$ | OH | OH | OH | — | OH | $L^1$ | $ON^{3-5}$ | 0 | 1 |
| 597 | $K^{1-1}$ | $K^{1-1}$ | $K^{1-1}$ | — | $OC_2H_4OH$ | OH | SH | SH | — | OH | $L^1$ | $ON^{3-5}$ | 0 | 1 |
| 598 | $K^{1-1}$ | $K^{1-1}$ | $K^{1-1}$ | — | $OC_2H_4OH$ | SH | SH | SH | — | OH | $L^1$ | $ON^{3-5}$ | 0 | 1 |
| 599 | $K^{1-1}$ | $K^{1-1}$ | $K^{1-1}$ | — | $OC_2H_4OH$ | OH | SH | SH | SH | OH | $L^1$ | $ON^{3-5}$ | 1 | 1 |
| 600 | $K^{1-1}$ | $K^{1-1}$ | $K^{1-1}$ | — | OH | SH | SH | SH | — | OH | $L^1$ | $ON^{3-5}$ | 0 | 1 |
| 601 | $K^{1-1}$ | $K^{1-1}$ | $K^{1-1}$ | — | $OC_2H_4OH$ | OH | OH | OH | — | OH | $L^1$ | $ON^{4-1}$ | 0 | 2 |
| 602 | $K^{1-1}$ | $K^{1-1}$ | $K^{1-1}$ | — | $OC_2H_4OH$ | OH | SH | SH | — | OH | $L^1$ | $ON^{4-1}$ | 0 | 2 |
| 603 | $K^{1-1}$ | $K^{1-1}$ | $K^{1-1}$ | — | $OC_2H_4OH$ | SH | SH | SH | — | OH | $L^1$ | $ON^{4-1}$ | 0 | 2 |
| 604 | $K^{1-1}$ | $K^{1-1}$ | $K^{1-1}$ | $K^{1-1}$ | $OC_2H_4OH$ | OH | SH | SH | SH | OH | $L^1$ | $ON^{4-1}$ | 1 | 2 |
| 605 | $K^{1-1}$ | $K^{1-1}$ | $K^{1-1}$ | — | OH | SH | SH | SH | — | OH | $L^1$ | $ON^{4-1}$ | 0 | 2 |
| 606 | $K^{2-1}$ | $K^{1-1}$ | $K^{3-1}$ | — | $OC_2H_4OH$ | OH | OH | OH | — | OH | $L^2$ | $ON^{4-1}$ | 0 | 1 |
| 607 | $K^{1-1}$ | $K^{1-1}$ | $K^{1-1}$ | — | $OC_2H_4OH$ | OH | SH | SH | — | OH | $L^2$ | $ON^{4-1}$ | 0 | 1 |
| 608 | $K^{1-1}$ | $K^{1-1}$ | $K^{1-1}$ | — | $OC_2H_4OH$ | SH | SH | SH | — | OH | $L^2$ | $ON^{4-1}$ | 0 | 1 |
| 609 | $K^{1-1}$ | $K^{1-1}$ | $K^{1-1}$ | $K^{1-1}$ | $OC_2H_4OH$ | OH | SH | SH | SH | OH | $L^2$ | $ON^{4-1}$ | 1 | 1 |
| 610 | $K^{1-1}$ | $K^{1-1}$ | $K^{1-1}$ | — | OH | SH | SH | SH | — | OH | $L^2$ | $ON^{4-1}$ | 0 | 1 |
| 611 | $K^{2-1}$ | $K^{1-1}$ | $K^{3-1}$ | — | $OC_2H_4OH$ | OH | OH | OH | — | OH | $L^1$ | $ON^{4-2}$ | 0 | 2 |
| 612 | $K^{1-1}$ | $K^{1-1}$ | $K^{1-1}$ | — | $OC_2H_4OH$ | OH | SH | SH | — | OH | $L^1$ | $ON^{4-2}$ | 0 | 2 |
| 613 | $K^{1-1}$ | $K^{1-1}$ | $K^{1-1}$ | — | $OC_2H_4OH$ | SH | SH | SH | — | OH | $L^1$ | $ON^{4-2}$ | 0 | 2 |
| 614 | $K^{1-1}$ | $K^{1-1}$ | $K^{1-1}$ | $K^{1-1}$ | $OC_2H_4OH$ | OH | SH | SH | SH | OH | $L^1$ | $ON^{4-2}$ | 1 | 2 |
| 615 | $K^{1-1}$ | $K^{1-1}$ | $K^{1-1}$ | — | OH | SH | SH | SH | — | OH | $L^1$ | $ON^{4-2}$ | 0 | 2 |
| 616 | $K^{2-1}$ | $K^{1-1}$ | $K^{3-1}$ | — | $OC_2H_4OH$ | OH | OH | OH | — | OH | $L^2$ | $ON^{4-2}$ | 0 | 1 |
| 617 | $K^{1-1}$ | $K^{1-1}$ | $K^{1-1}$ | — | $OC_2H_4OH$ | OH | SH | SH | — | OH | $L^2$ | $ON^{4-2}$ | 0 | 1 |
| 618 | $K^{1-1}$ | $K^{1-1}$ | $K^{1-1}$ | — | $OC_2H_4OH$ | SH | SH | SH | — | OH | $L^2$ | $ON^{4-2}$ | 0 | 1 |
| 619 | $K^{1-1}$ | $K^{1-1}$ | $K^{1-1}$ | $K^{1-1}$ | $OC_2H_4OH$ | OH | SH | SH | SH | OH | $L^2$ | $ON^{4-2}$ | 1 | 1 |
| 620 | $K^{1-1}$ | $K^{1-1}$ | $K^{1-1}$ | — | OH | SH | SH | SH | — | OH | $L^2$ | $ON^{4-2}$ | 0 | 1 |
| 621 | $K^{2-1}$ | $K^{1-1}$ | $K^{3-1}$ | — | $OC_2H_4OH$ | OH | OH | OH | — | OH | $L^1$ | $ON^{4-3}$ | 0 | 2 |
| 622 | $K^{1-1}$ | $K^{1-1}$ | $K^{1-1}$ | — | $OC_2H_4OH$ | OH | SH | SH | — | OH | $L^1$ | $ON^{4-3}$ | 0 | 2 |
| 623 | $K^{1-1}$ | $K^{1-1}$ | $K^{1-1}$ | — | $OC_2H_4OH$ | SH | SH | SH | — | OH | $L^1$ | $ON^{4-3}$ | 0 | 2 |
| 624 | $K^{1-1}$ | $K^{1-1}$ | $K^{1-1}$ | $K^{1-1}$ | $OC_2H_4OH$ | OH | SH | SH | SH | OH | $L^1$ | $ON^{4-3}$ | 1 | 2 |
| 625 | $K^{1-1}$ | $K^{1-1}$ | $K^{1-1}$ | — | OH | SH | SH | SH | — | OH | $L^1$ | $ON^{4-3}$ | 0 | 2 |
| 626 | $K^{2-1}$ | $K^{1-1}$ | $K^{1-1}$ | — | $OC_2H_4OH$ | OH | OH | OH | — | OH | $L^2$ | $ON^{4-3}$ | 0 | 1 |

TABLE 1-continued

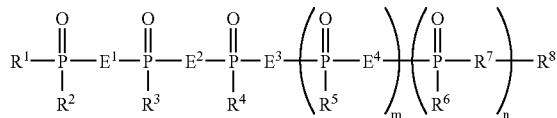

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 627 | $K^{1-1}$ | $K^{1-1}$ | $K^{1-1}$ | — | $OC_2H_4OH$ | OH | SH | SH | — | OH | $L^2$ | $ON^{4-3}$ | 0 | 1 |
| 628 | $K^{1-1}$ | $K^{1-1}$ | $K^{1-1}$ | — | $OC_2H_4OH$ | SH | SH | SH | — | OH | $L^2$ | $ON^{4-3}$ | 0 | 1 |
| 629 | $K^{1-1}$ | $K^{1-1}$ | $K^{1-1}$ | $K^{1-1}$ | $OC_2H_4OH$ | OH | SH | SH | SH | OH | $L^2$ | $ON^{4-3}$ | 1 | 1 |
| 630 | $K^{1-1}$ | $K^{1-1}$ | $K^{1-1}$ | — | OH | SH | SH | SH | — | OH | $L^2$ | $ON^{4-3}$ | 0 | 1 |
| 631 | $K^{3-1}$ | $K^{1-1}$ | $K^{1-1}$ | — | $OC_2H_4OH$ | OH | OH | OH | — | OH | $L^1$ | $ON^{4-4}$ | 0 | 2 |
| 632 | $K^{1-1}$ | $K^{1-1}$ | $K^{1-1}$ | — | $OC_2H_4OH$ | OH | SH | SH | — | OH | $L^1$ | $ON^{4-4}$ | 0 | 2 |
| 633 | $K^{1-1}$ | $K^{1-1}$ | $K^{1-1}$ | — | $OC_2H_4OH$ | SH | SH | SH | — | OH | $L^1$ | $ON^{4-4}$ | 0 | 2 |
| 634 | $K^{1-1}$ | $K^{1-1}$ | $K^{1-1}$ | $K^{1-1}$ | $OC_2H_4OH$ | OH | SH | SH | SH | OH | $L^1$ | $ON^{4-4}$ | 1 | 2 |
| 635 | $K^{1-1}$ | $K^{1-1}$ | $K^{1-1}$ | — | OH | SH | SH | SH | — | OH | $L^1$ | $ON^{4-4}$ | 0 | 2 |
| 636 | $K^{2-1}$ | $K^{1-1}$ | $K^{1-1}$ | — | $OC_2H_4OH$ | OH | OH | OH | — | OH | $L^2$ | $ON^{4-4}$ | 0 | 1 |
| 637 | $K^{1-1}$ | $K^{1-1}$ | $K^{1-1}$ | — | $OC_2H_4OH$ | OH | SH | SH | — | OH | $L^2$ | $ON^{4-4}$ | 0 | 1 |
| 638 | $K^{1-1}$ | $K^{1-1}$ | $K^{1-1}$ | — | $OC_2H_4OH$ | SH | SH | SH | — | OH | $L^2$ | $ON^{4-4}$ | 0 | 1 |
| 639 | $K^{1-1}$ | $K^{1-1}$ | $K^{1-1}$ | $K^{1-1}$ | $OC_2H_4OH$ | OH | SH | SH | SH | OH | $L^2$ | $ON^{4-4}$ | 1 | 1 |
| 640 | $K^{1-1}$ | $K^{1-1}$ | $K^{1-1}$ | — | OH | SH | SH | SH | — | OH | $L^2$ | $ON^{4-4}$ | 0 | 1 |
| 641 | $K^{2-1}$ | $K^{1-1}$ | $K^{1-1}$ | — | $OC_2H_4OH$ | OH | OH | OH | — | OH | $L^1$ | $ON^{4-5}$ | 0 | 2 |
| 642 | $K^{1-1}$ | $K^{1-1}$ | $K^{1-1}$ | — | $OC_2H_4OH$ | OH | SH | SH | — | OH | $L^1$ | $ON^{4-5}$ | 0 | 2 |
| 643 | $K^{1-1}$ | $K^{1-1}$ | $K^{1-1}$ | — | $OC_2H_4OH$ | SH | SH | SH | — | OH | $L^1$ | $ON^{4-5}$ | 0 | 2 |
| 644 | $K^{1-1}$ | $K^{1-1}$ | $K^{1-1}$ | $K^{1-1}$ | $OC_2H_4OH$ | OH | SH | SH | SH | OH | $L^1$ | $ON^{4-5}$ | 1 | 2 |
| 645 | $K^{1-1}$ | $K^{1-1}$ | $K^{1-1}$ | — | OH | SH | SH | SH | — | OH | $L^1$ | $ON^{4-5}$ | 0 | 2 |
| 646 | $K^{2-1}$ | $K^{1-1}$ | $K^{3-1}$ | — | $OC_2H_4OH$ | OH | OH | OH | — | OH | $L^2$ | $ON^{4-5}$ | 0 | 1 |
| 647 | $K^{1-1}$ | $K^{1-1}$ | $K^{1-1}$ | — | $OC_2H_4OH$ | OH | SH | SH | — | OH | $L^2$ | $ON^{4-5}$ | 0 | 1 |
| 648 | $K^{1-1}$ | $K^{1-1}$ | $K^{1-1}$ | — | $OC_2H_4OH$ | SH | SH | SH | — | OH | $L^2$ | $ON^{4-5}$ | 0 | 1 |
| 649 | $K^{1-1}$ | $K^{1-1}$ | $K^{1-1}$ | $K^{1-1}$ | $OC_2H_4OH$ | OH | SH | SH | SH | OH | $L^2$ | $ON^{4-5}$ | 1 | 1 |
| 650 | $K^{1-1}$ | $K^{1-1}$ | $K^{1-1}$ | — | OH | SH | SH | SH | — | OH | $L^2$ | $ON^{4-5}$ | 0 | 1 |
| 651 | $K^{2-1}$ | $K^{1-1}$ | $K^{3-1}$ | — | $OC_2H_4OH$ | OH | OH | OH | — | OH | $L^1$ | $ON^{5-1}$ | 0 | 2 |
| 652 | $K^{1-1}$ | $K^{1-1}$ | $K^{1-1}$ | — | $OC_2H_4OH$ | OH | SH | SH | — | OH | $L^1$ | $ON^{5-1}$ | 0 | 2 |
| 653 | $K^{1-1}$ | $K^{1-1}$ | $K^{1-1}$ | — | $OC_2H_4OH$ | SH | SH | SH | — | OH | $L^1$ | $ON^{5-1}$ | 0 | 2 |
| 654 | $K^{1-1}$ | $K^{1-1}$ | $K^{1-1}$ | $K^{1-1}$ | $OC_2H_4OH$ | OH | SH | SH | SH | OH | $L^1$ | $ON^{5-1}$ | 1 | 2 |
| 655 | $K^{1-1}$ | $K^{1-1}$ | $K^{1-1}$ | — | OH | SH | SH | SH | — | OH | $L^1$ | $ON^{5-1}$ | 0 | 2 |
| 656 | $K^{2-1}$ | $K^{1-1}$ | $K^{3-1}$ | — | $OC_2H_4OH$ | OH | OH | OH | — | OH | $L^2$ | $ON^{5-1}$ | 0 | 1 |
| 657 | $K^{1-1}$ | $K^{1-1}$ | $K^{1-1}$ | — | $OC_2H_4OH$ | OH | SH | SH | — | OH | $L^2$ | $ON^{5-1}$ | 0 | 1 |
| 658 | $K^{1-1}$ | $K^{1-1}$ | $K^{1-1}$ | — | $OC_2H_4OH$ | SH | SH | SH | — | OH | $L^2$ | $ON^{5-1}$ | 0 | 1 |
| 659 | $K^{1-1}$ | $K^{1-1}$ | $K^{1-1}$ | $K^{1-1}$ | $OC_2H_4OH$ | OH | SH | SH | SH | OH | $L^2$ | $ON^{5-1}$ | 1 | 1 |
| 660 | $K^{1-1}$ | $K^{1-1}$ | $K^{1-1}$ | — | OH | SH | SH | SH | — | OH | $L^2$ | $ON^{5-1}$ | 0 | 1 |
| 661 | $K^{2-1}$ | $K^{1-1}$ | $K^{3-1}$ | — | $OC_2H_4OH$ | OH | OH | OH | — | OH | $L^1$ | $ON^{5-2}$ | 0 | 2 |
| 662 | $K^{1-1}$ | $K^{1-1}$ | $K^{1-1}$ | — | $OC_2H_4OH$ | OH | SH | SH | — | OH | $L^1$ | $ON^{5-2}$ | 0 | 2 |
| 663 | $K^{1-1}$ | $K^{1-1}$ | $K^{1-1}$ | — | $OC_2H_4OH$ | SH | SH | SH | — | OH | $L^1$ | $ON^{5-2}$ | 0 | 2 |
| 664 | $K^{1-1}$ | $K^{1-1}$ | $K^{1-1}$ | $K^{1-1}$ | $OC_2H_4OH$ | OH | SH | SH | SH | OH | $L^1$ | $ON^{5-2}$ | 1 | 2 |
| 665 | $K^{1-1}$ | $K^{1-1}$ | $K^{1-1}$ | — | OH | SH | SH | SH | — | OH | $L^1$ | $ON^{5-2}$ | 0 | 2 |
| 666 | $K^{2-1}$ | $K^{1-1}$ | $K^{3-1}$ | — | $OC_2H_4OH$ | OH | OH | OH | — | OH | $L^2$ | $ON^{5-2}$ | 0 | 1 |
| 667 | $K^{1-1}$ | $K^{1-1}$ | $K^{1-1}$ | — | $OC_2H_4OH$ | OH | SH | SH | — | OH | $L^2$ | $ON^{5-2}$ | 0 | 1 |
| 668 | $K^{1-1}$ | $K^{1-1}$ | $K^{1-1}$ | — | $OC_2H_4OH$ | SH | SH | SH | — | OH | $L^2$ | $ON^{5-2}$ | 0 | 1 |
| 669 | $K^{1-1}$ | $K^{1-1}$ | $K^{1-1}$ | $K^{1-1}$ | $OC_2H_4OH$ | OH | SH | SH | SH | OH | $L^2$ | $ON^{5-2}$ | 1 | 1 |
| 670 | $K^{1-1}$ | $K^{1-1}$ | $K^{1-1}$ | — | OH | SH | SH | SH | — | OH | $L^2$ | $ON^{5-2}$ | 0 | 1 |
| 671 | $K^{2-1}$ | $K^{1-1}$ | $K^{3-1}$ | — | $OC_2H_4OH$ | OH | OH | OH | — | OH | $L^1$ | $ON^{5-3}$ | 0 | 2 |
| 672 | $K^{1-1}$ | $K^{1-1}$ | $K^{1-1}$ | — | $OC_2H_4OH$ | OH | SH | SH | — | OH | $L^1$ | $ON^{5-3}$ | 0 | 2 |
| 673 | $K^{1-1}$ | $K^{1-1}$ | $K^{1-1}$ | — | $OC_2H_4OH$ | SH | SH | SH | — | OH | $L^1$ | $ON^{5-3}$ | 0 | 2 |
| 674 | $K^{1-1}$ | $K^{1-1}$ | $K^{1-1}$ | $K^{1-1}$ | $OC_2H_4OH$ | OH | SH | SH | SH | OH | $L^1$ | $ON^{5-3}$ | 1 | 2 |
| 675 | $K^{1-1}$ | $K^{1-1}$ | $K^{1-1}$ | — | OH | SH | SH | SH | — | OH | $L^1$ | $ON^{5-3}$ | 0 | 2 |
| 676 | $K^{2-1}$ | $K^{1-1}$ | $K^{3-1}$ | — | $OC_2H_4OH$ | OH | OH | OH | — | OH | $L^2$ | $ON^{5-3}$ | 0 | 1 |
| 677 | $K^{1-1}$ | $K^{1-1}$ | $K^{1-1}$ | — | $OC_2H_4OH$ | OH | SH | SH | — | OH | $L^2$ | $ON^{5-3}$ | 0 | 1 |
| 678 | $K^{1-1}$ | $K^{1-1}$ | $K^{1-1}$ | — | $OC_2H_4OH$ | SH | SH | SH | — | OH | $L^2$ | $ON^{5-3}$ | 0 | 1 |
| 679 | $K^{1-1}$ | $K^{1-1}$ | $K^{1-1}$ | $K^{1-1}$ | $OC_2H_4OH$ | OH | SH | SH | SH | OH | $L^2$ | $ON^{5-3}$ | 1 | 1 |
| 680 | $K^{1-1}$ | $K^{1-1}$ | $K^{1-1}$ | — | OH | SH | SH | SH | — | OH | $L^2$ | $ON^{5-3}$ | 0 | 1 |
| 681 | $K^{2-1}$ | $K^{1-1}$ | $K^{3-1}$ | — | $OC_2H_4OH$ | OH | OH | OH | — | OH | $L^1$ | $ON^{5-4}$ | 0 | 2 |
| 682 | $K^{1-1}$ | $K^{1-1}$ | $K^{1-1}$ | — | $OC_2H_4OH$ | OH | SH | SH | — | OH | $L^1$ | $ON^{5-4}$ | 0 | 2 |
| 683 | $K^{1-1}$ | $K^{1-1}$ | $K^{1-1}$ | — | $OC_2H_4OH$ | SH | SH | SH | — | OH | $L^1$ | $ON^{5-4}$ | 0 | 2 |
| 684 | $K^{1-1}$ | $K^{1-1}$ | $K^{1-1}$ | $K^{1-1}$ | $OC_2H_4OH$ | OH | SH | SH | SH | OH | $L^1$ | $ON^{5-4}$ | 1 | 2 |
| 685 | $K^{1-1}$ | $K^{1-1}$ | $K^{1-1}$ | — | OH | SH | SH | SH | — | OH | $L^1$ | $ON^{5-4}$ | 0 | 2 |
| 686 | $K^{2-1}$ | $K^{1-1}$ | $K^{3-1}$ | — | $OC_2H_4OH$ | OH | OH | OH | — | OH | $L^2$ | $ON^{5-4}$ | 0 | 1 |
| 687 | $K^{1-1}$ | $K^{1-1}$ | $K^{1-1}$ | — | $OC_2H_4OH$ | OH | SH | SH | — | OH | $L^2$ | $ON^{5-4}$ | 0 | 1 |
| 688 | $K^{1-1}$ | $K^{1-1}$ | $K^{1-1}$ | — | $OC_2H_4OH$ | SH | SH | SH | — | OH | $L^2$ | $ON^{5-4}$ | 0 | 1 |
| 689 | $K^{1-1}$ | $K^{1-1}$ | $K^{1-1}$ | $K^{1-1}$ | $OC_2H_4OH$ | OH | SH | SH | SH | OH | $L^2$ | $ON^{5-4}$ | 1 | 1 |
| 690 | $K^{1-1}$ | $K^{1-1}$ | $K^{1-1}$ | — | OH | SH | SH | SH | — | OH | $L^2$ | $ON^{5-4}$ | 0 | 1 |
| 691 | $K^{2-1}$ | $K^{1-1}$ | $K^{3-1}$ | — | $OC_2H_4OH$ | OH | OH | OH | — | OH | $L^1$ | $ON^{5-5}$ | 0 | 2 |
| 692 | $K^{1-1}$ | $K^{1-1}$ | $K^{1-1}$ | — | $OC_2H_4OH$ | OH | SH | SH | — | OH | $L^1$ | $ON^{5-5}$ | 0 | 2 |
| 693 | $K^{1-1}$ | $K^{1-1}$ | $K^{1-1}$ | — | $OC_2H_4OH$ | SH | SH | SH | — | OH | $L^1$ | $ON^{5-5}$ | 0 | 2 |
| 694 | $K^{1-1}$ | $K^{1-1}$ | $K^{1-1}$ | $K^{1-1}$ | $OC_2H_4OH$ | OH | SH | SH | SH | OH | $L^1$ | $ON^{5-5}$ | 0 | 2 |

TABLE 1-continued

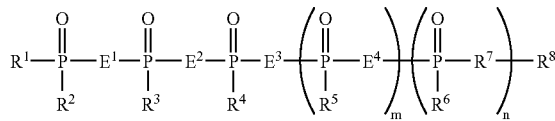

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 695 | $K^{1-1}$ | $K^{1-1}$ | $K^{1-1}$ | — | OH | SH | SH | SH | — | OH | $L^1$ | $ON^{5-5}$ | 0 | 2 |
| 696 | $K^{2-1}$ | $K^{1-1}$ | $K^{3-1}$ | — | $OC_2H_4OH$ | OH | OH | OH | — | OH | $L^2$ | $ON^{5-5}$ | 0 | 1 |
| 697 | $K^{1-1}$ | $K^{1-1}$ | $K^{1-1}$ | — | $OC_2H_4OH$ | OH | SH | SH | — | OH | $L^2$ | $ON^{5-5}$ | 0 | 1 |
| 698 | $K^{1-1}$ | $K^{1-1}$ | $K^{1-1}$ | — | $OC_2H_4OH$ | SH | SH | SH | — | OH | $L^2$ | $ON^{5-5}$ | 0 | 1 |
| 699 | $K^{1-1}$ | $K^{1-1}$ | $K^{1-1}$ | $K^{1-1}$ | $OC_2H_4OH$ | OH | SH | SH | SH | OH | $L^2$ | $ON^{5-5}$ | 0 | 1 |
| 700 | $K^{1-1}$ | $K^{1-1}$ | $K^{1-1}$ | — | OH | SH | SH | SH | — | OH | $L^2$ | $ON^{5-5}$ | 0 | 1 |
| 701 | $K^{2-1}$ | $K^{1-1}$ | $K^{3-1}$ | — | $OC_2H_4OH$ | OH | OH | OH | — | OH | $L^1$ | $ON^{6-1}$ | 0 | 2 |
| 702 | $K^{1-1}$ | $K^{1-1}$ | $K^{1-1}$ | — | $OC_2H_4OH$ | OH | SH | SH | — | OH | $L^1$ | $ON^{6-1}$ | 0 | 2 |
| 703 | $K^{1-1}$ | $K^{1-1}$ | $K^{1-1}$ | — | $OC_2H_4OH$ | SH | SH | SH | — | OH | $L^1$ | $ON^{6-1}$ | 0 | 2 |
| 704 | $K^{1-1}$ | $K^{1-1}$ | $K^{1-1}$ | $K^{1-1}$ | $OC_4H_4OH$ | OH | SH | SH | SH | OH | $L^1$ | $ON^{6-1}$ | 0 | 2 |
| 705 | $K^{1-1}$ | $K^{1-1}$ | $K^{1-1}$ | — | OH | SH | SH | SH | — | OH | $L^1$ | $ON^{6-1}$ | 0 | 2 |
| 706 | $K^{2-1}$ | $K^{1-1}$ | $K^{3-1}$ | — | $OC_2H_4OH$ | OH | OH | OH | — | OH | $L^2$ | $ON^{6-1}$ | 0 | 1 |
| 707 | $K^{1-1}$ | $K^{1-1}$ | $K^{1-1}$ | — | $OC_2H_4OH$ | OH | SH | SH | — | OH | $L^2$ | $ON^{6-1}$ | 0 | 1 |
| 708 | $K^{1-1}$ | $K^{1-1}$ | $K^{1-1}$ | — | $OC_2H_4OH$ | SH | SH | SH | — | OH | $L^2$ | $ON^{6-1}$ | 0 | 1 |
| 709 | $K^{1-1}$ | $K^{1-1}$ | $K^{1-1}$ | $K^{1-1}$ | $OC_2H_4OH$ | OH | SH | SH | SH | OH | $L^2$ | $ON^{6-1}$ | 1 | 1 |
| 710 | $K^{1-1}$ | $K^{1-1}$ | $K^{1-1}$ | — | OH | SH | SH | SH | — | OH | $L^2$ | $ON^{6-1}$ | 0 | 1 |
| 711 | $K^{2-1}$ | $K^{1-1}$ | $K^{3-1}$ | — | $OC_2H_4OH$ | OH | OH | OH | — | OH | $L^1$ | $ON^{6-2}$ | 0 | 2 |
| 712 | $K^{1-1}$ | $K^{1-1}$ | $K^{1-1}$ | — | $OC_2H_4OH$ | OH | SH | SH | — | OH | $L^1$ | $ON^{6-2}$ | 0 | 2 |
| 713 | $K^{1-1}$ | $K^{1-1}$ | $K^{1-1}$ | — | $OC_2H_4OH$ | SH | SH | SH | — | OH | $L^1$ | $ON^{6-2}$ | 0 | 2 |
| 714 | $K^{1-1}$ | $K^{1-1}$ | $K^{1-1}$ | $K^{1-1}$ | $OC_2H_4OH$ | OH | SH | SH | SH | OH | $L^1$ | $ON^{6-2}$ | 1 | 2 |
| 715 | $K^{1-1}$ | $K^{1-1}$ | $K^{1-1}$ | — | OH | SH | SH | SH | — | OH | $L^1$ | $ON^{6-2}$ | 0 | 2 |
| 716 | $K^{2-1}$ | $K^{1-1}$ | $K^{3-1}$ | — | $OC_2H_4OH$ | OH | OH | OH | — | OH | $L^2$ | $ON^{6-2}$ | 0 | 1 |
| 717 | $K^{1-1}$ | $K^{1-1}$ | $K^{1-1}$ | — | $OC_2H_4OH$ | OH | SH | SH | — | OH | $L^2$ | $ON^{6-2}$ | 0 | 1 |
| 718 | $K^{1-1}$ | $K^{1-1}$ | $K^{1-1}$ | — | $OC_2H_4OH$ | SH | SH | SH | — | OH | $L^2$ | $ON^{6-2}$ | 0 | 1 |
| 719 | $K^{1-1}$ | $K^{1-1}$ | $K^{1-1}$ | $K^{1-1}$ | $OC_2H_4OH$ | OH | SH | SH | SH | OH | $L^2$ | $ON^{6-2}$ | 1 | 1 |
| 720 | $K^{1-1}$ | $K^{1-1}$ | $K^{1-1}$ | — | OH | SH | SH | SH | — | OH | $L^2$ | $ON^{6-2}$ | 0 | 1 |
| 721 | $K^{2-1}$ | $K^{1-1}$ | $K^{3-1}$ | — | $OC_2H_4OH$ | OH | OH | OH | — | OH | $L^1$ | $ON^{6-3}$ | 0 | 2 |
| 722 | $K^{1-1}$ | $K^{1-1}$ | $K^{1-1}$ | — | $OC_2H_4OH$ | OH | SH | SH | — | OH | $L^1$ | $ON^{6-3}$ | 0 | 2 |
| 723 | $K^{1-1}$ | $K^{1-1}$ | $K^{1-1}$ | — | $OC_2H_4OH$ | SH | SH | SH | — | OH | $L^1$ | $ON^{6-3}$ | 0 | 2 |
| 724 | $K^{1-1}$ | $K^{1-1}$ | $K^{1-1}$ | $K^{1-1}$ | $OC_2H_4OH$ | OH | SH | SH | SH | OH | $L^1$ | $ON^{6-3}$ | 1 | 2 |
| 725 | $K^{1-1}$ | $K^{1-1}$ | $K^{1-1}$ | — | OH | SH | SH | SH | — | OH | $L^1$ | $ON^{6-3}$ | 0 | 2 |
| 726 | $K^{2-1}$ | $K^{1-1}$ | $K^{3-1}$ | — | $OC_2H_4OH$ | OH | OH | OH | — | OH | $L^2$ | $ON^{6-3}$ | 0 | 1 |
| 727 | $K^{1-1}$ | $K^{1-1}$ | $K^{1-1}$ | — | $OC_2H_4OH$ | OH | SH | SH | — | OH | $L^2$ | $ON^{6-3}$ | 0 | 1 |
| 728 | $K^{1-1}$ | $K^{1-1}$ | $K^{1-1}$ | — | $OC_2H_4OH$ | SH | SH | SH | — | OH | $L^2$ | $ON^{6-3}$ | 0 | 1 |
| 729 | $K^{1-1}$ | $K^{1-1}$ | $K^{1-1}$ | $K^{1-1}$ | $OC_2H_4OH$ | OH | SH | SH | SH | OH | $L^2$ | $ON^{6-3}$ | 1 | 1 |
| 730 | $K^{1-1}$ | $K^{1-1}$ | $K^{1-1}$ | — | OH | SH | SH | SH | — | OH | $L^2$ | $ON^{6-3}$ | 0 | 1 |
| 731 | $K^{2-1}$ | $K^{1-1}$ | $K^{3-1}$ | — | $OC_2H_4OH$ | OH | OH | OH | — | OH | $L^1$ | $ON^{6-4}$ | 0 | 2 |
| 732 | $K^{1-1}$ | $K^{1-1}$ | $K^{1-1}$ | — | $OC_2H_4OH$ | OH | SH | SH | — | OH | $L^1$ | $ON^{6-4}$ | 0 | 2 |
| 733 | $K^{1-1}$ | $K^{1-1}$ | $K^{1-1}$ | — | $OC_2H_4OH$ | SH | SH | SH | — | OH | $L^1$ | $ON^{6-4}$ | 0 | 2 |
| 734 | $K^{1-1}$ | $K^{1-1}$ | $K^{1-1}$ | $K^{1-1}$ | $OC_2H_4OH$ | OH | SH | SH | SH | OH | $L^1$ | $ON^{6-4}$ | 1 | 2 |
| 735 | $K^{1-1}$ | $K^{1-1}$ | $K^{1-1}$ | — | OH | SH | SH | SH | — | OH | $L^1$ | $ON^{6-4}$ | 0 | 2 |
| 736 | $K^{2-1}$ | $K^{1-1}$ | $K^{3-1}$ | — | $OC_2H_4OH$ | OH | OH | OH | — | OH | $L^2$ | $ON^{6-4}$ | 0 | 1 |
| 737 | $K^{1-1}$ | $K^{1-1}$ | $K^{1-1}$ | — | $OC_2H_4OH$ | OH | SH | SH | — | OH | $L^2$ | $ON^{6-4}$ | 0 | 1 |
| 738 | $K^{1-1}$ | $K^{1-1}$ | $K^{1-1}$ | — | $OC_2H_4OH$ | SH | SH | SH | — | OH | $L^2$ | $ON^{6-4}$ | 0 | 1 |
| 739 | $K^{1-1}$ | $K^{1-1}$ | $K^{1-1}$ | $K^{1-1}$ | $OC_2H_4OH$ | OH | SH | SH | SH | OH | $L^2$ | $ON^{6-4}$ | 1 | 1 |
| 740 | $K^{1-1}$ | $K^{1-1}$ | $K^{1-1}$ | — | SH | SH | SH | OH | — | OH | $L^2$ | $ON^{6-4}$ | 0 | 1 |
| 741 | $K^{2-1}$ | $K^{1-1}$ | $K^{3-1}$ | — | $OC_2H_4OH$ | OH | OH | OH | — | OH | $L^1$ | $ON^{6-5}$ | 0 | 2 |
| 742 | $K^{1-1}$ | $K^{1-1}$ | $K^{1-1}$ | — | $OC_2H_4OH$ | OH | SH | SH | — | OH | $L^1$ | $ON^{6-5}$ | 0 | 2 |
| 743 | $K^{1-1}$ | $K^{1-1}$ | $K^{1-1}$ | — | $OC_2H_4OH$ | SH | SH | SH | — | OH | $L^1$ | $ON^{6-5}$ | 0 | 2 |
| 744 | $K^{1-1}$ | $K^{1-1}$ | $K^{1-1}$ | $K^{1-1}$ | $OC_2H_4OH$ | OH | SH | SH | SH | OH | $L^1$ | $ON^{6-5}$ | 1 | 2 |
| 745 | $K^{1-1}$ | $K^{1-1}$ | $K^{1-1}$ | — | OH | SH | SH | SH | — | OH | $L^1$ | $ON^{6-5}$ | 0 | 2 |
| 746 | $K^{2-1}$ | $K^{1-1}$ | $K^{3-1}$ | — | $OC_2H_4OH$ | OH | OH | OH | — | OH | $L^2$ | $ON^{6-5}$ | 0 | 1 |
| 747 | $K^{1-1}$ | $K^{1-1}$ | $K^{1-1}$ | — | $OC_2H_4OH$ | OH | SH | SH | — | OH | $L^2$ | $ON^{6-5}$ | 0 | 1 |
| 748 | $K^{1-1}$ | $K^{1-1}$ | $K^{1-1}$ | — | $OC_2H_4OH$ | SH | SH | SH | — | OH | $L^2$ | $ON^{6-5}$ | 0 | 1 |
| 749 | $K^{1-1}$ | $K^{1-1}$ | $K^{1-1}$ | $K^{1-1}$ | $OC_2H_4OH$ | OH | SH | SH | SH | OH | $L^2$ | $ON^{6-5}$ | 1 | 1 |
| 750 | $K^{1-1}$ | $K^{1-1}$ | $K^{1-1}$ | — | OH | SH | SH | SH | — | OH | $L^2$ | $ON^{6-5}$ | 0 | 1 |
| 751 | $K^{2-1}$ | $K^{1-1}$ | $K^{3-1}$ | — | $OC_2H_4OH$ | OH | OH | OH | — | OH | $L^1$ | $ON^{7-1}$ | 0 | 2 |
| 752 | $K^{1-1}$ | $K^{1-1}$ | $K^{1-1}$ | — | $OC_2H_4OH$ | OH | SH | SH | — | OH | $L^1$ | $ON^{7-1}$ | 0 | 2 |
| 753 | $K^{1-1}$ | $K^{1-1}$ | $K^{1-1}$ | — | $OC_2H_4OH$ | SH | SH | SH | — | OH | $L^1$ | $ON^{7-1}$ | 0 | 2 |
| 754 | $K^{1-1}$ | $K^{1-1}$ | $K^{1-1}$ | $K^{1-1}$ | $OC_2H_4OH$ | OH | SH | SH | SH | OH | $L^1$ | $ON^{7-1}$ | 1 | 2 |
| 755 | $K^{1-1}$ | $K^{1-1}$ | $K^{1-1}$ | — | OH | SH | SH | SH | — | OH | $L^1$ | $ON^{7-1}$ | 0 | 2 |
| 756 | $K^{2-1}$ | $K^{1-1}$ | $K^{3-1}$ | — | $OC_2H_4OH$ | OH | OH | OH | — | OH | $L^2$ | $ON^{7-1}$ | 0 | 1 |
| 757 | $K^{1-1}$ | $K^{1-1}$ | $K^{1-1}$ | — | $OC_2H_4OH$ | OH | SH | SH | — | OH | $L^2$ | $ON^{7-1}$ | 0 | 1 |
| 758 | $K^{1-1}$ | $K^{1-1}$ | $K^{1-1}$ | — | $OC_2H_4OH$ | SH | SH | SH | — | OH | $L^2$ | $ON^{7-1}$ | 0 | 1 |
| 759 | $K^{1-1}$ | $K^{1-1}$ | $K^{1-1}$ | $K^{1-1}$ | $OC_2H_4OH$ | OH | SH | SH | SH | OH | $L^2$ | $ON^{7-1}$ | 1 | 1 |
| 760 | $K^{1-1}$ | $K^{1-1}$ | $K^{1-1}$ | — | OH | SH | SH | SH | — | OH | $L^2$ | $ON^{7-1}$ | 0 | 1 |
| 761 | $K^{2-1}$ | $K^{1-1}$ | $K^{3-1}$ | — | $OC_2H_4OH$ | OH | OH | OH | — | OH | $L^1$ | $ON^{7-2}$ | 0 | 2 |
| 762 | $K^{1-1}$ | $K^{1-1}$ | $K^{1-1}$ | — | $OC_2H_4OH$ | OH | SH | SH | — | OH | $L^1$ | $ON^{7-2}$ | 0 | 2 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 763 | $K^{1-1}$ | $K^{1-1}$ | $K^{1-1}$ | — | $OC_2H_4OH$ | SH | SH | SH | — | OH | $L^1$ | $ON^{7-2}$ | 0 | 2 |
| 764 | $K^{1-1}$ | $K^{1-1}$ | $K^{1-1}$ | $K^{1-1}$ | $OC_2H_4OH$ | OH | SH | SH | SH | OH | $L^1$ | $ON^{7-2}$ | 1 | 2 |
| 765 | $K^{1-1}$ | $K^{1-1}$ | $K^{1-1}$ | — | OH | SH | SH | SH | — | OH | $L^1$ | $ON^{7-2}$ | 0 | 2 |
| 766 | $K^{2-1}$ | $K^{1-1}$ | $K^{3-1}$ | — | $OC_2H_4OH$ | OH | OH | OH | — | OH | $L^2$ | $ON^{7-2}$ | 0 | 1 |
| 767 | $K^{1-1}$ | $K^{1-1}$ | $K^{1-1}$ | — | $OC_2H_4OH$ | OH | SH | SH | — | OH | $L^2$ | $ON^{7-2}$ | 0 | 1 |
| 768 | $K^{1-1}$ | $K^{1-1}$ | $K^{1-1}$ | — | $OC_2H_4OH$ | SH | SH | SH | — | OH | $L^2$ | $ON^{7-2}$ | 0 | 1 |
| 769 | $K^{1-1}$ | $K^{1-1}$ | $K^{1-1}$ | — | $OC_2H_4OH$ | OH | SH | SH | SH | OH | $L^2$ | $ON^{7-2}$ | 1 | 1 |
| 770 | $K^{1-1}$ | $K^{1-1}$ | $K^{1-1}$ | — | OH | SH | SH | SH | — | OH | $L^2$ | $ON^{7-2}$ | 0 | 1 |
| 771 | $K^{2-1}$ | $K^{1-1}$ | $K^{3-1}$ | — | $OC_2H_4OH$ | OH | OH | OH | — | OH | $L^1$ | $ON^{7-3}$ | 0 | 2 |
| 772 | $K^{1-1}$ | $K^{1-1}$ | $K^{1-1}$ | — | $OC_2H_4OH$ | OH | SH | SH | — | OH | $L^1$ | $ON^{7-3}$ | 0 | 2 |
| 773 | $K^{1-1}$ | $K^{1-1}$ | $K^{1-1}$ | — | $OC_2H_4OH$ | SH | SH | SH | — | OH | $L^1$ | $ON^{7-3}$ | 0 | 2 |
| 774 | $K^{1-1}$ | $K^{1-1}$ | $K^{1-1}$ | — | $OC_2H_4OH$ | OH | SH | SH | SH | OH | $L^1$ | $ON^{7-3}$ | 1 | 2 |
| 775 | $K^{1-1}$ | $K^{1-1}$ | $K^{1-1}$ | — | OH | SH | SH | SH | — | OH | $L^1$ | $ON^{7-3}$ | 0 | 2 |
| 776 | $K^{2-1}$ | $K^{1-1}$ | $K^{3-1}$ | — | $OC_2H_4OH$ | OH | OH | OH | — | OH | $L^2$ | $ON^{7-3}$ | 0 | 1 |
| 777 | $K^{1-1}$ | $K^{1-1}$ | $K^{1-1}$ | — | $OC_2H_4OH$ | OH | SH | SH | — | OH | $L^2$ | $ON^{7-3}$ | 0 | 1 |
| 778 | $K^{1-1}$ | $K^{1-1}$ | $K^{1-1}$ | — | $OC_2H_4OH$ | SH | SH | SH | — | OH | $L^2$ | $ON^{7-3}$ | 0 | 1 |
| 779 | $K^{1-1}$ | $K^{1-1}$ | $K^{1-1}$ | — | $OC_2H_4OH$ | OH | SH | SH | SH | OH | $L^2$ | $ON^{7-3}$ | 1 | 1 |
| 780 | $K^{1-1}$ | $K^{1-1}$ | $K^{1-1}$ | — | OH | SH | SH | SH | — | OH | $L^2$ | $ON^{7-3}$ | 0 | 1 |
| 781 | $K^{2-1}$ | $K^{1-1}$ | $K^{3-1}$ | — | $OC_2H_4OH$ | OH | OH | OH | — | OH | $L^1$ | $ON^{7-4}$ | 0 | 2 |
| 782 | $K^{1-1}$ | $K^{1-1}$ | $K^{1-1}$ | — | $OC_2H_4OH$ | OH | SH | SH | — | OH | $L^1$ | $ON^{7-4}$ | 0 | 2 |
| 783 | $K^{1-1}$ | $K^{1-1}$ | $K^{1-1}$ | — | $OC_2H_4OH$ | SH | SH | SH | — | OH | $L^1$ | $ON^{7-4}$ | 0 | 2 |
| 784 | $K^{1-1}$ | $K^{1-1}$ | $K^{1-1}$ | — | $OC_2H_4OH$ | OH | SH | SH | SH | OH | $L^1$ | $ON^{7-4}$ | 1 | 2 |
| 785 | $K^{1-1}$ | $K^{1-1}$ | $K^{1-1}$ | — | OH | SH | SH | SH | — | OH | $L^1$ | $ON^{7-4}$ | 0 | 2 |
| 786 | $K^{2-1}$ | $K^{1-1}$ | $K^{3-1}$ | — | $OC_2H_4OH$ | OH | OH | OH | — | OH | $L^2$ | $ON^{7-4}$ | 0 | 1 |
| 787 | $K^{1-1}$ | $K^{1-1}$ | $K^{1-1}$ | — | $OC_2H_4OH$ | OH | SH | SH | — | OH | $L^2$ | $ON^{7-4}$ | 0 | 1 |
| 788 | $K^{1-1}$ | $K^{1-1}$ | $K^{1-1}$ | — | $OC_2H_4OH$ | SH | SH | SH | — | OH | $L^2$ | $ON^{7-4}$ | 0 | 1 |
| 789 | $K^{1-1}$ | $K^{1-1}$ | $K^{1-1}$ | $K^{1-1}$ | $OC_2H_4OH$ | OH | SH | SH | SH | OH | $L^2$ | $ON^{7-4}$ | 1 | 1 |
| 790 | $K^{1-1}$ | $K^{1-1}$ | $K^{1-1}$ | — | OH | SH | SH | SH | — | OH | $L^2$ | $ON^{7-4}$ | 0 | 1 |
| 791 | $K^{2-1}$ | $K^{1-1}$ | $K^{3-1}$ | — | $OC_2H_4OH$ | OH | OH | OH | — | OH | $L^1$ | $ON^{7-5}$ | 0 | 2 |
| 792 | $K^{1-1}$ | $K^{1-1}$ | $K^{1-1}$ | — | $OC_2H_4OH$ | OH | SH | SH | — | OH | $L^1$ | $ON^{7-5}$ | 0 | 2 |
| 793 | $K^{1-1}$ | $K^{1-1}$ | $K^{1-1}$ | — | $OC_2H_4OH$ | SH | SH | SH | — | OH | $L^1$ | $ON^{7-5}$ | 0 | 2 |
| 794 | $K^{1-1}$ | $K^{1-1}$ | $K^{1-1}$ | $K^{1-1}$ | $OC_2H_4OH$ | OH | SH | SH | SH | OH | $L^1$ | $ON^{7-5}$ | 1 | 2 |
| 795 | $K^{1-1}$ | $K^{1-1}$ | $K^{1-1}$ | — | OH | SH | SH | SH | — | OH | $L^1$ | $ON^{7-5}$ | 0 | 2 |
| 796 | $K^{2-1}$ | $K^{1-1}$ | $K^{3-1}$ | — | $OC_2H_4OH$ | OH | OH | OH | — | OH | $L^2$ | $ON^{7-5}$ | 0 | 1 |
| 797 | $K^{1-1}$ | $K^{1-1}$ | $K^{1-1}$ | — | $OC_2H_4OH$ | OH | SH | SH | — | OH | $L^2$ | $ON^{7-5}$ | 0 | 1 |
| 798 | $K^{1-1}$ | $K^{1-1}$ | $K^{1-1}$ | — | $OC_2H_4OH$ | SH | SH | SH | — | OH | $L^2$ | $ON^{7-5}$ | 0 | 1 |
| 799 | $K^{1-1}$ | $K^{1-1}$ | $K^{1-1}$ | $K^{1-1}$ | $OC_2H_4OH$ | OH | SH | SH | SH | OH | $L^2$ | $ON^{7-5}$ | 1 | 1 |
| 800 | $K^{1-1}$ | $K^{1-1}$ | $K^{1-1}$ | — | OH | SH | SH | SH | — | OH | $L^2$ | $ON^{7-5}$ | 0 | 1 |
| 801 | $K^{2-1}$ | $K^{1-1}$ | $K^{3-1}$ | — | $OC_2H_4OH$ | OH | OH | OH | — | OH | $L^1$ | $ON^{8-1}$ | 0 | 2 |
| 802 | $K^{1-1}$ | $K^{1-1}$ | $K^{1-1}$ | — | $OC_2H_4OH$ | OH | SH | SH | — | OH | $L^1$ | $ON^{8-1}$ | 0 | 2 |
| 803 | $K^{1-1}$ | $K^{1-1}$ | $K^{1-1}$ | — | $OC_2H_4OH$ | SH | SH | SH | — | OH | $L^1$ | $ON^{8-1}$ | 0 | 2 |
| 804 | $K^{1-1}$ | $K^{1-1}$ | $K^{1-1}$ | $K^{1-1}$ | $OC_2H_4OH$ | OH | SH | SH | SH | OH | $L^1$ | $ON^{8-1}$ | 1 | 2 |
| 805 | $K^{1-1}$ | $K^{1-1}$ | $K^{1-1}$ | — | OH | SH | SH | SH | — | OH | $L^1$ | $ON^{8-1}$ | 0 | 2 |
| 806 | $K^{2-1}$ | $K^{1-1}$ | $K^{3-1}$ | — | $OC_2H_4OH$ | OH | OH | OH | — | OH | $L^2$ | $ON^{8-1}$ | 0 | 1 |
| 807 | $K^{1-1}$ | $K^{1-1}$ | $K^{1-1}$ | — | $OC_2H_4OH$ | OH | SH | SH | — | OH | $L^2$ | $ON^{8-1}$ | 0 | 1 |
| 808 | $K^{1-1}$ | $K^{1-1}$ | $K^{1-1}$ | — | $OC_2H_4OH$ | SH | SH | SH | — | OH | $L^2$ | $ON^{8-1}$ | 0 | 1 |
| 809 | $K^{1-1}$ | $K^{1-1}$ | $K^{1-1}$ | $K^{1-1}$ | $OC_2H_4OH$ | OH | SH | SH | SH | OH | $L^2$ | $ON^{8-1}$ | 1 | 1 |
| 810 | $K^{1-1}$ | $K^{1-1}$ | $K^{1-1}$ | — | OH | SH | SH | SH | — | OH | $L^2$ | $ON^{8-1}$ | 0 | 1 |
| 811 | $K^{2-1}$ | $K^{1-1}$ | $K^{3-1}$ | — | $OC_2H_4OH$ | OH | OH | OH | — | OH | $L^1$ | $ON^{8-2}$ | 0 | 2 |
| 812 | $K^{1-1}$ | $K^{1-1}$ | $K^{1-1}$ | — | $OC_2H_4OH$ | OH | SH | SH | — | OH | $L^1$ | $ON^{8-2}$ | 0 | 2 |
| 813 | $K^{1-1}$ | $K^{1-1}$ | $K^{1-1}$ | — | $OC_2H_4OH$ | SH | SH | SH | — | OH | $L^1$ | $ON^{8-2}$ | 0 | 2 |
| 814 | $K^{1-1}$ | $K^{1-1}$ | $K^{1-1}$ | $K^{1-1}$ | $OC_2H_4OH$ | OH | SH | SH | SH | OH | $L^1$ | $ON^{8-2}$ | 1 | 2 |
| 815 | $K^{1-1}$ | $K^{1-1}$ | $K^{1-1}$ | — | OH | SH | SH | SH | — | OH | $L^1$ | $ON^{8-2}$ | 0 | 2 |
| 816 | $K^{2-1}$ | $K^{1-1}$ | $K^{3-1}$ | — | $OC_2H_4OH$ | OH | OH | OH | — | OH | $L^2$ | $ON^{8-2}$ | 0 | 1 |
| 817 | $K^{1-1}$ | $K^{1-1}$ | $K^{1-1}$ | — | $OC_2H_4OH$ | OH | SH | SH | — | OH | $L^2$ | $ON^{8-2}$ | 0 | 1 |
| 818 | $K^{1-1}$ | $K^{1-1}$ | $K^{1-1}$ | — | $OC_2H_4OH$ | SH | SH | SH | — | OH | $L^2$ | $ON^{8-2}$ | 0 | 1 |
| 819 | $K^{1-1}$ | $K^{1-1}$ | $K^{1-1}$ | $K^{1-1}$ | $OC_2H_4OH$ | OH | SH | SH | SH | OH | $L^2$ | $ON^{8-2}$ | 1 | 1 |
| 820 | $K^{1-1}$ | $K^{1-1}$ | $K^{1-1}$ | — | OH | SH | SH | SH | — | OH | $L^2$ | $ON^{8-2}$ | 0 | 1 |
| 821 | $K^{2-1}$ | $K^{1-1}$ | $K^{3-1}$ | — | $OC_2H_4OH$ | OH | OH | OH | — | OH | $L^1$ | $ON^{8-3}$ | 0 | 2 |
| 822 | $K^{1-1}$ | $K^{1-1}$ | $K^{1-1}$ | — | $OC_2H_4OH$ | OH | SH | SH | — | OH | $L^1$ | $ON^{8-3}$ | 0 | 2 |
| 823 | $K^{1-1}$ | $K^{1-1}$ | $K^{1-1}$ | — | $OC_2H_4OH$ | SH | SH | SH | — | OH | $L^1$ | $ON^{8-3}$ | 0 | 2 |
| 824 | $K^{1-1}$ | $K^{1-1}$ | $K^{1-1}$ | $K^{1-1}$ | $OC_2H_4OH$ | OH | SH | SH | SH | OH | $L^1$ | $ON^{8-3}$ | 1 | 2 |
| 825 | $K^{1-1}$ | $K^{1-1}$ | $K^{1-1}$ | — | OH | SH | SH | SH | — | OH | $L^1$ | $ON^{8-3}$ | 0 | 2 |
| 826 | $K^{2-1}$ | $K^{1-1}$ | $K^{3-1}$ | — | $OC_2H_4OH$ | OH | OH | OH | — | OH | $L^2$ | $ON^{8-3}$ | 0 | 1 |
| 827 | $K^{1-1}$ | $K^{1-1}$ | $K^{1-1}$ | — | $OC_2H_4OH$ | OH | SH | SH | — | OH | $L^2$ | $ON^{8-3}$ | 0 | 1 |
| 828 | $K^{1-1}$ | $K^{1-1}$ | $K^{1-1}$ | — | $OC_2H_4OH$ | SH | SH | SH | — | OH | $L^2$ | $ON^{8-3}$ | 0 | 1 |
| 829 | $K^{1-1}$ | $K^{1-1}$ | $K^{1-1}$ | $K^{1-1}$ | $OC_2H_4OH$ | OH | SH | SH | SH | OH | $L^2$ | $ON^{8-3}$ | 1 | 1 |
| 830 | $K^{1-1}$ | $K^{1-1}$ | $K^{1-1}$ | — | OH | SH | SH | SH | — | OH | $L^2$ | $ON^{8-3}$ | 0 | 1 |

TABLE 1-continued

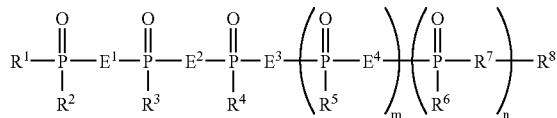

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 831 | $K^{2-1}$ | $K^{1-1}$ | $K^{3-1}$ | — | $OC_2H_4OH$ | OH | OH | OH | — | OH | $L^1$ | $ON^{8-4}$ | 0 | 2 |
| 832 | $K^{1-1}$ | $K^{1-1}$ | $K^{1-1}$ | — | $OC_2H_4OH$ | OH | SH | SH | — | OH | $L^1$ | $ON^{8-4}$ | 0 | 2 |
| 833 | $K^{1-1}$ | $K^{1-1}$ | $K^{1-1}$ | — | $OC_2H_4OH$ | SH | SH | SH | — | OH | $L^1$ | $ON^{8-4}$ | 0 | 2 |
| 834 | $K^{1-1}$ | $K^{1-1}$ | $K^{1-1}$ | $K^{1-1}$ | $OC_2H_4OH$ | OH | SH | SH | SH | OH | $L^1$ | $ON^{8-4}$ | 1 | 2 |
| 835 | $K^{1-1}$ | $K^{1-1}$ | $K^{1-1}$ | — | OH | SH | SH | SH | — | OH | $L^1$ | $ON^{8-4}$ | 0 | 2 |
| 836 | $K^{2-1}$ | $K^{1-1}$ | $K^{3-1}$ | — | $OC_2H_4OH$ | OH | OH | OH | — | OH | $L^2$ | $ON^{8-4}$ | 0 | 1 |
| 837 | $K^{1-1}$ | $K^{1-1}$ | $K^{1-1}$ | — | $OC_2H_4OH$ | OH | SH | SH | — | OH | $L^2$ | $ON^{8-4}$ | 0 | 1 |
| 838 | $K^{1-1}$ | $K^{1-1}$ | $K^{1-1}$ | — | $OC_2H_4OH$ | SH | SH | SH | — | OH | $L^2$ | $ON^{8-4}$ | 0 | 1 |
| 839 | $K^{1-1}$ | $K^{1-1}$ | $K^{1-1}$ | $K^{1-1}$ | $OC_2H_4OH$ | OH | SH | SH | SH | OH | $L^2$ | $ON^{8-4}$ | 1 | 1 |
| 840 | $K^{1-1}$ | $K^{1-1}$ | $K^{1-1}$ | — | OH | SH | SH | SH | — | OH | $L^2$ | $ON^{8-4}$ | 0 | 1 |
| 841 | $K^{2-1}$ | $K^{1-1}$ | $K^{3-1}$ | — | $OC_2H_4OH$ | OH | OH | OH | — | OH | $L^1$ | $ON^{8-5}$ | 0 | 2 |
| 842 | $K^{1-1}$ | $K^{1-1}$ | $K^{1-1}$ | — | $OC_2H_4OH$ | OH | SH | SH | — | OH | $L^1$ | $ON^{8-5}$ | 0 | 2 |
| 843 | $K^{1-1}$ | $K^{1-1}$ | $K^{1-1}$ | — | $OC_2H_4OH$ | SH | SH | SH | — | OH | $L^1$ | $ON^{8-5}$ | 0 | 2 |
| 844 | $K^{1-1}$ | $K^{1-1}$ | $K^{1-1}$ | $K^{1-1}$ | $OC_2H_4OH$ | OH | SH | SH | SH | OH | $L^1$ | $ON^{8-5}$ | 1 | 2 |
| 845 | $K^{1-1}$ | $K^{1-1}$ | $K^{1-1}$ | — | OH | SH | SH | SH | — | OH | $L^1$ | $ON^{8-5}$ | 0 | 2 |
| 846 | $K^{2-1}$ | $K^{1-1}$ | $K^{3-1}$ | — | $OC_2H_4OH$ | OH | OH | OH | — | OH | $L^2$ | $ON^{8-5}$ | 0 | 1 |
| 847 | $K^{1-1}$ | $K^{1-1}$ | $K^{1-1}$ | — | $OC_2H_4OH$ | OH | SH | SH | — | OH | $L^2$ | $ON^{8-5}$ | 0 | 1 |
| 848 | $K^{1-1}$ | $K^{1-1}$ | $K^{1-1}$ | — | $OC_2H_4OH$ | SH | SH | SH | — | OH | $L^2$ | $ON^{8-5}$ | 0 | 1 |
| 849 | $K^{1-1}$ | $K^{1-1}$ | $K^{1-1}$ | $K^{1-1}$ | $OC_2H_4OH$ | OH | SH | SH | SH | OH | $L^2$ | $ON^{8-5}$ | 1 | 1 |
| 850 | $K^{1-1}$ | $K^{1-1}$ | $K^{1-1}$ | — | OH | SH | SH | SH | — | OH | $L^2$ | $ON^{8-5}$ | 0 | 1 |
| 851 | $K^{2-1}$ | $K^{1-1}$ | $K^{3-1}$ | — | $OC_2H_4OH$ | OH | OH | OH | — | OH | $L^1$ | $ON^{9-1}$ | 0 | 2 |
| 852 | $K^{1-1}$ | $K^{1-1}$ | $K^{1-1}$ | — | $OC_2H_4OH$ | OH | SH | SH | — | OH | $L^1$ | $ON^{9-1}$ | 0 | 2 |
| 853 | $K^{1-1}$ | $K^{1-1}$ | $K^{1-1}$ | — | $OC_2H_4OH$ | SH | SH | SH | — | OH | $L^1$ | $ON^{9-1}$ | 0 | 2 |
| 854 | $K^{1-1}$ | $K^{1-1}$ | $K^{1-1}$ | $K^{1-1}$ | $OC_2H_4OH$ | OH | SH | SH | SH | OH | $L^1$ | $ON^{9-1}$ | 1 | 2 |
| 855 | $K^{1-1}$ | $K^{1-1}$ | $K^{1-1}$ | — | OH | SH | SH | SH | — | OH | $L^1$ | $ON^{9-1}$ | 0 | 2 |
| 856 | $K^{2-1}$ | $K^{1-1}$ | $K^{3-1}$ | — | $OC_2H_4OH$ | OH | OH | OH | — | OH | $L^2$ | $ON^{9-1}$ | 0 | 1 |
| 857 | $K^{1-1}$ | $K^{1-1}$ | $K^{1-1}$ | — | $OC_2H_4OH$ | OH | SH | SH | — | OH | $L^2$ | $ON^{9-1}$ | 0 | 1 |
| 858 | $K^{1-1}$ | $K^{1-1}$ | $K^{1-1}$ | — | $OC_2H_4OH$ | SH | SH | SH | — | OH | $L^2$ | $ON^{9-1}$ | 0 | 1 |
| 859 | $K^{1-1}$ | $K^{1-1}$ | $K^{1-1}$ | $K^{1-1}$ | $OC_2H_4OH$ | OH | SH | SH | SH | OH | $L^2$ | $ON^{9-1}$ | 1 | 1 |
| 860 | $K^{1-1}$ | $K^{1-1}$ | $K^{1-1}$ | — | OH | SH | SH | SH | — | OH | $L^2$ | $ON^{9-1}$ | 0 | 1 |
| 861 | $K^{2-1}$ | $K^{1-1}$ | $K^{3-1}$ | — | $OC_2H_4OH$ | OH | OH | OH | — | OH | $L^1$ | $ON^{9-2}$ | 0 | 2 |
| 862 | $K^{1-1}$ | $K^{1-1}$ | $K^{1-1}$ | — | $OC_2H_4OH$ | OH | SH | SH | — | OH | $L^1$ | $ON^{9-2}$ | 0 | 2 |
| 863 | $K^{1-1}$ | $K^{1-1}$ | $K^{1-1}$ | — | $OC_2H_4OH$ | SH | SH | SH | — | OH | $L^1$ | $ON^{9-2}$ | 0 | 2 |
| 864 | $K^{1-1}$ | $K^{1-1}$ | $K^{1-1}$ | $K^{1-1}$ | $OC_2H_4OH$ | OH | SH | SH | SH | OH | $L^1$ | $ON^{9-2}$ | 1 | 2 |
| 865 | $K^{1-1}$ | $K^{1-1}$ | $K^{1-1}$ | — | OH | SH | SH | SH | — | OH | $L^1$ | $ON^{9-2}$ | 0 | 2 |
| 866 | $K^{2-1}$ | $K^{1-1}$ | $K^{3-1}$ | — | $OC_2H_4OH$ | OH | OH | OH | — | OH | $L^2$ | $ON^{9-2}$ | 0 | 1 |
| 867 | $K^{1-1}$ | $K^{1-1}$ | $K^{1-1}$ | — | $OC_2H_4OH$ | OH | SH | SH | — | OH | $L^2$ | $ON^{9-2}$ | 0 | 1 |
| 868 | $K^{1-1}$ | $K^{1-1}$ | $K^{1-1}$ | — | $OC_2H_4OH$ | SH | SH | SH | — | OH | $L^2$ | $ON^{9-2}$ | 0 | 1 |
| 869 | $K^{1-1}$ | $K^{1-1}$ | $K^{1-1}$ | $K^{1-1}$ | $OC_2H_4OH$ | OH | SH | SH | SH | OH | $L^2$ | $ON^{9-2}$ | 1 | 1 |
| 870 | $K^{1-1}$ | $K^{1-1}$ | $K^{1-1}$ | — | OH | SH | SH | SH | — | OH | $L^2$ | $ON^{9-2}$ | 0 | 1 |
| 871 | $K^{2-1}$ | $K^{1-1}$ | $K^{3-1}$ | — | $OC_2H_4OH$ | OH | OH | OH | — | OH | $L^1$ | $ON^{9-3}$ | 0 | 2 |
| 872 | $K^{1-1}$ | $K^{1-1}$ | $K^{1-1}$ | — | $OC_2H_4OH$ | OH | SH | SH | — | OH | $L^1$ | $ON^{9-3}$ | 0 | 2 |
| 873 | $K^{1-1}$ | $K^{1-1}$ | $K^{1-1}$ | — | $OC_2H_4OH$ | SH | SH | SH | — | OH | $L^1$ | $ON^{9-3}$ | 0 | 2 |
| 874 | $K^{1-1}$ | $K^{1-1}$ | $K^{1-1}$ | $K^{1-1}$ | $OC_2H_4OH$ | OH | SH | SH | SH | OH | $L^1$ | $ON^{9-3}$ | 1 | 2 |
| 875 | $K^{1-1}$ | $K^{1-1}$ | $K^{1-1}$ | — | OH | SH | SH | SH | — | OH | $L^1$ | $ON^{9-3}$ | 0 | 2 |
| 876 | $K^{2-1}$ | $K^{1-1}$ | $K^{3-1}$ | — | $OC_2H_4OH$ | OH | OH | OH | — | OH | $L^2$ | $ON^{9-3}$ | 0 | 1 |
| 877 | $K^{1-1}$ | $K^{1-1}$ | $K^{1-1}$ | — | $OC_2H_4OH$ | OH | SH | SH | — | OH | $L^2$ | $ON^{9-3}$ | 0 | 1 |
| 878 | $K^{1-1}$ | $K^{1-1}$ | $K^{1-1}$ | — | $OC_2H_4OH$ | SH | SH | SH | — | OH | $L^2$ | $ON^{9-3}$ | 0 | 1 |
| 879 | $K^{1-1}$ | $K^{1-1}$ | $K^{1-1}$ | $K^{1-1}$ | $OC_2H_4OH$ | OH | SH | SH | SH | OH | $L^2$ | $ON^{9-3}$ | 1 | 1 |
| 880 | $K^{1-1}$ | $K^{1-1}$ | $K^{1-1}$ | — | OH | SH | SH | SH | — | OH | $L^2$ | $ON^{9-3}$ | 0 | 1 |
| 881 | $K^{2-1}$ | $K^{1-1}$ | $K^{3-1}$ | — | $OC_2H_4OH$ | OH | OH | OH | — | OH | $L^1$ | $ON^{9-4}$ | 0 | 2 |
| 882 | $K^{1-1}$ | $K^{1-1}$ | $K^{1-1}$ | — | $OC_2H_4OH$ | OH | SH | SH | — | OH | $L^1$ | $ON^{9-4}$ | 0 | 2 |
| 883 | $K^{1-1}$ | $K^{1-1}$ | $K^{1-1}$ | — | $OC_2H_4OH$ | SH | SH | SH | — | OH | $L^1$ | $ON^{9-4}$ | 0 | 2 |
| 884 | $K^{1-1}$ | $K^{1-1}$ | $K^{1-1}$ | $K^{1-1}$ | $OC_2H_4OH$ | OH | SH | SH | SH | OH | $L^1$ | $ON^{9-4}$ | 1 | 2 |
| 885 | $K^{1-1}$ | $K^{1-1}$ | $K^{1-1}$ | — | OH | SH | SH | SH | — | OH | $L^1$ | $ON^{9-4}$ | 0 | 2 |
| 886 | $K^{2-1}$ | $K^{1-1}$ | $K^{3-1}$ | — | $OC_2H_4OH$ | OH | OH | OH | — | OH | $L^2$ | $ON^{9-4}$ | 0 | 1 |
| 887 | $K^{1-1}$ | $K^{1-1}$ | $K^{1-1}$ | — | $OC_2H_4OH$ | OH | SH | SH | — | OH | $L^2$ | $ON^{9-4}$ | 0 | 1 |
| 888 | $K^{1-1}$ | $K^{1-1}$ | $K^{1-1}$ | — | $OC_2H_4OH$ | SH | SH | SH | — | OH | $L^2$ | $ON^{9-4}$ | 0 | 1 |
| 889 | $K^{1-1}$ | $K^{1-1}$ | $K^{1-1}$ | $K^{1-1}$ | $OC_2H_4OH$ | OH | SH | SH | SH | OH | $L^2$ | $ON^{9-4}$ | 1 | 1 |
| 890 | $K^{1-1}$ | $K^{1-1}$ | $K^{1-1}$ | — | OH | SH | SH | SH | — | OH | $L^2$ | $ON^{9-4}$ | 0 | 1 |
| 891 | $K^{2-1}$ | $K^{1-1}$ | $K^{3-1}$ | — | $OC_2H_4OH$ | OH | OH | OH | — | OH | $L^1$ | $ON^{9-5}$ | 0 | 2 |
| 892 | $K^{1-1}$ | $K^{1-1}$ | $K^{1-1}$ | — | $OC_2H_4OH$ | OH | SH | SH | — | OH | $L^1$ | $ON^{9-5}$ | 0 | 2 |
| 893 | $K^{1-1}$ | $K^{1-1}$ | $K^{1-1}$ | — | $OC_2H_4OH$ | SH | SH | SH | — | OH | $L^1$ | $ON^{9-5}$ | 0 | 2 |
| 894 | $K^{1-1}$ | $K^{1-1}$ | $K^{1-1}$ | $K^{1-1}$ | $OC_2H_4OH$ | OH | SH | SH | SH | OH | $L^1$ | $ON^{9-5}$ | 1 | 2 |
| 895 | $K^{1-1}$ | $K^{1-1}$ | $K^{1-1}$ | — | OH | SH | SH | SH | — | OH | $L^1$ | $ON^{9-5}$ | 0 | 2 |
| 896 | $K^{2-1}$ | $K^{1-1}$ | $K^{3-1}$ | — | $OC_2H_4OH$ | OH | OH | OH | — | OH | $L^2$ | $ON^{9-5}$ | 0 | 1 |
| 897 | $K^{1-1}$ | $K^{1-1}$ | $K^{1-1}$ | — | $OC_2H_4OH$ | OH | SH | SH | — | OH | $L^2$ | $ON^{9-5}$ | 0 | 1 |
| 898 | $K^{1-1}$ | $K^{1-1}$ | $K^{1-1}$ | — | $OC_2H_4OH$ | SH | SH | SH | — | OH | $L^2$ | $ON^{9-5}$ | 0 | 1 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 899 | $K^{1-1}$ | $K^{1-1}$ | $K^{1-1}$ | $K^{1-1}$ | $OC_2H_4OH$ | OH | SH | SH | SH | OH | $L^2$ | $ON^{9-5}$ | 1 | 1 |
| 900 | $K^{1-1}$ | $K^{1-1}$ | $K^{1-1}$ | — | OH | SH | SH | SH | — | OH | $L^2$ | $ON^{9-5}$ | 0 | 1 |
| 901 | $K^{2-1}$ | $K^{1-1}$ | $K^{3-1}$ | — | $OC_2H_4OH$ | OH | POMS | OH | — | — | — | H | — | — |
| 902 | $K^{2-1}$ | $K^{1-1}$ | $K^{3-1}$ | — | OH | POMS | POMS | OH | — | — | — | H | — | — |
| 903 | $K^{2-1}$ | $K^{1-1}$ | $K^{3-1}$ | — | $OC_2H_4OH$ | POMS | POMS | OH | — | — | — | H | — | — |
| 904 | $K^{2-1}$ | $K^{1-1}$ | $K^{3-2}$ | — | $OC_2H_4OH$ | OH | POMS | OH | — | — | — | H | — | — |
| 905 | $K^{2-1}$ | $K^{1-1}$ | $K^{3-2}$ | — | OH | POMS | POMS | OH | — | — | — | H | — | — |
| 906 | $K^{2-1}$ | $K^{1-1}$ | $K^{3-2}$ | — | $OC_2H_4OH$ | POMS | POMS | OH | — | — | — | H | — | — |
| 907 | $K^{1-1}$ | $K^{1-1}$ | $K^{3-1}$ | — | $OC_2H_4OH$ | OH | POMS | OH | — | — | — | H | — | — |
| 908 | $K^{1-1}$ | $K^{1-1}$ | $K^{3-1}$ | — | $OC_2H_4OH$ | POMS | POMS | OH | — | — | — | H | — | — |
| 909 | $K^{1-1}$ | $K^{1-1}$ | $K^{3-1}$ | — | OH | POMS | POMS | OH | — | — | — | H | — | — |
| 910 | $K^{1-1}$ | $K^{1-1}$ | $K^{3-2}$ | — | $OC_2H_4OH$ | OH | POMS | OH | — | — | — | H | — | — |
| 911 | $K^{1-1}$ | $K^{1-1}$ | $K^{3-2}$ | — | $OC_2H_4OH$ | POMS | POMS | OH | — | — | — | H | — | — |
| 912 | $K^{1-1}$ | $K^{1-1}$ | $K^{3-2}$ | — | OH | POMS | POMS | OH | — | — | — | H | — | — |
| 913 | $K^{2-1}$ | $K^{1-1}$ | $K^{1-1}$ | — | $OC_2H_4OH$ | OH | OH | POMS | — | — | — | H | — | — |
| 914 | $K^{2-1}$ | $K^{1-1}$ | $K^{1-1}$ | — | OH | POMS | OH | POMS | — | — | — | H | — | — |
| 915 | $K^{2-1}$ | $K^{1-1}$ | $K^{1-1}$ | — | $OC_2H_4OH$ | POMS | OH | POMS | — | — | — | H | — | — |
| 916 | $K^{2-1}$ | $K^{1-1}$ | $K^{1-2}$ | — | $OC_2H_4OH$ | OH | OH | POMS | — | — | — | H | — | — |
| 917 | $K^{2-1}$ | $K^{1-1}$ | $K^{1-2}$ | — | OH | POMS | OH | POMS | — | — | — | H | — | — |
| 918 | $K^{2-1}$ | $K^{1-1}$ | $K^{1-2}$ | — | $OC_2H_4OH$ | POMS | OH | POMS | — | — | — | H | — | — |
| 919 | $K^{2-1}$ | $K^{1-1}$ | $K^{3-1}$ | — | OH | ATES | ATES | OH | — | — | — | H | — | — |
| 920 | $K^{2-1}$ | $K^{1-1}$ | $K^{3-1}$ | — | $OC_2H_4OH$ | ATES | ATES | OH | — | — | — | H | — | — |
| 921 | $K^{2-1}$ | $K^{1-1}$ | $K^{3-2}$ | — | $OC_2H_4OH$ | OH | ATES | OH | — | — | — | H | — | — |
| 922 | $K^{2-1}$ | $K^{1-1}$ | $K^{3-2}$ | — | OH | ATES | ATES | OH | — | — | — | H | — | — |
| 923 | $K^{2-1}$ | $K^{1-1}$ | $K^{3-2}$ | — | $OC_2H_4OH$ | ATES | ATES | OH | — | — | — | H | — | — |
| 924 | $K^{1-1}$ | $K^{1-1}$ | $K^{3-1}$ | — | $OC_2H_4OH$ | OH | ATES | OH | — | — | — | H | — | — |
| 925 | $K^{1-1}$ | $K^{1-1}$ | $K^{3-1}$ | — | $OC_2H_4OH$ | ATES | ATES | OH | — | — | — | H | — | — |
| 926 | $K^{1-1}$ | $K^{1-1}$ | $K^{3-1}$ | — | OH | ATES | ATES | OH | — | — | — | H | — | — |
| 927 | $K^{1-1}$ | $K^{1-1}$ | $K^{3-2}$ | — | $OC_2H_4OH$ | OH | ATES | OH | — | — | — | H | — | — |
| 928 | $K^{1-1}$ | $K^{1-1}$ | $K^{3-2}$ | — | $OC_2H_4OH$ | ATES | ATES | OH | — | — | — | H | — | — |
| 929 | $K^{1-1}$ | $K^{1-1}$ | $K^{3-2}$ | — | OH | ATES | ATES | OH | — | — | — | H | — | — |
| 930 | $K^{2-1}$ | $K^{1-1}$ | $K^{1-1}$ | — | $OC_2H_4OH$ | OH | OH | ATES | — | — | — | H | — | — |
| 931 | $K^{2-1}$ | $K^{1-1}$ | $K^{1-1}$ | — | OH | ATES | OH | ATES | — | — | — | H | — | — |
| 932 | $K^{2-1}$ | $K^{1-1}$ | $K^{1-1}$ | — | $OC_2H_4OH$ | ATES | OH | ATES | — | — | — | H | — | — |
| 933 | $K^{2-1}$ | $K^{1-1}$ | $K^{1-2}$ | — | $OC_2H_4OH$ | OH | OH | ATES | — | — | — | H | — | — |
| 934 | $K^{2-1}$ | $K^{1-1}$ | $K^{1-2}$ | — | OH | ATES | OH | ATES | — | — | — | H | — | — |
| 935 | $K^{2-1}$ | $K^{1-1}$ | $K^{1-2}$ | — | $OC_2H_4OH$ | ATES | OH | ATES | — | — | — | H | — | — |
| 936 | $K^{2-1}$ | $K^{1-1}$ | $K^{3-1}$ | — | OH | PTES | PTES | OH | — | — | — | H | — | — |
| 937 | $K^{2-1}$ | $K^{1-1}$ | $K^{3-1}$ | — | $OC_2H_4OH$ | PTES | PTES | OH | — | — | — | H | — | — |
| 938 | $K^{2-1}$ | $K^{1-1}$ | $K^{3-2}$ | — | $OC_2H_4OH$ | OH | PTES | OH | — | — | — | H | — | — |
| 939 | $K^{2-1}$ | $K^{1-1}$ | $K^{3-2}$ | — | OH | PTES | PTES | OH | — | — | — | H | — | — |
| 940 | $K^{2-1}$ | $K^{1-1}$ | $K^{3-2}$ | — | $OC_2H_4OH$ | PTES | PTES | OH | — | — | — | H | — | — |
| 941 | $K^{1-1}$ | $K^{1-1}$ | $K^{3-1}$ | — | $OC_2H_4OH$ | OH | PTES | OH | — | — | — | H | — | — |
| 942 | $K^{1-1}$ | $K^{1-1}$ | $K^{3-1}$ | — | $OC_2H_4OH$ | PTES | PTES | OH | — | — | — | H | — | — |
| 943 | $K^{1-1}$ | $K^{1-1}$ | $K^{3-1}$ | — | OH | PTES | PTES | OH | — | — | — | H | — | — |
| 944 | $K^{1-1}$ | $K^{1-1}$ | $K^{3-2}$ | — | $OC_2H_4OH$ | OH | PTES | OH | — | — | — | H | — | — |
| 945 | $K^{1-1}$ | $K^{1-1}$ | $K^{3-2}$ | — | $OC_2H_4OH$ | PTES | PTES | OH | — | — | — | H | — | — |
| 946 | $K^{1-1}$ | $K^{1-1}$ | $K^{3-2}$ | — | OH | PTES | PTES | OH | — | — | — | H | — | — |
| 947 | $K^{2-1}$ | $K^{1-1}$ | $K^{1-1}$ | — | $OC_2H_4OH$ | OH | OH | PTES | — | — | — | H | — | — |
| 948 | $K^{2-1}$ | $K^{1-1}$ | $K^{1-1}$ | — | OH | PTES | OH | PTES | — | — | — | H | — | — |
| 949 | $K^{2-1}$ | $K^{1-1}$ | $K^{1-1}$ | — | $OC_2H_4OH$ | PTES | OH | PTES | — | — | — | H | — | — |
| 950 | $K^{2-1}$ | $K^{1-1}$ | $K^{1-1}$ | — | $OC_2H_4OH$ | OH | OH | PTES | — | — | — | H | — | — |
| 951 | $K^{2-1}$ | $K^{1-1}$ | $K^{1-1}$ | — | OH | PTES | OH | PTES | — | — | — | H | — | — |
| 952 | $K^{2-1}$ | $K^{1-1}$ | $K^{1-2}$ | — | $OC_2H_4OH$ | PTES | OH | PTES | — | — | — | H | — | — |
| 953 | $K^{2-1}$ | $K^{1-1}$ | $K^{3-1}$ | — | OH | SH | SH | OH | — | — | — | H | 0 | 0 |
| 954 | $K^{1-1}$ | $K^{1-1}$ | $K^{3-1}$ | — | OH | SH | SH | OH | — | — | — | H | 0 | 0 |
| 955 | $K^{2-1}$ | $K^{1-1}$ | $K^{3-1}$ | — | OH | POMS | SH | OH | — | — | — | H | 0 | 0 |
| 956 | $K^{1-1}$ | $K^{1-1}$ | $K^{3-1}$ | — | OH | POMS | SH | OH | — | — | — | H | 0 | 0 |
| 957 | $K^{2-1}$ | $K^{1-1}$ | $K^{3-1}$ | — | OH | ATES | SH | OH | — | — | — | H | 0 | 0 |
| 958 | $K^{1-1}$ | $K^{1-1}$ | $K^{3-1}$ | — | OH | ATES | SH | OH | — | — | — | H | 0 | 0 |
| 959 | $K^{2-1}$ | $K^{1-1}$ | $K^{4-1}$ | — | SH | OH | OH | OH | — | — | — | H | 0 | 0 |
| 960 | $K^{1-1}$ | $K^{1-1}$ | $K^{4-1}$ | — | SH | OH | SH | OH | — | — | — | H | 0 | 0 |
| 961 | $K^{2-1}$ | $K^{1-1}$ | $K^{4-3}$ | — | SH | OH | OH | OH | — | — | — | H | 0 | 0 |
| 962 | $K^{1-1}$ | $K^{1-1}$ | $K^{4-3}$ | — | SH | OH | SH | OH | — | — | — | H | 0 | 0 |
| 963 | $K^{2-1}$ | $K^{1-1}$ | $K^{2-1}$ | — | SH | OH | OH | SH | — | — | — | H | 0 | 0 |
| 964 | $K^{2-1}$ | $K^{1-1}$ | $K^{3-1}$ | — | $SC_2H_4OC(O)tBu$ | OH | OH | OH | — | — | — | H | 0 | 0 |
| 965 | $K^{2-1}$ | $K^{1-1}$ | $K^{3-1}$ | — | $SC_2H_4OC(O)Ph$ | OH | OH | OH | — | — | — | H | 0 | 0 |
| 966 | $K^{2-1}$ | $K^{1-1}$ | $K^{3-1}$ | — | $SC_2H_4C^{20}$ | OH | OH | OH | — | — | — | H | 0 | 0 |

TABLE 1-continued

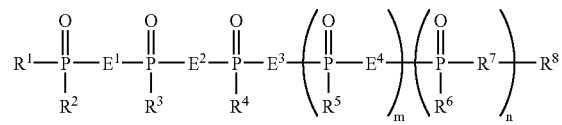

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 967 | $K^{2-1}$ | $K^{1-1}$ | $K^{3-1}$ | — | $SC_2H_4C^{18}$ | OH | OH | OH | — | — | — | H | 0 | 0 |
| 968 | $K^{2-1}$ | $K^{1-1}$ | $K^{3-1}$ | — | $SC_2H_4C^{14}$ | OH | OH | OH | — | — | — | H | 0 | 0 |
| 969 | $K^{2-1}$ | $K^{1-1}$ | $K^{3-1}$ | — | $SC_2H_4C^{10}$ | OH | OH | OH | — | — | — | H | 0 | 0 |
| 970 | $K^{2-1}$ | $K^{1-1}$ | $K^{3-1}$ | — | $S(CH_2)_3C^{20}$ | OH | OH | OH | — | — | — | H | 0 | 0 |
| 971 | $K^{2-1}$ | $K^{1-1}$ | $K^{3-1}$ | — | $S(CH_2)_3C^{18}$ | OH | OH | OH | — | — | — | H | 0 | 0 |
| 972 | $K^{2-1}$ | $K^{1-1}$ | $K^{3-1}$ | — | $S(CH_2)_3C^{14}$ | OH | OH | OH | — | — | — | H | 0 | 0 |
| 973 | $K^{2-1}$ | $K^{1-1}$ | $K^{3-1}$ | — | $S(CH_2)_3C^{10}$ | OH | OH | OH | — | — | — | H | 0 | 0 |
| 974 | $K^{2-1}$ | $K^{1-1}$ | $K^{3-1}$ | — | $S(CH_2)_4C^{20}$ | OH | OH | OH | — | — | — | H | 0 | 0 |
| 975 | $K^{2-1}$ | $K^{1-1}$ | $K^{3-1}$ | — | $S(CH_2)_4C^{18}$ | OH | OH | OH | — | — | — | H | 0 | 0 |
| 976 | $K^{2-1}$ | $K^{1-1}$ | $K^{3-1}$ | — | $S(CH_2)_4C^{14}$ | OH | OH | OH | — | — | — | H | 0 | 0 |
| 977 | $K^{2-1}$ | $K^{1-1}$ | $K^{3-1}$ | — | $S(CH_2)_4C^{10}$ | OH | OH | OH | — | — | — | H | 0 | 0 |
| 978 | $K^{1-1}$ | $K^{1-1}$ | $K^{3-1}$ | — | $SC_2H_4C^{20}$ | OH | SH | OH | — | — | — | H | 0 | 0 |
| 979 | $K^{1-1}$ | $K^{1-1}$ | $K^{3-1}$ | — | $SC_2H_4C^{18}$ | OH | SH | OH | — | — | — | H | 0 | 0 |
| 980 | $K^{1-1}$ | $K^{1-1}$ | $K^{3-1}$ | — | $SC_2H_4C^{14}$ | OH | SH | OH | — | — | — | H | 0 | 0 |
| 981 | $K^{1-1}$ | $K^{1-1}$ | $K^{3-1}$ | — | $SC_2H_4C^{10}$ | OH | SH | OH | — | — | — | H | 0 | 0 |
| 982 | $K^{1-1}$ | $K^{1-1}$ | $K^{3-1}$ | — | $S(CH_2)_3C^{20}$ | OH | SH | OH | — | — | — | H | 0 | 0 |
| 983 | $K^{1-1}$ | $K^{1-1}$ | $K^{3-1}$ | — | $S(CH_2)_3C^{18}$ | OH | SH | OH | — | — | — | H | 0 | 0 |
| 984 | $K^{1-1}$ | $K^{1-1}$ | $K^{3-1}$ | — | $S(CH_2)_3C^{14}$ | OH | SH | OH | — | — | — | H | 0 | 0 |
| 985 | $K^{1-1}$ | $K^{1-1}$ | $K^{3-1}$ | — | $S(CH_2)_3C^{10}$ | OH | SH | OH | — | — | — | H | 0 | 0 |
| 986 | $K^{1-1}$ | $K^{1-1}$ | $K^{3-1}$ | — | $S(CH_2)_4C^{20}$ | OH | SH | OH | — | — | — | H | 0 | 0 |
| 987 | $K^{1-1}$ | $K^{1-1}$ | $K^{3-1}$ | — | $S(CH_2)_4C^{18}$ | OH | SH | OH | — | — | — | H | 0 | 0 |
| 988 | $K^{1-1}$ | $K^{1-1}$ | $K^{3-1}$ | — | $S(CH_2)_4C^{14}$ | OH | SH | OH | — | — | — | H | 0 | 0 |
| 989 | $K^{1-1}$ | $K^{1-1}$ | $K^{3-1}$ | — | $S(CH_2)_4C^{10}$ | OH | SH | OH | — | — | — | H | 0 | 0 |
| 990 | $K^{2-1}$ | $K^{1-1}$ | $K^{4-1}$ | — | $SC_2H_4C^{20}$ | OH | OH | OH | — | — | — | H | 0 | 0 |
| 991 | $K^{2-1}$ | $K^{1-1}$ | $K^{4-1}$ | — | $SC_2H_4C^{18}$ | OH | OH | OH | — | — | — | H | 0 | 0 |
| 992 | $K^{2-1}$ | $K^{1-1}$ | $K^{4-1}$ | — | $SC_2H_4C^{14}$ | OH | OH | OH | — | — | — | H | 0 | 0 |
| 993 | $K^{2-1}$ | $K^{1-1}$ | $K^{4-1}$ | — | $SC_2H_4C^{10}$ | OH | OH | OH | — | — | — | H | 0 | 0 |
| 994 | $K^{2-1}$ | $K^{1-1}$ | $K^{4-1}$ | — | $S(CH_2)_3C^{20}$ | OH | OH | OH | — | — | — | H | 0 | 0 |
| 995 | $K^{2-1}$ | $K^{1-1}$ | $K^{4-1}$ | — | $S(CH_2)_3C^{18}$ | OH | OH | OH | — | — | — | H | 0 | 0 |
| 996 | $K^{2-1}$ | $K^{1-1}$ | $K^{4-1}$ | — | $S(CH_2)_3C^{14}$ | OH | OH | OH | — | — | — | H | 0 | 0 |
| 997 | $K^{2-1}$ | $K^{1-1}$ | $K^{4-1}$ | — | $S(CH_2)_3C^{10}$ | OH | OH | OH | — | — | — | H | 0 | 0 |
| 998 | $K^{2-1}$ | $K^{1-1}$ | $K^{4-1}$ | — | $S(CH_2)_4C^{10}$ | OH | OH | OH | — | — | — | H | 0 | 0 |
| 999 | $K^{2-1}$ | $K^{1-1}$ | $K^{4-1}$ | — | $S(CH_2)_4C^{18}$ | OH | OH | OH | — | — | — | H | 0 | 0 |
| 1000 | $K^{2-1}$ | $K^{1-1}$ | $K^{4-1}$ | — | $S(CH_2)_4C^{14}$ | OH | OH | OH | — | — | — | H | 0 | 0 |
| 1001 | $K^{2-1}$ | $K^{1-1}$ | $K^{4-1}$ | — | $S(CH_2)_4C^{10}$ | OH | OH | OH | — | — | — | H | 0 | 0 |
| 1002 | $K^{1-1}$ | $K^{1-1}$ | $K^{4-1}$ | — | $SC_2H_4C^{20}$ | OH | SH | OH | — | — | — | H | 0 | 0 |
| 1003 | $K^{1-1}$ | $K^{1-1}$ | $K^{4-1}$ | — | $SC_2H_4C^{18}$ | OH | SH | OH | — | — | — | H | 0 | 0 |
| 1004 | $K^{1-1}$ | $K^{1-1}$ | $K^{4-1}$ | — | $SC_2H_4C^{14}$ | OH | SH | OH | — | — | — | H | 0 | 0 |
| 1005 | $K^{1-1}$ | $K^{1-1}$ | $K^{4-1}$ | — | $SC_2H_4C^{10}$ | OH | SH | OH | — | — | — | H | 0 | 0 |
| 1006 | $K^{1-1}$ | $K^{1-1}$ | $K^{4-1}$ | — | $S(CH_2)_3C^{20}$ | OH | SH | OH | — | — | — | H | 0 | 0 |
| 1007 | $K^{1-1}$ | $K^{1-1}$ | $K^{4-1}$ | — | $S(CH_2)_3C^{18}$ | OH | SH | OH | — | — | — | H | 0 | 0 |
| 1008 | $K^{1-1}$ | $K^{1-1}$ | $K^{4-1}$ | — | $S(CH_2)_3C^{14}$ | OH | SH | OH | — | — | — | H | 0 | 0 |
| 1009 | $K^{1-1}$ | $K^{1-1}$ | $K^{4-1}$ | — | $S(CH_2)_3C^{10}$ | OH | SH | OH | — | — | — | H | 0 | 0 |
| 1010 | $K^{1-1}$ | $K^{1-1}$ | $K^{4-1}$ | — | $S(CH_2)_4C^{20}$ | OH | SH | OH | — | — | — | H | 0 | 0 |
| 1011 | $K^{1-1}$ | $K^{1-1}$ | $K^{4-1}$ | — | $S(CH_2)_4C^{18}$ | OH | SH | OH | — | — | — | H | 0 | 0 |
| 1012 | $K^{1-1}$ | $K^{1-1}$ | $K^{4-1}$ | — | $S(CH_2)_4C^{14}$ | OH | SH | OH | — | — | — | H | 0 | 0 |
| 1013 | $K^{1-1}$ | $K^{1-1}$ | $K^{4-1}$ | — | $S(CH_2)_4C^{10}$ | OH | SH | OH | — | — | — | H | 0 | 0 |
| 1014 | $K^{2-1}$ | $K^{1-1}$ | $K^{4-3}$ | — | $SC_2H_4C^{20}$ | OH | OH | OH | — | — | — | H | 0 | 0 |
| 1015 | $K^{2-1}$ | $K^{1-1}$ | $K^{4-3}$ | — | $SC_2H_4C^{18}$ | OH | OH | OH | — | — | — | H | 0 | 0 |
| 1016 | $K^{2-1}$ | $K^{1-1}$ | $K^{4-3}$ | — | $SC_2H_4C^{14}$ | OH | OH | OH | — | — | — | H | 0 | 0 |
| 1017 | $K^{2-1}$ | $K^{1-1}$ | $K^{4-3}$ | — | $SC_2H_4C^{10}$ | OH | OH | OH | — | — | — | H | 0 | 0 |
| 1018 | $K^{2-1}$ | $K^{1-1}$ | $K^{4-3}$ | — | $S(CH_2)_3C^{20}$ | OH | OH | OH | — | — | — | H | 0 | 0 |
| 1019 | $K^{2-1}$ | $K^{1-1}$ | $K^{4-3}$ | — | $S(CH_2)_3C^{18}$ | OH | OH | OH | — | — | — | H | 0 | 0 |
| 1020 | $K^{2-1}$ | $K^{1-1}$ | $K^{4-3}$ | — | $S(CH_2)_3C^{14}$ | OH | OH | OH | — | — | — | H | 0 | 0 |
| 1021 | $K^{2-1}$ | $K^{1-1}$ | $K^{4-3}$ | — | $S(CH_2)_3C^{10}$ | OH | OH | OH | — | — | — | H | 0 | 0 |
| 1022 | $K^{2-1}$ | $K^{1-1}$ | $K^{4-3}$ | — | $S(CH_2)_4C^{20}$ | OH | OH | OH | — | — | — | H | 0 | 0 |
| 1023 | $K^{2-1}$ | $K^{1-1}$ | $K^{4-3}$ | — | $S(CH_2)_4C^{18}$ | OH | OH | OH | — | — | — | H | 0 | 0 |
| 1024 | $K^{2-1}$ | $K^{1-1}$ | $K^{4-3}$ | — | $S(CH_2)_4C^{14}$ | OH | OH | OH | — | — | — | H | 0 | 0 |
| 1025 | $K^{2-1}$ | $K^{1-1}$ | $K^{4-3}$ | — | $S(CH_2)_4C^{10}$ | OH | OH | OH | — | — | — | H | 0 | 0 |
| 1026 | $K^{1-1}$ | $K^{1-1}$ | $K^{4-3}$ | — | $SC_2H_4C^{20}$ | OH | SH | OH | — | — | — | H | 0 | 0 |
| 1027 | $K^{1-1}$ | $K^{1-1}$ | $K^{4-3}$ | — | $SC_2H_4C^{18}$ | OH | SH | OH | — | — | — | H | 0 | 0 |
| 1028 | $K^{1-1}$ | $K^{1-1}$ | $K^{4-3}$ | — | $SC_2H_4C^{14}$ | OH | SH | OH | — | — | — | H | 0 | 0 |
| 1029 | $K^{1-1}$ | $K^{1-1}$ | $K^{4-3}$ | — | $SC_2H_4C^{10}$ | OH | SH | OH | — | — | — | H | 0 | 0 |
| 1030 | $K^{1-1}$ | $K^{1-1}$ | $K^{4-3}$ | — | $S(CH_2)_3C^{20}$ | OH | SH | OH | — | — | — | H | 0 | 0 |
| 1031 | $K^{1-1}$ | $K^{1-1}$ | $K^{4-3}$ | — | $S(CH_2)_3C^{18}$ | OH | SH | OH | — | — | — | H | 0 | 0 |
| 1032 | $K^{1-1}$ | $K^{1-1}$ | $K^{4-3}$ | — | $S(CH_2)_3C^{14}$ | OH | SH | OH | — | — | — | H | 0 | 0 |
| 1033 | $K^{1-1}$ | $K^{1-1}$ | $K^{4-3}$ | — | $S(CH_2)_3C^{10}$ | OH | SH | OH | — | — | — | H | 0 | 0 |
| 1034 | $K^{1-1}$ | $K^{1-1}$ | $K^{4-3}$ | — | $S(CH_2)_4C^{20}$ | OH | SH | OH | — | — | — | H | 0 | 0 |

TABLE 1-continued $$R^1-\underset{R^2}{\underset{|}{\overset{\overset{O}{\|}}{P}}}-E^1-\underset{R^3}{\underset{|}{\overset{\overset{O}{\|}}{P}}}-E^2-\underset{R^4}{\underset{|}{\overset{\overset{O}{\|}}{P}}}-E^3\left(\underset{R^5}{\underset{|}{\overset{\overset{O}{\|}}{P}}}-E^4\right)_m\left(\underset{R^6}{\underset{|}{\overset{\overset{O}{\|}}{P}}}-R^7\right)_n R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1035 | $K^{1-1}$ | $K^{1-1}$ | $K^{4-3}$ | — | $S(CH_2)_4C^{18}$ | OH | SH | OH | — | — | — | H | 0 | 0 |
| 1036 | $K^{1-1}$ | $K^{1-1}$ | $K^{4-3}$ | — | $S(CH_2)_4C^{14}$ | OH | SH | OH | — | — | — | H | 0 | 0 |
| 1037 | $K^{1-1}$ | $K^{1-1}$ | $K^{4-3}$ | — | $S(CH_2)_4C^{10}$ | OH | SH | OH | — | — | — | H | 0 | 0 |
| 1038 | $K^{2-1}$ | $K^{1-1}$ | $K^{2-1}$ | — | $SC_2H_4C^{20}$ | OH | OH | SH | — | — | — | H | 0 | 0 |
| 1039 | $K^{2-1}$ | $K^{1-1}$ | $K^{2-1}$ | — | $SC_2H_4C^{18}$ | OH | OH | SH | — | — | — | H | 0 | 0 |
| 1040 | $K^{2-1}$ | $K^{1-1}$ | $K^{2-1}$ | — | $SC_2H_4C^{14}$ | OH | OH | SH | — | — | — | H | 0 | 0 |
| 1041 | $K^{2-1}$ | $K^{1-1}$ | $K^{2-1}$ | — | $SC_2H_4C^{10}$ | OH | OH | SH | — | — | — | H | 0 | 0 |
| 1042 | $K^{2-1}$ | $K^{1-1}$ | $K^{2-1}$ | — | $S(CH_2)_3C^{20}$ | OH | OH | SH | — | — | — | H | 0 | 0 |
| 1043 | $K^{2-1}$ | $K^{1-1}$ | $K^{2-1}$ | — | $S(CH_2)_3C^{18}$ | OH | OH | SH | — | — | — | H | 0 | 0 |
| 1044 | $K^{2-1}$ | $K^{1-1}$ | $K^{2-1}$ | — | $S(CH_2)_3C^{14}$ | OH | OH | SH | — | — | — | H | 0 | 0 |
| 1045 | $K^{2-1}$ | $K^{1-1}$ | $K^{2-1}$ | — | $S(CH_2)_3C^{10}$ | OH | OH | SH | — | — | — | H | 0 | 0 |
| 1046 | $K^{2-1}$ | $K^{1-1}$ | $K^{2-1}$ | — | $S(CH_2)_4C^{20}$ | OH | OH | SH | — | — | — | H | 0 | 0 |
| 1047 | $K^{2-1}$ | $K^{1-1}$ | $K^{2-1}$ | — | $S(CH_2)_4C^{18}$ | OH | OH | SH | — | — | — | H | 0 | 0 |
| 1048 | $K^{2-1}$ | $K^{1-1}$ | $K^{2-1}$ | — | $S(CH_2)_4C^{14}$ | OH | OH | SH | — | — | — | H | 0 | 0 |
| 1049 | $K^{2-1}$ | $K^{1-1}$ | $K^{2-1}$ | — | $S(CH_2)_4C^{10}$ | OH | OH | SH | — | — | — | H | 0 | 0 |
| 1050 | $K^{1-1}$ | $K^{1-1}$ | $K^{1-1}$ | — | $SC_2H_4C^{20}$ | OH | SH | SH | — | — | — | H | 0 | 0 |
| 1051 | $K^{1-1}$ | $K^{1-1}$ | $K^{1-1}$ | — | $SC_2H_4C^{18}$ | OH | SH | SH | — | — | — | H | 0 | 0 |
| 1052 | $K^{1-1}$ | $K^{1-1}$ | $K^{1-1}$ | — | $SC_2H_4C^{14}$ | OH | SH | SH | — | — | — | H | 0 | 0 |
| 1053 | $K^{1-1}$ | $K^{1-1}$ | $K^{1-1}$ | — | $SC_2H_4C^{10}$ | OH | SH | SH | — | — | — | H | 0 | 0 |
| 1054 | $K^{1-1}$ | $K^{1-1}$ | $K^{1-1}$ | — | $S(CH_2)_3C^{20}$ | OH | SH | SH | — | — | — | H | 0 | 0 |
| 1055 | $K^{1-1}$ | $K^{1-1}$ | $K^{1-1}$ | — | $S(CH_2)_3C^{18}$ | OH | SH | SH | — | — | — | H | 0 | 0 |
| 1056 | $K^{1-1}$ | $K^{1-1}$ | $K^{1-1}$ | — | $S(CH_2)_3C^{14}$ | OH | SH | SH | — | — | — | H | 0 | 0 |
| 1057 | $K^{1-1}$ | $K^{1-1}$ | $K^{1-1}$ | — | $S(CH_2)_3C^{10}$ | OH | SH | SH | — | — | — | H | 0 | 0 |
| 1058 | $K^{1-1}$ | $K^{1-1}$ | $K^{1-1}$ | — | $S(CH_2)_4C^{20}$ | OH | SH | SH | — | — | — | H | 0 | 0 |
| 1059 | $K^{1-1}$ | $K^{1-1}$ | $K^{1-1}$ | — | $S(CH_2)_4C^{18}$ | OH | SH | SH | — | — | — | H | 0 | 0 |
| 1060 | $K^{1-1}$ | $K^{1-1}$ | $K^{1-1}$ | — | $S(CH_2)_4C^{14}$ | OH | SH | SH | — | — | — | H | 0 | 0 |
| 1061 | $K^{1-1}$ | $K^{1-1}$ | $K^{1-1}$ | — | $S(CH_2)_4C^{10}$ | OH | SH | SH | — | — | — | H | 0 | 0 |
| 1062 | $K^{1-1}$ | $K^{1-1}$ | $K^{1-1}$ | $K^{1-1}$ | $SC_2H_4C^{20}$ | OH | SH | SH | SH | — | — | H | 1 | 0 |
| 1063 | $K^{1-1}$ | $K^{1-1}$ | $K^{1-1}$ | $K^{1-1}$ | $SC_2H_4C^{18}$ | OH | SH | SH | SH | — | — | H | 1 | 0 |
| 1064 | $K^{1-1}$ | $K^{1-1}$ | $K^{1-1}$ | $K^{1-1}$ | $SC_2H_4C^{14}$ | OH | SH | SH | SH | — | — | H | 1 | 0 |
| 1065 | $K^{1-1}$ | $K^{1-1}$ | $K^{1-1}$ | $K^{1-1}$ | $SC_2H_4C^{10}$ | OH | SH | SH | SH | — | — | H | 1 | 0 |
| 1066 | $K^{1-1}$ | $K^{1-1}$ | $K^{1-1}$ | $K^{1-1}$ | $S(CH_2)_3C^{20}$ | OH | SH | SH | SH | — | — | H | 1 | 0 |
| 1067 | $K^{1-1}$ | $K^{1-1}$ | $K^{1-1}$ | $K^{1-1}$ | $S(CH_2)_3C^{18}$ | OH | SH | SH | SH | — | — | H | 1 | 0 |
| 1068 | $K^{1-1}$ | $K^{1-1}$ | $K^{1-1}$ | $K^{1-1}$ | $S(CH_2)_3C^{14}$ | OH | SH | SH | SH | — | — | H | 1 | 0 |
| 1069 | $K^{1-1}$ | $K^{1-1}$ | $K^{1-1}$ | $K^{1-1}$ | $S(CH_2)_3C^{10}$ | OH | SH | SH | SH | — | — | H | 1 | 0 |
| 1070 | $K^{1-1}$ | $K^{1-1}$ | $K^{1-1}$ | $K^{1-1}$ | $S(CH_2)_4C^{20}$ | OH | SH | SH | SH | — | — | H | 1 | 0 |
| 1071 | $K^{1-1}$ | $K^{1-1}$ | $K^{1-1}$ | $K^{1-1}$ | $S(CH_2)_4C^{18}$ | OH | SH | SH | SH | — | — | H | 1 | 0 |
| 1072 | $K^{1-1}$ | $K^{1-1}$ | $K^{1-1}$ | $K^{1-1}$ | $S(CH_2)_4C^{14}$ | OH | SH | SH | SH | — | — | H | 1 | 0 |
| 1073 | $K^{1-1}$ | $K^{1-1}$ | $K^{1-1}$ | $K^{1-1}$ | $S(CH_2)_4C^{10}$ | OH | SH | SH | SH | — | — | H | 1 | 0 |
| 1074 | $K^{2-1}$ | $K^{1-1}$ | $K^{3-1}$ | — | OH | SH | OH | OH | — | OH | S | H | 0 | 1 |
| 1075 | $K^{2-1}$ | $K^{1-1}$ | $K^{3-1}$ | — | $OC_2H_4OH$ | OH | OH | OH | — | OH | S | H | 0 | 1 |
| 1076 | $K^{2-1}$ | $K^{1-1}$ | $K^{3-1}$ | — | $O(CH_2)_3OH$ | OH | OH | OH | — | OH | S | H | 0 | 1 |
| 1077 | $K^{2-1}$ | $K^{1-1}$ | $K^{3-1}$ | — | $O(CH_2)_4OH$ | OH | OH | OH | — | OH | S | H | 0 | 1 |
| 1078 | $K^{2-1}$ | $K^{1-1}$ | $K^{3-1}$ | — | OH | SH | SH | OH | — | OH | S | H | 0 | 1 |
| 1079 | $K^{2-1}$ | $K^{1-1}$ | $K^{3-1}$ | — | $OC_2H_4OH$ | OH | SH | OH | — | OH | S | H | 0 | 1 |
| 1080 | $K^{2-1}$ | $K^{1-1}$ | $K^{3-1}$ | — | $O(CH_2)_3OH$ | OH | SH | OH | — | OH | S | H | 0 | 1 |
| 1081 | $K^{2-1}$ | $K^{1-1}$ | $K^{3-1}$ | — | $O(CH_2)_4OH$ | OH | SH | OH | — | OH | S | H | 0 | 1 |
| 1082 | $K^{2-1}$ | $K^{1-1}$ | $K^{4-1}$ | — | OH | SH | OH | OH | — | OH | S | H | 0 | 1 |
| 1083 | $K^{2-1}$ | $K^{1-1}$ | $K^{4-1}$ | — | $OC_2H_4OH$ | OH | OH | OH | — | OH | S | H | 0 | 1 |
| 1084 | $K^{2-1}$ | $K^{1-1}$ | $K^{4-1}$ | — | $O(CH_2)_3OH$ | OH | OH | OH | — | OH | S | H | 0 | 1 |
| 1085 | $K^{2-1}$ | $K^{1-1}$ | $K^{4-1}$ | — | $O(CH_2)_4OH$ | OH | OH | OH | — | OH | S | H | 0 | 1 |
| 1086 | $K^{2-1}$ | $K^{1-1}$ | $K^{4-1}$ | — | OH | SH | SH | OH | — | OH | S | H | 0 | 1 |
| 1087 | $K^{2-1}$ | $K^{1-1}$ | $K^{4-1}$ | — | $OC_2H_4OH$ | OH | SH | OH | — | OH | S | H | 0 | 1 |
| 1088 | $K^{2-1}$ | $K^{1-1}$ | $K^{4-1}$ | — | $O(CH_2)_3OH$ | OH | SH | OH | — | OH | S | H | 0 | 1 |
| 1089 | $K^{2-1}$ | $K^{1-1}$ | $K^{4-1}$ | — | $O(CH_2)_4OH$ | OH | SH | OH | — | OH | S | H | 0 | 1 |
| 1090 | $K^{2-1}$ | $K^{1-1}$ | $K^{4-3}$ | — | OH | SH | OH | OH | — | OH | S | H | 0 | 1 |
| 1091 | $K^{2-1}$ | $K^{1-1}$ | $K^{4-3}$ | — | $OC_2H_4OH$ | OH | OH | OH | — | OH | S | H | 0 | 1 |
| 1092 | $K^{2-1}$ | $K^{1-1}$ | $K^{4-3}$ | — | $O(CH_2)_3OH$ | OH | OH | OH | — | OH | S | H | 0 | 1 |
| 1093 | $K^{2-1}$ | $K^{1-1}$ | $K^{4-3}$ | — | $O(CH_2)_4OH$ | OH | OH | OH | — | OH | S | H | 0 | 1 |
| 1094 | $K^{2-1}$ | $K^{1-1}$ | $K^{4-3}$ | — | OH | SH | SH | OH | — | OH | S | H | 0 | 1 |
| 1095 | $K^{2-1}$ | $K^{1-1}$ | $K^{4-3}$ | — | $OC_2H_4OH$ | OH | SH | OH | — | OH | S | H | 0 | 1 |
| 1096 | $K^{2-1}$ | $K^{1-1}$ | $K^{4-3}$ | — | $O(CH_2)_3OH$ | OH | SH | OH | — | OH | S | H | 0 | 1 |
| 1097 | $K^{2-1}$ | $K^{1-1}$ | $K^{4-3}$ | — | $O(CH_2)_4OH$ | OH | SH | OH | — | OH | S | H | 0 | 1 |
| 1098 | $K^{2-1}$ | $K^{1-1}$ | $K^{2-1}$ | — | OH | SH | OH | SH | — | OH | S | H | 0 | 1 |
| 1099 | $K^{2-1}$ | $K^{1-1}$ | $K^{2-1}$ | — | $OC_2H_4OH$ | OH | OH | SH | — | OH | S | H | 0 | 1 |
| 1100 | $K^{2-1}$ | $K^{1-1}$ | $K^{2-1}$ | — | $O(CH_2)_3OH$ | OH | OH | SH | — | OH | S | H | 0 | 1 |
| 1101 | $K^{2-1}$ | $K^{1-1}$ | $K^{2-1}$ | — | $O(CH_2)_4OH$ | OH | OH | SH | — | OH | S | H | 0 | 1 |
| 1102 | $K^{1-1}$ | $K^{1-1}$ | $K^{1-1}$ | — | OH | SH | SH | SH | — | OH | S | H | 0 | 1 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3+\underset{\underset{R^5}{|}}{\overset{\overset{O}{\|}}{P}}-E^4\underset{m}{\Big)}\Big(\underset{\underset{R^6}{|}}{\overset{\overset{O}{\|}}{P}}-R^7\Big)_n-R^8$$

| Exemplified Compound No. | E¹ | E² | E³ | E⁴ | R¹ | R² | R³ | R⁴ | R⁵ | R⁶ | R⁷ | R⁸ | m | n |
|---|---|---|---|---|---|---|---|---|---|---|---|---|---|---|
| 1103 | K$^{1-1}$ | K$^{1-1}$ | K$^{1-1}$ | — | OC$_2$H$_4$OH | OH | SH | SH | — | OH | S | H | 0 | 1 |
| 1104 | K$^{1-1}$ | K$^{1-1}$ | K$^{1-1}$ | — | O(CH$_2$)$_3$OH | OH | SH | SH | — | OH | S | H | 0 | 1 |
| 1105 | K$^{1-1}$ | K$^{1-1}$ | K$^{1-1}$ | — | O(CH$_2$)$_4$OH | OH | SH | SH | — | OH | S | H | 0 | 1 |
| 1106 | K$^{1-1}$ | K$^{1-1}$ | K$^{1-1}$ | K$^{1-1}$ | OH | SH | SH | SH | SH | OH | S | H | 1 | 1 |
| 1107 | K$^{1-1}$ | K$^{1-1}$ | K$^{1-1}$ | K$^{1-1}$ | OC$_2$H$_4$OH | OH | SH | SH | SH | OH | S | H | 1 | 1 |
| 1108 | K$^{1-1}$ | K$^{1-1}$ | K$^{1-1}$ | K$^{1-1}$ | O(CH$_2$)$_3$OH | OH | SH | SH | SH | OH | S | H | 1 | 1 |
| 1109 | K$^{1-1}$ | K$^{1-1}$ | K$^{1-1}$ | K$^{1-1}$ | O(CH$_2$)$_4$OH | OH | SH | SH | SH | OH | S | H | 1 | 1 |
| 1110 | K$^{2-1}$ | K$^{1-1}$ | K$^{3-1}$ | — | OC$_2$H$_4$OH | OH | OH | OH | — | SC$_2$H$_4$C$^{20}$ | O | H | 0 | 1 |
| 1111 | K$^{2-1}$ | K$^{1-1}$ | K$^{3-1}$ | — | OC$_2$H$_4$OH | OH | OH | OH | — | SC$_2$H$_4$C$^{18}$ | O | H | 0 | 1 |
| 1112 | K$^{2-1}$ | K$^{1-1}$ | K$^{3-1}$ | — | OC$_2$H$_4$OH | OH | OH | OH | — | SC$_2$H$_4$C$^{14}$ | O | H | 0 | 1 |
| 1113 | K$^{2-1}$ | K$^{1-1}$ | K$^{3-1}$ | — | OC$_2$H$_4$OH | OH | OH | OH | — | SC$_2$H$_4$C$^{10}$ | O | H | 0 | 1 |
| 1114 | K$^{2-1}$ | K$^{1-1}$ | K$^{3-1}$ | — | O(CH$_2$)$_3$OH | OH | OH | OH | — | S(CH$_2$)$_3$C$^{20}$ | O | H | 0 | 1 |
| 1115 | K$^{2-1}$ | K$^{1-1}$ | K$^{3-1}$ | — | O(CH$_2$)$_3$OH | OH | OH | OH | — | S(CH$_2$)$_3$C$^{18}$ | O | H | 0 | 1 |
| 1116 | K$^{2-1}$ | K$^{1-1}$ | K$^{3-1}$ | — | O(CH$_2$)$_3$OH | OH | OH | OH | — | S(CH$_2$)$_3$C$^{14}$ | O | H | 0 | 1 |
| 1117 | K$^{2-1}$ | K$^{1-1}$ | K$^{3-1}$ | — | O(CH$_2$)$_3$OH | OH | OH | OH | — | S(CH$_2$)$_3$C$^{10}$ | O | H | 0 | 1 |
| 1118 | K$^{2-1}$ | K$^{1-1}$ | K$^{3-1}$ | — | O(CH$_2$)$_4$OH | OH | OH | OH | — | S(CH$_2$)$_4$C$^{20}$ | O | H | 0 | 1 |
| 1119 | K$^{2-1}$ | K$^{1-1}$ | K$^{3-1}$ | — | O(CH$_2$)$_4$OH | OH | OH | OH | — | S(CH$_2$)$_4$C$^{18}$ | O | H | 0 | 1 |
| 1120 | K$^{2-1}$ | K$^{1-1}$ | K$^{3-1}$ | — | O(CH$_2$)$_4$OH | OH | OH | OH | — | S(CH$_2$)$_4$C$^{14}$ | O | H | 0 | 1 |
| 1121 | K$^{2-1}$ | K$^{1-1}$ | K$^{3-1}$ | — | O(CH$_2$)$_4$OH | OH | OH | OH | — | S(CH$_2$)$_4$C$^{10}$ | O | H | 0 | 1 |
| 1122 | K$^{1-1}$ | K$^{1-1}$ | K$^{3-1}$ | — | OC$_2$H$_4$OH | OH | SH | OH | — | SC$_2$H$_4$C$^{20}$ | O | H | 0 | 1 |
| 1123 | K$^{1-1}$ | K$^{1-1}$ | K$^{3-1}$ | — | OC$_2$H$_4$OH | OH | SH | OH | — | SC$_2$H$_4$C$^{18}$ | O | H | 0 | 1 |
| 1124 | K$^{1-1}$ | K$^{1-1}$ | K$^{3-1}$ | — | OC$_2$H$_4$OH | OH | SH | OH | — | SC$_2$H$_4$C$^{14}$ | O | H | 0 | 1 |
| 1125 | K$^{1-1}$ | K$^{1-1}$ | K$^{3-1}$ | — | OC$_2$H$_4$OH | OH | SH | OH | — | SC$_2$H$_4$C$^{10}$ | O | H | 0 | 1 |
| 1126 | K$^{1-1}$ | K$^{1-1}$ | K$^{3-1}$ | — | O(CH$_2$)$_3$OH | OH | SH | OH | — | S(CH$_2$)$_3$C$^{20}$ | O | H | 0 | 1 |
| 1127 | K$^{1-1}$ | K$^{1-1}$ | K$^{3-1}$ | — | O(CH$_2$)$_3$OH | OH | SH | OH | — | S(CH$_2$)$_3$C$^{18}$ | O | H | 0 | 1 |
| 1128 | K$^{1-1}$ | K$^{1-1}$ | K$^{3-1}$ | — | O(CH$_2$)$_3$OH | OH | SH | OH | — | S(CH$_2$)$_3$C$^{14}$ | O | H | 0 | 1 |
| 1129 | K$^{1-1}$ | K$^{1-1}$ | K$^{3-1}$ | — | O(CH$_2$)$_3$OH | OH | SH | OH | — | S(CH$_2$)$_3$C$^{10}$ | O | H | 0 | 1 |
| 1130 | K$^{1-1}$ | K$^{1-1}$ | K$^{3-1}$ | — | O(CH$_2$)$_4$OH | OH | SH | OH | — | S(CH$_2$)$_4$C$^{20}$ | O | H | 0 | 1 |
| 1131 | K$^{1-1}$ | K$^{1-1}$ | K$^{3-1}$ | — | O(CH$_2$)$_4$OH | OH | SH | OH | — | S(CH$_2$)$_4$C$^{18}$ | O | H | 0 | 1 |
| 1132 | K$^{1-1}$ | K$^{1-1}$ | K$^{3-1}$ | — | O(CH$_2$)$_4$OH | OH | SH | OH | — | S(CH$_2$)$_4$C$^{14}$ | O | H | 0 | 1 |
| 1133 | K$^{1-1}$ | K$^{1-1}$ | K$^{3-1}$ | — | O(CH$_2$)$_4$OH | OH | SH | OH | — | S(CH$_2$)$_4$C$^{10}$ | O | H | 0 | 1 |
| 1134 | K$^{2-1}$ | K$^{1-1}$ | K$^{4-1}$ | — | OC$_2$H$_4$OH | OH | OH | OH | — | SC$_2$H$_4$C$^{20}$ | O | H | 0 | 1 |
| 1135 | K$^{2-1}$ | K$^{1-1}$ | K$^{4-1}$ | — | OC$_2$H$_4$OH | OH | OH | OH | — | SC$_2$H$_4$C$^{18}$ | O | H | 0 | 1 |
| 1136 | K$^{2-1}$ | K$^{1-1}$ | K$^{4-1}$ | — | OC$_2$H$_4$OH | OH | OH | OH | — | SC$_2$H$_4$C$^{14}$ | O | H | 0 | 1 |
| 1137 | K$^{2-1}$ | K$^{1-1}$ | K$^{4-1}$ | — | OC$_2$H$_4$OH | OH | OH | OH | — | SC$_2$H$_4$C$^{10}$ | O | H | 0 | 1 |
| 1138 | K$^{2-1}$ | K$^{1-1}$ | K$^{4-1}$ | — | O(CH$_2$)$_3$OH | OH | OH | OH | — | S(CH$_2$)$_3$C$^{20}$ | O | H | 0 | 1 |
| 1139 | K$^{2-1}$ | K$^{1-1}$ | K$^{4-1}$ | — | O(CH$_2$)$_3$OH | OH | OH | OH | — | S(CH$_2$)$_3$C$^{18}$ | O | H | 0 | 1 |
| 1140 | K$^{2-1}$ | K$^{1-1}$ | K$^{4-1}$ | — | O(CH$_2$)$_3$OH | OH | OH | OH | — | S(CH$_2$)$_3$C$^{14}$ | O | H | 0 | 1 |
| 1141 | K$^{2-1}$ | K$^{1-1}$ | K$^{4-1}$ | — | O(CH$_2$)$_3$OH | OH | OH | OH | — | S(CH$_2$)$_3$C$^{10}$ | O | H | 0 | 1 |
| 1142 | K$^{2-1}$ | K$^{1-1}$ | K$^{4-1}$ | — | O(CH$_2$)$_4$OH | OH | OH | OH | — | S(CH$_2$)$_4$C$^{20}$ | O | H | 0 | 1 |
| 1143 | K$^{2-1}$ | K$^{1-1}$ | K$^{4-1}$ | — | O(CH$_2$)$_4$OH | OH | OH | OH | — | S(CH$_2$)$_4$C$^{18}$ | O | H | 0 | 1 |
| 1144 | K$^{2-1}$ | K$^{1-1}$ | K$^{4-1}$ | — | O(CH$_2$)$_4$OH | OH | OH | OH | — | S(CH$_2$)$_4$C$^{14}$ | O | H | 0 | 1 |
| 1145 | K$^{2-1}$ | K$^{1-1}$ | K$^{4-1}$ | — | O(CH$_2$)$_4$OH | OH | OH | OH | — | S(CH$_2$)$_4$C$^{10}$ | O | H | 0 | 1 |
| 1146 | K$^{1-1}$ | K$^{1-1}$ | K$^{4-1}$ | — | OC$_2$H$_4$OH | OH | SH | OH | — | SC$_2$H$_4$C$^{20}$ | O | H | 0 | 1 |
| 1147 | K$^{1-1}$ | K$^{1-1}$ | K$^{4-1}$ | — | OC$_2$H$_4$OH | OH | SH | OH | — | SC$_2$H$_4$C$^{18}$ | O | H | 0 | 1 |
| 1148 | K$^{1-1}$ | K$^{1-1}$ | K$^{4-1}$ | — | OC$_2$H$_4$OH | OH | SH | OH | — | SC$_2$H$_4$C$^{14}$ | O | H | 0 | 1 |
| 1149 | K$^{1-1}$ | K$^{1-1}$ | K$^{4-1}$ | — | OC$_2$H$_4$OH | OH | SH | OH | — | SC$_2$H$_4$C$^{10}$ | O | H | 0 | 1 |
| 1150 | K$^{1-1}$ | K$^{1-1}$ | K$^{4-1}$ | — | O(CH$_2$)$_3$OH | OH | SH | OH | — | S(CH$_2$)$_3$C$^{20}$ | O | H | 0 | 1 |
| 1151 | K$^{1-1}$ | K$^{1-1}$ | K$^{4-1}$ | — | O(CH$_2$)$_3$OH | OH | SH | OH | — | S(CH$_2$)$_3$C$^{18}$ | O | H | 0 | 1 |
| 1152 | K$^{1-1}$ | K$^{1-1}$ | K$^{4-1}$ | — | O(CH$_2$)$_3$OH | OH | SH | OH | — | S(CH$_2$)$_3$C$^{14}$ | O | H | 0 | 1 |
| 1153 | K$^{1-1}$ | K$^{1-1}$ | K$^{4-1}$ | — | O(CH$_2$)$_3$OH | OH | SH | OH | — | S(CH$_2$)$_3$C$^{10}$ | O | H | 0 | 1 |
| 1154 | K$^{1-1}$ | K$^{1-1}$ | K$^{4-1}$ | — | O(CH$_2$)$_4$OH | OH | SH | OH | — | S(CH$_2$)$_4$C$^{20}$ | O | H | 0 | 1 |
| 1155 | K$^{1-1}$ | K$^{1-1}$ | K$^{4-1}$ | — | O(CH$_2$)$_4$OH | OH | SH | OH | — | S(CH$_2$)$_4$C$^{18}$ | O | H | 0 | 1 |
| 1156 | K$^{1-1}$ | K$^{1-1}$ | K$^{4-1}$ | — | O(CH$_2$)$_4$OH | OH | SH | OH | — | S(CH$_2$)$_4$C$^{14}$ | O | H | 0 | 1 |
| 1157 | K$^{1-1}$ | K$^{1-1}$ | K$^{4-1}$ | — | O(CH$_2$)$_4$OH | OH | SH | OH | — | S(CH$_2$)$_4$C$^{10}$ | O | H | 0 | 1 |
| 1158 | K$^{2-1}$ | K$^{1-1}$ | K$^{4-3}$ | — | OC$_2$H$_4$OH | OH | OH | OH | — | SC$_2$H$_4$C$^{20}$ | O | H | 0 | 1 |
| 1159 | K$^{2-2}$ | K$^{1-2}$ | K$^{4-3}$ | — | OC$_2$H$_4$OH | OH | OH | OH | — | SC$_2$H$_4$C$^{18}$ | O | H | 0 | 1 |
| 1160 | K$^{2-3}$ | K$^{1-3}$ | K$^{4-3}$ | — | OC$_2$H$_4$OH | OH | OH | OH | — | SC$_2$H$_4$C$^{14}$ | O | H | 0 | 1 |
| 1161 | K$^{2-4}$ | K$^{1-4}$ | K$^{4-3}$ | — | OC$_2$H$_4$OH | OH | OH | OH | — | SC$_2$H$_4$C$^{10}$ | O | H | 0 | 1 |
| 1162 | K$^{2-1}$ | K$^{1-1}$ | K$^{4-3}$ | — | O(CH$_2$)$_3$OH | OH | OH | OH | — | S(CH$_2$)$_3$C$^{20}$ | O | H | 0 | 1 |
| 1163 | K$^{2-2}$ | K$^{1-2}$ | K$^{4-3}$ | — | O(CH$_2$)$_3$OH | OH | OH | OH | — | S(CH$_2$)$_3$C$^{18}$ | O | H | 0 | 1 |
| 1164 | K$^{2-3}$ | K$^{1-3}$ | K$^{4-3}$ | — | O(CH$_2$)$_3$OH | OH | OH | OH | — | S(CH$_2$)$_3$C$^{14}$ | O | H | 0 | 1 |
| 1165 | K$^{2-4}$ | K$^{1-4}$ | K$^{4-3}$ | — | O(CH$_2$)$_3$OH | OH | OH | OH | — | S(CH$_2$)$_3$C$^{10}$ | O | H | 0 | 1 |
| 1166 | K$^{2-1}$ | K$^{1-1}$ | K$^{4-3}$ | — | O(CH$_2$)$_4$OH | OH | OH | OH | — | S(CH$_2$)$_4$C$^{20}$ | O | H | 0 | 1 |
| 1167 | K$^{2-2}$ | K$^{1-2}$ | K$^{4-3}$ | — | O(CH$_2$)$_4$OH | OH | OH | OH | — | S(CH$_2$)$_4$C$^{18}$ | O | H | 0 | 1 |
| 1168 | K$^{2-3}$ | K$^{1-3}$ | K$^{4-3}$ | — | O(CH$_2$)$_4$OH | OH | OH | OH | — | S(CH$_2$)$_4$C$^{14}$ | O | H | 0 | 1 |
| 1169 | K$^{2-4}$ | K$^{1-4}$ | K$^{4-3}$ | — | O(CH$_2$)$_4$OH | OH | OH | OH | — | S(CH$_2$)$_4$C$^{10}$ | O | H | 0 | 1 |
| 1170 | K$^{1-1}$ | K$^{1-1}$ | K$^{4-3}$ | — | OC$_2$H$_4$OH | OH | SH | OH | — | SC$_2$H$_4$C$^{20}$ | O | H | 0 | 1 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1171 | $K^{1-1}$ | $K^{1-1}$ | $K^{4-3}$ | — | $OC_2H_4OH$ | OH | SH | OH | — | $SC_2H_4C^{18}$ | O | H | 0 | 1 |
| 1172 | $K^{1-1}$ | $K^{1-1}$ | $K^{4-3}$ | — | $OC_2H_4OH$ | OH | SH | OH | — | $SC_2H_4C^{14}$ | O | H | 0 | 1 |
| 1173 | $K^{1-1}$ | $K^{1-1}$ | $K^{4-3}$ | — | $OC_2H_4OH$ | OH | SH | OH | — | $SC_2H_4C^{10}$ | O | H | 0 | 1 |
| 1174 | $K^{1-1}$ | $K^{1-1}$ | $K^{4-3}$ | — | $O(CH_2)_3OH$ | OH | SH | OH | — | $S(CH_2)_3C^{20}$ | O | H | 0 | 1 |
| 1175 | $K^{1-1}$ | $K^{1-1}$ | $K^{4-3}$ | — | $O(CH_2)_3OH$ | OH | SH | OH | — | $S(CH_2)_3C^{18}$ | O | H | 0 | 1 |
| 1176 | $K^{1-1}$ | $K^{1-1}$ | $K^{4-3}$ | — | $O(CH_2)_3OH$ | OH | SH | OH | — | $S(CH_2)_3C^{14}$ | O | H | 0 | 1 |
| 1177 | $K^{1-1}$ | $K^{1-1}$ | $K^{4-3}$ | — | $O(CH_2)_3OH$ | OH | SH | OH | — | $S(CH_2)_3C^{10}$ | O | H | 0 | 1 |
| 1178 | $K^{1-1}$ | $K^{1-1}$ | $K^{4-3}$ | — | $O(CH_2)_4OH$ | OH | SH | OH | — | $S(CH_2)_4C^{20}$ | O | H | 0 | 1 |
| 1179 | $K^{1-1}$ | $K^{1-1}$ | $K^{4-3}$ | — | $O(CH_2)_4OH$ | OH | SH | OH | — | $S(CH_2)_4C^{18}$ | O | H | 0 | 1 |
| 1180 | $K^{1-1}$ | $K^{1-1}$ | $K^{4-3}$ | — | $O(CH_2)_4OH$ | OH | SH | OH | — | $S(CH_2)_4C^{14}$ | O | H | 0 | 1 |
| 1181 | $K^{1-1}$ | $K^{1-1}$ | $K^{4-3}$ | — | $O(CH_2)_4OH$ | OH | SH | OH | — | $S(CH_2)_4C^{10}$ | O | H | 0 | 1 |
| 1182 | $K^{2-1}$ | $K^{1-1}$ | $K^{2-1}$ | — | $OC_2H_4OH$ | OH | OH | SH | — | $SC_2H_4C^{20}$ | O | H | 0 | 1 |
| 1183 | $K^{2-1}$ | $K^{1-1}$ | $K^{2-1}$ | — | $OC_2H_4OH$ | OH | OH | SH | — | $SC_2H_4C^{18}$ | O | H | 0 | 1 |
| 1184 | $K^{2-1}$ | $K^{1-1}$ | $K^{2-1}$ | — | $OC_2H_4OH$ | OH | OH | SH | — | $SC_2H_4C^{14}$ | O | H | 0 | 1 |
| 1185 | $K^{2-1}$ | $K^{1-1}$ | $K^{2-1}$ | — | $OC_2H_4OH$ | OH | OH | SH | — | $SC_2H_4C^{10}$ | O | H | 0 | 1 |
| 1186 | $K^{2-1}$ | $K^{1-1}$ | $K^{2-1}$ | — | $O(CH_2)_3OH$ | OH | OH | SH | — | $S(CH_2)_3C^{20}$ | O | H | 0 | 1 |
| 1187 | $K^{2-1}$ | $K^{1-1}$ | $K^{2-1}$ | — | $O(CH_2)_3OH$ | OH | OH | SH | — | $S(CH_2)_3C^{18}$ | O | H | 0 | 1 |
| 1188 | $K^{2-1}$ | $K^{1-1}$ | $K^{2-1}$ | — | $O(CH_2)_3OH$ | OH | OH | SH | — | $S(CH_2)_3C^{14}$ | O | H | 0 | 1 |
| 1189 | $K^{2-1}$ | $K^{1-1}$ | $K^{2-1}$ | — | $O(CH_2)_3OH$ | OH | OH | SH | — | $S(CH_2)_3C^{10}$ | O | H | 0 | 1 |
| 1190 | $K^{2-1}$ | $K^{1-1}$ | $K^{2-1}$ | — | $O(CH_2)_4OH$ | OH | OH | SH | — | $S(CH_2)_4C^{20}$ | O | H | 0 | 1 |
| 1191 | $K^{2-1}$ | $K^{1-1}$ | $K^{2-1}$ | — | $O(CH_2)_4OH$ | OH | OH | SH | — | $S(CH_2)_4C^{18}$ | O | H | 0 | 1 |
| 1192 | $K^{2-1}$ | $K^{1-1}$ | $K^{2-1}$ | — | $O(CH_2)_4OH$ | OH | OH | SH | — | $S(CH_2)_4C^{14}$ | O | H | 0 | 1 |
| 1193 | $K^{2-1}$ | $K^{1-1}$ | $K^{2-1}$ | — | $O(CH_2)_4OH$ | OH | OH | SH | — | $S(CH_2)_4C^{10}$ | O | H | 0 | 1 |
| 1194 | $K^{1-1}$ | $K^{1-1}$ | $K^{1-1}$ | — | $OC_2H_4OH$ | OH | SH | SH | — | $SC_2H_4C^{20}$ | O | H | 0 | 1 |
| 1195 | $K^{1-1}$ | $K^{1-1}$ | $K^{1-1}$ | — | $OC_2H_4OH$ | OH | SH | SH | — | $SC_2H_4C^{18}$ | O | H | 0 | 1 |
| 1196 | $K^{1-1}$ | $K^{1-1}$ | $K^{1-1}$ | — | $OC_2H_4OH$ | OH | SH | SH | — | $SC_2H_4C^{14}$ | O | H | 0 | 1 |
| 1197 | $K^{1-1}$ | $K^{1-1}$ | $K^{1-1}$ | — | $OC_2H_4OH$ | OH | SH | SH | — | $SC_2H_4C^{10}$ | O | H | 0 | 1 |
| 1198 | $K^{1-1}$ | $K^{1-1}$ | $K^{1-1}$ | — | $O(CH_2)_3OH$ | OH | SH | SH | — | $S(CH_2)_3C^{20}$ | O | H | 0 | 1 |
| 1199 | $K^{1-1}$ | $K^{1-1}$ | $K^{1-1}$ | — | $O(CH_2)_3OH$ | OH | SH | SH | — | $S(CH_2)_3C^{18}$ | O | H | 0 | 1 |
| 1200 | $K^{1-1}$ | $K^{1-1}$ | $K^{1-1}$ | — | $O(CH_2)_3OH$ | OH | SH | SH | — | $S(CH_2)_3C^{14}$ | O | H | 0 | 1 |
| 1201 | $K^{1-1}$ | $K^{1-1}$ | $K^{1-1}$ | — | $O(CH_2)_3OH$ | OH | SH | SH | — | $S(CH_2)_3C^{10}$ | O | H | 0 | 1 |
| 1202 | $K^{1-1}$ | $K^{1-1}$ | $K^{1-1}$ | — | $O(CH_2)_4OH$ | OH | SH | SH | — | $S(CH_2)_4C^{20}$ | O | H | 0 | 1 |
| 1203 | $K^{1-1}$ | $K^{1-1}$ | $K^{1-1}$ | — | $O(CH_2)_4OH$ | OH | SH | SH | — | $S(CH_2)_4C^{18}$ | O | H | 0 | 1 |
| 1204 | $K^{1-1}$ | $K^{1-1}$ | $K^{1-1}$ | — | $O(CH_2)_4OH$ | OH | SH | SH | — | $S(CH_2)_4C^{14}$ | O | H | 0 | 1 |
| 1205 | $K^{1-1}$ | $K^{1-1}$ | $K^{1-1}$ | — | $O(CH_2)_4OH$ | OH | SH | SH | — | $S(CH_2)_4C^{10}$ | O | H | 0 | 1 |
| 1206 | $K^{1-1}$ | $K^{1-1}$ | $K^{1-1}$ | $K^{1-1}$ | $OC_2H_4OH$ | OH | SH | SH | SH | $SC_2H_4C^{20}$ | O | H | 1 | 1 |
| 1207 | $K^{1-1}$ | $K^{1-1}$ | $K^{1-1}$ | $K^{1-1}$ | $OC_2H_4OH$ | OH | SH | SH | SH | $SC_2H_4C^{18}$ | O | H | 1 | 1 |
| 1208 | $K^{1-1}$ | $K^{1-1}$ | $K^{1-1}$ | $K^{1-1}$ | $OC_2H_4OH$ | OH | SH | SH | SH | $SC_2H_4C^{14}$ | O | H | 1 | 1 |
| 1209 | $K^{1-1}$ | $K^{1-1}$ | $K^{1-1}$ | $K^{1-1}$ | $OC_2H_4OH$ | OH | SH | SH | SH | $SC_2H_4C^{10}$ | O | H | 1 | 1 |
| 1210 | $K^{1-1}$ | $K^{1-1}$ | $K^{1-1}$ | $K^{1-1}$ | $O(CH_2)_3OH$ | OH | SH | SH | SH | $S(CH_2)_3C^{20}$ | O | H | 1 | 1 |
| 1211 | $K^{1-1}$ | $K^{1-1}$ | $K^{1-1}$ | $K^{1-1}$ | $O(CH_2)_3OH$ | OH | SH | SH | SH | $S(CH_2)_3C^{18}$ | O | H | 1 | 1 |
| 1212 | $K^{1-1}$ | $K^{1-1}$ | $K^{1-1}$ | $K^{1-1}$ | $O(CH_2)_3OH$ | OH | SH | SH | SH | $S(CH_2)_3C^{14}$ | O | H | 1 | 1 |
| 1213 | $K^{1-1}$ | $K^{1-1}$ | $K^{1-1}$ | $K^{1-1}$ | $O(CH_2)_3OH$ | OH | SH | SH | SH | $S(CH_2)_3C^{10}$ | O | H | 1 | 1 |
| 1214 | $K^{1-1}$ | $K^{1-1}$ | $K^{1-1}$ | $K^{1-1}$ | $O(CH_2)_4OH$ | OH | SH | SH | SH | $S(CH_2)_4C^{20}$ | O | H | 1 | 1 |
| 1215 | $K^{1-1}$ | $K^{1-1}$ | $K^{1-1}$ | $K^{1-1}$ | $O(CH_2)_4OH$ | OH | SH | SH | SH | $S(CH_2)_4C^{18}$ | O | H | 1 | 1 |
| 1216 | $K^{1-1}$ | $K^{1-1}$ | $K^{1-1}$ | $K^{1-1}$ | $O(CH_2)_4OH$ | OH | SH | SH | SH | $S(CH_2)_4C^{14}$ | O | H | 1 | 1 |
| 1217 | $K^{1-1}$ | $K^{1-1}$ | $K^{1-1}$ | $K^{1-1}$ | $O(CH_2)_4OH$ | OH | SH | SH | SH | $S(CH_2)_4C^{10}$ | O | H | 1 | 1 |
| 1218 | $K^{2-1}$ | $K^{1-1}$ | $K^{3-1}$ | — | $SC_2H_4C^{20}$ | OH | OH | OH | — | $SC_2H_4C^{20}$ | O | H | 0 | 1 |
| 1219 | $K^{2-1}$ | $K^{1-1}$ | $K^{3-1}$ | — | $SC_2H_4C^{18}$ | OH | OH | OH | — | $SC_2H_4C^{18}$ | O | H | 0 | 1 |
| 1220 | $K^{2-1}$ | $K^{1-1}$ | $K^{3-1}$ | — | $SC_2H_4C^{14}$ | OH | OH | OH | — | $SC_2H_4C^{14}$ | O | H | 0 | 1 |
| 1221 | $K^{2-1}$ | $K^{1-1}$ | $K^{3-1}$ | — | $SC_2H_4C^{10}$ | OH | OH | OH | — | $SC_2H_4C^{10}$ | O | H | 0 | 1 |
| 1222 | $K^{2-1}$ | $K^{1-1}$ | $K^{3-1}$ | — | $S(CH_2)_3C^{20}$ | OH | OH | OH | — | $S(CH_2)_3C^{20}$ | O | H | 0 | 1 |
| 1223 | $K^{2-1}$ | $K^{1-1}$ | $K^{3-1}$ | — | $S(CH_2)_3C^{18}$ | OH | OH | OH | — | $S(CH_2)_3C^{18}$ | O | H | 0 | 1 |
| 1224 | $K^{2-1}$ | $K^{1-1}$ | $K^{3-1}$ | — | $S(CH_2)_3C^{14}$ | OH | OH | OH | — | $S(CH_2)_3C^{14}$ | O | H | 0 | 1 |
| 1225 | $K^{2-1}$ | $K^{1-1}$ | $K^{3-1}$ | — | $S(CH_2)_3C^{10}$ | OH | OH | OH | — | $S(CH_2)_3C^{10}$ | O | H | 0 | 1 |
| 1226 | $K^{2-1}$ | $K^{1-1}$ | $K^{3-1}$ | — | $S(CH_2)_4C^{20}$ | OH | OH | OH | — | $S(CH_2)_4C^{20}$ | O | H | 0 | 1 |
| 1227 | $K^{2-1}$ | $K^{1-1}$ | $K^{3-1}$ | — | $S(CH_2)_4C^{18}$ | OH | OH | OH | — | $S(CH_2)_4C^{18}$ | O | H | 0 | 1 |
| 1228 | $K^{2-1}$ | $K^{1-1}$ | $K^{3-1}$ | — | $S(CH_2)_4C^{14}$ | OH | OH | OH | — | $S(CH_2)_4C^{14}$ | O | H | 0 | 1 |
| 1229 | $K^{2-1}$ | $K^{1-1}$ | $K^{3-1}$ | — | $S(CH_2)_4C^{10}$ | OH | OH | OH | — | $S(CH_2)_4C^{10}$ | O | H | 0 | 1 |
| 1230 | $K^{1-1}$ | $K^{1-1}$ | $K^{3-1}$ | — | $SC_2H_4C^{20}$ | OH | SH | OH | — | $SC_2H_4C^{20}$ | O | H | 0 | 1 |
| 1231 | $K^{1-1}$ | $K^{1-1}$ | $K^{3-1}$ | — | $SC_2H_4C^{18}$ | OH | SH | OH | — | $SC_2H_4C^{18}$ | O | H | 0 | 1 |
| 1232 | $K^{1-1}$ | $K^{1-1}$ | $K^{3-1}$ | — | $SC_2H_4C^{14}$ | OH | SH | OH | — | $SC_2H_4C^{14}$ | O | H | 0 | 1 |
| 1233 | $K^{1-1}$ | $K^{1-1}$ | $K^{3-1}$ | — | $SC_2H_4C^{10}$ | OH | SH | OH | — | $SC_2H_4C^{10}$ | O | H | 0 | 1 |
| 1234 | $K^{1-1}$ | $K^{1-1}$ | $K^{3-1}$ | — | $S(CH_2)_3C^{20}$ | OH | SH | OH | — | $S(CH_2)_3C^{20}$ | O | H | 0 | 1 |
| 1235 | $K^{1-1}$ | $K^{1-1}$ | $K^{3-1}$ | — | $S(CH_2)_3C^{18}$ | OH | SH | OH | — | $S(CH_2)_3C^{18}$ | O | H | 0 | 1 |
| 1236 | $K^{1-1}$ | $K^{1-1}$ | $K^{3-1}$ | — | $S(CH_2)_3C^{14}$ | OH | SH | OH | — | $S(CH_2)_3C^{14}$ | O | H | 0 | 1 |
| 1237 | $K^{1-1}$ | $K^{1-1}$ | $K^{3-1}$ | — | $S(CH_2)_3C^{10}$ | OH | SH | OH | — | $S(CH_2)_3C^{10}$ | O | H | 0 | 1 |
| 1238 | $K^{1-1}$ | $K^{1-1}$ | $K^{3-1}$ | — | $S(CH_2)_4C^{20}$ | OH | SH | OH | — | $S(CH_2)_4C^{20}$ | O | H | 0 | 1 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1239 | $K^{1-1}$ | $K^{1-1}$ | $K^{3-1}$ | — | $S(CH_2)_4C^{18}$ | OH | SH | OH | — | $S(CH_2)_4C^{18}$ | O | H | 0 | 1 |
| 1240 | $K^{1-1}$ | $K^{1-1}$ | $K^{3-1}$ | — | $S(CH_2)_4C^{14}$ | OH | SH | OH | — | $S(CH_2)_4C^{14}$ | O | H | 0 | 1 |
| 1241 | $K^{1-1}$ | $K^{1-1}$ | $K^{3-1}$ | — | $S(CH_2)_4C^{10}$ | OH | SH | OH | — | $S(CH_2)_4C^{10}$ | O | H | 0 | 1 |
| 1242 | $K^{2-1}$ | $K^{1-1}$ | $K^{4-1}$ | — | $SC_2H_4C^{20}$ | OH | OH | OH | — | $SC_2H_4C^{20}$ | O | H | 0 | 1 |
| 1243 | $K^{2-1}$ | $K^{1-1}$ | $K^{4-1}$ | — | $SC_2H_4C^{18}$ | OH | OH | OH | — | $SC_2H_4C^{18}$ | O | H | 0 | 1 |
| 1244 | $K^{2-1}$ | $K^{1-1}$ | $K^{4-1}$ | — | $SC_2H_4C^{14}$ | OH | OH | OH | — | $SC_2H_4C^{14}$ | O | H | 0 | 1 |
| 1245 | $K^{2-1}$ | $K^{1-1}$ | $K^{4-1}$ | — | $SC_2H_4C^{10}$ | OH | OH | OH | — | $SC_2H_4C^{10}$ | O | H | 0 | 1 |
| 1246 | $K^{2-1}$ | $K^{1-1}$ | $K^{4-1}$ | — | $S(CH_2)_3C^{20}$ | OH | OH | OH | — | $S(CH_2)_3C^{20}$ | O | H | 0 | 1 |
| 1247 | $K^{2-1}$ | $K^{1-1}$ | $K^{4-1}$ | — | $S(CH_2)_3C^{18}$ | OH | OH | OH | — | $S(CH_2)_3C^{18}$ | O | H | 0 | 1 |
| 1248 | $K^{2-1}$ | $K^{1-1}$ | $K^{4-1}$ | — | $S(CH_2)_3C^{14}$ | OH | OH | OH | — | $S(CH_2)_3C^{14}$ | O | H | 0 | 1 |
| 1249 | $K^{2-1}$ | $K^{1-1}$ | $K^{4-1}$ | — | $S(CH_2)_3C^{10}$ | OH | OH | OH | — | $S(CH_2)_3C^{10}$ | O | H | 0 | 1 |
| 1250 | $K^{2-1}$ | $K^{1-1}$ | $K^{4-1}$ | — | $S(CH_2)_4C^{20}$ | OH | OH | OH | — | $S(CH_2)_4C^{20}$ | O | H | 0 | 1 |
| 1251 | $K^{2-1}$ | $K^{1-1}$ | $K^{4-1}$ | — | $S(CH_2)_4C^{18}$ | OH | OH | OH | — | $S(CH_2)_4C^{18}$ | O | H | 0 | 1 |
| 1252 | $K^{2-1}$ | $K^{1-1}$ | $K^{4-1}$ | — | $S(CH_2)_4C^{14}$ | OH | OH | OH | — | $S(CH_2)_4C^{14}$ | O | H | 0 | 1 |
| 1253 | $K^{2-1}$ | $K^{1-1}$ | $K^{4-1}$ | — | $S(CH_2)_4C^{10}$ | OH | OH | OH | — | $S(CH_2)_4C^{10}$ | O | H | 0 | 1 |
| 1254 | $K^{1-1}$ | $K^{1-1}$ | $K^{4-1}$ | — | $SC_2H_4C^{20}$ | OH | SH | OH | — | $SC_2H_4C^{20}$ | O | H | 0 | 1 |
| 1255 | $K^{1-1}$ | $K^{1-1}$ | $K^{4-1}$ | — | $SC_2H_4C^{18}$ | OH | SH | OH | — | $SC_2H_4C^{18}$ | O | H | 0 | 1 |
| 1256 | $K^{1-1}$ | $K^{1-1}$ | $K^{4-1}$ | — | $SC_2H_4C^{14}$ | OH | SH | OH | — | $SC_2H_4C^{14}$ | O | H | 0 | 1 |
| 1257 | $K^{1-1}$ | $K^{1-1}$ | $K^{4-1}$ | — | $SC_2H_4C^{10}$ | OH | SH | OH | — | $SC_2H_4C^{10}$ | O | H | 0 | 1 |
| 1258 | $K^{1-1}$ | $K^{1-1}$ | $K^{4-1}$ | — | $S(CH_2)_3C^{20}$ | OH | SH | OH | — | $S(CH_2)_3C^{20}$ | O | H | 0 | 1 |
| 1259 | $K^{1-1}$ | $K^{1-1}$ | $K^{4-1}$ | — | $S(CH_2)_3C^{18}$ | OH | SH | OH | — | $S(CH_2)_3C^{18}$ | O | H | 0 | 1 |
| 1260 | $K^{1-1}$ | $K^{1-1}$ | $K^{4-1}$ | — | $S(CH_2)_3C^{14}$ | OH | SH | OH | — | $S(CH_2)_3C^{14}$ | O | H | 0 | 1 |
| 1261 | $K^{1-1}$ | $K^{1-1}$ | $K^{4-1}$ | — | $S(CH_2)_3C^{10}$ | OH | SH | OH | — | $S(CH_2)_3C^{10}$ | O | H | 0 | 1 |
| 1262 | $K^{1-1}$ | $K^{1-1}$ | $K^{4-1}$ | — | $S(CH_2)_4C^{20}$ | OH | SH | OH | — | $S(CH_2)_4C^{20}$ | O | H | 0 | 1 |
| 1263 | $K^{1-1}$ | $K^{1-1}$ | $K^{4-1}$ | — | $S(CH_2)_4C^{18}$ | OH | SH | OH | — | $S(CH_2)_4C^{18}$ | O | H | 0 | 1 |
| 1264 | $K^{1-1}$ | $K^{1-1}$ | $K^{4-1}$ | — | $S(CH_2)_4C^{14}$ | OH | SH | OH | — | $S(CH_2)_4C^{14}$ | O | H | 0 | 1 |
| 1265 | $K^{1-1}$ | $K^{1-1}$ | $K^{4-1}$ | — | $S(CH_2)_4C^{10}$ | OH | SH | OH | — | $S(CH_2)_4C^{10}$ | O | H | 0 | 1 |
| 1266 | $K^{2-1}$ | $K^{1-1}$ | $K^{4-3}$ | — | $SC_2H_4C^{20}$ | OH | OH | OH | — | $SC_2H_4C^{20}$ | O | H | 0 | 1 |
| 1267 | $K^{2-2}$ | $K^{1-2}$ | $K^{4-3}$ | — | $SC_2H_4C^{18}$ | OH | OH | OH | — | $SC_2H_4C^{18}$ | O | H | 0 | 1 |
| 1268 | $K^{2-3}$ | $K^{1-3}$ | $K^{4-3}$ | — | $SC_2H_4C^{14}$ | OH | OH | OH | — | $SC_2H_4C^{14}$ | O | H | 0 | 1 |
| 1269 | $K^{2-4}$ | $K^{1-4}$ | $K^{4-3}$ | — | $SC_2H_4C^{10}$ | OH | OH | OH | — | $SC_2H_4C^{10}$ | O | H | 0 | 1 |
| 1270 | $K^{2-1}$ | $K^{1-1}$ | $K^{4-3}$ | — | $S(CH_2)_3C^{20}$ | OH | OH | OH | — | $S(CH_2)_3C^{20}$ | O | H | 0 | 1 |
| 1271 | $K^{2-2}$ | $K^{1-2}$ | $K^{4-3}$ | — | $S(CH_2)_3C^{18}$ | OH | OH | OH | — | $S(CH_2)_3C^{18}$ | O | H | 0 | 1 |
| 1272 | $K^{2-3}$ | $K^{1-3}$ | $K^{4-3}$ | — | $S(CH_2)_3C^{14}$ | OH | OH | OH | — | $S(CH_2)_3C^{14}$ | O | H | 0 | 1 |
| 1273 | $K^{2-4}$ | $K^{1-4}$ | $K^{4-3}$ | — | $S(CH_2)_3C^{10}$ | OH | OH | OH | — | $S(CH_2)_3C^{10}$ | O | H | 0 | 1 |
| 1274 | $K^{2-1}$ | $K^{1-1}$ | $K^{4-3}$ | — | $S(CH_2)_4C^{20}$ | OH | OH | OH | — | $S(CH_2)_4C^{20}$ | O | H | 0 | 1 |
| 1275 | $K^{2-2}$ | $K^{1-2}$ | $K^{4-3}$ | — | $S(CH_2)_4C^{18}$ | OH | OH | OH | — | $S(CH_2)_4C^{18}$ | O | H | 0 | 1 |
| 1276 | $K^{2-3}$ | $K^{1-3}$ | $K^{4-3}$ | — | $S(CH_2)_4C^{14}$ | OH | OH | OH | — | $S(CH_2)_4C^{14}$ | O | H | 0 | 1 |
| 1277 | $K^{2-4}$ | $K^{1-4}$ | $K^{4-3}$ | — | $S(CH_2)_4C^{10}$ | OH | OH | OH | — | $S(CH_2)_4C^{10}$ | O | H | 0 | 1 |
| 1278 | $K^{1-1}$ | $K^{1-1}$ | $K^{4-3}$ | — | $SC_2H_4C^{20}$ | OH | SH | OH | — | $SC_2H_4C^{20}$ | O | H | 0 | 1 |
| 1279 | $K^{1-1}$ | $K^{1-1}$ | $K^{4-3}$ | — | $SC_2H_4C^{18}$ | OH | SH | OH | — | $SC_2H_4C^{18}$ | O | H | 0 | 1 |
| 1280 | $K^{1-1}$ | $K^{1-1}$ | $K^{4-3}$ | — | $SC_2H_4C^{14}$ | OH | SH | OH | — | $SC_2H_4C^{14}$ | O | H | 0 | 1 |
| 1281 | $K^{1-1}$ | $K^{1-1}$ | $K^{4-3}$ | — | $SC_2H_4C^{10}$ | OH | SH | OH | — | $SC_2H_4C^{10}$ | O | H | 0 | 1 |
| 1282 | $K^{1-1}$ | $K^{1-1}$ | $K^{4-3}$ | — | $S(CH_2)_3C^{20}$ | OH | SH | OH | — | $S(CH_2)_3C^{20}$ | O | H | 0 | 1 |
| 1283 | $K^{1-1}$ | $K^{1-1}$ | $K^{4-3}$ | — | $S(CH_2)_3C^{18}$ | OH | SH | OH | — | $S(CH_2)_3C^{18}$ | O | H | 0 | 1 |
| 1284 | $K^{1-1}$ | $K^{1-1}$ | $K^{4-3}$ | — | $S(CH_2)_3C^{14}$ | OH | SH | OH | — | $S(CH_2)_3C^{14}$ | O | H | 0 | 1 |
| 1285 | $K^{1-1}$ | $K^{1-1}$ | $K^{4-3}$ | — | $S(CH_2)_3C^{10}$ | OH | SH | OH | — | $S(CH_2)_3C^{10}$ | O | H | 0 | 1 |
| 1286 | $K^{1-1}$ | $K^{1-1}$ | $K^{4-3}$ | — | $S(CH_2)_4C^{20}$ | OH | SH | OH | — | $S(CH_2)_4C^{20}$ | O | H | 0 | 1 |
| 1287 | $K^{1-1}$ | $K^{1-1}$ | $K^{4-3}$ | — | $S(CH_2)_4C^{18}$ | OH | SH | OH | — | $S(CH_2)_4C^{18}$ | O | H | 0 | 1 |
| 1288 | $K^{1-1}$ | $K^{1-1}$ | $K^{4-3}$ | — | $S(CH_2)_4C^{14}$ | OH | SH | OH | — | $S(CH_2)_4C^{14}$ | O | H | 0 | 1 |
| 1289 | $K^{1-1}$ | $K^{1-1}$ | $K^{4-3}$ | — | $S(CH_2)_4C^{10}$ | OH | SH | OH | — | $S(CH_2)_4C^{10}$ | O | H | 0 | 1 |
| 1290 | $K^{2-1}$ | $K^{1-1}$ | $K^{2-1}$ | — | $SC_2H_4C^{20}$ | OH | OH | SH | — | $SC_2H_4C^{20}$ | O | H | 0 | 1 |
| 1291 | $K^{2-1}$ | $K^{1-1}$ | $K^{2-1}$ | — | $SC_2H_4C^{18}$ | OH | OH | SH | — | $SC_2H_4C^{18}$ | O | H | 0 | 1 |
| 1292 | $K^{2-1}$ | $K^{1-1}$ | $K^{2-1}$ | — | $SC_2H_4C^{14}$ | OH | OH | SH | — | $SC_2H_4C^{14}$ | O | H | 0 | 1 |
| 1293 | $K^{2-1}$ | $K^{1-1}$ | $K^{2-1}$ | — | $SC_2H_4C^{10}$ | OH | OH | SH | — | $SC_2H_4C^{10}$ | O | H | 0 | 1 |
| 1294 | $K^{2-1}$ | $K^{1-1}$ | $K^{2-1}$ | — | $S(CH_2)_3C^{20}$ | OH | OH | SH | — | $S(CH_2)_3C^{20}$ | O | H | 0 | 1 |
| 1295 | $K^{2-1}$ | $K^{1-1}$ | $K^{2-1}$ | — | $S(CH_2)_3C^{18}$ | OH | OH | SH | — | $S(CH_2)_3C^{18}$ | O | H | 0 | 1 |
| 1296 | $K^{2-1}$ | $K^{1-1}$ | $K^{2-1}$ | — | $S(CH_2)_3C^{14}$ | OH | OH | SH | — | $S(CH_2)_3C^{14}$ | O | H | 0 | 1 |
| 1297 | $K^{2-1}$ | $K^{1-1}$ | $K^{2-1}$ | — | $S(CH_2)_3C^{10}$ | OH | OH | SH | — | $S(CH_2)_3C^{10}$ | O | H | 0 | 1 |
| 1298 | $K^{2-1}$ | $K^{1-1}$ | $K^{2-1}$ | — | $S(CH_2)_4C_{20}$ | OH | OH | SH | — | $S(CH_2)_4C^{20}$ | O | H | 0 | 1 |
| 1299 | $K^{2-1}$ | $K^{1-1}$ | $K^{2-1}$ | — | $S(CH_2)_4C^{18}$ | OH | OH | SH | — | $S(CH_2)_4C^{18}$ | O | H | 0 | 1 |
| 1300 | $K^{2-1}$ | $K^{1-1}$ | $K^{2-1}$ | — | $S(CH_2)_4C^{14}$ | OH | OH | SH | — | $S(CH_2)_4C^{14}$ | O | H | 0 | 1 |
| 1301 | $K^{2-1}$ | $K^{1-1}$ | $K^{2-1}$ | — | $S(CH_2)_4C^{10}$ | OH | OH | SH | — | $S(CH_2)_4C^{10}$ | O | H | 0 | 1 |
| 1302 | $K^{1-1}$ | $K^{1-1}$ | $K^{1-1}$ | — | $SC_2H_4C^{20}$ | OH | SH | SH | — | $SC_2H_4C^{20}$ | O | H | 0 | 1 |
| 1303 | $K^{1-1}$ | $K^{1-1}$ | $K^{1-1}$ | — | $SC_2H_4C^{18}$ | OH | SH | SH | — | $SC_2H_4C^{18}$ | O | H | 0 | 1 |
| 1304 | $K^{1-1}$ | $K^{1-1}$ | $K^{1-1}$ | — | $SC_2H_4C^{14}$ | OH | SH | SH | — | $SC_2H_4C^{14}$ | O | H | 0 | 1 |
| 1305 | $K^{1-1}$ | $K^{1-1}$ | $K^{1-1}$ | — | $SC_2H_4C^{10}$ | OH | SH | SH | — | $SC_2H_4C^{10}$ | O | H | 0 | 1 |
| 1306 | $K^{1-1}$ | $K^{1-1}$ | $K^{1-1}$ | — | $S(CH_2)_3C^{20}$ | OH | SH | SH | — | $S(CH_2)_3C^{20}$ | O | H | 0 | 1 |

TABLE 1-continued $$R^1-\underset{\underset{R^2}{|}}{\overset{\overset{O}{\|}}{P}}-E^1-\underset{\underset{R^3}{|}}{\overset{\overset{O}{\|}}{P}}-E^2-\underset{\underset{R^4}{|}}{\overset{\overset{O}{\|}}{P}}-E^3-\left(\underset{\underset{R^5}{|}}{\overset{\overset{O}{\|}}{P}}-E^4\right)_m\left(\underset{\underset{R^6}{|}}{\overset{\overset{O}{\|}}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1307 | $K^{1-1}$ | $K^{1-1}$ | $K^{1-1}$ | — | $S(CH_2)_3C^{18}$ | OH | SH | SH | — | $S(CH_2)_3C^{18}$ | O | H | 0 | 1 |
| 1308 | $K^{1-1}$ | $K^{1-1}$ | $K^{1-1}$ | — | $S(CH_2)_3C^{14}$ | OH | SH | SH | — | $S(CH_2)_3C^{14}$ | O | H | 0 | 1 |
| 1309 | $K^{1-1}$ | $K^{1-1}$ | $K^{1-1}$ | — | $S(CH_2)_3C^{10}$ | OH | SH | SH | — | $S(CH_2)_3C^{10}$ | O | H | 0 | 1 |
| 1310 | $K^{1-1}$ | $K^{1-1}$ | $K^{1-1}$ | — | $S(CH_2)_4C^{20}$ | OH | SH | SH | — | $S(CH_2)_4C^{20}$ | O | H | 0 | 1 |
| 1311 | $K^{1-1}$ | $K^{1-1}$ | $K^{1-1}$ | — | $S(CH_2)_4C^{18}$ | OH | SH | SH | — | $S(CH_2)_4C^{18}$ | O | H | 0 | 1 |
| 1312 | $K^{1-1}$ | $K^{1-1}$ | $K^{1-1}$ | — | $S(CH_2)_4C^{14}$ | OH | SH | SH | — | $S(CH_2)_4C^{14}$ | O | H | 0 | 1 |
| 1313 | $K^{1-1}$ | $K^{1-1}$ | $K^{1-1}$ | — | $S(CH_2)_4C^{10}$ | OH | SH | SH | — | $S(CH_2)_4C^{10}$ | O | H | 0 | 1 |
| 1314 | $K^{1-1}$ | $K^{1-1}$ | $K^{1-1}$ | $K^{1-1}$ | $SC_2H_4C^{20}$ | OH | SH | SH | SH | $SC_2H_4C^{20}$ | O | H | 1 | 1 |
| 1315 | $K^{1-1}$ | $K^{1-1}$ | $K^{1-1}$ | $K^{1-1}$ | $SC_2H_4C^{18}$ | OH | SH | SH | SH | $SC_2H_4C^{18}$ | O | H | 1 | 1 |
| 1316 | $K^{1-1}$ | $K^{1-1}$ | $K^{1-1}$ | $K^{1-1}$ | $SC_2H_4C^{14}$ | OH | SH | SH | SH | $SC_2H_4C^{14}$ | O | H | 1 | 1 |
| 1317 | $K^{1-1}$ | $K^{1-1}$ | $K^{1-1}$ | $K^{1-1}$ | $SC_2H_4C^{10}$ | OH | SH | SH | SH | $SC_2H_4C^{10}$ | O | H | 1 | 1 |
| 1318 | $K^{1-1}$ | $K^{1-1}$ | $K^{1-1}$ | $K^{1-1}$ | $S(CH_2)_3C^{20}$ | OH | SH | SH | SH | $S(CH_2)_3C^{20}$ | O | H | 1 | 1 |
| 1319 | $K^{1-1}$ | $K^{1-1}$ | $K^{1-1}$ | $K^{1-1}$ | $S(CH_2)_3C^{18}$ | OH | SH | SH | SH | $S(CH_2)_3C^{18}$ | O | H | 1 | 1 |
| 1320 | $K^{1-1}$ | $K^{1-1}$ | $K^{1-1}$ | $K^{1-1}$ | $S(CH_2)_3C^{14}$ | OH | SH | SH | SH | $S(CH_2)_3C^{14}$ | O | H | 1 | 1 |
| 1321 | $K^{1-1}$ | $K^{1-1}$ | $K^{1-1}$ | $K^{1-1}$ | $S(CH_2)_3C^{10}$ | OH | SH | SH | SH | $S(CH_2)_3C^{10}$ | O | H | 1 | 1 |
| 1322 | $K^{1-1}$ | $K^{1-1}$ | $K^{1-1}$ | $K^{1-1}$ | $S(CH_2)_4C^{20}$ | OH | SH | SH | SH | $S(CH_2)_4C^{20}$ | O | H | 1 | 1 |
| 1323 | $K^{1-1}$ | $K^{1-1}$ | $K^{1-1}$ | $K^{1-1}$ | $S(CH_2)_4C^{18}$ | OH | SH | SH | SH | $S(CH_2)_4C^{18}$ | O | H | 1 | 1 |
| 1324 | $K^{1-1}$ | $K^{1-1}$ | $K^{1-1}$ | $K^{1-1}$ | $S(CH_2)_4C^{14}$ | OH | SH | SH | SH | $S(CH_2)_4C^{14}$ | O | H | 1 | 1 |
| 1325 | $K^{1-1}$ | $K^{1-1}$ | $K^{1-1}$ | $K^{1-1}$ | $S(CH_2)_4C^{10}$ | OH | SH | SH | SH | $S(CH_2)_4C^{10}$ | O | H | 1 | 1 |
| 1326 | $K^{2-1}$ | $K^{1-1}$ | $K^{3-2}$ | $K^{1-1}$ | $SC_2H_4C^{20}$ | OH | OH | OH | — | — | — | H | 0 | 0 |
| 1327 | $K^{2-1}$ | $K^{1-1}$ | $K^{3-2}$ | — | $SC_2H_4C^{18}$ | OH | OH | OH | — | — | — | H | 0 | 0 |
| 1328 | $K^{1-1}$ | $K^{1-1}$ | $K^{3-2}$ | — | $SC_2H_4C^{20}$ | OH | SH | OH | — | — | — | H | 0 | 0 |
| 1329 | $K^{1-1}$ | $K^{1-1}$ | $K^{3-2}$ | — | $SC_2H_4C^{18}$ | OH | SH | OH | — | — | — | H | 0 | 0 |
| 1330 | $K^{2-1}$ | $K^{1-1}$ | $K^{4-2}$ | — | $SC_2H_4C^{20}$ | OH | OH | OH | — | — | — | H | 0 | 0 |
| 1331 | $K^{2-1}$ | $K^{1-1}$ | $K^{4-2}$ | — | $SC_2H_4C^{18}$ | OH | OH | OH | — | — | — | H | 0 | 0 |
| 1332 | $K^{1-1}$ | $K^{1-1}$ | $K^{4-2}$ | — | $SC_2H_4C^{20}$ | OH | SH | OH | — | — | — | H | 0 | 0 |
| 1333 | $K^{1-1}$ | $K^{1-1}$ | $K^{4-2}$ | — | $SC_2H_4C^{18}$ | OH | SH | OH | — | — | — | H | 0 | 0 |
| 1334 | $K^{2-1}$ | $K^{1-1}$ | $K^{4-4}$ | — | $SC_2H_4C^{20}$ | OH | OH | OH | — | — | — | H | 0 | 0 |
| 1335 | $K^{2-1}$ | $K^{1-1}$ | $K^{4-4}$ | — | $SC_2H_4C^{18}$ | OH | OH | OH | — | — | — | H | 0 | 0 |
| 1336 | $K^{1-1}$ | $K^{1-1}$ | $K^{4-4}$ | — | $SC_2H_4C^{20}$ | OH | SH | OH | — | — | — | H | 0 | 0 |
| 1337 | $K^{1-1}$ | $K^{1-1}$ | $K^{4-4}$ | — | $SC_2H_4C^{18}$ | OH | SH | OH | — | — | — | H | 0 | 0 |
| 1338 | $K^{2-1}$ | $K^{1-1}$ | $K^{2-2}$ | — | $SC_2H_4C^{20}$ | OH | OH | SH | — | — | — | H | 0 | 0 |
| 1339 | $K^{2-1}$ | $K^{1-1}$ | $K^{2-2}$ | — | $SC_2H_4C^{18}$ | OH | OH | SH | — | — | — | H | 0 | 0 |
| 1340 | $K^{1-1}$ | $K^{1-1}$ | $K^{1-2}$ | — | $SC_2H_4C^{20}$ | OH | SH | SH | — | — | — | H | 0 | 0 |
| 1341 | $K^{1-1}$ | $K^{1-1}$ | $K^{1-2}$ | — | $SC_2H_4C^{18}$ | OH | SH | SH | — | — | — | H | 0 | 0 |
| 1342 | $K^{1-1}$ | $K^{1-1}$ | $K^{1-2}$ | $K^{1-1}$ | $SC_2H_4C^{20}$ | OH | SH | SH | SH | — | — | H | 1 | 0 |
| 1343 | $K^{1-1}$ | $K^{1-1}$ | $K^{1-2}$ | $K^{1-1}$ | $SC_2H_4C^{18}$ | OH | SH | SH | SH | — | — | H | 1 | 0 |
| 1344 | $K^{2-1}$ | $K^{1-1}$ | $K^{3-2}$ | — | $OC_2H_4OH$ | OH | OH | OH | — | $SC_2H_4C^{20}$ | O | H | 0 | 1 |
| 1345 | $K^{2-1}$ | $K^{1-1}$ | $K^{3-2}$ | — | $OC_2H_4OH$ | OH | OH | OH | — | $SC_2H_4C^{18}$ | O | H | 0 | 1 |
| 1346 | $K^{1-1}$ | $K^{1-1}$ | $K^{3-2}$ | — | $OC_2H_4OH$ | OH | SH | OH | — | $SC_2H_4C^{20}$ | O | H | 0 | 1 |
| 1347 | $K^{1-1}$ | $K^{1-1}$ | $K^{3-2}$ | — | $OC_2H_4OH$ | OH | SH | OH | — | $SC_2H_4C^{18}$ | O | H | 0 | 1 |
| 1348 | $K^{2-1}$ | $K^{1-1}$ | $K^{4-2}$ | — | $OC_2H_4OH$ | OH | OH | OH | — | $SC_2H_4C^{20}$ | O | H | 0 | 1 |
| 1349 | $K^{2-1}$ | $K^{1-1}$ | $K^{4-2}$ | — | $OC_2H_4OH$ | OH | OH | OH | — | $SC_2H_4C^{18}$ | O | H | 0 | 1 |
| 1350 | $K^{1-1}$ | $K^{1-1}$ | $K^{4-2}$ | — | $OC_2H_4OH$ | OH | SH | OH | — | $SC_2H_4C^{20}$ | O | H | 0 | 1 |
| 1351 | $K^{1-1}$ | $K^{1-1}$ | $K^{4-2}$ | — | $OC_2H_4OH$ | OH | SH | OH | — | $SC_2H_4C^{18}$ | O | H | 0 | 1 |
| 1352 | $K^{2-1}$ | $K^{1-1}$ | $K^{4-4}$ | — | $OC_2H_4OH$ | OH | OH | OH | — | $SC_2H_4C^{20}$ | O | H | 0 | 1 |
| 1353 | $K^{2-1}$ | $K^{1-2}$ | $K^{4-4}$ | — | $OC_2H_4OH$ | OH | OH | OH | — | $SC_2H_4C^{18}$ | O | H | 0 | 1 |
| 1354 | $K^{1-1}$ | $K^{1-1}$ | $K^{4-4}$ | — | $OC_2H_4OH$ | OH | SH | OH | — | $SC_2H_4C^{20}$ | O | H | 0 | 1 |
| 1355 | $K^{1-1}$ | $K^{1-1}$ | $K^{4-4}$ | — | $OC_2H_4OH$ | OH | SH | OH | — | $SC_2H_4C^{18}$ | O | H | 0 | 1 |
| 1356 | $K^{2-1}$ | $K^{1-1}$ | $K^{2-2}$ | — | $OC_2H_4OH$ | OH | OH | SH | — | $SC_2H_4C^{20}$ | O | H | 0 | 1 |
| 1357 | $K^{2-1}$ | $K^{1-1}$ | $K^{2-2}$ | — | $OC_2H_4OH$ | OH | OH | SH | — | $SC_2H_4C^{18}$ | O | H | 0 | 1 |
| 1358 | $K^{1-1}$ | $K^{1-1}$ | $K^{1-2}$ | — | $OC_2H_4OH$ | OH | SH | SH | — | $SC_2H_4C^{20}$ | O | H | 0 | 1 |
| 1359 | $K^{1-1}$ | $K^{1-1}$ | $K^{1-2}$ | — | $OC_2H_4OH$ | OH | SH | SH | — | $SC_2H_4C^{18}$ | O | H | 0 | 1 |
| 1360 | $K^{1-1}$ | $K^{1-1}$ | $K^{1-2}$ | $K^{1-1}$ | $OC_2H_4OH$ | OH | SH | SH | SH | $SC_2H_4C^{20}$ | O | H | 1 | 1 |
| 1361 | $K^{1-1}$ | $K^{1-1}$ | $K^{1-2}$ | $K^{1-1}$ | $OC_2H_4OH$ | OH | SH | SH | SH | $SC_2H_4C^{18}$ | O | H | 1 | 1 |
| 1362 | $K^{1-1}$ | $K^{1-1}$ | $K^{3-1}$ | — | $OC_2H_4OH$ | OH | OH | OH | — | — | — | H | 0 | 0 |
| 1363 | $K^{2-1}$ | $K^{1-1}$ | $K^{3-1}$ | — | $OC_2H_4OH$ | OH | SH | OH | — | — | — | H | 0 | 0 |
| 1364 | $K^{1-1}$ | $K^{1-1}$ | $K^{4-1}$ | — | $OC_2H_4OH$ | OH | OH | OH | — | — | — | H | 0 | 0 |
| 1365 | $K^{2-1}$ | $K^{1-1}$ | $K^{4-1}$ | — | $OC_2H_4OH$ | OH | SH | OH | — | — | — | H | 0 | 0 |
| 1366 | $K^{1-1}$ | $K^{1-1}$ | $K^{4-3}$ | — | $OC_2H_4OH$ | OH | OH | OH | — | — | — | H | 0 | 0 |
| 1367 | $K^{2-1}$ | $K^{1-1}$ | $K^{4-3}$ | — | $OC_2H_4OH$ | OH | SH | OH | — | — | — | H | 0 | 0 |
| 1368 | $K^{1-1}$ | $K^{1-1}$ | $K^{2-1}$ | — | $OC_2H_4OH$ | OH | OH | SH | — | — | — | H | 0 | 0 |
| 1369 | $K^{2-1}$ | $K^{1-1}$ | $K^{3-1}$ | — | $SC_2H_4OH$ | OH | OH | OH | — | — | — | H | 0 | 0 |
| 1370 | $K^{2-1}$ | $K^{1-1}$ | $K^{3-1}$ | — | $SC_2H_4OH$ | OH | SH | OH | — | — | — | H | 0 | 0 |
| 1371 | $K^{1-1}$ | $K^{1-1}$ | $K^{3-1}$ | — | $SC_2H_4OH$ | OH | SH | OH | — | — | — | H | 0 | 0 |
| 1372 | $K^{2-1}$ | $K^{1-1}$ | $K^{4-1}$ | — | $SC_2H_4OH$ | OH | OH | OH | — | — | — | H | 0 | 0 |
| 1373 | $K^{1-1}$ | $K^{1-1}$ | $K^{4-1}$ | — | $SC_2H_4OH$ | OH | SH | OH | — | — | — | H | 0 | 0 |
| 1374 | $K^{2-1}$ | $K^{1-1}$ | $K^{4-3}$ | — | $SC_2H_4OH$ | OH | OH | OH | — | — | — | H | 0 | 0 |

TABLE 1-continued $$R^1-\overset{\overset{O}{\|}}{\underset{R^2}{P}}-E^1-\overset{\overset{O}{\|}}{\underset{R^3}{P}}-E^2-\overset{\overset{O}{\|}}{\underset{R^4}{P}}-E^3-\left(\overset{\overset{O}{\|}}{\underset{R^5}{P}}-E^4\right)_m\left(\overset{\overset{O}{\|}}{\underset{R^6}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1375 | $K^{1-1}$ | $K^{1-1}$ | $K^{4-3}$ | — | $SC_2H_4OH$ | OH | SH | OH | — | — | — | H | 0 | 0 |
| 1376 | $K^{2-1}$ | $K^{1-1}$ | $K^{2-1}$ | — | $SC_2H_4OH$ | OH | OH | SH | — | — | — | H | 0 | 0 |
| 1377 | $K^{2-1}$ | $K^{1-1}$ | $K^{3-1}$ | — | $S(CH_2)_3OH$ | OH | OH | OH | — | — | — | H | 0 | 0 |
| 1378 | $K^{2-1}$ | $K^{1-1}$ | $K^{3-1}$ | — | $S(CH_2)_3OH$ | OH | SH | OH | — | — | — | H | 0 | 0 |
| 1379 | $K^{1-1}$ | $K^{1-1}$ | $K^{3-1}$ | — | $S(CH_2)_3OH$ | OH | SH | OH | — | — | — | H | 0 | 0 |
| 1380 | $K^{2-1}$ | $K^{1-1}$ | $K^{4-1}$ | — | $S(CH_2)_3OH$ | OH | OH | OH | — | — | — | H | 0 | 0 |
| 1381 | $K^{2-1}$ | $K^{1-1}$ | $K^{4-1}$ | — | $S(CH_2)_3OH$ | OH | SH | OH | — | — | — | H | 0 | 0 |
| 1382 | $K^{2-1}$ | $K^{1-1}$ | $K^{4-3}$ | — | $S(CH_2)_3OH$ | OH | OH | OH | — | — | — | H | 0 | 0 |
| 1383 | $K^{1-1}$ | $K^{1-1}$ | $K^{4-3}$ | — | $S(CH_2)_3OH$ | OH | SH | OH | — | — | — | H | 0 | 0 |
| 1384 | $K^{2-1}$ | $K^{1-1}$ | $K^{2-1}$ | — | $S(CH_2)_3OH$ | OH | OH | SH | — | — | — | H | 0 | 0 |
| 1385 | $K^{2-1}$ | $K^{1-1}$ | $K^{3-1}$ | — | $S(CH_2)_4OH$ | OH | OH | OH | — | — | — | H | 0 | 0 |
| 1386 | $K^{2-1}$ | $K^{1-1}$ | $K^{3-1}$ | — | $S(CH_2)_4OH$ | OH | SH | OH | — | — | — | H | 0 | 0 |
| 1387 | $K^{1-1}$ | $K^{1-1}$ | $K^{3-1}$ | — | $S(CH_2)_4OH$ | OH | SH | OH | — | — | — | H | 0 | 0 |
| 1388 | $K^{2-1}$ | $K^{1-1}$ | $K^{4-1}$ | — | $S(CH_2)_4OH$ | OH | OH | OH | — | — | — | H | 0 | 0 |
| 1389 | $K^{2-1}$ | $K^{1-1}$ | $K^{4-1}$ | — | $S(CH_2)_4OH$ | OH | SH | OH | — | — | — | H | 0 | 0 |
| 1390 | $K^{2-1}$ | $K^{1-1}$ | $K^{4-3}$ | — | $S(CH_2)_4OH$ | OH | OH | OH | — | — | — | H | 0 | 0 |
| 1391 | $K^{1-1}$ | $K^{1-1}$ | $K^{4-3}$ | — | $S(CH_2)_4OH$ | OH | SH | OH | — | — | — | H | 0 | 0 |
| 1392 | $K^{2-1}$ | $K^{1-1}$ | $K^{2-1}$ | — | $S(CH_2)_4OH$ | OH | OH | SH | — | — | — | H | 0 | 0 |
| 1393 | $K^{2-1}$ | $K^{1-1}$ | $K^{3-1}$ | — | $SC_2H_4OH$ | OH | OH | OH | — | $SC_2H_4OH$ | O | H | 0 | 1 |
| 1394 | $K^{2-1}$ | $K^{1-1}$ | $K^{3-1}$ | — | $OC_2H_4OH$ | OH | OH | OH | — | $SC_2H_4OH$ | O | H | 0 | 1 |
| 1395 | $K^{2-1}$ | $K^{1-1}$ | $K^{3-1}$ | — | $O(CH_2)_3OH$ | OH | OH | OH | — | $S(CH_2)_3OH$ | O | H | 0 | 1 |
| 1396 | $K^{2-1}$ | $K^{1-1}$ | $K^{3-1}$ | — | $O(CH_2)_4OH$ | OH | OH | OH | — | $S(CH_2)_4OH$ | O | H | 0 | 1 |
| 1397 | $K^{1-1}$ | $K^{1-1}$ | $K^{3-1}$ | — | $SC_2H_4OH$ | OH | SH | OH | — | $SC_2H_4OH$ | O | H | 0 | 1 |
| 1398 | $K^{1-1}$ | $K^{1-1}$ | $K^{3-1}$ | — | $OC_2H_4OH$ | OH | SH | OH | — | $SC_2H_4OH$ | O | H | 0 | 1 |
| 1399 | $K^{1-1}$ | $K^{1-1}$ | $K^{3-1}$ | — | $O(CH_2)_3OH$ | OH | SH | OH | — | $S(CH_2)_3OH$ | O | H | 0 | 1 |
| 1400 | $K^{1-1}$ | $K^{1-1}$ | $K^{3-1}$ | — | $O(CH_2)_4OH$ | OH | SH | OH | — | $S(CH_2)_4OH$ | O | H | 0 | 1 |
| 1401 | $K^{2-1}$ | $K^{1-1}$ | $K^{4-1}$ | — | $SC_2H_4OH$ | OH | OH | OH | — | $SC_2H_4OH$ | O | H | 0 | 1 |
| 1402 | $K^{2-1}$ | $K^{1-1}$ | $K^{4-1}$ | — | $OC_2H_4OH$ | OH | OH | OH | — | $SC_2H_4OH$ | O | H | 0 | 1 |
| 1403 | $K^{2-1}$ | $K^{1-1}$ | $K^{4-1}$ | — | $O(CH_2)_3OH$ | OH | OH | OH | — | $S(CH_2)_3OH$ | O | H | 0 | 1 |
| 1404 | $K^{2-1}$ | $K^{1-1}$ | $K^{4-1}$ | — | $O(CH_2)_4OH$ | OH | OH | OH | — | $S(CH_2)_4OH$ | O | H | 0 | 1 |
| 1405 | $K^{1-1}$ | $K^{1-1}$ | $K^{4-1}$ | — | $SC_2H_4OH$ | OH | SH | OH | — | $SC_2H_4OH$ | O | H | 0 | 1 |
| 1406 | $K^{1-1}$ | $K^{1-1}$ | $K^{4-1}$ | — | $OC_2H_4OH$ | OH | SH | OH | — | $SC_2H_4OH$ | O | H | 0 | 1 |
| 1407 | $K^{1-1}$ | $K^{1-1}$ | $K^{4-1}$ | — | $O(CH_2)_3OH$ | OH | SH | OH | — | $S(CH_2)_3OH$ | O | H | 0 | 1 |
| 1408 | $K^{1-1}$ | $K^{1-1}$ | $K^{4-1}$ | — | $O(CH_2)_4OH$ | OH | SH | OH | — | $S(CH_2)_4OH$ | O | H | 0 | 1 |
| 1409 | $K^{2-1}$ | $K^{1-1}$ | $K^{4-3}$ | — | $SC_2H_4OH$ | OH | OH | OH | — | $SC_2H_4OH$ | O | H | 0 | 1 |
| 1410 | $K^{2-1}$ | $K^{1-1}$ | $K^{4-3}$ | — | $OC_2H_4OH$ | OH | OH | OH | — | $SC_2H_4OH$ | O | H | 0 | 1 |
| 1411 | $K^{2-1}$ | $K^{1-1}$ | $K^{4-3}$ | — | $O(CH_2)_3OH$ | OH | OH | OH | — | $S(CH_2)_3OH$ | O | H | 0 | 1 |
| 1412 | $K^{2-1}$ | $K^{1-1}$ | $K^{4-3}$ | — | $O(CH_2)_4OH$ | OH | OH | OH | — | $S(CH_2)_4OH$ | O | H | 0 | 1 |
| 1413 | $K^{1-1}$ | $K^{1-1}$ | $K^{4-3}$ | — | $SC_2H_4OH$ | OH | SH | OH | — | $SC_2H_4OH$ | O | H | 0 | 1 |
| 1414 | $K^{1-1}$ | $K^{1-1}$ | $K^{4-3}$ | — | $OC_2H_4OH$ | OH | SH | OH | — | $SC_2H_4OH$ | O | H | 0 | 1 |
| 1415 | $K^{1-1}$ | $K^{1-1}$ | $K^{4-3}$ | — | $O(CH_2)_3OH$ | OH | SH | OH | — | $S(CH_2)_3OH$ | O | H | 0 | 1 |
| 1416 | $K^{1-1}$ | $K^{1-1}$ | $K^{4-3}$ | — | $O(CH_2)_4OH$ | OH | SH | OH | — | $S(CH_2)_4OH$ | O | H | 0 | 1 |
| 1417 | $K^{2-1}$ | $K^{1-1}$ | $K^{2-1}$ | — | $SC_2H_4OH$ | OH | OH | SH | — | $SC_2H_4OH$ | O | H | 0 | 1 |
| 1418 | $K^{2-1}$ | $K^{1-1}$ | $K^{2-1}$ | — | $OC_2H_4OH$ | OH | OH | SH | — | $SC_2H_4OH$ | O | H | 0 | 1 |
| 1419 | $K^{2-1}$ | $K^{1-1}$ | $K^{2-1}$ | — | $O(CH_2)_3OH$ | OH | OH | SH | — | $S(CH_2)_3OH$ | O | H | 0 | 1 |
| 1420 | $K^{2-1}$ | $K^{1-1}$ | $K^{2-1}$ | — | $O(CH_2)_4OH$ | OH | OH | SH | — | $S(CH_2)_4OH$ | O | H | 0 | 1 |
| 1421 | $K^{1-1}$ | $K^{1-1}$ | $K^{1-1}$ | — | $SC_2H_4OH$ | OH | SH | SH | — | $SC_2H_4OH$ | O | H | 0 | 1 |
| 1422 | $K^{1-1}$ | $K^{1-1}$ | $K^{1-1}$ | — | $OC_2H_4OH$ | OH | SH | SH | — | $SC_2H_4OH$ | O | H | 0 | 1 |
| 1423 | $K^{1-1}$ | $K^{1-1}$ | $K^{1-1}$ | — | $O(CH_2)_3OH$ | OH | SH | SH | — | $S(CH_2)_3OH$ | O | H | 0 | 1 |
| 1424 | $K^{1-1}$ | $K^{1-1}$ | $K^{1-1}$ | — | $O(CH_2)_4OH$ | OH | SH | SH | — | $S(CH_2)_4OH$ | O | H | 0 | 1 |
| 1425 | $K^{1-1}$ | $K^{1-1}$ | $K^{1-1}$ | $K^{1-1}$ | $SC_2H_4OH$ | OH | SH | SH | SH | $SC_2H_4OH$ | O | H | 1 | 1 |
| 1426 | $K^{1-1}$ | $K^{1-1}$ | $K^{1-1}$ | $K^{1-1}$ | $OC_2H_4OH$ | OH | SH | SH | SH | $SC_2H_4OH$ | O | H | 1 | 1 |
| 1427 | $K^{1-1}$ | $K^{1-1}$ | $K^{1-1}$ | $K^{1-1}$ | $O(CH_2)_3OH$ | OH | SH | SH | SH | $S(CH_2)_3OH$ | O | H | 1 | 1 |
| 1428 | $K^{1-1}$ | $K^{1-1}$ | $K^{1-1}$ | $K^{1-1}$ | $O(CH_2)_4OH$ | OH | SH | SH | SH | $S(CH_2)_4OH$ | O | H | 1 | 1 |
| 1429 | $K^{2-1}$ | $K^{1-1}$ | $K^{3-1}$ | — | $OC_2H_4OH$ | OH | OH | OH | — | OH | $L^1$ | $ON^{1-6}$ | 0 | 2 |
| 1430 | $K^{1-1}$ | $K^{1-1}$ | $K^{1-1}$ | — | $OC_2H_4OH$ | SH | SH | OH | — | OH | $L^1$ | $ON^{1-6}$ | 0 | 2 |
| 1431 | $K^{1-1}$ | $K^{1-1}$ | $K^{1-1}$ | — | $OC_2H_4OH$ | SH | SH | SH | — | OH | $L^1$ | $ON^{1-6}$ | 0 | 2 |
| 1432 | $K^{1-1}$ | $K^{1-1}$ | $K^{1-1}$ | $K^{1-1}$ | $OC_2H_4OH$ | OH | SH | SH | SH | OH | $L^1$ | $ON^{1-6}$ | 1 | 2 |
| 1433 | $K^{1-1}$ | $K^{1-1}$ | $K^{1-1}$ | — | OH | SH | SH | SH | — | OH | $L^1$ | $ON^{1-6}$ | 0 | 2 |
| 1434 | $K^{2-1}$ | $K^{1-1}$ | $K^{3-1}$ | — | $OC_2H_4OH$ | OH | OH | OH | — | OH | $L^2$ | $ON^{1-6}$ | 0 | 1 |
| 1435 | $K^{1-1}$ | $K^{1-1}$ | $K^{1-1}$ | — | $OC_2H_4OH$ | OH | SH | SH | — | OH | $L^2$ | $ON^{1-6}$ | 0 | 1 |
| 1436 | $K^{1-1}$ | $K^{1-1}$ | $K^{1-1}$ | — | $OC_2H_4OH$ | SH | SH | SH | — | OH | $L^2$ | $ON^{1-6}$ | 0 | 1 |
| 1437 | $K^{1-1}$ | $K^{1-1}$ | $K^{1-1}$ | $K^{1-1}$ | $OC_2H_4OH$ | OH | SH | SH | SH | OH | $L^2$ | $ON^{1-6}$ | 1 | 1 |
| 1438 | $K^{1-1}$ | $K^{1-1}$ | $K^{1-1}$ | — | OH | SH | SH | SH | — | OH | $L^2$ | $ON^{1-6}$ | 0 | 1 |
| 1439 | $K^{2-1}$ | $K^{1-1}$ | $K^{3-1}$ | — | $OC_2H_4OH$ | OH | OH | OH | — | OH | $L^1$ | $ON^{1-7}$ | 0 | 2 |
| 1440 | $K^{1-1}$ | $K^{1-1}$ | $K^{1-1}$ | — | $OC_2H_4OH$ | OH | SH | SH | — | OH | $L^1$ | $ON^{1-7}$ | 0 | 2 |
| 1441 | $K^{1-1}$ | $K^{1-1}$ | $K^{1-1}$ | — | $OC_2H_4OH$ | SH | SH | SH | — | OH | $L^1$ | $ON^{1-7}$ | 0 | 2 |
| 1442 | $K^{1-1}$ | $K^{1-1}$ | $K^{1-1}$ | $K^{1-1}$ | $OC_2H_4OH$ | OH | SH | SH | SH | OH | $L^1$ | $ON^{1-7}$ | 1 | 2 |

TABLE 1-continued

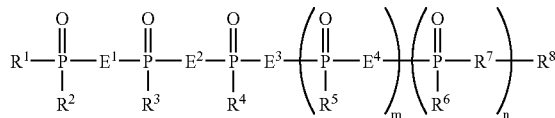

| Exemplified Compound No. | E$^1$ | E$^2$ | E$^3$ | E$^4$ | R$^1$ | R$^2$ | R$^3$ | R$^4$ | R$^5$ | R$^6$ | R$^7$ | R$^8$ | m | n |
|---|---|---|---|---|---|---|---|---|---|---|---|---|---|---|
| 1443 | K$^{1-1}$ | K$^{1-1}$ | K$^{1-1}$ | — | OH | SH | SH | SH | — | OH | L$^1$ | ON$^{1-7}$ | 0 | 2 |
| 1444 | K$^{2-1}$ | K$^{1-1}$ | K$^{3-1}$ | — | OC$_2$H$_4$OH | OH | OH | OH | — | OH | L$^2$ | ON$^{1-7}$ | 0 | 1 |
| 1445 | K$^{1-1}$ | K$^{1-1}$ | K$^{1-1}$ | — | OC$_2$H$_4$OH | OH | SH | SH | — | OH | L$^2$ | ON$^{1-7}$ | 0 | 1 |
| 1446 | K$^{1-1}$ | K$^{1-1}$ | K$^{1-1}$ | — | OC$_2$H$_4$OH | SH | SH | SH | — | OH | L$^2$ | ON$^{1-7}$ | 0 | 1 |
| 1447 | K$^{1-1}$ | K$^{1-1}$ | K$^{1-1}$ | K$^{1-1}$ | OC$_2$H$_4$OH | OH | SH | SH | SH | OH | L$^2$ | ON$^{1-7}$ | 1 | 1 |
| 1448 | K$^{1-1}$ | K$^{1-1}$ | K$^{1-1}$ | — | OH | SH | SH | SH | — | OH | L$^2$ | ON$^{1-7}$ | 0 | 1 |
| 1449 | K$^{2-1}$ | K$^{1-1}$ | K$^{3-1}$ | — | OC$_2$H$_4$OH | OH | OH | OH | — | OH | L$^1$ | ON$^{2-6}$ | 0 | 2 |
| 1450 | K$^{1-1}$ | K$^{1-1}$ | K$^{1-1}$ | — | OC$_2$H$_4$OH | OH | SH | SH | — | OH | L$^1$ | ON$^{2-6}$ | 0 | 2 |
| 1451 | K$^{1-1}$ | K$^{1-1}$ | K$^{1-1}$ | — | OC$_2$H$_4$OH | SH | SH | SH | — | OH | L$^1$ | ON$^{2-6}$ | 0 | 2 |
| 1452 | K$^{1-1}$ | K$^{1-1}$ | K$^{1-1}$ | K$^{1-1}$ | OC$_2$H$_4$OH | OH | SH | SH | SH | OH | L$^1$ | ON$^{2-6}$ | 1 | 2 |
| 1453 | K$^{1-1}$ | K$^{1-1}$ | K$^{1-1}$ | — | OH | SH | SH | SH | — | OH | L$^1$ | ON$^{2-6}$ | 0 | 2 |
| 1454 | K$^{2-1}$ | K$^{1-1}$ | K$^{3-1}$ | — | OC$_2$H$_4$OH | OH | OH | OH | — | OH | L$^2$ | ON$^{2-6}$ | 0 | 1 |
| 1455 | K$^{1-1}$ | K$^{1-1}$ | K$^{1-1}$ | — | OC$_2$H$_4$OH | OH | SH | SH | — | OH | L$^2$ | ON$^{2-6}$ | 0 | 1 |
| 1456 | K$^{1-1}$ | K$^{1-1}$ | K$^{1-1}$ | — | OC$_2$H$_4$OH | SH | SH | SH | — | OH | L$^2$ | ON$^{2-6}$ | 0 | 1 |
| 1457 | K$^{1-1}$ | K$^{1-1}$ | K$^{1-1}$ | K$^{1-1}$ | OC$_2$H$_4$OH | OH | SH | SH | SH | OH | L$^2$ | ON$^{2-6}$ | 1 | 1 |
| 1458 | K$^{1-1}$ | K$^{1-1}$ | K$^{1-1}$ | — | OH | SH | SH | SH | — | OH | L$^2$ | ON$^{2-6}$ | 0 | 1 |
| 1459 | K$^{2-1}$ | K$^{1-1}$ | K$^{3-1}$ | — | OC$_2$H$_4$OH | OH | OH | OH | — | OH | L$^1$ | ON$^{2-7}$ | 0 | 2 |
| 1460 | K$^{1-1}$ | K$^{1-1}$ | K$^{1-1}$ | — | OC$_2$H$_4$OH | OH | SH | SH | — | OH | L$^1$ | ON$^{2-7}$ | 0 | 2 |
| 1461 | K$^{1-1}$ | K$^{1-1}$ | K$^{1-1}$ | — | OC$_2$H$_4$OH | SH | SH | SH | — | OH | L$^1$ | ON$^{2-7}$ | 0 | 2 |
| 1462 | K$^{1-1}$ | K$^{1-1}$ | K$^{1-1}$ | K$^{1-1}$ | OC$_2$H$_4$OH | OH | SH | SH | SH | OH | L$^1$ | ON$^{2-7}$ | 1 | 2 |
| 1463 | K$^{1-1}$ | K$^{1-1}$ | K$^{1-1}$ | — | OH | SH | SH | SH | — | OH | L$^1$ | ON$^{2-7}$ | 0 | 2 |
| 1464 | K$^{2-1}$ | K$^{1-1}$ | K$^{3-1}$ | — | OC$_2$H$_4$OH | OH | OH | OH | — | OH | L$^2$ | ON$^{2-7}$ | 0 | 1 |
| 1465 | K$^{1-1}$ | K$^{1-1}$ | K$^{1-1}$ | — | OC$_2$H$_4$OH | OH | SH | SH | — | OH | L$^2$ | ON$^{2-7}$ | 0 | 1 |
| 1466 | K$^{1-1}$ | K$^{1-1}$ | K$^{1-1}$ | — | OC$_2$H$_4$OH | SH | SH | SH | — | OH | L$^2$ | ON$^{2-7}$ | 0 | 1 |
| 1467 | K$^{1-1}$ | K$^{1-1}$ | K$^{1-1}$ | K$^{1-1}$ | OC$_2$H$_4$OH | OH | SH | SH | SH | OH | L$^2$ | ON$^{2-7}$ | 1 | 1 |
| 1468 | K$^{1-1}$ | K$^{1-1}$ | K$^{1-1}$ | — | OH | SH | SH | SH | — | OH | L$^2$ | ON$^{2-7}$ | 0 | 1 |
| 1469 | K$^{2-1}$ | K$^{1-1}$ | K$^{3-1}$ | — | OC$_2$H$_4$OH | OH | OH | OH | — | OH | L$^1$ | ON$^{3-6}$ | 0 | 2 |
| 1470 | K$^{1-1}$ | K$^{1-1}$ | K$^{1-1}$ | — | OC$_2$H$_4$OH | OH | SH | SH | — | OH | L$^1$ | ON$^{3-6}$ | 0 | 2 |
| 1471 | K$^{1-1}$ | K$^{1-1}$ | K$^{1-1}$ | — | OC$_2$H$_4$OH | SH | SH | SH | — | OH | L$^1$ | ON$^{3-6}$ | 0 | 2 |
| 1472 | K$^{1-1}$ | K$^{1-1}$ | K$^{1-1}$ | K$^{1-1}$ | OC$_2$H$_4$OH | OH | SH | SH | SH | OH | L$^1$ | ON$^{3-6}$ | 1 | 2 |
| 1473 | K$^{1-1}$ | K$^{1-1}$ | K$^{1-1}$ | — | OH | SH | SH | SH | — | OH | L$^1$ | ON$^{3-6}$ | 0 | 2 |
| 1474 | K$^{2-1}$ | K$^{1-1}$ | K$^{3-1}$ | — | OC$_2$H$_4$OH | OH | OH | OH | — | OH | L$^2$ | ON$^{3-6}$ | 0 | 1 |
| 1475 | K$^{1-1}$ | K$^{1-1}$ | K$^{1-1}$ | — | OC$_2$H$_4$OH | OH | SH | SH | — | OH | L$^2$ | ON$^{3-6}$ | 0 | 1 |
| 1476 | K$^{1-1}$ | K$^{1-1}$ | K$^{1-1}$ | — | OC$_2$H$_4$OH | SH | SH | SH | — | OH | L$^2$ | ON$^{3-6}$ | 0 | 1 |
| 1477 | K$^{1-1}$ | K$^{1-1}$ | K$^{1-1}$ | K$^{1-1}$ | OC$_2$H$_4$OH | OH | SH | SH | SH | OH | L$^2$ | ON$^{3-6}$ | 1 | 1 |
| 1478 | K$^{1-1}$ | K$^{1-1}$ | K$^{1-1}$ | — | OH | SH | SH | SH | — | OH | L$^2$ | ON$^{3-6}$ | 0 | 1 |
| 1479 | K$^{2-1}$ | K$^{1-1}$ | K$^{3-1}$ | — | OC$_2$H$_4$OH | OH | OH | OH | — | OH | L$^1$ | ON$^{3-7}$ | 0 | 2 |
| 1480 | K$^{1-1}$ | K$^{1-1}$ | K$^{1-1}$ | — | OC$_2$H$_4$OH | OH | SH | SH | — | OH | L$^1$ | ON$^{3-7}$ | 0 | 2 |
| 1481 | K$^{1-1}$ | K$^{1-1}$ | K$^{1-1}$ | — | OC$_2$H$_4$OH | SH | SH | SH | — | OH | L$^1$ | ON$^{3-7}$ | 0 | 2 |
| 1482 | K$^{1-1}$ | K$^{1-1}$ | K$^{1-1}$ | K$^{1-1}$ | OC$_2$H$_4$OH | OH | SH | SH | SH | OH | L$^1$ | ON$^{3-7}$ | 1 | 2 |
| 1483 | K$^{1-1}$ | K$^{1-1}$ | K$^{1-1}$ | — | OH | SH | SH | SH | — | OH | L$^1$ | ON$^{3-7}$ | 0 | 2 |
| 1484 | K$^{2-1}$ | K$^{1-1}$ | K$^{3-1}$ | — | OC$_2$H$_4$OH | OH | OH | OH | — | OH | L$^2$ | ON$^{3-7}$ | 0 | 1 |
| 1485 | K$^{1-1}$ | K$^{1-1}$ | K$^{1-1}$ | — | OC$_2$H$_4$OH | OH | SH | SH | — | OH | L$^2$ | ON$^{3-7}$ | 0 | 1 |
| 1486 | K$^{1-1}$ | K$^{1-1}$ | K$^{1-1}$ | — | OC$_2$H$_4$OH | SH | SH | SH | — | OH | L$^2$ | ON$^{3-7}$ | 0 | 1 |
| 1487 | K$^{1-1}$ | K$^{1-1}$ | K$^{1-1}$ | K$^{1-1}$ | OC$_2$H$_4$OH | OH | SH | SH | SH | OH | L$^2$ | ON$^{3-7}$ | 1 | 1 |
| 1488 | K$^{1-1}$ | K$^{1-1}$ | K$^{1-1}$ | — | OH | SH | SH | SH | — | OH | L$^2$ | ON$^{3-7}$ | 0 | 1 |
| 1489 | K$^{2-1}$ | K$^{1-1}$ | K$^{2-1}$ | — | OC$_2$H$_4$OH | OH | OH | OH | — | OH | L$^1$ | ON$^{4-6}$ | 0 | 2 |
| 1490 | K$^{1-1}$ | K$^{1-1}$ | K$^{1-1}$ | — | OC$_2$H$_4$OH | OH | SH | SH | — | OH | L$^1$ | ON$^{4-6}$ | 0 | 2 |
| 1491 | K$^{1-1}$ | K$^{1-1}$ | K$^{1-1}$ | — | OC$_2$H$_4$OH | SH | SH | SH | — | OH | L$^1$ | ON$^{4-6}$ | 0 | 2 |
| 1492 | K$^{1-1}$ | K$^{1-1}$ | K$^{1-1}$ | K$^{1-1}$ | OC$_2$H$_4$OH | OH | SH | SH | SH | OH | L$^1$ | ON$^{4-6}$ | 1 | 2 |
| 1493 | K$^{1-1}$ | K$^{1-1}$ | K$^{1-1}$ | — | OH | SH | SH | SH | — | OH | L$^1$ | ON$^{4-6}$ | 0 | 2 |
| 1494 | K$^{2-1}$ | K$^{1-1}$ | K$^{2-1}$ | — | OC$_2$H$_4$OH | OH | OH | OH | — | OH | L$^2$ | ON$^{4-6}$ | 0 | 1 |
| 1495 | K$^{1-1}$ | K$^{1-1}$ | K$^{1-1}$ | — | OC$_2$H$_4$OH | OH | SH | SH | — | OH | L$^2$ | ON$^{4-6}$ | 0 | 1 |
| 1496 | K$^{1-1}$ | K$^{1-1}$ | K$^{1-1}$ | — | OC$_2$H$_4$OH | SH | SH | SH | — | OH | L$^2$ | ON$^{4-6}$ | 0 | 1 |
| 1497 | K$^{1-1}$ | K$^{1-1}$ | K$^{1-1}$ | K$^{1-1}$ | OC$_2$H$_4$OH | OH | SH | SH | SH | OH | L$^2$ | ON$^{4-6}$ | 1 | 1 |
| 1498 | K$^{1-1}$ | K$^{1-1}$ | K$^{1-1}$ | — | OH | SH | SH | SH | — | OH | L$^2$ | ON$^{4-6}$ | 0 | 1 |
| 1499 | K$^{2-1}$ | K$^{1-1}$ | K$^{2-1}$ | — | OC$_2$H$_4$OH | OH | OH | OH | — | OH | L$^1$ | ON$^{4-7}$ | 0 | 2 |
| 1500 | K$^{1-1}$ | K$^{1-1}$ | K$^{1-1}$ | — | OC$_2$H$_4$OH | OH | SH | SH | — | OH | L$^1$ | ON$^{4-7}$ | 0 | 2 |
| 1501 | K$^{1-1}$ | K$^{1-1}$ | K$^{1-1}$ | — | OC$_2$H$_4$OH | SH | SH | SH | — | OH | L$^1$ | ON$^{4-7}$ | 0 | 2 |
| 1502 | K$^{1-1}$ | K$^{1-1}$ | K$^{1-1}$ | K$^{1-1}$ | OC$_2$H$_4$OH | OH | SH | SH | SH | OH | L$^1$ | ON$^{4-7}$ | 1 | 2 |
| 1503 | K$^{1-1}$ | K$^{1-1}$ | K$^{1-1}$ | — | OH | SH | SH | SH | — | OH | L$^1$ | ON$^{4-7}$ | 0 | 2 |
| 1504 | K$^{2-1}$ | K$^{1-1}$ | K$^{2-1}$ | — | OC$_2$H$_4$OH | OH | OH | OH | — | OH | L$^2$ | ON$^{4-7}$ | 0 | 1 |
| 1505 | K$^{1-1}$ | K$^{1-1}$ | K$^{1-1}$ | — | OC$_2$H$_4$OH | OH | SH | SH | — | OH | L$^2$ | ON$^{4-7}$ | 0 | 1 |
| 1506 | K$^{1-1}$ | K$^{1-1}$ | K$^{1-1}$ | — | OC$_2$H$_4$OH | SH | SH | SH | — | OH | L$^2$ | ON$^{4-7}$ | 0 | 1 |
| 1507 | K$^{1-1}$ | K$^{1-1}$ | K$^{1-1}$ | K$^{1-1}$ | OC$_2$H$_4$OH | OH | SH | SH | SH | OH | L$^2$ | ON$^{4-7}$ | 1 | 1 |
| 1508 | K$^{1-1}$ | K$^{1-1}$ | K$^{1-1}$ | — | OH | SH | SH | SH | — | OH | L$^2$ | ON$^{4-7}$ | 0 | 1 |
| 1509 | K$^{2-1}$ | K$^{1-1}$ | K$^{3-1}$ | — | OC$_2$H$_4$OH | OH | OH | OH | — | OH | L$^1$ | ON$^{5-6}$ | 0 | 2 |
| 1510 | K$^{1-1}$ | K$^{1-1}$ | K$^{1-1}$ | — | OC$_2$H$_4$OH | OH | SH | SH | — | OH | L$^1$ | ON$^{5-6}$ | 0 | 2 |

TABLE 1-continued

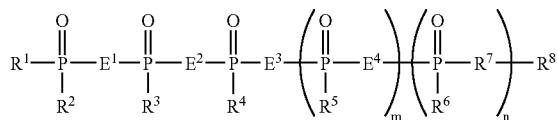

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1511 | $K^{1-1}$ | $K^{1-1}$ | $K^{1-1}$ | — | $OC_2H_4OH$ | SH | SH | SH | — | OH | $L^1$ | $ON^{5-6}$ | 0 | 2 |
| 1512 | $K^{1-1}$ | $K^{1-1}$ | $K^{1-1}$ | $K^{1-1}$ | $OC_2H_4OH$ | OH | SH | SH | SH | OH | $L^1$ | $ON^{5-6}$ | 1 | 2 |
| 1513 | $K^{1-1}$ | $K^{1-1}$ | $K^{1-1}$ | — | OH | SH | SH | SH | — | OH | $L^1$ | $ON^{5-6}$ | 0 | 2 |
| 1514 | $K^{2-1}$ | $K^{1-1}$ | $K^{3-1}$ | — | $OC_2H_4OH$ | OH | OH | OH | — | OH | $L^2$ | $ON^{5-6}$ | 0 | 1 |
| 1515 | $K^{1-1}$ | $K^{1-1}$ | $K^{1-1}$ | — | $OC_2H_4OH$ | OH | SH | SH | — | OH | $L^2$ | $ON^{5-6}$ | 0 | 1 |
| 1516 | $K^{1-1}$ | $K^{1-1}$ | $K^{1-1}$ | — | $OC_2H_4OH$ | SH | SH | SH | — | OH | $L^2$ | $ON^{5-6}$ | 0 | 1 |
| 1517 | $K^{1-1}$ | $K^{1-1}$ | $K^{1-1}$ | $K^{1-1}$ | $OC_2H_4OH$ | OH | SH | SH | SH | OH | $L^2$ | $ON^{5-6}$ | 1 | 1 |
| 1518 | $K^{1-1}$ | $K^{1-1}$ | $K^{1-1}$ | — | OH | SH | SH | SH | — | OH | $L^2$ | $ON^{5-6}$ | 0 | 1 |
| 1519 | $K^{2-1}$ | $K^{1-1}$ | $K^{3-1}$ | — | $OC_2H_4OH$ | OH | OH | OH | — | OH | $L^1$ | $ON^{5-7}$ | 0 | 2 |
| 1520 | $K^{1-1}$ | $K^{1-1}$ | $K^{1-1}$ | — | $OC_2H_4OH$ | OH | SH | SH | — | OH | $L^1$ | $ON^{5-7}$ | 0 | 2 |
| 1521 | $K^{1-1}$ | $K^{1-1}$ | $K^{1-1}$ | — | $OC_2H_4OH$ | SH | SH | SH | — | OH | $L^1$ | $ON^{5-7}$ | 0 | 2 |
| 1522 | $K^{1-1}$ | $K^{1-1}$ | $K^{1-1}$ | $K^{1-1}$ | $OC_2H_4OH$ | OH | SH | SH | SH | OH | $L^1$ | $ON^{5-7}$ | 1 | 2 |
| 1523 | $K^{1-1}$ | $K^{1-1}$ | $K^{1-1}$ | — | OH | SH | SH | SH | — | OH | $L^1$ | $ON^{5-7}$ | 0 | 2 |
| 1524 | $K^{2-1}$ | $K^{1-1}$ | $K^{3-1}$ | — | $OC_2H_4OH$ | OH | OH | OH | — | OH | $L^2$ | $ON^{5-7}$ | 0 | 1 |
| 1525 | $K^{1-1}$ | $K^{1-1}$ | $K^{1-1}$ | — | $OC_2H_4OH$ | OH | SH | SH | — | OH | $L^2$ | $ON^{5-7}$ | 0 | 1 |
| 1526 | $K^{1-1}$ | $K^{1-1}$ | $K^{1-1}$ | — | $OC_2H_4OH$ | SH | SH | SH | — | OH | $L^2$ | $ON^{5-7}$ | 0 | 1 |
| 1527 | $K^{1-1}$ | $K^{1-1}$ | $K^{1-1}$ | $K^{1-1}$ | $OC_2H_4OH$ | OH | SH | SH | SH | OH | $L^2$ | $ON^{5-7}$ | 1 | 1 |
| 1528 | $K^{1-1}$ | $K^{1-1}$ | $K^{1-1}$ | — | OH | SH | SH | SH | — | OH | $L^2$ | $ON^{5-7}$ | 0 | 1 |
| 1529 | $K^{2-1}$ | $K^{1-1}$ | $K^{3-1}$ | — | $OC_2H_4OH$ | OH | OH | OH | — | OH | $L^1$ | $ON^{6-6}$ | 0 | 2 |
| 1530 | $K^{1-1}$ | $K^{1-1}$ | $K^{1-1}$ | — | $OC_2H_4OH$ | OH | SH | SH | — | OH | $L^1$ | $ON^{6-6}$ | 0 | 2 |
| 1531 | $K^{1-1}$ | $K^{1-1}$ | $K^{1-1}$ | — | $OC_2H_4OH$ | SH | SH | SH | — | OH | $L^1$ | $ON^{6-6}$ | 0 | 2 |
| 1532 | $K^{1-1}$ | $K^{1-1}$ | $K^{1-1}$ | $K^{1-1}$ | $OC_2H_4OH$ | OH | SH | SH | SH | OH | $L^1$ | $ON^{6-6}$ | 1 | 2 |
| 1533 | $K^{1-1}$ | $K^{1-1}$ | $K^{1-1}$ | — | OH | SH | SH | SH | — | OH | $L^1$ | $ON^{6-6}$ | 0 | 2 |
| 1534 | $K^{2-1}$ | $K^{1-1}$ | $K^{3-1}$ | — | $OC_2H_4OH$ | OH | OH | OH | — | OH | $L^2$ | $ON^{6-6}$ | 0 | 1 |
| 1535 | $K^{1-1}$ | $K^{1-1}$ | $K^{1-1}$ | — | $OC_2H_4OH$ | OH | SH | SH | — | OH | $L^2$ | $ON^{6-6}$ | 0 | 1 |
| 1536 | $K^{1-1}$ | $K^{1-1}$ | $K^{1-1}$ | — | $OC_2H_4OH$ | SH | SH | SH | — | OH | $L^2$ | $ON^{6-6}$ | 0 | 1 |
| 1537 | $K^{1-1}$ | $K^{1-1}$ | $K^{1-1}$ | $K^{1-1}$ | $OC_2H_4OH$ | OH | SH | SH | SH | OH | $L^2$ | $ON^{6-6}$ | 1 | 1 |
| 1538 | $K^{1-1}$ | $K^{1-1}$ | $K^{1-1}$ | — | OH | SH | SH | SH | — | OH | $L^2$ | $ON^{6-6}$ | 0 | 1 |
| 1539 | $K^{2-1}$ | $K^{1-1}$ | $K^{3-1}$ | — | $OC_2H_4OH$ | OH | OH | OH | — | OH | $L^1$ | $ON^{6-7}$ | 0 | 2 |
| 1540 | $K^{1-1}$ | $K^{1-1}$ | $K^{1-1}$ | — | $OC_2H_4OH$ | OH | SH | SH | — | OH | $L^1$ | $ON^{6-7}$ | 0 | 2 |
| 1541 | $K^{1-1}$ | $K^{1-1}$ | $K^{1-1}$ | — | $OC_2H_4OH$ | SH | SH | SH | — | OH | $L^1$ | $ON^{6-7}$ | 0 | 2 |
| 1542 | $K^{1-1}$ | $K^{1-1}$ | $K^{1-1}$ | $K^{1-1}$ | $OC_2H_4OH$ | OH | SH | SH | SH | OH | $L^1$ | $ON^{6-7}$ | 1 | 2 |
| 1543 | $K^{1-1}$ | $K^{1-1}$ | $K^{1-1}$ | — | OH | SH | SH | SH | — | OH | $L^1$ | $ON^{6-7}$ | 0 | 2 |
| 1544 | $K^{2-1}$ | $K^{1-1}$ | $K^{3-1}$ | — | $OC_2H_4OH$ | OH | OH | OH | — | OH | $L^2$ | $ON^{6-7}$ | 0 | 1 |
| 1545 | $K^{1-1}$ | $K^{1-1}$ | $K^{1-1}$ | — | $OC_2H_4OH$ | OH | SH | SH | — | OH | $L^2$ | $ON^{6-7}$ | 0 | 1 |
| 1546 | $K^{1-1}$ | $K^{1-1}$ | $K^{1-1}$ | — | $OC_2H_4OH$ | SH | SH | SH | — | OH | $L^2$ | $ON^{6-7}$ | 0 | 1 |
| 1547 | $K^{1-1}$ | $K^{1-1}$ | $K^{1-1}$ | $K^{1-1}$ | $OC_2H_4OH$ | OH | SH | SH | SH | OH | $L^2$ | $ON^{6-7}$ | 1 | 1 |
| 1548 | $K^{1-1}$ | $K^{1-1}$ | $K^{1-1}$ | — | OH | SH | SH | SH | — | OH | $L^2$ | $ON^{6-7}$ | 0 | 1 |
| 1549 | $K^{2-1}$ | $K^{1-1}$ | $K^{3-1}$ | — | $OC_2H_4OH$ | OH | OH | OH | — | OH | $L^1$ | $ON^{7-6}$ | 0 | 2 |
| 1550 | $K^{1-1}$ | $K^{1-1}$ | $K^{1-1}$ | — | $OC_2H_4OH$ | OH | SH | SH | — | OH | $L^1$ | $ON^{7-6}$ | 0 | 2 |
| 1551 | $K^{1-1}$ | $K^{1-1}$ | $K^{1-1}$ | — | $OC_2H_4OH$ | SH | SH | SH | — | OH | $L^1$ | $ON^{7-6}$ | 0 | 2 |
| 1552 | $K^{1-1}$ | $K^{1-1}$ | $K^{1-1}$ | $K^{1-1}$ | $OC_2H_4OH$ | OH | SH | SH | SH | OH | $L^1$ | $ON^{7-6}$ | 1 | 2 |
| 1553 | $K^{1-1}$ | $K^{1-1}$ | $K^{1-1}$ | — | OH | SH | SH | SH | — | OH | $L^1$ | $ON^{7-6}$ | 0 | 2 |
| 1554 | $K^{2-1}$ | $K^{1-1}$ | $K^{3-1}$ | — | $OC_2H_4OH$ | OH | OH | OH | — | OH | $L^2$ | $ON^{7-6}$ | 0 | 1 |
| 1555 | $K^{1-1}$ | $K^{1-1}$ | $K^{1-1}$ | — | $OC_2H_4OH$ | OH | SH | SH | — | OH | $L^2$ | $ON^{7-6}$ | 0 | 1 |
| 1556 | $K^{1-1}$ | $K^{1-1}$ | $K^{1-1}$ | — | $OC_2H_4OH$ | SH | SH | SH | — | OH | $L^2$ | $ON^{7-6}$ | 0 | 1 |
| 1557 | $K^{1-1}$ | $K^{1-1}$ | $K^{1-1}$ | $K^{1-1}$ | $OC_2H_4OH$ | OH | SH | SH | SH | OH | $L^2$ | $ON^{7-6}$ | 1 | 1 |
| 1558 | $K^{1-1}$ | $K^{1-1}$ | $K^{1-1}$ | — | OH | SH | SH | SH | — | OH | $L^2$ | $ON^{7-6}$ | 0 | 1 |
| 1559 | $K^{2-1}$ | $K^{1-1}$ | $K^{3-1}$ | — | $OC_2H_4OH$ | OH | OH | OH | — | OH | $L^1$ | $ON^{7-7}$ | 0 | 2 |
| 1560 | $K^{1-1}$ | $K^{1-1}$ | $K^{1-1}$ | — | $OC_2H_4OH$ | OH | SH | SH | — | OH | $L^1$ | $ON^{7-7}$ | 0 | 2 |
| 1561 | $K^{1-1}$ | $K^{1-1}$ | $K^{1-1}$ | — | $OC_2H_4OH$ | SH | SH | SH | — | OH | $L^1$ | $ON^{7-7}$ | 0 | 2 |
| 1562 | $K^{1-1}$ | $K^{1-1}$ | $K^{1-1}$ | $K^{1-1}$ | $OC_2H_4OH$ | OH | SH | SH | SH | OH | $L^1$ | $ON^{7-7}$ | 1 | 2 |
| 1563 | $K^{1-1}$ | $K^{1-1}$ | $K^{1-1}$ | — | OH | SH | SH | SH | — | OH | $L^1$ | $ON^{7-7}$ | 0 | 2 |
| 1564 | $K^{2-1}$ | $K^{1-1}$ | $K^{3-1}$ | — | $OC_2H_4OH$ | OH | OH | OH | — | OH | $L^2$ | $ON^{7-7}$ | 0 | 1 |
| 1565 | $K^{1-1}$ | $K^{1-1}$ | $K^{1-1}$ | — | $OC_2H_4OH$ | OH | SH | SH | — | OH | $L^2$ | $ON^{7-7}$ | 0 | 1 |
| 1566 | $K^{1-1}$ | $K^{1-1}$ | $K^{1-1}$ | — | $OC_2H_4OH$ | SH | SH | SH | — | OH | $L^2$ | $ON^{7-7}$ | 0 | 1 |
| 1567 | $K^{1-1}$ | $K^{1-1}$ | $K^{1-1}$ | $K^{1-1}$ | $OC_2H_4OH$ | OH | SH | SH | SH | OH | $L^2$ | $ON^{7-7}$ | 1 | 1 |
| 1568 | $K^{1-1}$ | $K^{1-1}$ | $K^{1-1}$ | — | OH | SH | SH | SH | — | OH | $L^2$ | $ON^{7-7}$ | 0 | 1 |
| 1569 | $K^{2-1}$ | $K^{1-1}$ | $K^{3-1}$ | — | $OC_2H_4OH$ | OH | OH | OH | — | OH | $L^1$ | $ON^{8-6}$ | 0 | 2 |
| 1570 | $K^{1-1}$ | $K^{1-1}$ | $K^{1-1}$ | — | $OC_2H_4OH$ | OH | SH | SH | — | OH | $L^1$ | $ON^{8-6}$ | 0 | 2 |
| 1571 | $K^{1-1}$ | $K^{1-1}$ | $K^{1-1}$ | — | $OC_2H_4OH$ | SH | SH | SH | — | OH | $L^1$ | $ON^{8-6}$ | 0 | 2 |
| 1572 | $K^{1-1}$ | $K^{1-1}$ | $K^{1-1}$ | $K^{1-1}$ | $OC_2H_4OH$ | OH | SH | SH | SH | OH | $L^1$ | $ON^{8-6}$ | 1 | 2 |
| 1573 | $K^{1-1}$ | $K^{1-1}$ | $K^{1-1}$ | — | OH | SH | SH | SH | — | OH | $L^1$ | $ON^{8-6}$ | 0 | 2 |
| 1574 | $K^{2-1}$ | $K^{1-1}$ | $K^{3-1}$ | — | $OC_2H_4OH$ | OH | OH | OH | — | OH | $L^2$ | $ON^{8-6}$ | 0 | 1 |
| 1575 | $K^{1-1}$ | $K^{1-1}$ | $K^{1-1}$ | — | $OC_2H_4OH$ | OH | SH | SH | — | OH | $L^2$ | $ON^{8-6}$ | 0 | 1 |
| 1576 | $K^{1-1}$ | $K^{1-1}$ | $K^{1-1}$ | — | $OC_2H_4OH$ | SH | SH | SH | — | OH | $L^2$ | $ON^{8-6}$ | 0 | 1 |
| 1577 | $K^{1-1}$ | $K^{1-1}$ | $K^{1-1}$ | $K^{1-1}$ | $OC_2H_4OH$ | OH | SH | SH | SH | OH | $L^2$ | $ON^{8-6}$ | 1 | 1 |
| 1578 | $K^{1-1}$ | $K^{1-1}$ | $K^{1-1}$ | — | OH | SH | SH | SH | — | OH | $L^2$ | $ON^{8-6}$ | 0 | 1 |

TABLE 1-continued

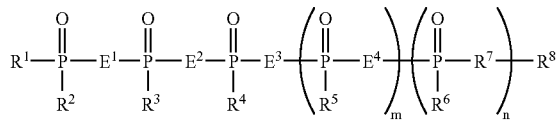

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1579 | $K^{2-1}$ | $K^{1-1}$ | $K^{3-1}$ | — | $OC_2H_4OH$ | OH | OH | OH | — | OH | $L^1$ | $ON^{8-7}$ | 0 | 2 |
| 1580 | $K^{1-1}$ | $K^{1-1}$ | $K^{1-1}$ | — | $OC_2H_4OH$ | OH | SH | SH | — | OH | $L^1$ | $ON^{8-7}$ | 0 | 2 |
| 1581 | $K^{1-1}$ | $K^{1-1}$ | $K^{1-1}$ | — | $OC_2H_4OH$ | SH | SH | SH | — | OH | $L^1$ | $ON^{8-7}$ | 0 | 2 |
| 1582 | $K^{1-1}$ | $K^{1-1}$ | $K^{1-1}$ | $K^{1-1}$ | $OC_2H_4OH$ | OH | SH | SH | SH | OH | $L^1$ | $ON^{8-7}$ | 1 | 2 |
| 1583 | $K^{1-1}$ | $K^{1-1}$ | $K^{1-1}$ | — | OH | SH | SH | SH | — | OH | $L^1$ | $ON^{8-7}$ | 0 | 2 |
| 1584 | $K^{2-1}$ | $K^{1-1}$ | $K^{3-1}$ | — | $OC_2H_4OH$ | OH | OH | OH | — | OH | $L^2$ | $ON^{8-7}$ | 0 | 1 |
| 1585 | $K^{1-1}$ | $K^{1-1}$ | $K^{1-1}$ | — | $OC_2H_4OH$ | OH | SH | SH | — | OH | $L^2$ | $ON^{8-7}$ | 0 | 1 |
| 1586 | $K^{1-1}$ | $K^{1-1}$ | $K^{1-1}$ | — | $OC_2H_4OH$ | SH | SH | SH | — | OH | $L^2$ | $ON^{8-7}$ | 0 | 1 |
| 1587 | $K^{1-1}$ | $K^{1-1}$ | $K^{1-1}$ | $K^{1-1}$ | $OC_2H_4OH$ | OH | SH | SH | SH | OH | $L^2$ | $ON^{8-7}$ | 1 | 1 |
| 1588 | $K^{1-1}$ | $K^{1-1}$ | $K^{1-1}$ | — | OH | SH | SH | SH | — | OH | $L^2$ | $ON^{8-7}$ | 0 | 1 |
| 1589 | $K^{2-1}$ | $K^{1-1}$ | $K^{3-1}$ | — | $OC_2H_4OH$ | OH | OH | OH | — | OH | $L^1$ | $ON^{9-6}$ | 0 | 2 |
| 1590 | $K^{1-1}$ | $K^{1-1}$ | $K^{1-1}$ | — | $OC_2H_4OH$ | OH | SH | SH | — | OH | $L^1$ | $ON^{9-6}$ | 0 | 2 |
| 1591 | $K^{1-1}$ | $K^{1-1}$ | $K^{1-1}$ | — | $OC_2H_4OH$ | SH | SH | SH | — | OH | $L^1$ | $ON^{9-6}$ | 0 | 2 |
| 1592 | $K^{1-1}$ | $K^{1-1}$ | $K^{1-1}$ | $K^{1-1}$ | $OC_2H_4OH$ | OH | SH | SH | SH | OH | $L^1$ | $ON^{9-6}$ | 1 | 2 |
| 1593 | $K^{1-1}$ | $K^{1-1}$ | $K^{1-1}$ | — | OH | SH | SH | SH | — | OH | $L^1$ | $ON^{9-6}$ | 0 | 2 |
| 1594 | $K^{2-1}$ | $K^{1-1}$ | $K^{3-1}$ | — | $OC_2H_4OH$ | OH | OH | OH | — | OH | $L^2$ | $ON^{9-6}$ | 0 | 1 |
| 1595 | $K^{1-1}$ | $K^{1-1}$ | $K^{1-1}$ | — | $OC_2H_4OH$ | OH | SH | SH | — | OH | $L^2$ | $ON^{9-6}$ | 0 | 1 |
| 1596 | $K^{1-1}$ | $K^{1-1}$ | $K^{1-1}$ | — | $OC_2H_4OH$ | SH | SH | SH | — | OH | $L^2$ | $ON^{9-6}$ | 0 | 1 |
| 1597 | $K^{1-1}$ | $K^{1-1}$ | $K^{1-1}$ | $K^{1-1}$ | $OC_2H_4OH$ | OH | SH | SH | SH | OH | $L^2$ | $ON^{9-6}$ | 1 | 1 |
| 1598 | $K^{1-1}$ | $K^{1-1}$ | $K^{1-1}$ | — | OH | SH | SH | SH | — | OH | $L^2$ | $ON^{9-6}$ | 0 | 1 |
| 1599 | $K^{2-1}$ | $K^{1-1}$ | $K^{3-1}$ | — | $OC_2H_4OH$ | OH | OH | OH | — | OH | $L^1$ | $ON^{9-7}$ | 0 | 2 |
| 1600 | $K^{1-1}$ | $K^{1-1}$ | $K^{1-1}$ | — | $OC_2H_4OH$ | OH | SH | SH | — | OH | $L^1$ | $ON^{9-7}$ | 0 | 2 |
| 1601 | $K^{1-1}$ | $K^{1-1}$ | $K^{1-1}$ | — | $OC_2H_4OH$ | SH | SH | SH | — | OH | $L^1$ | $ON^{9-7}$ | 0 | 2 |
| 1602 | $K^{1-1}$ | $K^{1-1}$ | $K^{1-1}$ | $K^{1-1}$ | $OC_2H_4OH$ | OH | SH | SH | SH | OH | $L^1$ | $ON^{9-7}$ | 1 | 2 |
| 1603 | $K^{1-1}$ | $K^{1-1}$ | $K^{1-1}$ | — | OH | SH | SH | SH | — | OH | $L^1$ | $ON^{9-7}$ | 0 | 2 |
| 1604 | $K^{2-1}$ | $K^{1-1}$ | $K^{3-1}$ | — | $OC_2H_4OH$ | OH | OH | OH | — | OH | $L^2$ | $ON^{9-7}$ | 0 | 1 |
| 1605 | $K^{1-1}$ | $K^{1-1}$ | $K^{1-1}$ | — | $OC_2H_4OH$ | OH | SH | SH | — | OH | $L^2$ | $ON^{9-7}$ | 0 | 1 |
| 1606 | $K^{1-1}$ | $K^{1-1}$ | $K^{1-1}$ | — | $OC_2H_4OH$ | SH | SH | SH | — | OH | $L^2$ | $ON^{9-7}$ | 0 | 1 |
| 1607 | $K^{1-1}$ | $K^{1-1}$ | $K^{1-1}$ | $K^{1-1}$ | $OC_2H_4OH$ | OH | SH | SH | SH | OH | $L^2$ | $ON^{9-7}$ | 1 | 1 |
| 1608 | $K^{1-1}$ | $K^{1-1}$ | $K^{1-1}$ | — | OH | SH | SH | SH | — | OH | $L^2$ | $ON^{9-7}$ | 0 | 1 |
| 1609 | $K^{2-1}$ | $K^{1-1}$ | $K^{4-1}$ | — | $OC_2H_4OH$ | OH | OH | OH | — | OH | $L^1$ | $ON^{1-6}$ | 0 | 2 |
| 1610 | $K^{2-1}$ | $K^{1-1}$ | $K^{4-1}$ | — | $OC_2H_4OH$ | OH | OH | OH | — | OH | $L^2$ | $ON^{1-6}$ | 0 | 1 |
| 1611 | $K^{2-1}$ | $K^{1-1}$ | $K^{4-1}$ | — | $OC_2H_4OH$ | OH | OH | OH | — | OH | $L^1$ | $ON^{1-7}$ | 0 | 2 |
| 1612 | $K^{2-1}$ | $K^{1-1}$ | $K^{4-1}$ | — | $OC_2H_4OH$ | OH | OH | OH | — | OH | $L^2$ | $ON^{1-7}$ | 0 | 1 |
| 1613 | $K^{2-1}$ | $K^{1-1}$ | $K^{4-1}$ | — | $OC_2H_4OH$ | OH | OH | OH | — | OH | $L^1$ | $ON^{2-6}$ | 0 | 2 |
| 1614 | $K^{2-1}$ | $K^{1-1}$ | $K^{4-1}$ | — | $OC_2H_4OH$ | OH | OH | OH | — | OH | $L^2$ | $ON^{2-6}$ | 0 | 1 |
| 1615 | $K^{2-1}$ | $K^{1-1}$ | $K^{4-1}$ | — | $OC_2H_4OH$ | OH | OH | OH | — | OH | $L^1$ | $ON^{2-7}$ | 0 | 2 |
| 1616 | $K^{2-1}$ | $K^{1-1}$ | $K^{4-1}$ | — | $OC_2H_4OH$ | OH | OH | OH | — | OH | $L^2$ | $ON^{2-7}$ | 0 | 1 |
| 1617 | $K^{2-1}$ | $K^{1-1}$ | $K^{4-1}$ | — | $OC_2H_4OH$ | OH | OH | OH | — | OH | $L^1$ | $ON^{3-6}$ | 0 | 2 |
| 1618 | $K^{2-1}$ | $K^{1-1}$ | $K^{4-1}$ | — | $OC_2H_4OH$ | OH | OH | OH | — | OH | $L^2$ | $ON^{3-6}$ | 0 | 1 |
| 1619 | $K^{2-1}$ | $K^{1-1}$ | $K^{4-1}$ | — | $OC_2H_4OH$ | OH | OH | OH | — | OH | $L^1$ | $ON^{3-7}$ | 0 | 2 |
| 1620 | $K^{2-1}$ | $K^{1-1}$ | $K^{4-1}$ | — | $OC_2H_4OH$ | OH | OH | OH | — | OH | $L^2$ | $ON^{3-7}$ | 0 | 1 |
| 1621 | $K^{2-1}$ | $K^{1-1}$ | $K^{4-1}$ | — | $OC_2H_4OH$ | OH | OH | OH | — | OH | $L^1$ | $ON^{4-6}$ | 0 | 2 |
| 1622 | $K^{2-1}$ | $K^{1-1}$ | $K^{4-1}$ | — | $OC_2H_4OH$ | OH | OH | OH | — | OH | $L^2$ | $ON^{4-6}$ | 0 | 1 |
| 1623 | $K^{2-1}$ | $K^{1-1}$ | $K^{4-1}$ | — | $OC_2H_4OH$ | OH | OH | OH | — | OH | $L^1$ | $ON^{4-7}$ | 0 | 2 |
| 1624 | $K^{2-1}$ | $K^{1-1}$ | $K^{4-1}$ | — | $OC_2H_4OH$ | OH | OH | OH | — | OH | $L^2$ | $ON^{4-7}$ | 0 | 1 |
| 1625 | $K^{2-1}$ | $K^{1-1}$ | $K^{4-1}$ | — | $OC_2H_4OH$ | OH | OH | OH | — | OH | $L^1$ | $ON^{5-6}$ | 0 | 2 |
| 1626 | $K^{2-1}$ | $K^{1-1}$ | $K^{4-1}$ | — | $OC_2H_4OH$ | OH | OH | OH | — | OH | $L^2$ | $ON^{5-6}$ | 0 | 1 |
| 1627 | $K^{2-1}$ | $K^{1-1}$ | $K^{4-1}$ | — | $OC_2H_4OH$ | OH | OH | OH | — | OH | $L^1$ | $ON^{5-7}$ | 0 | 2 |
| 1628 | $K^{2-1}$ | $K^{1-1}$ | $K^{4-1}$ | — | $OC_2H_4OH$ | OH | OH | OH | — | OH | $L^2$ | $ON^{5-7}$ | 0 | 1 |
| 1629 | $K^{2-1}$ | $K^{1-1}$ | $K^{4-1}$ | — | $OC_2H_4OH$ | OH | OH | OH | — | OH | $L^1$ | $ON^{6-6}$ | 0 | 2 |
| 1630 | $K^{2-1}$ | $K^{1-1}$ | $K^{4-1}$ | — | $OC_2H_4OH$ | OH | OH | OH | — | OH | $L^2$ | $ON^{6-6}$ | 0 | 1 |
| 1631 | $K^{2-1}$ | $K^{1-1}$ | $K^{4-1}$ | — | $OC_2H_4OH$ | OH | OH | OH | — | OH | $L^1$ | $ON^{6-7}$ | 0 | 2 |
| 1632 | $K^{2-1}$ | $K^{1-1}$ | $K^{4-1}$ | — | $OC_2H_4OH$ | OH | OH | OH | — | OH | $L^2$ | $ON^{6-7}$ | 0 | 1 |
| 1633 | $K^{2-1}$ | $K^{1-1}$ | $K^{4-1}$ | — | $OC_2H_4OH$ | OH | OH | OH | — | OH | $L^1$ | $ON^{7-6}$ | 0 | 2 |
| 1634 | $K^{2-1}$ | $K^{1-1}$ | $K^{4-1}$ | — | $OC_2H_4OH$ | OH | OH | OH | — | OH | $L^2$ | $ON^{7-6}$ | 0 | 1 |
| 1635 | $K^{2-1}$ | $K^{1-1}$ | $K^{4-1}$ | — | $OC_2H_4OH$ | OH | OH | OH | — | OH | $L^1$ | $ON^{7-7}$ | 0 | 2 |
| 1636 | $K^{2-1}$ | $K^{1-1}$ | $K^{4-1}$ | — | $OC_2H_4OH$ | OH | OH | OH | — | OH | $L^2$ | $ON^{7-7}$ | 0 | 1 |
| 1637 | $K^{2-1}$ | $K^{1-1}$ | $K^{4-1}$ | — | $OC_2H_4OH$ | OH | OH | OH | — | OH | $L^1$ | $ON^{8-6}$ | 0 | 2 |
| 1638 | $K^{2-1}$ | $K^{1-1}$ | $K^{4-1}$ | — | $OC_2H_4OH$ | OH | OH | OH | — | OH | $L^2$ | $ON^{8-6}$ | 0 | 1 |
| 1639 | $K^{2-1}$ | $K^{1-1}$ | $K^{4-1}$ | — | $OC_2H_4OH$ | OH | OH | OH | — | OH | $L^1$ | $ON^{8-7}$ | 0 | 2 |
| 1640 | $K^{2-1}$ | $K^{1-1}$ | $K^{4-1}$ | — | $OC_2H_4OH$ | OH | OH | OH | — | OH | $L^2$ | $ON^{8-7}$ | 0 | 1 |
| 1641 | $K^{2-1}$ | $K^{1-1}$ | $K^{4-1}$ | — | $OC_2H_4OH$ | OH | OH | OH | — | OH | $L^1$ | $ON^{9-6}$ | 0 | 2 |
| 1642 | $K^{2-1}$ | $K^{1-1}$ | $K^{4-1}$ | — | $OC_2H_4OH$ | OH | OH | OH | — | OH | $L^2$ | $ON^{9-6}$ | 0 | 1 |
| 1643 | $K^{2-1}$ | $K^{1-1}$ | $K^{4-1}$ | — | $OC_2H_4OH$ | OH | OH | OH | — | OH | $L^1$ | $ON^{9-7}$ | 0 | 2 |
| 1644 | $K^{2-1}$ | $K^{1-1}$ | $K^{4-1}$ | — | $OC_2H_4OH$ | OH | OH | OH | — | OH | $L^2$ | $ON^{9-7}$ | 0 | 1 |
| 1645 | $K^{2-1}$ | $K^{1-1}$ | $K^{3-1}$ | — | $OC_2H_4OH$ | OH | SH | SH | — | SH | O | H | 0 | 1 |
| 1646 | $K^{2-1}$ | $K^{1-1}$ | $K^{3-1}$ | — | $OC_2H_4OH$ | OH | OH | SH | — | SH | O | H | 0 | 1 |

TABLE 1-continued

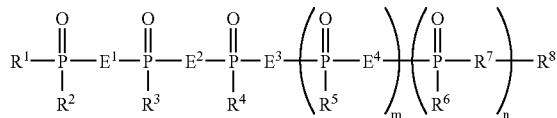

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1647 | $K^{1-1}$ | $K^{1-1}$ | $K^{3-1}$ | — | $OC_2H_4OH$ | OH | SH | SH | — | SH | O | H | 0 | 1 |
| 1648 | $K^{2-1}$ | $K^{1-1}$ | $K^{3-1}$ | — | $OC_2H_4OH$ | OH | SH | SH | — | $SC_2H_4C^{20}$ | O | H | 0 | 1 |
| 1649 | $K^{2-1}$ | $K^{1-1}$ | $K^{3-1}$ | — | $OC_2H_4OH$ | OH | OH | SH | — | $SC_2H_4C^{20}$ | O | H | 0 | 1 |
| 1650 | $K^{1-1}$ | $K^{1-1}$ | $K^{3-1}$ | — | $OC_2H_4OH$ | OH | SH | SH | — | $SC_2H_4C^{20}$ | O | H | 0 | 1 |
| 1651 | $K^{2-1}$ | $K^{1-1}$ | $K^{3-1}$ | — | $OC_2H_4OH$ | OH | SH | SH | — | $SC_2H_4C^{18}$ | O | H | 0 | 1 |
| 1652 | $K^{2-1}$ | $K^{1-1}$ | $K^{3-1}$ | — | $OC_2H_4OH$ | OH | OH | SH | — | $SC_2H_4C^{18}$ | O | H | 0 | 1 |
| 1653 | $K^{1-1}$ | $K^{1-1}$ | $K^{3-1}$ | — | $OC_2H_4OH$ | OH | SH | SH | — | $SC_2H_4C^{18}$ | O | H | 0 | 1 |
| 1654 | $K^{2-1}$ | $K^{1-1}$ | $K^{3-2}$ | — | $OC_2H_4OH$ | OH | SH | SH | — | SH | O | H | 0 | 1 |
| 1655 | $K^{2-1}$ | $K^{1-1}$ | $K^{3-2}$ | — | $OC_2H_4OH$ | OH | OH | SH | — | SH | O | H | 0 | 1 |
| 1656 | $K^{1-1}$ | $K^{1-1}$ | $K^{3-2}$ | — | $OC_2H_4OH$ | OH | SH | SH | — | SH | O | H | 0 | 1 |
| 1657 | $K^{2-1}$ | $K^{1-1}$ | $K^{3-2}$ | — | $OC_2H_4OH$ | OH | SH | SH | — | $SC_2H_4C^{20}$ | O | H | 0 | 1 |
| 1658 | $K^{2-1}$ | $K^{1-1}$ | $K^{3-2}$ | — | $OC_2H_4OH$ | OH | OH | SH | — | $SC_2H_4C^{20}$ | O | H | 0 | 1 |
| 1659 | $K^{1-1}$ | $K^{1-1}$ | $K^{3-2}$ | — | $OC_2H_4OH$ | OH | SH | SH | — | $SC_2H_4C^{20}$ | O | H | 0 | 1 |
| 1660 | $K^{2-1}$ | $K^{1-1}$ | $K^{3-2}$ | — | $OC_2H_4OH$ | OH | SH | SH | — | $SC_2H_4C^{18}$ | O | H | 0 | 1 |
| 1661 | $K^{2-1}$ | $K^{1-1}$ | $K^{3-2}$ | — | $OC_2H_4OH$ | OH | OH | SH | — | $SC_2H_4C^{18}$ | O | H | 0 | 1 |
| 1662 | $K^{1-1}$ | $K^{1-1}$ | $K^{3-2}$ | — | $OC_2H_4OH$ | OH | SH | SH | — | $SC_2H_4C^{18}$ | O | H | 0 | 1 |
| 1663 | $K^{2-1}$ | $K^{1-1}$ | $K^{4-1}$ | — | $OC_2H_4OH$ | OH | SH | SH | — | SH | O | H | 0 | 1 |
| 1664 | $K^{2-1}$ | $K^{1-1}$ | $K^{4-1}$ | — | $OC_2H_4OH$ | OH | OH | SH | — | SH | O | H | 0 | 1 |
| 1665 | $K^{1-1}$ | $K^{1-1}$ | $K^{4-1}$ | — | $OC_2H_4OH$ | OH | SH | SH | — | SH | O | H | 0 | 1 |
| 1666 | $K^{2-1}$ | $K^{1-1}$ | $K^{4-1}$ | — | $OC_2H_4OH$ | OH | SH | SH | — | $SC_2H_4C^{20}$ | O | H | 0 | 1 |
| 1667 | $K^{2-1}$ | $K^{1-1}$ | $K^{4-1}$ | — | $OC_2H_4OH$ | OH | OH | SH | — | $SC_2H_4C^{20}$ | O | H | 0 | 1 |
| 1668 | $K^{1-1}$ | $K^{1-1}$ | $K^{4-1}$ | — | $OC_2H_4OH$ | OH | SH | SH | — | $SC_2H_4C^{20}$ | O | H | 0 | 1 |
| 1669 | $K^{2-1}$ | $K^{1-1}$ | $K^{4-1}$ | — | $OC_2H_4OH$ | OH | SH | SH | — | $SC_2H_4C^{18}$ | O | H | 0 | 1 |
| 1670 | $K^{2-1}$ | $K^{1-1}$ | $K^{4-1}$ | — | $OC_2H_4OH$ | OH | OH | SH | — | $SC_2H_4C^{18}$ | O | H | 0 | 1 |
| 1671 | $K^{1-1}$ | $K^{1-1}$ | $K^{4-1}$ | — | $OC_2H_4OH$ | OH | SH | SH | — | $SC_2H_4C^{18}$ | O | H | 0 | 1 |
| 1672 | $K^{2-1}$ | $K^{1-1}$ | $K^{4-2}$ | — | $OC_2H_4OH$ | OH | SH | SH | — | SH | O | H | 0 | 1 |
| 1673 | $K^{2-1}$ | $K^{1-1}$ | $K^{4-2}$ | — | $OC_2H_4OH$ | OH | OH | SH | — | SH | O | H | 0 | 1 |
| 1674 | $K^{1-1}$ | $K^{1-1}$ | $K^{4-2}$ | — | $OC_2H_4OH$ | OH | SH | SH | — | SH | O | H | 0 | 1 |
| 1675 | $K^{2-1}$ | $K^{1-1}$ | $K^{4-2}$ | — | $OC_2H_4OH$ | OH | SH | SH | — | $SC_2H_4C^{20}$ | O | H | 0 | 1 |
| 1676 | $K^{2-1}$ | $K^{1-1}$ | $K^{4-2}$ | — | $OC_2H_4OH$ | OH | OH | SH | — | $SC_2H_4C^{20}$ | O | H | 0 | 1 |
| 1677 | $K^{1-1}$ | $K^{1-1}$ | $K^{4-2}$ | — | $OC_2H_4OH$ | OH | SH | SH | — | $SC_2H_4C^{20}$ | O | H | 0 | 1 |
| 1678 | $K^{2-1}$ | $K^{1-1}$ | $K^{4-2}$ | — | $OC_2H_4OH$ | OH | SH | SH | — | $SC_2H_4C^{18}$ | O | H | 0 | 1 |
| 1679 | $K^{2-1}$ | $K^{1-1}$ | $K^{4-2}$ | — | $OC_2H_4OH$ | OH | OH | SH | — | $SC_2H_4C^{18}$ | O | H | 0 | 1 |
| 1680 | $K^{1-1}$ | $K^{1-1}$ | $K^{4-2}$ | — | $OC_2H_4OH$ | OH | SH | SH | — | $SC_2H_4C^{18}$ | O | H | 0 | 1 |
| 1681 | $K^{2-1}$ | $K^{1-1}$ | $K^{4-3}$ | — | $OC_2H_4OH$ | OH | SH | SH | — | SH | O | H | 0 | 1 |
| 1682 | $K^{2-1}$ | $K^{1-1}$ | $K^{4-3}$ | — | $OC_2H_4OH$ | OH | OH | SH | — | SH | O | H | 0 | 1 |
| 1683 | $K^{1-1}$ | $K^{1-1}$ | $K^{4-3}$ | — | $OC_2H_4OH$ | OH | SH | SH | — | SH | O | H | 0 | 1 |
| 1684 | $K^{2-1}$ | $K^{1-1}$ | $K^{4-3}$ | — | $OC_2H_4OH$ | OH | SH | SH | — | $SC_2H_4C^{20}$ | O | H | 0 | 1 |
| 1685 | $K^{2-1}$ | $K^{1-1}$ | $K^{4-3}$ | — | $OC_2H_4OH$ | OH | OH | SH | — | $SC_2H_4C^{20}$ | O | H | 0 | 1 |
| 1686 | $K^{1-1}$ | $K^{1-1}$ | $K^{4-3}$ | — | $OC_2H_4OH$ | OH | SH | SH | — | $SC_2H_4C^{20}$ | O | H | 0 | 1 |
| 1687 | $K^{2-1}$ | $K^{1-1}$ | $K^{4-3}$ | — | $OC_2H_4OH$ | OH | SH | SH | — | $SC_2H_4C^{18}$ | O | H | 0 | 1 |
| 1688 | $K^{2-1}$ | $K^{1-1}$ | $K^{4-3}$ | — | $OC_2H_4OH$ | OH | OH | SH | — | $SC_2H_4C^{18}$ | O | H | 0 | 1 |
| 1689 | $K^{1-1}$ | $K^{1-1}$ | $K^{4-3}$ | — | $OC_2H_4OH$ | OH | SH | SH | — | $SC_2H_4C^{18}$ | O | H | 0 | 1 |
| 1690 | $K^{2-1}$ | $K^{1-1}$ | $K^{2-1}$ | — | $OC_2H_4OH$ | OH | SH | SH | — | SH | O | H | 0 | 1 |
| 1691 | $K^{2-1}$ | $K^{1-1}$ | $K^{2-1}$ | — | $OC_2H_4OH$ | OH | SH | SH | — | $SC_2H_4C^{20}$ | O | H | 0 | 1 |
| 1692 | $K^{2-1}$ | $K^{1-1}$ | $K^{2-1}$ | — | $OC_2H_4OH$ | OH | SH | SH | — | $SC_2H_4C^{18}$ | O | H | 0 | 1 |
| 1693 | $K^{2-1}$ | $K^{1-1}$ | $K^{3-1}$ | — | $OC_2H_4OH$ | SH | SH | SH | — | SH | O | H | 0 | 1 |
| 1694 | $K^{1-1}$ | $K^{1-1}$ | $K^{3-1}$ | — | $OC_2H_4OH$ | SH | SH | SH | — | SH | O | H | 0 | 1 |
| 1695 | $K^{2-1}$ | $K^{1-1}$ | $K^{3-1}$ | — | $OC_2H_4OH$ | SH | SH | SH | — | $SC_2H_4C^{20}$ | O | H | 0 | 1 |
| 1696 | $K^{1-1}$ | $K^{1-1}$ | $K^{3-1}$ | — | $OC_2H_4OH$ | SH | SH | SH | — | $SC_2H_4C^{20}$ | O | H | 0 | 1 |
| 1697 | $K^{2-1}$ | $K^{1-1}$ | $K^{3-1}$ | — | $OC_2H_4OH$ | SH | SH | SH | — | $SC_2H_4C^{18}$ | O | H | 0 | 1 |
| 1698 | $K^{1-1}$ | $K^{1-1}$ | $K^{3-1}$ | — | $OC_2H_4OH$ | SH | SH | SH | — | $SC_2H_4C^{18}$ | O | H | 0 | 1 |
| 1699 | $K^{2-1}$ | $K^{1-1}$ | $K^{3-2}$ | — | $OC_2H_4OH$ | SH | SH | SH | — | SH | O | H | 0 | 1 |
| 1700 | $K^{1-1}$ | $K^{1-1}$ | $K^{3-2}$ | — | $OC_2H_4OH$ | SH | SH | SH | — | SH | O | H | 0 | 1 |
| 1701 | $K^{2-1}$ | $K^{1-1}$ | $K^{3-2}$ | — | $OC_2H_4OH$ | SH | SH | SH | — | $SC_2H_4C^{20}$ | O | H | 0 | 1 |
| 1702 | $K^{1-1}$ | $K^{1-1}$ | $K^{3-2}$ | — | $OC_2H_4OH$ | SH | SH | SH | — | $SC_2H_4C^{20}$ | O | H | 0 | 1 |
| 1703 | $K^{2-1}$ | $K^{1-1}$ | $K^{3-2}$ | — | $OC_2H_4OH$ | SH | SH | SH | — | $SC_2H_4C^{18}$ | O | H | 0 | 1 |
| 1704 | $K^{1-1}$ | $K^{1-1}$ | $K^{3-2}$ | — | $OC_2H_4OH$ | SH | SH | SH | — | $SC_2H_4C^{18}$ | O | H | 0 | 1 |
| 1705 | $K^{2-1}$ | $K^{1-1}$ | $K^{4-1}$ | — | $OC_2H_4OH$ | SH | SH | SH | — | SH | O | H | 0 | 1 |
| 1706 | $K^{1-1}$ | $K^{1-1}$ | $K^{4-1}$ | — | $OC_2H_4OH$ | SH | SH | SH | — | SH | O | H | 0 | 1 |
| 1707 | $K^{2-1}$ | $K^{1-1}$ | $K^{4-1}$ | — | $OC_2H_4OH$ | SH | SH | SH | — | $SC_2H_4C^{20}$ | O | H | 0 | 1 |
| 1708 | $K^{2-1}$ | $K^{1-1}$ | $K^{4-1}$ | — | $OC_2H_4OH$ | SH | SH | SH | — | $SC_2H_4C^{20}$ | O | H | 0 | 1 |
| 1709 | $K^{2-1}$ | $K^{1-1}$ | $K^{4-1}$ | — | $OC_2H_4OH$ | SH | SH | SH | — | $SC_2H_4C^{18}$ | O | H | 0 | 1 |
| 1710 | $K^{1-1}$ | $K^{1-1}$ | $K^{4-1}$ | — | $OC_2H_4OH$ | SH | SH | SH | — | $SC_2H_4C^{18}$ | O | H | 0 | 1 |
| 1711 | $K^{2-1}$ | $K^{1-1}$ | $K^{4-2}$ | — | $OC_2H_4OH$ | SH | SH | SH | — | SH | O | H | 0 | 1 |
| 1712 | $K^{1-1}$ | $K^{1-1}$ | $K^{4-2}$ | — | $OC_2H_4OH$ | SH | SH | SH | — | SH | O | H | 0 | 1 |
| 1713 | $K^{2-1}$ | $K^{1-1}$ | $K^{4-2}$ | — | $OC_2H_4OH$ | SH | SH | SH | — | $SC_2H_4C^{20}$ | O | H | 0 | 1 |
| 1714 | $K^{1-1}$ | $K^{1-1}$ | $K^{4-2}$ | — | $OC_2H_4OH$ | SH | SH | SH | — | $SC_2H_4C^{20}$ | O | H | 0 | 1 |

TABLE 1-continued

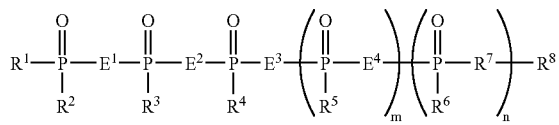

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1715 | $K^{2-1}$ | $K^{1-1}$ | $K^{4-2}$ | — | $OC_2H_4OH$ | SH | SH | SH | — | $SC_2H_4C^{18}$ | O | H | 0 | 1 |
| 1716 | $K^{1-1}$ | $K^{1-1}$ | $K^{4-2}$ | — | $OC_2H_4OH$ | SH | SH | SH | — | $SC_2H_4C^{18}$ | O | H | 0 | 1 |
| 1717 | $K^{2-1}$ | $K^{1-1}$ | $K^{4-3}$ | — | $OC_2H_4OH$ | SH | SH | SH | — | SH | O | H | 0 | 1 |
| 1718 | $K^{1-1}$ | $K^{1-1}$ | $K^{4-3}$ | — | $OC_2H_4OH$ | SH | SH | SH | — | SH | O | H | 0 | 1 |
| 1719 | $K^{2-1}$ | $K^{1-1}$ | $K^{4-3}$ | — | $OC_2H_4OH$ | SH | SH | SH | — | $SC_2H_4C^{20}$ | O | H | 0 | 1 |
| 1720 | $K^{1-1}$ | $K^{1-1}$ | $K^{4-3}$ | — | $OC_2H_4OH$ | SH | SH | SH | — | $SC_2H_4C^{20}$ | O | H | 0 | 1 |
| 1721 | $K^{2-1}$ | $K^{1-1}$ | $K^{4-3}$ | — | $OC_2H_4OH$ | SH | SH | SH | — | $SC_2H_4C^{18}$ | O | H | 0 | 1 |
| 1722 | $K^{1-1}$ | $K^{1-1}$ | $K^{4-3}$ | — | $OC_2H_4OH$ | SH | SH | SH | — | $SC_2H_4C^{18}$ | O | H | 0 | 1 |
| 1723 | $K^{2-1}$ | $K^{1-1}$ | $K^{2-1}$ | — | $OC_2H_4OH$ | SH | SH | SH | — | SH | O | H | 0 | 1 |
| 1724 | $K^{1-1}$ | $K^{1-1}$ | $K^{2-1}$ | — | $OC_2H_4OH$ | SH | SH | SH | — | SH | O | H | 0 | 1 |
| 1725 | $K^{2-1}$ | $K^{1-1}$ | $K^{2-1}$ | — | $OC_2H_4OH$ | SH | SH | SH | — | $SC_2H_4C^{20}$ | O | H | 0 | 1 |
| 1726 | $K^{1-1}$ | $K^{1-1}$ | $K^{2-1}$ | — | $OC_2H_4OH$ | SH | SH | SH | — | $SC_2H_4C^{20}$ | O | H | 0 | 1 |
| 1727 | $K^{2-1}$ | $K^{1-1}$ | $K^{2-1}$ | — | $OC_2H_4OH$ | SH | SH | SH | — | $SC_2H_4C^{18}$ | O | H | 0 | 1 |
| 1728 | $K^{1-1}$ | $K^{1-1}$ | $K^{2-1}$ | — | $OC_2H_4OH$ | SH | SH | SH | — | $SC_2H_4C^{18}$ | O | H | 0 | 1 |
| 1729 | $K^{2-1}$ | $K^{1-1}$ | $K^{3-1}$ | — | $OC_2H_4OH$ | OH | SH | SH | — | SH | $L^1$ | $ON^{1-6}$ | 0 | 2 |
| 1730 | $K^{1-1}$ | $K^{1-1}$ | $K^{3-1}$ | — | $OC_2H_4OH$ | OH | SH | SH | — | SH | $L^1$ | $ON^{1-6}$ | 0 | 2 |
| 1731 | $K^{2-1}$ | $K^{1-1}$ | $K^{4-1}$ | — | $OC_2H_4OH$ | OH | SH | SH | — | SH | $L^1$ | $ON^{1-6}$ | 0 | 2 |
| 1732 | $K^{1-1}$ | $K^{1-1}$ | $K^{4-1}$ | — | $OC_2H_4OH$ | OH | SH | SH | — | SH | $L^1$ | $ON^{1-6}$ | 0 | 2 |
| 1733 | $K^{2-1}$ | $K^{1-1}$ | $K^{2-1}$ | — | $OC_2H_4OH$ | OH | SH | SH | — | SH | $L^1$ | $ON^{1-6}$ | 0 | 2 |
| 1734 | $K^{1-1}$ | $K^{1-1}$ | $K^{3-1}$ | — | $OC_2H_4OH$ | SH | SH | SH | — | SH | $L^1$ | $ON^{1-6}$ | 0 | 2 |
| 1735 | $K^{2-1}$ | $K^{1-1}$ | $K^{3-1}$ | — | $OC_2H_4OH$ | SH | SH | SH | — | SH | $L^1$ | $ON^{1-6}$ | 0 | 2 |
| 1736 | $K^{1-1}$ | $K^{1-1}$ | $K^{4-1}$ | — | $OC_2H_4OH$ | SH | SH | SH | — | SH | $L^1$ | $ON^{1-6}$ | 0 | 2 |
| 1737 | $K^{2-1}$ | $K^{1-1}$ | $K^{4-1}$ | — | $OC_2H_4OH$ | SH | SH | SH | — | SH | $L^1$ | $ON^{1-6}$ | 0 | 2 |
| 1738 | $K^{1-1}$ | $K^{1-1}$ | $K^{2-1}$ | — | $OC_2H_4OH$ | SH | SH | SH | — | SH | $L^1$ | $ON^{1-6}$ | 0 | 2 |
| 1739 | $K^{2-1}$ | $K^{1-1}$ | $K^{3-1}$ | — | $OC_2H_4OH$ | OH | SH | SH | — | SH | $L^2$ | $ON^{1-6}$ | 0 | 1 |
| 1740 | $K^{1-1}$ | $K^{1-1}$ | $K^{3-1}$ | — | $OC_2H_4OH$ | OH | SH | SH | — | SH | $L^2$ | $ON^{1-6}$ | 0 | 1 |
| 1741 | $K^{2-1}$ | $K^{1-1}$ | $K^{4-1}$ | — | $OC_2H_4OH$ | OH | SH | SH | — | SH | $L^2$ | $ON^{1-6}$ | 0 | 1 |
| 1742 | $K^{1-1}$ | $K^{1-1}$ | $K^{4-1}$ | — | $OC_2H_4OH$ | OH | SH | SH | — | SH | $L^2$ | $ON^{1-6}$ | 0 | 1 |
| 1743 | $K^{2-1}$ | $K^{1-1}$ | $K^{2-1}$ | — | $OC_2H_4OH$ | OH | SH | SH | — | SH | $L^2$ | $ON^{1-6}$ | 0 | 1 |
| 1744 | $K^{1-1}$ | $K^{1-1}$ | $K^{3-1}$ | — | $OC_2H_4OH$ | SH | SH | SH | — | SH | $L^2$ | $ON^{1-6}$ | 0 | 1 |
| 1745 | $K^{2-1}$ | $K^{1-1}$ | $K^{3-1}$ | — | $OC_2H_4OH$ | SH | SH | SH | — | SH | $L^2$ | $ON^{1-6}$ | 0 | 1 |
| 1746 | $K^{1-1}$ | $K^{1-1}$ | $K^{4-1}$ | — | $OC_2H_4OH$ | SH | SH | SH | — | SH | $L^2$ | $ON^{1-6}$ | 0 | 1 |
| 1747 | $K^{2-1}$ | $K^{1-1}$ | $K^{4-1}$ | — | $OC_2H_4OH$ | SH | SH | SH | — | SH | $L^2$ | $ON^{1-6}$ | 0 | 1 |
| 1748 | $K^{1-1}$ | $K^{1-1}$ | $K^{2-1}$ | — | $OC_2H_4OH$ | SH | SH | SH | — | SH | $L^2$ | $ON^{1-6}$ | 0 | 1 |
| 1749 | $K^{2-1}$ | $K^{1-1}$ | $K^{3-1}$ | — | $OC_2H_4OH$ | OH | SH | SH | — | SH | $L^1$ | $ON^{2-6}$ | 0 | 2 |
| 1750 | $K^{1-1}$ | $K^{1-1}$ | $K^{3-1}$ | — | $OC_2H_4OH$ | OH | SH | SH | — | SH | $L^1$ | $ON^{2-6}$ | 0 | 2 |
| 1751 | $K^{2-1}$ | $K^{1-1}$ | $K^{4-1}$ | — | $OC_2H_4OH$ | OH | SH | SH | — | SH | $L^1$ | $ON^{2-6}$ | 0 | 2 |
| 1752 | $K^{1-1}$ | $K^{1-1}$ | $K^{4-1}$ | — | $OC_2H_4OH$ | OH | SH | SH | — | SH | $L^1$ | $ON^{2-6}$ | 0 | 2 |
| 1753 | $K^{2-1}$ | $K^{1-1}$ | $K^{2-1}$ | — | $OC_2H_4OH$ | OH | SH | SH | — | SH | $L^1$ | $ON^{2-6}$ | 0 | 2 |
| 1754 | $K^{1-1}$ | $K^{1-1}$ | $K^{3-1}$ | — | $OC_2H_4OH$ | SH | SH | SH | — | SH | $L^1$ | $ON^{2-6}$ | 0 | 2 |
| 1755 | $K^{1-1}$ | $K^{1-1}$ | $K^{3-1}$ | — | $OC_2H_4OH$ | SH | SH | SH | — | SH | $L^1$ | $ON^{2-6}$ | 0 | 2 |
| 1756 | $K^{2-1}$ | $K^{1-1}$ | $K^{4-1}$ | — | $OC_2H_4OH$ | SH | SH | SH | — | SH | $L^1$ | $ON^{2-6}$ | 0 | 2 |
| 1757 | $K^{2-1}$ | $K^{1-1}$ | $K^{4-1}$ | — | $OC_2H_4OH$ | SH | SH | SH | — | SH | $L^1$ | $ON^{2-6}$ | 0 | 2 |
| 1758 | $K^{1-1}$ | $K^{1-1}$ | $K^{2-1}$ | — | $OC_2H_4OH$ | SH | SH | SH | — | SH | $L^1$ | $ON^{2-6}$ | 0 | 2 |
| 1759 | $K^{2-1}$ | $K^{1-1}$ | $K^{3-1}$ | — | $OC_2H_4OH$ | OH | SH | SH | — | SH | $L^2$ | $ON^{2-6}$ | 0 | 1 |
| 1760 | $K^{1-1}$ | $K^{1-1}$ | $K^{3-1}$ | — | $OC_2H_4OH$ | OH | SH | SH | — | SH | $L^2$ | $ON^{2-6}$ | 0 | 1 |
| 1761 | $K^{2-1}$ | $K^{1-1}$ | $K^{4-1}$ | — | $OC_2H_4OH$ | OH | SH | SH | — | SH | $L^2$ | $ON^{2-6}$ | 0 | 1 |
| 1762 | $K^{1-1}$ | $K^{1-1}$ | $K^{4-1}$ | — | $OC_2H_4OH$ | OH | SH | SH | — | SH | $L^2$ | $ON^{2-6}$ | 0 | 1 |
| 1763 | $K^{2-1}$ | $K^{1-1}$ | $K^{2-1}$ | — | $OC_2H_4OH$ | OH | SH | SH | — | SH | $L^2$ | $ON^{2-6}$ | 0 | 1 |
| 1764 | $K^{1-1}$ | $K^{1-1}$ | $K^{3-1}$ | — | $OC_2H_4OH$ | SH | SH | SH | — | SH | $L^2$ | $ON^{2-6}$ | 0 | 1 |
| 1765 | $K^{2-1}$ | $K^{1-1}$ | $K^{3-1}$ | — | $OC_2H_4OH$ | SH | SH | SH | — | SH | $L^2$ | $ON^{2-6}$ | 0 | 1 |
| 1766 | $K^{1-1}$ | $K^{1-1}$ | $K^{4-1}$ | — | $OC_2H_4OH$ | SH | SH | SH | — | SH | $L^2$ | $ON^{2-6}$ | 0 | 1 |
| 1767 | $K^{2-1}$ | $K^{1-1}$ | $K^{4-1}$ | — | $OC_2H_4OH$ | SH | SH | SH | — | SH | $L^2$ | $ON^{2-6}$ | 0 | 1 |
| 1768 | $K^{1-1}$ | $K^{1-1}$ | $K^{2-1}$ | — | $OC_2H_4OH$ | SH | SH | SH | — | SH | $L^2$ | $ON^{2-6}$ | 0 | 1 |
| 1769 | $K^{2-1}$ | $K^{1-1}$ | $K^{3-1}$ | — | $OC_2H_4OH$ | OH | SH | SH | — | SH | $L^1$ | $ON^{3-6}$ | 0 | 2 |
| 1770 | $K^{1-1}$ | $K^{1-1}$ | $K^{3-1}$ | — | $OC_2H_4OH$ | OH | SH | SH | — | SH | $L^1$ | $ON^{3-6}$ | 0 | 2 |
| 1771 | $K^{2-1}$ | $K^{1-1}$ | $K^{4-1}$ | — | $OC_2H_4OH$ | OH | SH | SH | — | SH | $L^1$ | $ON^{3-6}$ | 0 | 2 |
| 1772 | $K^{1-1}$ | $K^{1-1}$ | $K^{4-1}$ | — | $OC_2H_4OH$ | OH | SH | SH | — | SH | $L^1$ | $ON^{3-6}$ | 0 | 2 |
| 1773 | $K^{2-1}$ | $K^{1-1}$ | $K^{2-1}$ | — | $OC_2H_4OH$ | OH | SH | SH | — | SH | $L^1$ | $ON^{3-6}$ | 0 | 2 |
| 1774 | $K^{1-1}$ | $K^{1-1}$ | $K^{3-1}$ | — | $OC_2H_4OH$ | SH | SH | SH | — | SH | $L^1$ | $ON^{3-6}$ | 0 | 2 |
| 1775 | $K^{2-1}$ | $K^{1-1}$ | $K^{3-1}$ | — | $OC_2H_4OH$ | SH | SH | SH | — | SH | $L^1$ | $ON^{3-6}$ | 0 | 2 |
| 1776 | $K^{1-1}$ | $K^{1-1}$ | $K^{4-1}$ | — | $OC_2H_4OH$ | SH | SH | SH | — | SH | $L^1$ | $ON^{3-6}$ | 0 | 2 |
| 1777 | $K^{2-1}$ | $K^{1-1}$ | $K^{4-1}$ | — | $OC_2H_4OH$ | SH | SH | SH | — | SH | $L^1$ | $ON^{3-6}$ | 0 | 2 |
| 1778 | $K^{1-1}$ | $K^{1-1}$ | $K^{2-1}$ | — | $OC_2H_4OH$ | SH | SH | SH | — | SH | $L^1$ | $ON^{3-6}$ | 0 | 2 |
| 1779 | $K^{2-1}$ | $K^{1-1}$ | $K^{3-1}$ | — | $OC_2H_4OH$ | OH | SH | SH | — | SH | $L^2$ | $ON^{3-6}$ | 0 | 1 |
| 1780 | $K^{1-1}$ | $K^{1-1}$ | $K^{3-1}$ | — | $OC_2H_4OH$ | OH | SH | SH | — | SH | $L^2$ | $ON^{3-6}$ | 0 | 1 |
| 1781 | $K^{2-1}$ | $K^{1-1}$ | $K^{4-1}$ | — | $OC_2H_4OH$ | OH | SH | SH | — | SH | $L^2$ | $ON^{3-6}$ | 0 | 1 |
| 1782 | $K^{1-1}$ | $K^{1-1}$ | $K^{4-1}$ | — | $OC_2H_4OH$ | OH | SH | SH | — | SH | $L^2$ | $ON^{3-6}$ | 0 | 1 |

TABLE 1-continued

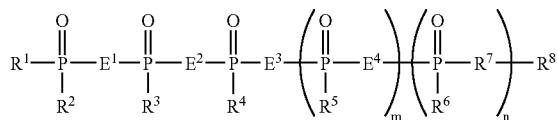

| Exemplified Compound No. | E¹ | E² | E³ | E⁴ | R¹ | R² | R³ | R⁴ | R⁵ | R⁶ | R⁷ | R⁸ | m | n |
|---|---|---|---|---|---|---|---|---|---|---|---|---|---|---|
| 1783 | $K^{2-1}$ | $K^{1-1}$ | $K^{2-1}$ | — | $OC_2H_4OH$ | OH | SH | SH | — | SH | $L^2$ | $ON^{3-6}$ | 0 | 1 |
| 1784 | $K^{2-1}$ | $K^{1-1}$ | $K^{3-1}$ | — | $OC_2H_4OH$ | SH | SH | SH | — | SH | $L^2$ | $ON^{3-6}$ | 0 | 1 |
| 1785 | $K^{1-1}$ | $K^{1-1}$ | $K^{3-1}$ | — | $OC_2H_4OH$ | SH | SH | SH | — | SH | $L^2$ | $ON^{3-6}$ | 0 | 1 |
| 1786 | $K^{2-1}$ | $K^{1-1}$ | $K^{4-1}$ | — | $OC_2H_4OH$ | SH | SH | SH | — | SH | $L^2$ | $ON^{3-6}$ | 0 | 1 |
| 1787 | $K^{1-1}$ | $K^{1-1}$ | $K^{4-1}$ | — | $OC_2H_4OH$ | SH | SH | SH | — | SH | $L^2$ | $ON^{3-6}$ | 0 | 1 |
| 1788 | $K^{2-1}$ | $K^{1-1}$ | $K^{2-1}$ | — | $OC_2H_4OH$ | SH | SH | SH | — | SH | $L^2$ | $ON^{3-6}$ | 0 | 1 |
| 1789 | $K^{2-1}$ | $K^{1-1}$ | $K^{3-1}$ | — | $OC_2H_4OH$ | OH | SH | SH | — | SH | $L^1$ | $ON^{4-6}$ | 0 | 2 |
| 1790 | $K^{1-1}$ | $K^{1-1}$ | $K^{3-1}$ | — | $OC_2H_4OH$ | OH | SH | SH | — | SH | $L^1$ | $ON^{4-6}$ | 0 | 2 |
| 1791 | $K^{2-1}$ | $K^{1-1}$ | $K^{4-1}$ | — | $OC_2H_4OH$ | OH | SH | SH | — | SH | $L^1$ | $ON^{4-6}$ | 0 | 2 |
| 1792 | $K^{1-1}$ | $K^{1-1}$ | $K^{4-1}$ | — | $OC_2H_4OH$ | OH | SH | SH | — | SH | $L^1$ | $ON^{4-6}$ | 0 | 2 |
| 1793 | $K^{2-1}$ | $K^{1-1}$ | $K^{2-1}$ | — | $OC_2H_4OH$ | OH | SH | SH | — | SH | $L^1$ | $ON^{4-6}$ | 0 | 2 |
| 1794 | $K^{2-1}$ | $K^{1-1}$ | $K^{3-1}$ | — | $OC_2H_4OH$ | SH | SH | SH | — | SH | $L^1$ | $ON^{4-6}$ | 0 | 2 |
| 1795 | $K^{1-1}$ | $K^{1-1}$ | $K^{3-1}$ | — | $OC_2H_4OH$ | SH | SH | SH | — | SH | $L^1$ | $ON^{4-6}$ | 0 | 2 |
| 1796 | $K^{2-1}$ | $K^{1-1}$ | $K^{4-1}$ | — | $OC_2H_4OH$ | SH | SH | SH | — | SH | $L^1$ | $ON^{4-6}$ | 0 | 2 |
| 1797 | $K^{1-1}$ | $K^{1-1}$ | $K^{4-1}$ | — | $OC_2H_4OH$ | SH | SH | SH | — | SH | $L^1$ | $ON^{4-6}$ | 0 | 2 |
| 1798 | $K^{2-1}$ | $K^{1-1}$ | $K^{2-1}$ | — | $OC_2H_4OH$ | SH | SH | SH | — | SH | $L^1$ | $ON^{4-6}$ | 0 | 2 |
| 1799 | $K^{2-1}$ | $K^{1-1}$ | $K^{3-1}$ | — | $OC_2H_4OH$ | OH | SH | SH | — | SH | $L^2$ | $ON^{4-6}$ | 0 | 1 |
| 1800 | $K^{1-1}$ | $K^{1-1}$ | $K^{3-1}$ | — | $OC_2H_4OH$ | OH | SH | SH | — | SH | $L^2$ | $ON^{4-6}$ | 0 | 1 |
| 1801 | $K^{2-1}$ | $K^{1-1}$ | $K^{4-1}$ | — | $OC_2H_4OH$ | OH | SH | SH | — | SH | $L^2$ | $ON^{4-6}$ | 0 | 1 |
| 1802 | $K^{1-1}$ | $K^{1-1}$ | $K^{4-1}$ | — | $OC_2H_4OH$ | OH | SH | SH | — | SH | $L^2$ | $ON^{4-6}$ | 0 | 1 |
| 1803 | $K^{2-1}$ | $K^{1-1}$ | $K^{2-1}$ | — | $OC_2H_4OH$ | OH | SH | SH | — | SH | $L^2$ | $ON^{4-6}$ | 0 | 1 |
| 1804 | $K^{2-1}$ | $K^{1-1}$ | $K^{3-1}$ | — | $OC_2H_4OH$ | SH | SH | SH | — | SH | $L^2$ | $ON^{4-6}$ | 0 | 1 |
| 1805 | $K^{1-1}$ | $K^{1-1}$ | $K^{3-1}$ | — | $OC_2H_4OH$ | SH | SH | SH | — | SH | $L^2$ | $ON^{4-6}$ | 0 | 1 |
| 1806 | $K^{2-1}$ | $K^{1-1}$ | $K^{4-1}$ | — | $OC_2H_4OH$ | SH | SH | SH | — | SH | $L^2$ | $ON^{4-6}$ | 0 | 1 |
| 1807 | $K^{1-1}$ | $K^{1-1}$ | $K^{4-1}$ | — | $OC_2H_4OH$ | SH | SH | SH | — | SH | $L^2$ | $ON^{4-6}$ | 0 | 1 |
| 1808 | $K^{2-1}$ | $K^{1-1}$ | $K^{2-1}$ | — | $OC_2H_4OH$ | SH | SH | SH | — | SH | $L^2$ | $ON^{4-6}$ | 0 | 1 |
| 1809 | $K^{2-1}$ | $K^{1-1}$ | $K^{3-1}$ | — | $OC_2H_4OH$ | OH | SH | SH | — | SH | $L^1$ | $ON^{5-6}$ | 0 | 2 |
| 1810 | $K^{1-1}$ | $K^{1-1}$ | $K^{3-1}$ | — | $OC_2H_4OH$ | OH | SH | SH | — | SH | $L^1$ | $ON^{5-6}$ | 0 | 2 |
| 1811 | $K^{2-1}$ | $K^{1-1}$ | $K^{4-1}$ | — | $OC_2H_4OH$ | OH | SH | SH | — | SH | $L^1$ | $ON^{5-6}$ | 0 | 2 |
| 1812 | $K^{1-1}$ | $K^{1-1}$ | $K^{4-1}$ | — | $OC_2H_4OH$ | OH | SH | SH | — | SH | $L^1$ | $ON^{5-6}$ | 0 | 2 |
| 1813 | $K^{2-1}$ | $K^{1-1}$ | $K^{2-1}$ | — | $OC_2K_4OH$ | OH | SH | SH | — | SH | $L^1$ | $ON^{5-6}$ | 0 | 2 |
| 1814 | $K^{2-1}$ | $K^{1-1}$ | $K^{3-1}$ | — | $OC_2H_4OH$ | SH | SH | SH | — | SH | $L^1$ | $ON^{5-6}$ | 0 | 2 |
| 1815 | $K^{1-1}$ | $K^{1-1}$ | $K^{3-1}$ | — | $OC_2H_4OH$ | SH | SH | SH | — | SH | $L^1$ | $ON^{5-6}$ | 0 | 2 |
| 1816 | $K^{2-1}$ | $K^{1-1}$ | $K^{4-1}$ | — | $OC_2H_4OH$ | SH | SH | SH | — | SH | $L^1$ | $ON^{5-6}$ | 0 | 2 |
| 1817 | $K^{1-1}$ | $K^{1-1}$ | $K^{4-1}$ | — | $OC_2H_4OH$ | SH | SH | SH | — | SH | $L^1$ | $ON^{5-6}$ | 0 | 2 |
| 1818 | $K^{2-1}$ | $K^{1-1}$ | $K^{2-1}$ | — | $OC_2H_4OH$ | SH | SH | SH | — | SH | $L^1$ | $ON^{5-6}$ | 0 | 2 |
| 1819 | $K^{2-1}$ | $K^{1-1}$ | $K^{3-1}$ | — | $OC_2H_4OH$ | OH | SH | SH | — | SH | $L^2$ | $ON^{5-6}$ | 0 | 1 |
| 1820 | $K^{1-1}$ | $K^{1-1}$ | $K^{3-1}$ | — | $OC_2H_4OH$ | OH | SH | SH | — | SH | $L^2$ | $ON^{5-6}$ | 0 | 1 |
| 1821 | $K^{2-1}$ | $K^{1-1}$ | $K^{4-1}$ | — | $OC_2H_4OH$ | OH | SH | SH | — | SH | $L^2$ | $ON^{5-6}$ | 0 | 1 |
| 1822 | $K^{1-1}$ | $K^{1-1}$ | $K^{4-1}$ | — | $OC_2H_4OH$ | OH | SH | SH | — | SH | $L^2$ | $ON^{5-6}$ | 0 | 1 |
| 1823 | $K^{2-1}$ | $K^{1-1}$ | $K^{2-1}$ | — | $OC_2H_4OH$ | OH | SH | SH | — | SH | $L^2$ | $ON^{5-6}$ | 0 | 1 |
| 1824 | $K^{2-1}$ | $K^{1-1}$ | $K^{3-1}$ | — | $OC_2H_4OH$ | SH | SH | SH | — | SH | $L^2$ | $ON^{5-6}$ | 0 | 1 |
| 1825 | $K^{1-1}$ | $K^{1-1}$ | $K^{3-1}$ | — | $OC_2H_4OH$ | SH | SH | SH | — | SH | $L^2$ | $ON^{5-6}$ | 0 | 1 |
| 1826 | $K^{2-1}$ | $K^{1-1}$ | $K^{4-1}$ | — | $OC_2H_4OH$ | SH | SH | SH | — | SH | $L^2$ | $ON^{5-6}$ | 0 | 1 |
| 1827 | $K^{1-1}$ | $K^{1-1}$ | $K^{4-1}$ | — | $OC_2H_4OH$ | SH | SH | SH | — | SH | $L^2$ | $ON^{5-6}$ | 0 | 1 |
| 1828 | $K^{2-1}$ | $K^{1-1}$ | $K^{2-1}$ | — | $OC_2H_4OH$ | SH | SH | SH | — | SH | $L^2$ | $ON^{5-6}$ | 0 | 1 |
| 1829 | $K^{2-1}$ | $K^{1-1}$ | $K^{3-1}$ | — | $OC_2H_4OH$ | OH | SH | SH | — | SH | $L^1$ | $ON^{6-6}$ | 0 | 2 |
| 1830 | $K^{1-1}$ | $K^{1-1}$ | $K^{3-1}$ | — | $OC_2H_4OH$ | OH | SH | SH | — | SH | $L^1$ | $ON^{6-6}$ | 0 | 2 |
| 1831 | $K^{2-1}$ | $K^{1-1}$ | $K^{4-1}$ | — | $OC_2H_4OH$ | OH | SH | SH | — | SH | $L^1$ | $ON^{6-6}$ | 0 | 2 |
| 1832 | $K^{1-1}$ | $K^{1-1}$ | $K^{4-1}$ | — | $OC_2H_4OH$ | OH | SH | SH | — | SH | $L^1$ | $ON^{6-6}$ | 0 | 2 |
| 1833 | $K^{2-1}$ | $K^{1-1}$ | $K^{2-1}$ | — | $OC_2H_4OH$ | OH | SH | SH | — | SH | $L^1$ | $ON^{6-6}$ | 0 | 2 |
| 1834 | $K^{2-1}$ | $K^{1-1}$ | $K^{3-1}$ | — | $OC_2H_4OH$ | SH | SH | SH | — | SH | $L^1$ | $ON^{6-6}$ | 0 | 2 |
| 1835 | $K^{1-1}$ | $K^{1-1}$ | $K^{3-1}$ | — | $OC_2H_4OH$ | SH | SH | SH | — | SH | $L^1$ | $ON^{6-6}$ | 0 | 2 |
| 1836 | $K^{2-1}$ | $K^{1-1}$ | $K^{4-1}$ | — | $OC_2H_4OH$ | SH | SH | SH | — | SH | $L^1$ | $ON^{6-6}$ | 0 | 2 |
| 1837 | $K^{1-1}$ | $K^{1-1}$ | $K^{4-1}$ | — | $OC_2H_4OH$ | SH | SH | SH | — | SH | $L^1$ | $ON^{6-6}$ | 0 | 2 |
| 1838 | $K^{2-1}$ | $K^{1-1}$ | $K^{2-1}$ | — | $OC_2H_4OH$ | SH | SH | SH | — | SH | $L^1$ | $ON^{6-6}$ | 0 | 2 |
| 1839 | $K^{2-1}$ | $K^{1-1}$ | $K^{3-1}$ | — | $OC_2H_4OH$ | OH | SH | SH | — | SH | $L^2$ | $ON^{6-6}$ | 0 | 1 |
| 1840 | $K^{1-1}$ | $K^{1-1}$ | $K^{3-1}$ | — | $OC_2H_4OH$ | OH | SH | SH | — | SH | $L^2$ | $ON^{6-6}$ | 0 | 1 |
| 1841 | $K^{2-1}$ | $K^{1-1}$ | $K^{4-1}$ | — | $OC_2H_4OH$ | OH | SH | SH | — | SH | $L^2$ | $ON^{6-6}$ | 0 | 1 |
| 1842 | $K^{1-1}$ | $K^{1-1}$ | $K^{4-1}$ | — | $OC_2H_4OH$ | OH | SH | SH | — | SH | $L^2$ | $ON^{6-6}$ | 0 | 1 |
| 1843 | $K^{2-1}$ | $K^{1-1}$ | $K^{2-1}$ | — | $OC_2H_4OH$ | OH | SH | SH | — | SH | $L^2$ | $ON^{6-6}$ | 0 | 1 |
| 1844 | $K^{2-1}$ | $K^{1-1}$ | $K^{3-1}$ | — | $OC_2H_4OH$ | SH | SH | SH | — | SH | $L^2$ | $ON^{6-6}$ | 0 | 1 |
| 1845 | $K^{1-1}$ | $K^{1-1}$ | $K^{3-1}$ | — | $OC_2H_4OH$ | SH | SH | SH | — | SH | $L^2$ | $ON^{6-6}$ | 0 | 1 |
| 1846 | $K^{2-1}$ | $K^{1-1}$ | $K^{4-1}$ | — | $OC_2H_4OH$ | SH | SH | SH | — | SH | $L^2$ | $ON^{6-6}$ | 0 | 1 |
| 1847 | $K^{1-1}$ | $K^{1-1}$ | $K^{4-1}$ | — | $OC_2H_4OH$ | SH | SH | SH | — | SH | $L^2$ | $ON^{6-6}$ | 0 | 1 |
| 1848 | $K^{2-1}$ | $K^{1-1}$ | $K^{2-1}$ | — | $OC_2H_4OH$ | SH | SH | SH | — | SH | $L^2$ | $ON^{6-6}$ | 0 | 1 |
| 1849 | $K^{2-1}$ | $K^{1-1}$ | $K^{3-1}$ | — | $OC_2H_4OH$ | OH | SH | SH | — | SH | $L^1$ | $ON^{7-6}$ | 0 | 2 |
| 1850 | $K^{1-1}$ | $K^{1-1}$ | $K^{3-1}$ | — | $OC_2H_4OH$ | OH | SH | SH | — | SH | $L^1$ | $ON^{7-6}$ | 0 | 2 |

TABLE 1-continued

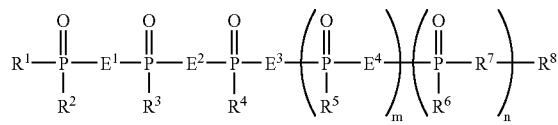

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1851 | $K^{2-1}$ | $K^{1-1}$ | $K^{4-1}$ | — | $OC_2H_4OH$ | OH | SH | SH | — | SH | $L^1$ | $ON^{7-6}$ | 0 | 2 |
| 1852 | $K^{1-1}$ | $K^{1-1}$ | $K^{4-1}$ | — | $OC_2H_4OH$ | OH | SH | SH | — | SH | $L^1$ | $ON^{7-6}$ | 0 | 2 |
| 1853 | $K^{2-1}$ | $K^{1-1}$ | $K^{2-1}$ | — | $OC_2H_4OH$ | OH | SH | SH | — | SH | $L^1$ | $ON^{7-6}$ | 0 | 2 |
| 1854 | $K^{2-1}$ | $K^{1-1}$ | $K^{3-1}$ | — | $OC_2H_4OH$ | SH | SH | SH | — | SH | $L^1$ | $ON^{7-6}$ | 0 | 2 |
| 1855 | $K^{1-1}$ | $K^{1-1}$ | $K^{3-1}$ | — | $OC_2H_4OH$ | SH | SH | SH | — | SH | $L^1$ | $ON^{7-6}$ | 0 | 2 |
| 1856 | $K^{2-1}$ | $K^{1-1}$ | $K^{4-1}$ | — | $OC_2H_4OH$ | SH | SH | SH | — | SH | $L^1$ | $ON^{7-6}$ | 0 | 2 |
| 1857 | $K^{1-1}$ | $K^{1-1}$ | $K^{4-1}$ | — | $OC_2H_4OH$ | SH | SH | SH | — | SH | $L^1$ | $ON^{7-6}$ | 0 | 2 |
| 1858 | $K^{2-1}$ | $K^{1-1}$ | $K^{2-1}$ | — | $OC_2H_4OH$ | SH | SH | SH | — | SH | $L^1$ | $ON^{7-6}$ | 0 | 2 |
| 1859 | $K^{2-1}$ | $K^{1-1}$ | $K^{3-1}$ | — | $OC_2H_4OH$ | OH | SH | SH | — | SH | $L^2$ | $ON^{7-6}$ | 0 | 1 |
| 1860 | $K^{1-1}$ | $K^{1-1}$ | $K^{3-1}$ | — | $OC_2H_4OH$ | OH | SH | SH | — | SH | $L^2$ | $ON^{7-6}$ | 0 | 1 |
| 1861 | $K^{2-1}$ | $K^{1-1}$ | $K^{4-1}$ | — | $OC_2H_4OH$ | OH | SH | SH | — | SH | $L^2$ | $ON^{7-6}$ | 0 | 1 |
| 1862 | $K^{1-1}$ | $K^{1-1}$ | $K^{4-1}$ | — | $OC_2H_4OH$ | OH | SH | SH | — | SH | $L^2$ | $ON^{7-6}$ | 0 | 1 |
| 1863 | $K^{2-1}$ | $K^{1-1}$ | $K^{2-1}$ | — | $OC_2H_4OH$ | OH | SH | SH | — | SH | $L^2$ | $ON^{7-6}$ | 0 | 1 |
| 1864 | $K^{2-1}$ | $K^{1-1}$ | $K^{3-1}$ | — | $OC_2H_4OH$ | SH | SH | SH | — | SH | $L^2$ | $ON^{7-6}$ | 0 | 1 |
| 1865 | $K^{1-1}$ | $K^{1-1}$ | $K^{3-1}$ | — | $OC_2H_4OH$ | SH | SH | SH | — | SH | $L^2$ | $ON^{7-6}$ | 0 | 1 |
| 1866 | $K^{2-1}$ | $K^{1-1}$ | $K^{4-1}$ | — | $OC_2H_4OH$ | SH | SH | SH | — | SH | $L^2$ | $ON^{7-6}$ | 0 | 1 |
| 1867 | $K^{1-1}$ | $K^{1-1}$ | $K^{4-1}$ | — | $OC_2H_4OH$ | SH | SH | SH | — | SH | $L^2$ | $ON^{7-6}$ | 0 | 1 |
| 1868 | $K^{2-1}$ | $K^{1-1}$ | $K^{2-1}$ | — | $OC_2H_4OH$ | SH | SH | SH | — | SH | $L^2$ | $ON^{7-6}$ | 0 | 1 |
| 1869 | $K^{2-1}$ | $K^{1-1}$ | $K^{3-1}$ | — | $OC_2H_4OH$ | OH | SH | SH | — | SH | $L^1$ | $ON^{8-6}$ | 0 | 2 |
| 1870 | $K^{1-1}$ | $K^{1-1}$ | $K^{3-1}$ | — | $OC_2H_4OH$ | OH | SH | SH | — | SH | $L^1$ | $ON^{8-6}$ | 0 | 2 |
| 1871 | $K^{2-1}$ | $K^{1-1}$ | $K^{4-1}$ | — | $OC_2H_4OH$ | OH | SH | SH | — | SH | $L^1$ | $ON^{8-6}$ | 0 | 2 |
| 1872 | $K^{1-1}$ | $K^{1-1}$ | $K^{4-1}$ | — | $OC_2H_4OH$ | OH | SH | SH | — | SH | $L^1$ | $ON^{8-6}$ | 0 | 2 |
| 1873 | $K^{2-1}$ | $K^{1-1}$ | $K^{2-1}$ | — | $OC_2H_4OH$ | OH | SH | SH | — | SH | $L^1$ | $ON^{8-6}$ | 0 | 2 |
| 1874 | $K^{2-1}$ | $K^{1-1}$ | $K^{3-1}$ | — | $OC_2H_4OH$ | SH | SH | SH | — | SH | $L^1$ | $ON^{8-6}$ | 0 | 2 |
| 1875 | $K^{1-1}$ | $K^{1-1}$ | $K^{3-1}$ | — | $OC_2H_4OH$ | SH | SH | SH | — | SH | $L^1$ | $ON^{8-6}$ | 0 | 2 |
| 1876 | $K^{2-1}$ | $K^{1-1}$ | $K^{4-1}$ | — | $OC_2H_4OH$ | SH | SH | SH | — | SH | $L^1$ | $ON^{8-6}$ | 0 | 2 |
| 1877 | $K^{1-1}$ | $K^{1-1}$ | $K^{4-1}$ | — | $OC_2H_4OH$ | SH | SH | SH | — | SH | $L^1$ | $ON^{8-6}$ | 0 | 2 |
| 1878 | $K^{2-1}$ | $K^{1-1}$ | $K^{2-1}$ | — | $OC_2H_4OH$ | SH | SH | SH | — | SH | $L^1$ | $ON^{8-6}$ | 0 | 2 |
| 1879 | $K^{2-1}$ | $K^{1-1}$ | $K^{3-1}$ | — | $OC_2H_4OH$ | OH | SH | SH | — | SH | $L^2$ | $ON^{8-6}$ | 0 | 1 |
| 1880 | $K^{1-1}$ | $K^{1-1}$ | $K^{3-1}$ | — | $OC_2H_4OH$ | OH | SH | SH | — | SH | $L^2$ | $ON^{8-6}$ | 0 | 1 |
| 1881 | $K^{2-1}$ | $K^{1-1}$ | $K^{4-1}$ | — | $OC_2H_4OH$ | OH | SH | SH | — | SH | $L^2$ | $ON^{8-6}$ | 0 | 1 |
| 1882 | $K^{1-1}$ | $K^{1-1}$ | $K^{4-1}$ | — | $OC_2H_4OH$ | OH | SH | SH | — | SH | $L^2$ | $ON^{8-6}$ | 0 | 1 |
| 1883 | $K^{2-1}$ | $K^{1-1}$ | $K^{2-1}$ | — | $OC_2H_4OH$ | OH | SH | SH | — | SH | $L^2$ | $ON^{8-6}$ | 0 | 1 |
| 1884 | $K^{2-1}$ | $K^{1-1}$ | $K^{3-1}$ | — | $OC_2H_4OH$ | SH | SH | SH | — | SH | $L^2$ | $ON^{8-6}$ | 0 | 1 |
| 1885 | $K^{1-1}$ | $K^{1-1}$ | $K^{3-1}$ | — | $OC_2H_4OH$ | SH | SH | SH | — | SH | $L^2$ | $ON^{8-6}$ | 0 | 1 |
| 1886 | $K^{2-1}$ | $K^{1-1}$ | $K^{4-1}$ | — | $OC_2H_4OH$ | SH | SH | SH | — | SH | $L^2$ | $ON^{8-6}$ | 0 | 1 |
| 1887 | $K^{1-1}$ | $K^{1-1}$ | $K^{4-1}$ | — | $OC_2H_4OH$ | SH | SH | SH | — | SH | $L^2$ | $ON^{8-6}$ | 0 | 1 |
| 1888 | $K^{2-1}$ | $K^{1-1}$ | $K^{2-1}$ | — | $OC_2H_4OH$ | SH | SH | SH | — | SH | $L^2$ | $ON^{8-6}$ | 0 | 1 |
| 1889 | $K^{2-1}$ | $K^{1-1}$ | $K^{3-1}$ | — | $OC_2H_4OH$ | OH | SH | SH | — | SH | $L^1$ | $ON^{9-6}$ | 0 | 2 |
| 1890 | $K^{1-1}$ | $K^{1-1}$ | $K^{3-1}$ | — | $OC_2H_4OH$ | OH | SH | SH | — | SH | $L^1$ | $ON^{9-6}$ | 0 | 2 |
| 1891 | $K^{2-1}$ | $K^{1-1}$ | $K^{4-1}$ | — | $OC_2H_4OH$ | OH | SH | SH | — | SH | $L^1$ | $ON^{9-6}$ | 0 | 2 |
| 1892 | $K^{1-1}$ | $K^{1-1}$ | $K^{4-1}$ | — | $OC_2H_4OH$ | OH | SH | SH | — | SH | $L^1$ | $ON^{9-6}$ | 0 | 2 |
| 1893 | $K^{2-1}$ | $K^{1-1}$ | $K^{2-1}$ | — | $OC_2H_4OH$ | OH | SH | SH | — | SH | $L^1$ | $ON^{9-6}$ | 0 | 2 |
| 1894 | $K^{2-1}$ | $K^{1-1}$ | $K^{3-1}$ | — | $OC_2H_4OH$ | SH | SH | SH | — | SH | $L^1$ | $ON^{9-6}$ | 0 | 2 |
| 1895 | $K^{1-1}$ | $K^{1-1}$ | $K^{3-1}$ | — | $OC_2H_4OH$ | SH | SH | SH | — | SH | $L^1$ | $ON^{9-6}$ | 0 | 2 |
| 1896 | $K^{2-1}$ | $K^{1-1}$ | $K^{4-1}$ | — | $OC_2H_4OH$ | SH | SH | SH | — | SH | $L^1$ | $ON^{9-6}$ | 0 | 2 |
| 1897 | $K^{1-1}$ | $K^{1-1}$ | $K^{4-1}$ | — | $OC_2H_4OH$ | SH | SH | SH | — | SH | $L^1$ | $ON^{9-6}$ | 0 | 2 |
| 1898 | $K^{2-1}$ | $K^{1-1}$ | $K^{2-1}$ | — | $OC_2H_4OH$ | SH | SH | SH | — | SH | $L^1$ | $ON^{9-6}$ | 0 | 2 |
| 1899 | $K^{2-1}$ | $K^{1-1}$ | $K^{3-1}$ | — | $OC_2H_4OH$ | OH | SH | SH | — | SH | $L^2$ | $ON^{9-6}$ | 0 | 1 |
| 1900 | $K^{1-1}$ | $K^{1-1}$ | $K^{3-1}$ | — | $OC_2H_4OH$ | OH | SH | SH | — | SH | $L^2$ | $ON^{9-6}$ | 0 | 1 |
| 1901 | $K^{2-1}$ | $K^{1-1}$ | $K^{4-1}$ | — | $OC_2H_4OH$ | OH | SH | SH | — | SH | $L^2$ | $ON^{9-6}$ | 0 | 1 |
| 1902 | $K^{1-1}$ | $K^{1-1}$ | $K^{4-1}$ | — | $OC_2H_4OH$ | OH | SH | SH | — | SH | $L^2$ | $ON^{9-6}$ | 0 | 1 |
| 1903 | $K^{2-1}$ | $K^{1-1}$ | $K^{2-1}$ | — | $OC_2H_4OH$ | OH | SH | SH | — | SH | $L^2$ | $ON^{9-6}$ | 0 | 1 |
| 1904 | $K^{2-1}$ | $K^{1-1}$ | $K^{3-1}$ | — | $OC_2H_4OH$ | SH | SH | SH | — | SH | $L^2$ | $ON^{9-6}$ | 0 | 1 |
| 1905 | $K^{1-1}$ | $K^{1-1}$ | $K^{3-1}$ | — | $OC_2H_4OH$ | SH | SH | SH | — | SH | $L^2$ | $ON^{9-6}$ | 0 | 1 |
| 1906 | $K^{2-1}$ | $K^{1-1}$ | $K^{4-1}$ | — | $OC_2H_4OH$ | SH | SH | SH | — | SH | $L^2$ | $ON^{9-6}$ | 0 | 1 |
| 1907 | $K^{1-1}$ | $K^{1-1}$ | $K^{4-1}$ | — | $OC_2H_4OH$ | SH | SH | SH | — | SH | $L^2$ | $ON^{9-6}$ | 0 | 1 |
| 1908 | $K^{2-1}$ | $K^{1-1}$ | $K^{2-1}$ | — | $OC_2H_4OH$ | SH | SH | SH | — | SH | $L^2$ | $ON^{9-6}$ | 0 | 1 |
| 1909 | $K^{2-1}$ | $K^{1-1}$ | $K^{3-1}$ | — | $OC_2H_4OH$ | OH | SH | SH | — | SH | $L^1$ | $ON^{10-1}$ | 0 | 2 |
| 1910 | $K^{1-1}$ | $K^{1-1}$ | $K^{3-1}$ | — | $OC_2H_4OH$ | OH | SH | SH | — | SH | $L^1$ | $ON^{10-1}$ | 0 | 2 |
| 1911 | $K^{2-1}$ | $K^{1-1}$ | $K^{4-1}$ | — | $OC_2H_4OH$ | OH | SH | SH | — | SH | $L^1$ | $ON^{10-1}$ | 0 | 2 |
| 1912 | $K^{1-1}$ | $K^{1-1}$ | $K^{4-1}$ | — | $OC_2H_4OH$ | OH | SH | SH | — | SH | $L^1$ | $ON^{10-1}$ | 0 | 2 |
| 1913 | $K^{2-1}$ | $K^{1-1}$ | $K^{2-1}$ | — | $OC_2H_4OH$ | OH | SH | SH | — | SH | $L^1$ | $ON^{10-1}$ | 0 | 2 |
| 1914 | $K^{2-1}$ | $K^{1-1}$ | $K^{3-1}$ | — | $OC_2H_4OH$ | SH | SH | SH | — | SH | $L^1$ | $ON^{10-1}$ | 0 | 2 |
| 1915 | $K^{1-1}$ | $K^{1-1}$ | $K^{3-1}$ | — | $OC_2H_4OH$ | SH | SH | SH | — | SH | $L^1$ | $ON^{10-1}$ | 0 | 2 |
| 1916 | $K^{2-1}$ | $K^{1-1}$ | $K^{4-1}$ | — | $OC_2H_4OH$ | SH | SH | SH | — | SH | $L^1$ | $ON^{10-1}$ | 0 | 2 |
| 1917 | $K^{1-1}$ | $K^{1-1}$ | $K^{4-1}$ | — | $OC_2H_4OH$ | SH | SH | SH | — | SH | $L^1$ | $ON^{10-1}$ | 0 | 2 |
| 1918 | $K^{2-1}$ | $K^{1-1}$ | $K^{2-1}$ | — | $OC_2H_4OH$ | SH | SH | SH | — | SH | $L^1$ | $ON^{10-1}$ | 0 | 2 |

TABLE 1-continued $$R^1-\overset{\overset{O}{\|}}{\underset{R^2}{P}}-E^1-\overset{\overset{O}{\|}}{\underset{R^3}{P}}-E^2-\overset{\overset{O}{\|}}{\underset{R^4}{P}}-E^3-\left(\overset{\overset{O}{\|}}{\underset{R^5}{P}}-E^4\right)_m\left(\overset{\overset{O}{\|}}{\underset{R^6}{P}}-R^7\right)_n-R^8$$

| Exemplified Compound No. | $E^1$ | $E^2$ | $E^3$ | $E^4$ | $R^1$ | $R^2$ | $R^3$ | $R^4$ | $R^5$ | $R^6$ | $R^7$ | $R^8$ | m | n |
|---|---|---|---|---|---|---|---|---|---|---|---|---|---|---|
| 1919 | $K^{2-1}$ | $K^{1-1}$ | $K^{3-1}$ | — | $OC_2H_4OH$ | OH | SH | SH | — | SH | $L^2$ | $ON^{10-1}$ | 0 | 1 |
| 1920 | $K^{1-1}$ | $K^{1-1}$ | $K^{3-1}$ | — | $OC_2H_4OH$ | OH | SH | SH | — | SH | $L^2$ | $ON^{10-1}$ | 0 | 1 |
| 1921 | $K^{2-1}$ | $K^{1-1}$ | $K^{4-1}$ | — | $OC_2H_4OH$ | OH | SH | SH | — | SH | $L^2$ | $ON^{10-1}$ | 0 | 1 |
| 1922 | $K^{1-1}$ | $K^{1-1}$ | $K^{4-1}$ | — | $OC_2H_4OH$ | OH | SH | SH | — | SH | $L^2$ | $ON^{10-1}$ | 0 | 1 |
| 1923 | $K^{2-1}$ | $K^{1-1}$ | $K^{2-1}$ | — | $OC_2H_4OH$ | OH | SH | SH | — | SH | $L^2$ | $ON^{10-1}$ | 0 | 1 |
| 1924 | $K^{2-1}$ | $K^{1-1}$ | $K^{3-1}$ | — | $OC_2H_4OH$ | SH | SH | SH | — | SH | $L^2$ | $ON^{10-1}$ | 0 | 1 |
| 1925 | $K^{1-1}$ | $K^{1-1}$ | $K^{3-1}$ | — | $OC_2H_4OH$ | SH | SH | SH | — | SH | $L^2$ | $ON^{10-1}$ | 0 | 1 |
| 1926 | $K^{2-1}$ | $K^{1-1}$ | $K^{4-1}$ | — | $OC_2H_4OH$ | SH | SH | SH | — | SH | $L^2$ | $ON^{10-1}$ | 0 | 1 |
| 1927 | $K^{1-1}$ | $K^{1-1}$ | $K^{4-1}$ | — | $OC_2H_4OH$ | SH | SH | SH | — | SH | $L^2$ | $ON^{10-1}$ | 0 | 1 |
| 1928 | $K^{2-1}$ | $K^{1-1}$ | $K^{2-1}$ | — | $OC_2H_4OH$ | SH | SH | SH | — | SH | $L^2$ | $ON^{10-1}$ | 0 | 1 |
| 1929 | $K^{2-1}$ | $K^{1-1}$ | $K^{2-1}$ | — | $OC_2H_4OH$ | OH | OH | OH | — | OH | $L^1$ | $ON^{11-1}$ | 0 | 2 |
| 1930 | $K^{2-1}$ | $K^{1-1}$ | $K^{2-1}$ | — | $OC_2H_4OH$ | OH | OH | OH | — | OH | $L^1$ | $ON^{12-1}$ | 0 | 2 |
| 1931 | $K^{2-1}$ | $K^{1-1}$ | $K^{2-1}$ | — | $OC_2H_4OH$ | OH | OH | OH | — | OH | $L^1$ | $ON^{13-1}$ | 0 | 2 |
| 1932 | $K^{2-1}$ | $K^{1-1}$ | $K^{2-1}$ | — | $OC_2H_4OH$ | OH | OH | OH | — | OH | $L^1$ | $ON^{14-1}$ | 0 | 2 |
| 1933 | $K^{2-1}$ | $K^{1-1}$ | $K^{2-1}$ | — | $OC_2H_4OH$ | OH | OH | OH | — | OH | $L^1$ | $ON^{15-1}$ | 0 | 2 |
| 1934 | $K^{2-1}$ | $K^{1-1}$ | $K^{2-1}$ | — | $OC_2H_4OH$ | OH | OH | OH | — | OH | $L^1$ | $ON^{16-1}$ | 0 | 2 |
| 1935 | $K^{2-1}$ | $K^{1-1}$ | $K^{2-1}$ | — | $OC_2H_4OH$ | OH | OH | OH | — | OH | $L^1$ | $ON^{17-1}$ | 0 | 2 |
| 1936 | $K^{2-1}$ | $K^{1-1}$ | $K^{2-1}$ | — | $OC_2H_4OH$ | OH | OH | OH | — | OH | $L^2$ | $ON^{14-1}$ | 0 | 1 |
| 1937 | $K^{2-1}$ | $K^{1-1}$ | $K^{2-1}$ | — | $OC_2H_4OH$ | OH | OH | OH | — | — | — | H | 0 | 0 |
| 1938 | $K^{2-1}$ | $K^{1-1}$ | $K^{2-1}$ | — | $OC_2H_4OH$ | OH | OH | OH | — | $SC_2H_4C^{18}$ | O | H | 0 | 1 |
| 1939 | $K^{2-1}$ | $K^{1-1}$ | $K^{2-1}$ | — | $SC_2H_4C^{20}$ | OH SH | SH | — | — | — | — | H | 0 | 0 |
| 1940 | $K^{2-1}$ | $K^{1-1}$ | $K^{2-1}$ | — | $SC_2H_4C^{18}$ | OH SH | SH | — | — | — | — | H | 0 | 0 |
| 1941 | $K^{2-1}$ | $K^{1-1}$ | $K^{2-1}$ | — | $SC_2H_4C^{18}$ | OH SH | SH | — | — | — | — | H | 0 | 0 |
| 1942 | $K^{2-1}$ | $K^{1-1}$ | $K^{2-1}$ | — | $SC_2H_4C^{20}$ | SH SH | SH | — | — | — | — | H | 0 | 0 |
| 1943 | $K^{2-1}$ | $K^{1-1}$ | $K^{2-1}$ | — | $SC_2H_4C^{18}$ | SH SH | SH | — | — | — | — | H | 0 | 0 |
| 1944 | $K^{2-1}$ | $K^{1-1}$ | $K^{2-1}$ | — | $SC_2H_4C^{18}$ | SH SH | SH | — | — | — | — | H | 0 | 0 |
| 1945 | $K^{2-1}$ | $K^{1-1}$ | $K^{2-1}$ | — | $OC_2H_4OH$ | OH SH | SH | — | $SC_2H_4OH$ | — | — | H | 0 | 1 |
| 1946 | $K^{2-1}$ | $K^{1-1}$ | $K^{2-1}$ | — | $OC_2H_4OH$ | SH SH | SH | — | $SC_2H_4OH$ | — | — | H | 0 | 1 |

In Table 1, Ph represents a phenyl group, Bn represents a benzyl group, Me represents a methyl group, Et represents an ethyl group, Pr represents an n-propyl group and tBu represents a tert-butyl group; and in Table 1, the groups described as $K^x$ represent groups having the following structure.

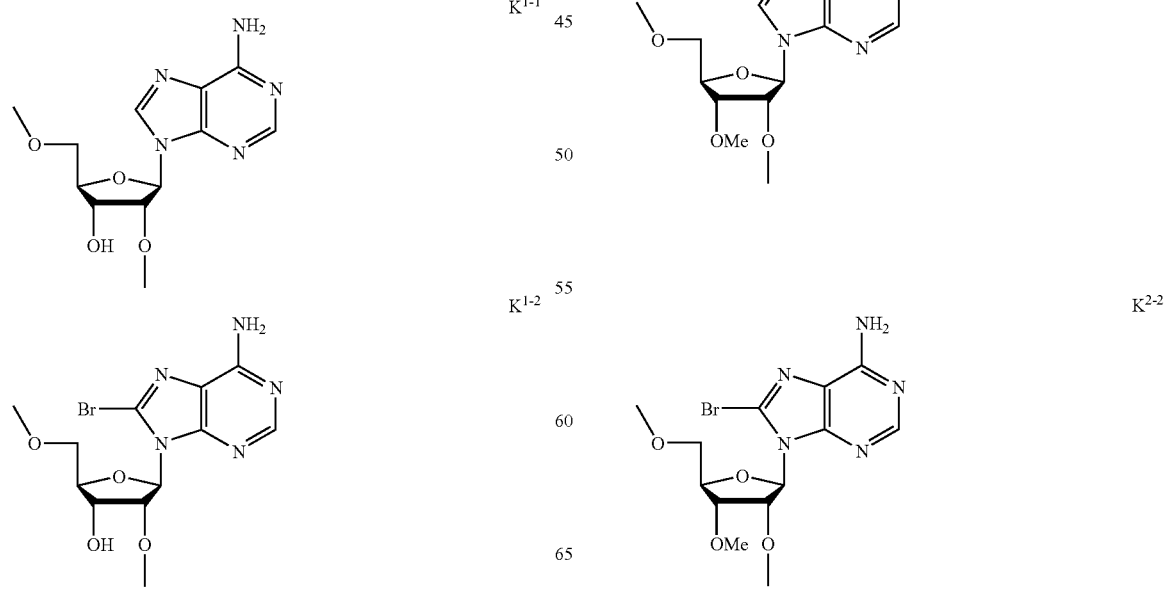

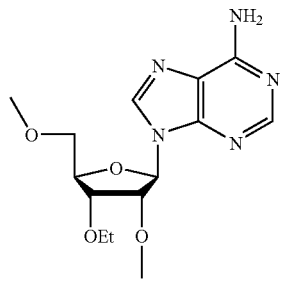 K²⁻³
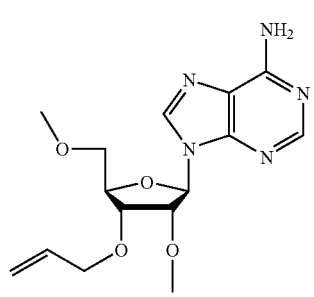 K²⁻⁴
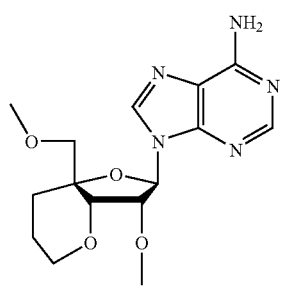 K³⁻¹
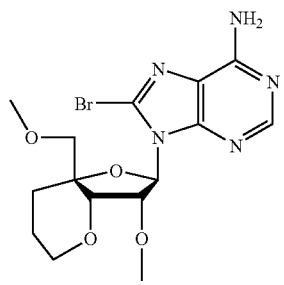 K³⁻²
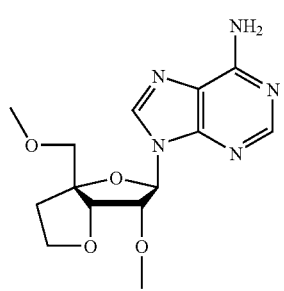 K³⁻³
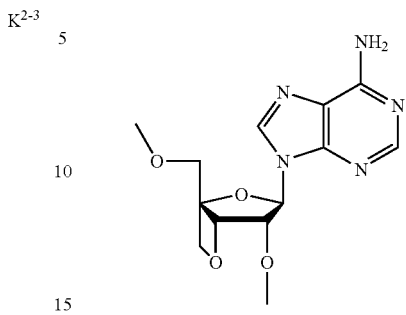 K³⁻⁴
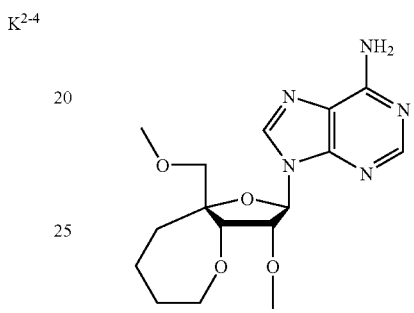 K³⁻⁵
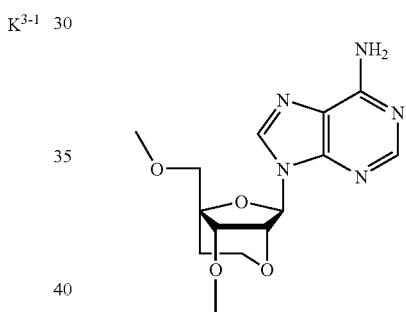 K⁴⁻¹
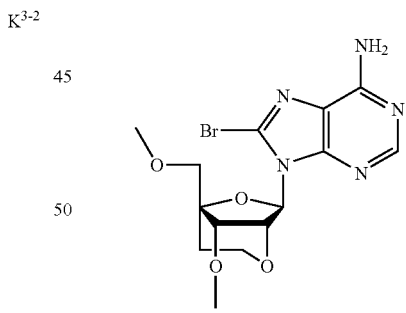 K⁴⁻²
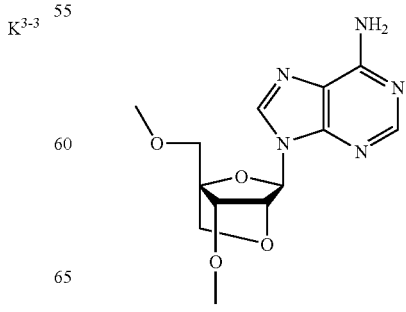 K⁴⁻³

-continued

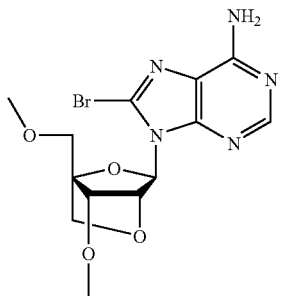

K<sup>4-4</sup>

Further, in Table 1, the groups described as Gly, POMO, POMS, ATE, PTE, ALM, $L^1$, $L^2$, $C^{20}$, $C^{18}$, $C^{14}$ and $C^{10}$ represent groups having the following structures respectively.

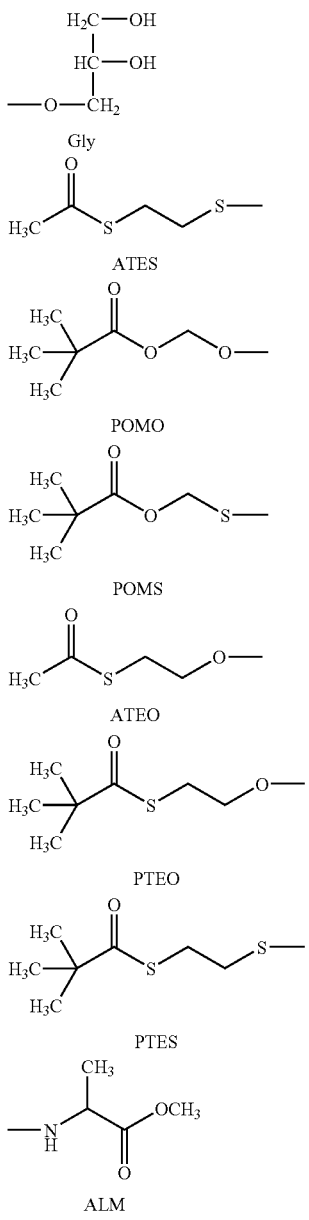

-continued

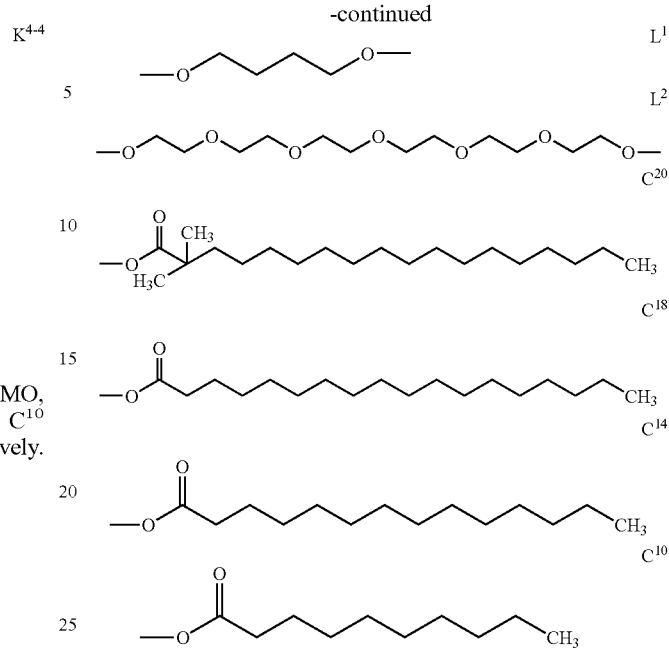

Further, in Table 1, the groups described as $ON^X$ represent oligonucleotide analogs having the structures defined below and bonded to $R^7$ at the terminal.

$ON^{1-1}$

—$G^e$-p-$C^e$-p-$G^e$-p-$C^e$-p-$G^e$-p-$G^e$-p-$G^e$-p-$G^e$-p-$A^e$-p-$G^e$-p-$C^e$-p-$A^e$-p-$A^e$-p-$A^e$-p-$A^e$-p-$G^e$-p-$C^e$-p-$A^e$-p-$C^e$-hp $ON^{1-2}$

—$G^e$-p-$C^e$-p-$G^e$-p-$C^e$-p-$G^e$-p-$G^e$-p-$G^e$-p-$G^e$-p-$A^e$-p-$G^e$-p-$C^e$-p-$A^e$-p-$A^e$-p-$A^e$-p-$A^e$-hp $ON^{1-3}$

—$A^e$-p-$G^e$-p-$C^e$-p-$A^e$-p-$A^e$-p-$A^e$-p-$A^e$-p-$G^e$-p-$C^e$-p-$A^e$-p-$C^e$-hp $ON^{1-4}$

—$G^e$-p-$C^e$-p-$G^e$-p-$C^e$-p-$G^e$-p-$G''$-s-$G''$-s-$G''$-s-$A''$-s-$G''$-s-$C''$-s-$A''$-s-$A''$-s-$A''$-s-$A^e$-p-$G^e$-p-$C^e$-p-$A^e$-p-$C^e$-hp $ON^{1-5}$

—$G^e$-p-$C^e$-p-$G^e$-p-$C^e$-p-$G^e$-p-$G''$-s-$G''$-s-$G''$-s-$A''$-s-$G''$-s-$C^e$-p-$A^e$-p-$A^e$-p-$A^e$-p-$A^e$-hp $ON^{1-6}$

—$G^e$-s-$C^e$-s-$G^e$-s-$C^e$-s-$G^e$-s-$G''$-s-$G''$-s-$G''$-s-$A''$-s-$G''$-s-$C''$-s-$A''$-s-$A''$-s-$A''$-s-$A^e$-s-$G^e$-s-$C^e$-s-$A^e$-s-$C^e$-hp $ON^{1-7}$

—$G^e$-s-$C^e$-s-$G^e$-s-$C^e$-s-$G^e$-s-$G''$-s-$G''$-s-$G''$-s-$A''$-s-$G''$-s-$C''$-s-$A''$-s-$A''$-s-$A''$-s-$A^e$-s-$G^e$-s-$C^e$-s-$A^e$-s-$C^e$-hp $ON^{2-1}$

—$G^e$-p-$C^e$-p-$C^e$-p-$C^e$-p-$A^e$-p-$C^e$-p-$C^e$-p-$G^e$-p-$G^e$-p-$G^e$-p-$T^e$-p-$C^e$-p-$C^e$-p-$A^e$-p-$C^e$-p-$C^e$-p-$A^e$-p-$T^e$-hp $ON^{2-2}$

—$C^e$-p-$A^e$-p-$C^e$-p-$C^e$-p-$G^e$-p-$G^e$-p-$G^e$-p-$T^e$-p-$C^e$-p-$C^e$-p-$A^e$-p-$C^e$-p-$C^e$-p-$A^e$-p-$T^e$-hp

ON²⁻³

—Cᵉ-p-Aᵉ-p-Cᵉ-p-Cᵉ-p-Gᵉ-p-Gᵉ-p-Gᵉ-p-Tᵉ-p-Cᵉ-p-Cᵉ-p-Aᵉ-p-Cᵉ-hp

ON²⁻⁴

—Gᵉ-p-Cᵉ-p-Cᵉ-p-Cᵉ-p-Aᵉ-p-Cⁿ-s-Cⁿ-s-Gⁿ-s-Gⁿ-s-Gⁿ-s-Tⁿ-s-Cⁿ-s-Cⁿ-s-Aᵉ-p-Cᵉ-p-Cᵉ-p-Aᵉ-p-Tᵉ-hp

ON²⁻⁵

—Cᵉ-p-Aᵉ-p-Cᵉ-p-Cᵉ-p-Gᵉ-p-Gⁿ-s-Gⁿ-s-Tⁿ-s-Cⁿ-s-Cⁿ-s-Aᵉ-p-Cᵉ-p-Cᵉ-p-Aᵉ-p-Tᵉ-hp

ON²⁻⁶

—Gᵉ-s-Cᵉ-s-Cᵉ-s-Cᵉ-s-Aᵉ-s-Cⁿ-s-Cⁿ-s-Gⁿ-s-Gⁿ-s-Gⁿ-s-Tⁿ-s-Cⁿ-s-Cⁿ-s-Aᵉ-s-Cᵉ-s-Cᵉ-s-Aᵉ-s-Tᵉ-hp

ON²⁻⁷

—Cᵉ-s-Aᵉ-s-Cᵉ-s-Cᵉ-s-Gᵉ-s-Gⁿ-s-Gⁿ-s-Tⁿ-s-Cⁿ-s-Cⁿ-s-Aᵉ-s-Cᵉ-s-Cᵉ-s-Aᵉ-s-Tᵉ-hp

ON³⁻¹

—Gᵉ-p-Tᵉ-p-Aᵉ-p-Cᵉ-p-Tᵉ-p-Aᵉ-p-Cᵉ-p-Tᵉ-p-Cᵉ-p-Cᵉ-p-Cᵉ-p-Tᵉ-p-Gᵉ-p-Cᵉ-p-Tᵉ-p-Tᵉ-p-Cᵉ-p-Tᵉ-p-Gᵉ-hp

ON³⁻²

—Cᵉ-p-Tᵉ-p-Aᵉ-p-Cᵉ-p-Tᵉ-p-Cᵉ-p-Cᵉ-p-Cᵉ-p-Tᵉ-p-Gᵉ-p-Cᵉ-p-Tᵉ-p-Tᵉ-p-Cᵉ-p-Tᵉ-p-Gᵉ-hp

ON³⁻³

—Cᵉ-p-Tᵉ-p-Aᵉ-p-Cᵉ-p-Tᵉ-p-Cᵉ-p-Cᵉ-p-Cᵉ-p-Tᵉ-p-Gᵉ-p-Cᵉ-p-Tᵉ-p-Tᵉ-hp

ON³⁻⁴

—Gᵉ-p-Tᵉ-p-Aᵉ-p-Cᵉ-p-Tᵉ-p-Aⁿ-s-Cⁿ-s-Tⁿ-s-Cⁿ-s-Cⁿ-s-Cⁿ-s-Tⁿ-s-Gⁿ-s-Cⁿ-s-Tᵉ-p-Tᵉ-p-Cᵉ-p-Tᵉ-p-Gᵉ-hp

ON³⁻⁵

—Cᵉ-p-Tᵉ-p-Aᵉ-p-Cᵉ-p-Tᵉ-p-Cⁿ-s-Cⁿ-s-Cⁿ-s-Tⁿ-s-Gⁿ-s-Cⁿ-s-Tᵉ-p-Tᵉ-p-Cᵉ-p-Tᵉ-p-Gᵉ-hp

ON³⁻⁶

—Gᵉ-s-Tᵉ-s-Aᵉ-s-Cᵉ-s-Tᵉ-s-Aⁿ-s-Cⁿ-s-Tⁿ-s-Cⁿ-s-Cⁿ-s-Cⁿ-s-Tⁿ-s-Gⁿ-s-Cⁿ-s-Tᵉ-s-Tᵉ-s-Cᵉ-s-Tᵉ-s-Gᵉ-hp

ON³⁻⁷

—Cᵉ-s-Tᵉ-s-Aᵉ-s-Cᵉ-s-Tᵉ-s-Cⁿ-s-Cⁿ-s-Cⁿ-s-Tⁿ-s-Gⁿ-s-Cⁿ-s-Tᵉ-s-Tᵉ-s-Cᵉ-s-Tᵉ-s-Gᵉ-hp

ON⁴⁻¹

—Gᵉ-p-Tᵉ-p-Tᵉ-p-Cᵉ-p-Tᵉ-p-Cᵉ-p-Gᵉ-p-Cᵉ-p-Tᵉ-p-Gᵉ-p-Gᵉ-p-Tᵉ-p-Gᵉ-p-Aᵉ-p-Gᵉ-p-Tᵉ-p-Tᵉ-p-Tᵉ-p-Cᵉ-p-Aᵉ-hp

ON⁴⁻²

—Cᵉ-p-Tᵉ-p-Cᵉ-p-Gᵉ-p-Cᵉ-p-Tᵉ-p-Gᵉ-p-Gᵉ-p-Tᵉ-p-Gᵉ-p-Aᵉ-p-Gᵉ-p-Tᵉ-p-Tᵉ-p-Tᵉ-p-Cᵉ-p-Aᵉ-hp

ON⁴⁻³

—Cᵉ-p-Tᵉ-p-Cᵉ-p-Gᵉ-p-Cᵉ-p-Tᵉ-p-Gᵉ-p-Gᵉ-p-Tᵉ-p-Gᵉ-p-Aᵉ-p-Gᵉ-p-Tᵉ-p-Tᵉ-hp

ON⁴⁻⁴

—Gᵉ-p-Tᵉ-p-Tᵉ-p-Cᵉ-p-Tᵉ-p-Cⁿ-s-Gⁿ-s-Cⁿ-s-Tⁿ-s-Gⁿ-s-Gⁿ-s-Tⁿ-s-Gⁿ-s-Aⁿ-s-Gⁿ-s-Tᵉ-p-Tᵉ-p-Tᵉ-p-Cᵉ-p-Aᵉ-hp

ON⁴⁻⁵

—Cᵉ-p-Tᵉ-p-Cᵉ-p-Gᵉ-p-Cᵉ-p-Tⁿ-s-Gⁿ-s-Gⁿ-s-Tⁿ-s-Gⁿ-s-Aⁿ-s-Gⁿ-s-Tᵉ-p-Tᵉ-p-Tᵉ-p-Cᵉ-p-Aᵉ-hp

ON⁴⁻⁶

—Gᵉ-s-Tᵉ-s-Tᵉ-s-Cᵉ-s-Tᵉ-s-Cⁿ-s-Gⁿ-s-Cⁿ-s-Tⁿ-s-Gⁿ-s-Gⁿ-s-Tⁿ-s-Gⁿ-s-Aⁿ-s-Gⁿ-s-Tᵉ-s-Tᵉ-s-Tᵉ-s-Cᵉ-s-Aᵉ-hp

ON⁴⁻⁷

—Cᵉ-s-Tᵉ-s-Cᵉ-s-Gᵉ-s-Cᵉ-s-Tⁿ-s-Gⁿ-s-Gⁿ-s-Tⁿ-s-Gⁿ-s-Aⁿ-s-Gⁿ-s-Tᵉ-s-Tᵉ-s-Tᵉ-s-Cᵉ-s-Aᵉ-hp

ON⁵⁻¹

—Gᵉ-p-Cᵉ-p-Cᵉ-p-Cᵉ-p-Aᵉ-p-Aᵉ-p-Gᵉ-p-Cᵉ-p-Tᵉ-p-Gᵉ-p-Gᵉ-p-Cᵉ-p-Aᵉ-p-Tᵉ-p-Cᵉ-p-Cᵉ-p-Gᵉ-p-Tᵉ-p-Cᵉ-p-Aᵉ-hp

ON⁵⁻²

—Cᵉ-p-Aᵉ-p-Aᵉ-p-Gᵉ-p-Cᵉ-p-Tᵉ-p-Gᵉ-p-Gᵉ-p-Cᵉ-p-Aᵉ-p-Tᵉ-p-Cᵉ-p-Cᵉ-p-Gᵉ-p-Tᵉ-p-Cᵉ-p-Aᵉ-hp

ON⁵⁻³

—Cᵉ-p-Aᵉ-p-Aᵉ-p-Gᵉ-p-Cᵉ-p-Tᵉ-p-Gᵉ-p-Gᵉ-p-Cᵉ-p-Aᵉ-p-Tᵉ-p-Cᵉ-p-Cᵉ-p-Gᵉ-hp

ON⁵⁻⁴

—Gᵉ-p-Cᵉ-p-Cᵉ-p-Cᵉ-p-Aᵉ-p-Aⁿ-s-Gⁿ-s-Cⁿ-s-Tⁿ-s-Gⁿ-s-Gⁿ-s-Cⁿ-s-Aⁿ-s-Tⁿ-s-Cⁿ-s-Cᵉ-p-Gᵉ-p-Tᵉ-p-Cᵉ-p-Aᵉ-hp

ON⁵⁻⁵

—Cᵉ-p-Aᵉ-p-Aᵉ-p-Gᵉ-p-Cᵉ-p-Tⁿ-s-Gⁿ-s-Gⁿ-s-Cⁿ-s-Aⁿ-s-Tⁿ-s-Cᵉ-s-Cᵉ-p-Gᵉ-p-Tᵉ-p-Cᵉ-p-Aᵉ-hp

ON⁵⁻⁶

—Gᵉ-s-Cᵉ-s-Cᵉ-s-Cᵉ-s-Aᵉ-s-Aⁿ-s-Gⁿ-s-Cⁿ-s-Tⁿ-s-Gⁿ-s-Gⁿ-s-Cⁿ-s-Aⁿ-s-Tⁿ-s-Cⁿ-s-Cᵉ-s-Gᵉ-s-Tᵉ-s-Cᵉ-s-Aᵉ-hp

ON⁵⁻⁷

—Cᵉ-s-Aᵉ-s-Aᵉ-s-Gᵉ-s-Cᵉ-s-Tⁿ-s-Gⁿ-s-Gⁿ-s-Cⁿ-s-Aⁿ-s-Tⁿ-s-Cⁿ-s-Cᵉ-s-Gᵉ-s-Tᵉ-s-Cᵉ-s-Aᵉ-hp

ON⁶⁻¹

—Tᵉ-p-Cᵉ-p-Cᵉ-p-Gᵉ-p-Tᵉ-p-Cᵉ-p-Aᵉ-p-Tᵉ-p-Cᵉ-p-Gᵉ-p-Cᵉ-p-Tᵉ-p-Cᵉ-p-Cᵉ-p-Tᵉ-p-Cᵉ-p-Aᵉ-p-Gᵉ-p-Gᵉ-p-Gᵉ-hp

OH⁶⁻²

—Gᵉ-p-Tᵉ-p-Cᵉ-p-Aᵉ-p-Tᵉ-p-Cᵉ-p-Gᵉ-p-Cᵉ-p-Tᵉ-p-Cᵉ-p-Cᵉ-p-Tᵉ-p-Cᵉ-p-Aᵉ-p-Gᵉ-p-Gᵉ-p-Gᵉ-hp

ON⁶⁻³

—Gᵉ-p-Tᵉ-p-Cᵉ-p-Aᵉ-p-Tᵉ-p-Cᵉ-p-Gᵉ-p-Cᵉ-p-Tᵉ-p-Cᵉ-p-Cᵉ-p-Tᵉ-p-Cᵉ-p-Aᵉ-hp

ON⁶⁻⁴

—Tᵉ-p-Cᵉ-p-Cᵉ-p-Gᵉ-p-Tᵉ-p-Cⁿ-s-Aⁿ-s-Tⁿ-s-Cⁿ-s-Gⁿ-s-Cⁿ-s-Tⁿ-s-Cⁿ-s-Cⁿ-s-Tⁿ-s-Cᵉ-p-Aᵉ-p-Gᵉ-p-Gᵉ-p-Gᵉ-hp

ON⁶⁻⁵

—Gᵉ-p-Tᵉ-p-Cᵉ-p-Aᵉ-p-Tᵉ-p-Cⁿ-s-Gⁿ-s-Cⁿ-s-Tⁿ-s-Cⁿ-s-Cⁿ-s-Tⁿ-s-Cᵉ-p-Aᵉ-p-Gᵉ-p-Gᵉ-p-Gᵉ-hp

ON⁶⁻⁶

—Tᵉ-s-Cᵉ-s-Cᵉ-s-Gᵉ-s-Tᵉ-s-Cⁿ-s-Aⁿ-s-Tⁿ-s-Cⁿ-s-Gⁿ-s-Cⁿ-s-Tⁿ-s-Cⁿ-s-Cⁿ-s-Tⁿ-s-Cᵉ-s-Aᵉ-s-Gᵉ-s-Gᵉ-s-Gᵉ-hp

ON$^{6-7}$

—G$^e$-s-T$^e$-s-C$^e$-s-A$^e$-s-T$^e$-s-C''-s-G''-s-C''-s-T''-s-C''-s-C''-s-T''-s-C$^e$-s-A$^e$-s-G$^e$-s-G$^e$-hp

ON$^{7-1}$

—G$^e$-p-C$^e$-p-T$^e$-p-G$^e$-p-A$^e$-p-T$^e$-p-T$^e$-p-A$^e$-p-G$^e$-p-A$^e$-p-G$^e$-p-A$^e$-p-G$^e$-p-A$^e$-p-G$^e$-p-G$^e$-p-T$^e$-p-C$^e$-p-C$^e$-p-C$^e$-hp

ON$^{7-2}$

—G$^e$-p-A$^e$-p-T$^e$-p-T$^e$-p-A$^e$-p-G$^e$-p-A$^e$-p-G$^e$-p-A$^e$-p-G$^e$-p-A$^e$-p-G$^e$-p-G$^e$-p-T$^e$-p-C$^e$-p-C$^e$-p-C$^e$-hp

ON$^{7-3}$

—G$^e$-p-A$^e$-p-T$^e$-p-T$^e$-p-A$^e$-p-G$^e$-p-A$^e$-p-G$^e$-p-A$^e$-p-G$^e$-p-A$^e$-p-G$^e$-p-G$^e$-p-T$^e$-hp

ON$^{7-4}$

—G$^e$-p-C$^e$-p-T$^e$-p-G$^e$-p-A$^e$-p-T''-s-T''-s-A''-s-G''-s-A''-s-G''-s-A''-s-G''-s-A''-s-G''-s-G$^e$-p-T$^e$-p-C$^e$-p-C$^e$-p-C$^e$-hp

ON$^{7-5}$

—G$^e$-p-A$^e$-p-T$^e$-p-T$^e$-p-A$^e$-p-G''-s-A''-s-G''-s-A''-s-G''-s-A''-s-G''-s-G$^e$-p-T$^e$-p-C$^e$-p-C$^e$-p-C$^e$-hp

ON$^{7-6}$

—G$^e$-s-C$^e$-s-T$^e$-s-G$^e$-s-A$^e$-s-T''-s-T''-s-A''-s-G''-s-A''-s-G''-s-A''-s-A''-s-G''-s-G$^e$-s-T$^e$-s-C$^e$-s-C$^e$-s-C$^e$-hp

ON$^{7-7}$

—G$^e$-p-A$^e$-p-T$^e$-p-T$^e$-p-A$^e$-p-G''-s-A''-s-G''-s-A''-s-G''-s-A''-s-G''-s-G$^e$-p-T$^e$-p-C$^e$-p-C$^e$-p-C$^e$-hp

ON$^{8-1}$

—G$^e$-p-C$^e$-p-T$^e$-p-C$^e$-p-C$^e$-p-T$^e$-p-T$^e$-p-C$^e$-p-C$^e$-p-A$^e$-p-C$^e$-p-T$^e$-p-G$^e$-p-A$^e$-p-T$^e$-p-C$^e$-p-C$^e$-p-T$^e$-p-G$^e$-p-C$^e$-hp

ON$^{8-2}$

—C$^e$-p-C$^e$-p-T$^e$-p-T$^e$-p-C$^e$-p-C$^e$-p-A$^e$-p-C$^e$-p-T$^e$-p-G$^e$-p-A$^e$-p-T$^e$-p-C$^e$-p-C$^e$-p-T$^e$-p-G$^e$-p-C$^e$-hp

ON$^{8-3}$

—C$^e$-p-C$^e$-p-T$^e$-p-T$^e$-p-C$^e$-p-C$^e$-p-A$^e$-p-C$^e$-p-T$^e$-p-G$^e$-p-A$^e$-p-T$^e$-p-C$^e$-p-C$^e$-hp

ON$^{8-4}$

—G$^e$-p-C$^e$-p-T$^e$-p-C$^e$-p-C$^e$-p-T''-s-T''-s-C''-s-C''-s-A''-s-C''-s-T''-s-G''-s-A''-s-T''-s-C$^e$-p-C$^e$-p-T$^e$-p-G$^e$-p-C$^e$-hp

ON$^{8-5}$

—C$^e$-p-C$^e$-p-T$^e$-p-T$^e$-p-C$^e$-p-C''-s-A''-s-C''-s-T''-s-G''-s-A''-s-T''-s-C$^e$-p-C$^e$-p-T$^e$-p-G$^e$-p-C$^e$-hp

ON$^{8-6}$

—G$^e$-s-C$^e$-s-T$^e$-s-C$^e$-s-C$^e$-s-T''-s-T''-s-C''-s-C''-s-A''-s-C''-s-T''-s-G''-s-A''-s-T''-s-C$^e$-s-C$^e$-s-T$^e$-s-G$^e$-s-C$^e$-hp

ON$^{8-7}$

—C$^e$-s-C$^e$-s-T$^e$-s-T$^e$-s-C$^e$-s-C''-s-A''-s-C''-s-T''-s-G''-s-A''-s-T''-s-C$^e$-s-C$^e$-s-T$^e$-s-G$^e$-s-C$^e$-hp

ON$^{9-1}$

—T$^e$-p-C$^e$-p-C$^e$-p-C$^e$-p-G$^e$-p-C$^e$-p-C$^e$-p-T$^e$-p-G$^e$-p-T$^e$-p-G$^e$-p-A$^e$-p-C$^e$-p-A$^e$-p-T$^e$-p-G$^e$-p-C$^e$-p-A$^e$-p-T$^e$-p-T$^e$-hp

ON$^{9-2}$

—C$^e$-p-G$^e$-p-C$^e$-p-C$^e$-p-T$^e$-p-G$^e$-p-T$^e$-p-G$^e$-p-A$^e$-p-C$^e$-p-A$^e$-p-T$^e$-p-G$^e$-p-C$^e$-p-A$^e$-p-T$^e$-p-T$^e$-hp

ON$^{9-3}$

—C$^e$-p-G$^e$-p-C$^e$-p-C$^e$-p-T$^e$-p-G$^e$-p-T$^e$-p-G$^e$-p-A$^e$-p-C$^e$-p-A$^e$-p-T$^e$-p-G$^e$-p-C$^e$-hp

ON$^{9-4}$

—T$^e$-p-C$^e$-p-C$^e$-p-C$^e$-p-G$^e$-p-C''-s-C''-s-T''-s-G''-s-T''-s-G''-s-A''-s-C''-s-A''-s-T''-s-G$^e$-p-C$^e$-p-A$^e$-p-T$^e$-p-T$^e$-hp

ON$^{9-5}$

—C$^e$-p-G$^e$-p-C$^e$-p-C$^e$-p-T$^e$-p-G''-s-T''-s-G''-s-A''-s-C''-s-A''-s-T''-s-G$^e$-p-C$^e$-p-A$^e$-p-T$^e$-p-T$^e$-hp

ON$^{9-6}$

—T$^e$-s-C$^e$-s-C$^e$-s-C$^e$-s-G$^e$-s-C''-s-C''-s-T''-s-G''-s-T''-s-G''-s-A''-s-C''-s-A''-s-T''-s-G$^e$-s-C$^e$-s-A$^e$-s-T$^e$-s-T$^e$-hp

ON$^{9-7}$

—C$^e$-s-G$^e$-s-C$^e$-s-C$^e$-s-T$^e$-s-G''-s-T''-s-G''-s-A''-s-C''-s-A''-s-T''-s-G$^e$-s-C$^e$-s-A$^e$-s-T$^e$-s-T$^e$-hp

ON$^{10-1}$

—T$^e$-s-A$^e$-s-G$^e$-s-G$^e$-s-G$^e$-s-T$^e$-s-T$^e$-s-A$^e$-s-G$^e$-s-A$^e$-s-C$^e$-s-A$^e$-s-A$^e$-s-G$^e$-hp

ON$^{11-1}$

-p-G$^e$-p-A$^e$-p-G$^e$-p-A$^e$-p-C$^e$-p-C''-p-C''-p-T''-p-G''-p-A''-p-A''-p-C''-p-A''-p-G''-p-T''-p-T$^e$-p-G$^e$-p-A$^e$-p-T$^e$-p-C$^e$-hp

ON$^{12-1}$

-p-T$^e$-p-C$^e$-p-T$^e$-p-T$^e$-p-G$^e$-p-G''-p-T''-p-T''-p-G''-p-T''-p-A''-p-A''-p-G''-p-A''-p-G''-p-A$^e$-p-G$^e$-p-A$^e$-p-G$^e$-p-A$^e$-hp

ON$^{13-1}$

-p-T$^e$-p-T$^e$-p-C$^e$-p-A$^e$-p-G$^e$-p-G''-p-C''-p-C''-p-T''-p-C''-p-C''-p-A''-p-T''-p-A''-p-T''-p-G$^e$-p-G$^e$-p-A$^e$-p-A$^e$-p-T$^e$-hp

ON$^{14-1}$

-p-G$^e$-p-T$^e$-p-T$^e$-p-C$^e$-p-T$^e$-p-C''-p-G''-p-C''-p-T''-p-G''-p-G''-p-T''-p-G''-p-A''-p-G''-p-T$^e$-p-T$^e$-p-T$^e$-p-C$^e$-p-A$^e$-hp

ON$^{15-1}$

-p-G$^e$-p-A$^e$-p-T$^e$-p-G$^e$-p-G$^e$-p-A''-p-A''-p-A''-p-T''-p-C''-p-T''-p-C''-p-T''-p-G''-p-C''-p-C$^e$-p-G$^e$-p-C$^e$-p-A$^e$-p-T$^e$-hp

ON$^{16-1}$

-p-A$^e$-p-T$^e$-p-G$^e$-p-G$^e$-p-C$^e$-p-A''-p-C''-p-C''-p-T''-p-C''-p-T''-p-T''-p-G''-p-T''-p-G''-p-G$^e$-p-A$^e$-p-C$^e$-p-C$^e$-p-A$^e$-hp

ON$^{17-1}$

-p-C$^e$-p-A$^e$-p-G$^e$-p-C$^e$-p-C$^e$-p-A''-p-T''-p-G''-p-G''-p-T''-p-C''-p-C''-p-C''-p-C''-p-C$^e$-p-C$^e$-p-C$^e$-p-A$^e$-p-A$^e$-hp

Further, the groups described as A'', G'', C'', T'', A$^e$, G$^e$, C$^e$, T$^e$, p, s and hp in the above represent groups having the following structure.

A$^n$ 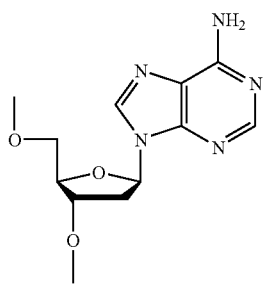

G$^n$ 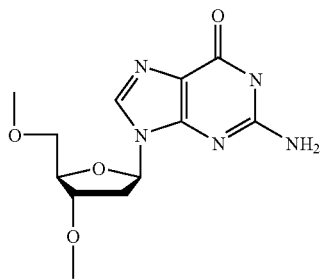

C$^n$ 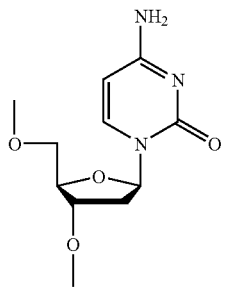

T$^n$ 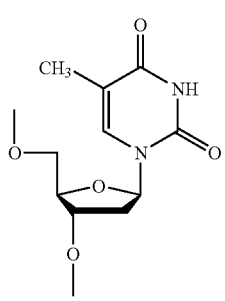

A$^e$ 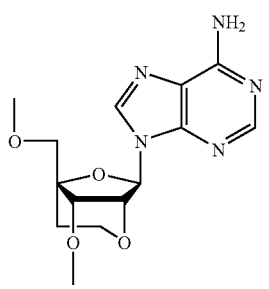

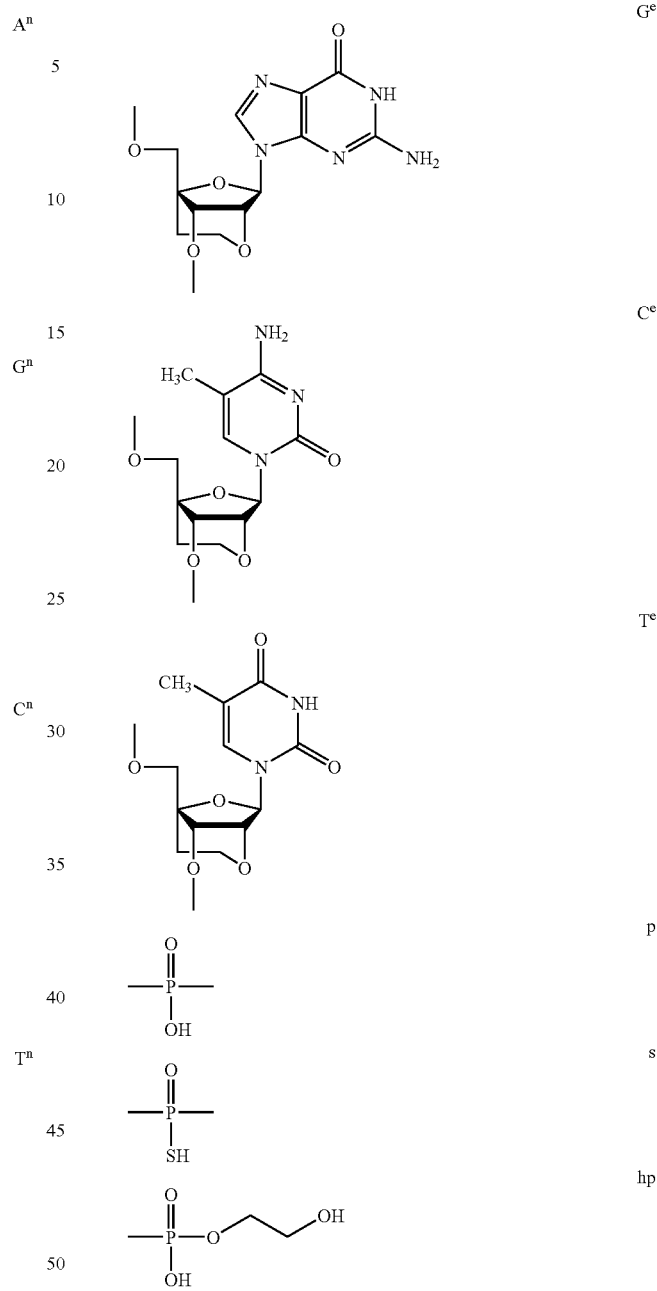

In the base sequences of the aforementioned oligonucleotide analogs, ON[1] is a sequence in human telomerase (GenBank Accession No. U86046, base sequence of the complementary chain of nucleotide numbers 170 to 188), ON[2] is a sequence in human breakpoint cluster region (BCR) mRNA (GenBank Accession No. NM-021574.1, base sequence of the complementary chain of nucleotide numbers 597 to 614), ON[3] is a sequence in interferon-inducible double-stranded RNA-dependent human protein kinase (PKR) mRNA (GenBank Accession No. NM-002759.1, base sequence of the complementary chain of nucleotide numbers 490 to 508), ON[4] is a sequence in human protein kinase C, alpha (PKCα) mRNA (GenBank Accession No. NM-002737.1, base sequence of the complementary chain of nucleotide numbers 2044 to 2063), ON⁵ is a sequence in human intercellular adhesion molecule (ICAM1) mRNA (GenBank Accession No. NM-000201.1, base sequence of the complementary chain of nucleotide numbers 2100 to 2119), ON⁶ is a sequence in human ras transforming protein gene (GenBank Accession No. M38453.1, base sequence of the complementary chain of nucleotide numbers 121 to 140), ON⁷ is a sequence in human tumor necrosis factor (TNF superfamily, member 2) (TNF) mRNA (GenBank Accession No. NM-000594.1, base sequence of the complementary chain of nucleotide numbers 279 to 298), ON⁸ is a sequence in human phosphotyrosyl-protein phosphatase (PTP-1B) mRNA (GenBank Accession No. M31724.1, base sequence of the complementary chain of nucleotide numbers 951 to 970), ON⁹ is a sequence in human c-raf-1 mRNA (GenBank Accession No. NM-002880.1, base sequence of the complementary chain of nucleotide numbers 2484 to 2503), and ON¹⁰ is a sequence in human telomerase mRNA (GenBank Accession No. U86046, base sequence of the complementary chain of nucleotide numbers 136 to 148).

In the above Table 1, the preferred compounds are 1, 2, 3, 4, 5, 6, 7, 8, 13, 22, 27, 28, 31, 39, 41, 42, 50, 52, 53, 61, 63, 64, 71, 73, 77, 79, 96, 98, 102, 104, 146, 148, 152, 154, 171, 173, 177, 179, 290, 292, 293, 305, 307, 310, 311, 312, 313, 314, 316, 319, 320, 325, 330, 334, 338, 339, 343, 344, 351, 356, 364, 369, 377, 382, 386, 390, 391, 395, 396, 403, 408, 416, 421, 424, 425, 428, 438, 441, 451, 452, 453, 454, 455, 461, 462, 463, 464, 465, 471, 472, 473, 474, 475, 481, 482, 483, 484, 485, 491, 492, 493, 494, 495, 501, 502, 503, 504, 505, 511, 512, 513, 514, 515, 521, 522, 523, 524, 525, 531, 532, 533, 534, 535, 541, 542, 543, 544, 545, 551, 552, 553, 554, 555, 561, 562, 563, 564, 565, 571, 572, 573, 574, 575, 581, 582, 583, 584, 585, 591, 592, 593, 594, 595, 601, 602, 603, 604, 605, 611, 612, 613, 614, 615, 621, 622, 623, 624, 625, 631, 632, 633, 634, 635, 641, 642, 643, 644, 645, 651, 652, 653, 654, 655, 661, 662, 663, 664, 665, 671, 672, 673, 674, 675, 681, 682, 683, 684, 685, 691, 692, 693, 694, 695, 701, 702, 703, 704, 705, 711, 712, 713, 714, 715, 721, 722, 723, 724, 725, 731, 732, 733, 734, 735, 741, 742, 743, 744, 745, 751, 752, 753, 754, 755, 761, 762, 763, 764, 765, 771, 772, 773, 774, 775, 781, 782, 783, 784, 785, 791, 792, 793, 794, 795, 801, 802, 803, 804, 805, 811, 812, 813, 814, 815, 821, 822, 823, 824, 825, 831, 832, 833, 834, 835, 841, 842, 843, 844, 845, 851, 852, 853, 854, 855, 861, 862, 863, 864, 865, 871, 872, 873, 874, 875, 881, 882, 883, 884, 885, 891, 892, 893, 894, 895, 901, 902, 903, 907, 908, 909, 913, 914, 915, 919, 920, 924, 925, 926, 930, 931, 932, 936, 937, 941, 942, 943, 947, 948, 949, 953, 954, 959, 960, 961, 962, 963, 966, 967, 978, 979, 990, 991, 1002, 1003, 1014, 1015, 1026, 1027, 1038, 1039, 1050, 1051, 1062, 1063, 1074, 1075, 1078, 1079, 1082, 1083, 1086, 1087, 1090, 1091, 1094, 1095, 1098, 1099, 1102, 1103, 1106, 1107, 1110, 1111, 1122, 1123, 1134, 1135, 1146, 1147, 1158, 1159, 1170, 1171, 1182, 1183, 1194, 1195, 1206, 1207, 1220, 1231, 1243, 1255, 1267, 1279, 1291, 1303, 1315, 1344, 1345, 1346, 1347, 1348, 1349, 1350, 1351, 1352, 1353, 1354, 1355, 1356, 1357, 1358, 1359, 1360, 1361, 1429, 1430, 1431, 1432, 1433, 1449, 1450, 1451, 1452, 1453, 1469, 1470, 1471, 1472, 1473, 1489, 1490, 1491, 1492, 1493, 1509, 1510, 1511, 1512, 1513, 1529, 1530, 1531, 1532, 1533, 1549, 1550, 1551, 1552., 1553, 1569, 1570, 1571, 1572, 1573, 1589, 1590, 1591, 1592, 1593, 1609, 1609, 1613, 1617, 1621, 1625, 1629, 1633, 1637, 1641, 1645, 1647, 1648, 1650, 1651, 1653, 1663, 1665, 1666, 1668, 1669, 1671, 1690, 1691, 1692, 1693, 1694, 1695, 1696, 1697, 1698, 1705, 1706, 1707, 1708, 1709, 1710, 1723, 1724, 1725, 1726, 1727, 1728, 1734, 1735, 1736, 1737, 1738, 1754, 1755, 1756, 1757, 1758, 1774, 1775, 1776, 1777, 1778 1794, 1795, 1796, 1797 1798, 1814, 1815, 1816, 1817, 1818, 1834, 1835, 1836, 1837 1838, 1854, 1855, 1856, 1857, 1858, 1874, 1875, 1876, 1877, 1878, 1894, 1895, 1896, 1897, 1898, 1914, 1915, 1916, 1917, and 1918, and more preferable compounds are 1, 2, 3, 4, 5, 8, 290, 305, 307, 338, 343, 364, 369, 390, 395, 416, 421, 451, 452, 455, 461, 462, 465, 471, 472, 475, 481, 482, 485, 491, 492, 495, 501, 502, 505, 511, 512, 515, 521, 522, 525, 531, 532, 535, 541, 542, 545, 551, 552, 555, 561, 562, 565, 571, 572, 575, 581, 582, 585, 591, 592, 595, 601, 602, 605, 611, 612, 615, 621, 622, 625, 631, 632, 635, 641, 642, 645, 651, 652, 655, 661, 662, 665, 671, 672, 675, 681, 682, 685, 691, 692, 695, 701, 702, 705, 711, 712, 715, 721, 722, 725, 731, 732, 735, 741, 742, 745, 751, 752, 755, 761, 762, 765, 771, 772, 775, 781, 782, 785, 791, 792, 795, 801, 802, 805, 811, 812, 815, 821, 822, 825, 831, 832, 835, 841, 842, 845, 851, 852, 855, 861, 862, 865, 871, 872, 875, 881, 882, 885, 891, 892, 895, 953, 954, 959, 960, 961, 962, 963, 966, 967, 978, 979, 990, 991, 1002, 1003, 1014, 1015, 1026, 1027, 1038, 1039, 1050, 1051, 1062, 1063, 1075, 1079, 1083, 1087, 1091, 1095, 1099, 1103, 1107, 1110, 1111, 1122, 1123, 1134, 1135, 1146, 1147, 1158, 1159, 1170, 1171, 1182, 1183, 1194, 1195, 1206, 1207, 1429, 1430, 1449, 1450, 1469, 1470, 1489, 1490, 1509, 1510, 1529, 1530, 1549, 1550, 1569, 1570, 1589, 1590, 1648, 1650, 1651, 1653, 1666, 1668, 1669, 1671, 1691, 1692, 1695, 1696, 1697, 1698, 1707, 1708, 1709, 1710, 1725, 1726, 1727, and 1728.

The compounds (1) of the present invention can be prepared by appropriately utilizing Process A, Process B, Process C, Process D, Process E, Process F, Process G, and Process H mentioned below.

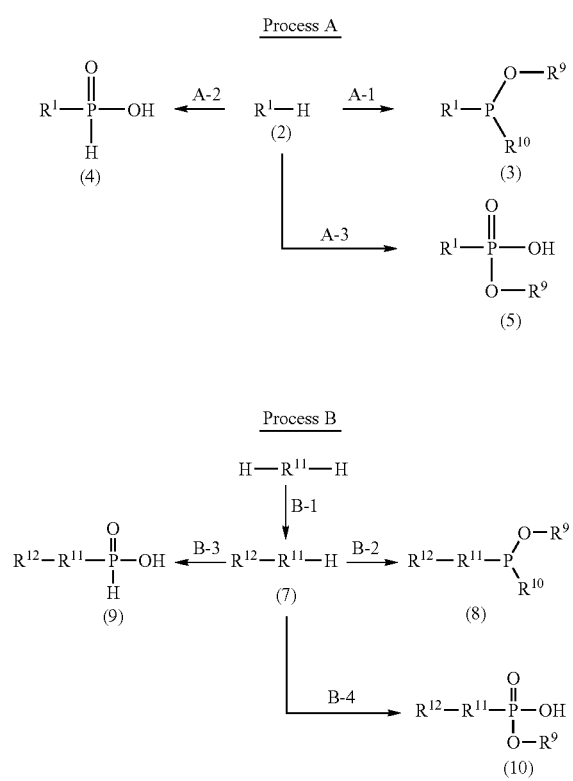

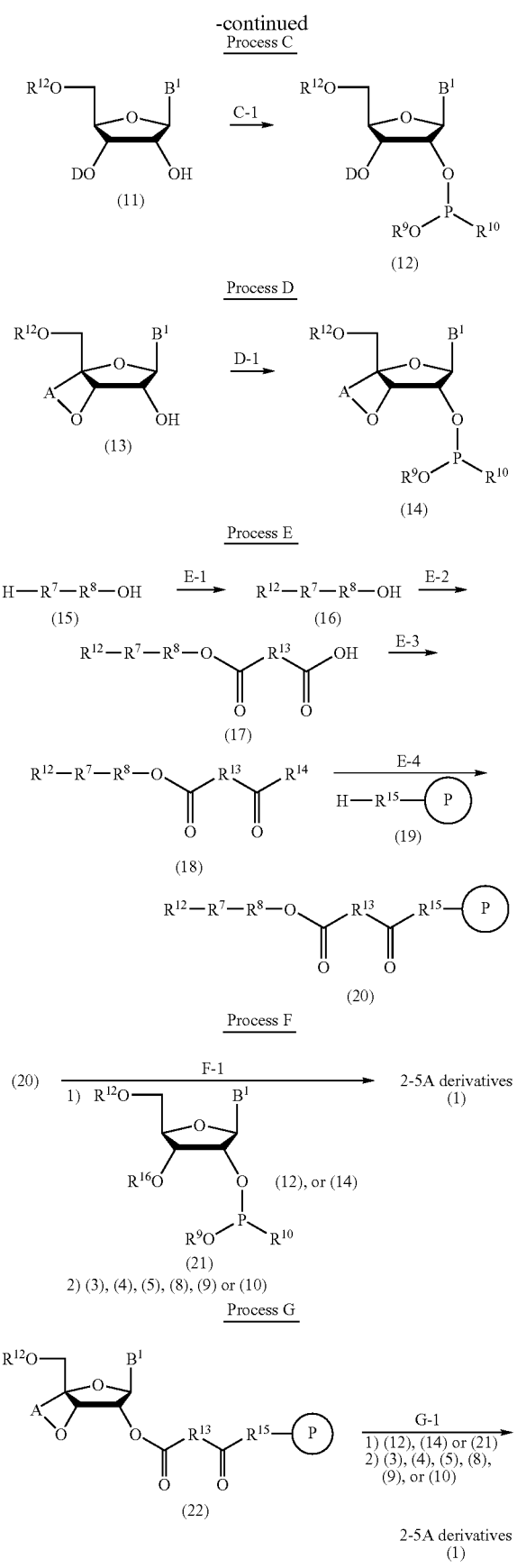
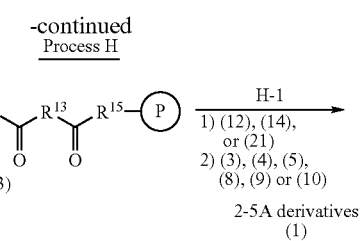

In Process A, Process B, Process C, Process D, Process E, Process F, Process G, and Process H, A, D, $R^1$, $R^7$, and $R^8$ have the same meanings as defined above; $R^9$ represents a protecting group for protecting a phosphoric acid group or a phosphorous acid group; $R^{10}$ represents a dialkylamino group (particularly a diisopropylamino group or a diethylamino group); $R^{11}$ represents an $R^1$ group which requires a protecting group in the synthesis of the 2-5A analog; $B^1$ represents a purin-9-yl group or a substituted purin-9-yl group having substituent(s) selected from the above Group α, but a group substituted by amino group is excluded. $R^{12}$ and $R^{16}$ are the same or different and represent a protecting group; $R^{13}$ represents a —(CH$_2$)h- group (h is an integer of from 2 to 8); $R^{14}$ represents a hydroxyl group, a phenyloxy group which may be substituted, or an ethyloxy group which may be substituted by halogen; $R^{15}$ represents an oxygen atom, a sulfur atom or an NH group; and HR$^{15}$—P (encircled) represents a high molecular weight compound.

The "protecting group" in the definition of $R^9$ can be, for example, a lower alkyl group such as methyl; a lower alkenyl group such as 2-propenyl; a cyano lower alkyl group such as 2-cyanoethyl; a lower alkoxylated lower alkoxymethyl group such as 2-methoxyethoxymethyl; a halogeno lower alkoxymethyl group such as 2,2,2-trichloroethoxymethyl and bis(2-chloroethoxy)methyl; a halogenated ethyl group such as 2,2,2-trichloroethyl; a methyl group substituted by an aryl group such as benzyl; a methyl group substituted by from 1 to 3 aryl groups whose aryl ring is substituted by lower alkyl, lower alkoxy, halogen or cyano group(s) such as 4-methylbenzyl, 2-nitrobenzyl, 4-nitrobenzyl, 4-chlorobenzyl, 4-bromobenzyl and 4-cyanobenzyl; an aryl group substituted by halogen atom(s), lower alkoxy group(s) or nitro group(s) such as 4-chlorophenyl, 2-chlorophenyl, 4-methoxyphenyl, 4-nitrophenyl and 2,4-dinitrophenyl; or a lower alkylcarbonyloxymethyl group such as pentanoyloxymethyl and pivaloyloxymethyl; and is preferably a methyl group, a 2-cyanoethyl group, a benzyl group, a 2-chlorophenyl group, a 4-chlorophenyl group, a 2-propenyl group or a pivaloyloxymethyl group.

The "protecting group" in the definition of $R^{12}$ and $R^{16}$ can be, for example, an "acyl type" protecting group including an "aliphatic acyl group" such as an alkylcarbonyl group, e.g., formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl; a carboxylated alkylcarbonyl group, e.g., succinoyl, glutaroyl and adipoyl; a halogeno lower alkylcarbonyl group, e.g., chloroacetyl, dichloroacetyl, trichloroacetyl and trifluoroacetyl; a lower alkoxy lower alkylcarbonyl group, e.g., methoxyacetyl; or an unsaturated alkylcarbonyl group, e.g., (E)-2-methyl-2-butenoyl; and an "aromatic acyl group" such as an arylcarbonyl group, e.g., benzoyl, α-naphthoyl and β-naphthoyl; a halogeno arylcarbonyl group, e.g., 2-bromobenzoyl and 4-chlorobenzoyl; a lower alkylated arylcarbonyl group, e.g., 2,4,6-trimethylbenzoyl and 4-toluoyl; a lower alkoxylated arylcarbonyl group, e.g., 4-anisoyl; a carboxylated arylcarbonyl group, e.g., 2-carboxybenzoyl, 3-carboxybenzoyl and 4-carboxybenzoyl; a nitrated arylcarbonyl group, e.g., 4-nitrobenzoyl and 2-nitrobenzoyl; a lower alkoxycarbonylated arylcarbonyl group, e.g., 2-(methoxycarbonyl)benzoyl; or an arylated arylcarbonyl group, e.g., 4-phenylbenzoyl;

a "lower alkyl group" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl;

a "lower alkenyl group" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl;

a "tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl;

a "tetrahydrofuranyl or tetrahydrothiofuranyl group" such as tetrahydrofuran-2-yl and tetrahydrothiofuran-2-yl;

a "silyl group" such as a tri-lower alkylsilyl group, e.g., trimethylsilyl, triethylsilyl, isopropyldimethylsilyl, t-butyldimethylsilyl, methyldiisopropylsilyl, methyldi-t-butylsilyl and triisopropylsilyl; or a tri-lower alkylsilyl group substituted by 1 or 2 aryl groups, e.g., diphenylmethylsilyl, diphenylbutylsilyl, diphenylisopropylsilyl and phenyldiisopropylsilyl;

a "lower alkoxymethyl group" such as methoxymethyl, 1,1-dimethyl-1-methoxymethyl, ethoxymethyl, propoxymethyl, isopropoxymethyl, butoxymethyl and t-butoxymethyl;

a "lower alkoxylated lower alkoxymethyl group" such as 2-methoxyethoxymethyl;

a "halogeno lower alkoxymethyl" such as 2,2,2-trichloroethoxymethyl and bis(2-chloroethoxy)methyl;

a "lower alkoxylated ethyl group" such as 1-ethoxyethyl and 1-(isopropoxy)ethyl;

a "halogenated ethyl group" such as 2,2,2-trichloroethyl;

a "methyl group substituted by from 1 to 3 aryl groups" such as benzyl, α-naphthylmethyl, β-naphthylmethyl, diphenylmethyl, triphenylmethyl, α-naphthyldiphenylmethyl and 9-anthrylmethyl;

a "methyl group substituted by from 1 to 3 aryl groups whose aryl ring is substituted by lower alkyl, lower alkoxy, halogen or cyano group(s)" such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl and 4-cyanobenzyl;

a "lower alkoxycarbonyl group" such as methoxycarbonyl, ethoxycarbonyl, t-butoxycarbonyl and isobutoxycarbonyl;

an "aryl group substituted by halogen atom(s), lower alkoxy group(s) or nitro group(s)" such as 4-chlorophenyl, 2-chlorophenyl, 4-methoxyphenyl, 4-nitrophenyl and 2,4-dinitrophenyl;

a "lower alkoxycarbonyl group substituted by halogen or tri-lower alkylsilyl group(s)" such as 2,2,2-trichloroethoxycarbonyl and 2-trimethylsilylethoxycarbonyl;

an "alkenyloxycarbonyl group" such as vinyloxycarbonyl and aryloxycarbonyl; or an "aralkyloxycarbonyl group whose aryl ring may be substituted by 1 or 2 lower alkoxy or nitro groups" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl.

In the following, the respective steps of Process A, Process B, Process C, Process D, Process E, Process F, Process G, and Process H will be explained in detail.

(Step A-1)

The present step is a step, wherein compound (3) is produced by reacting compound (2) with a mono-substituted chloro(alkoxy)phosphine, di-substituted alkoxyphosphine, mono-substituted chloro(benzyloxy)phosphine, or di-substituted benzyloxyphosphine normally used for amidite formation, in an inert solvent.

The solvent to be used is not particularly limited so long as it does not affect the reaction, but can preferably be an ether such as tetrahydrofuran, diethyl ether or dioxane; or a halogenated hydrocarbon such as methylene chloride, chloroform, carbon tetrachloride, dichloroethane, chlorobenzene or dichlorobenzene.

The mono-substituted chloro(alkoxy)phosphine to be used can be, for example, a phosphine such as chloro(morpholino)methoxyphosphine, chloro(morpholino)cyanoethoxyphosphine, chloro(dimethylamino)methoxyphosphine, chloro(dimethylamino)cyanoethoxyphosphine, chloro(diisopropylamino)methoxyphosphine or chloro(diisopropylamino)cyanoethoxyphosphine, and is preferably chloro(morpholino)methoxyphosphine, chloro(morpholino)cyanoethoxyphosphine, chloro(diisopropylamino)methoxyphosphine or chloro(diisopropylamino)cyanoethoxyphosphine.

In the case of using a mono-substituted chloro(alkoxy)phosphine, a deoxidizer is used. In that case, the deoxidizer to be used can be a heterocyclic amine such as pyridine or dimethylaminopyridine; or an aliphatic amine such as trimethylamine, triethylamine, diisopropylamine or diisopropylethylamine, and is preferably an aliphatic amine (particularly diisopropylethylamine).

The di-substituted alkoxyphosphine to be used can be, for example, a phosphine such as bis(diisopropylamino)cyanoethoxyphosphine, bis(diethylamino)methanesulfonylethoxyphosphine, bis(diisopropylamino)(2,2,2-trichloroethoxy)phosphine or bis(diisopropylamino)(4-chlorophenylmethoxy)phosphine, and is preferably bis(diisopropylamino)cyanoethoxyphosphine.

In the case of using a di-substituted alkoxyphosphine, an acid or an organic salt is used. In that case, the acid to be used is tetrazol, acetic acid or p-toluenesulfonic acid, and the organic salt to be used is tetrazol diisopropylamine salt, acetic acid diisopropylamine salt or p-toluenesulfonic acid diisopropylamine salt, preferably tetrazol or tetrazol diisopropylamine salt.

The mono-substituted chloro(benzyloxy)phosphine to be used can be, for example, a phosphine such as chloro(morpholino)benzyloxyphosphine, chloro(dimethylamino)methoxyphosphine, chloro(dimethylamino)benzyloxyphosphine or chloro(diisopropylamino)benzyloxyphosphine, and is preferably chloro(diisopropylamino)benzyloxyphosphine.

In the case of using a mono-substituted chloro(benzyloxy) phosphine, a deoxidizer is used. In that case, the deoxidizer to be used can be a heterocyclic amine such as pyridine or dimethylaminopyridine; or an aliphatic amine such as trimethylamine, triethylamine, diisopropylamine or diisopropylethylamine, and is preferably an aliphatic amine (particularly diisopropylethylamine).

The di-substituted benzyloxyphosphine to be used can be, for example, a phosphine such as bis(diisopropylamino)benzyloxyphosphine or bis(diethylamino)benzyloxyphosphine, and is preferably bis(diisopropylamino)benzyloxyphosphine.

In the case of using a di-substituted benzyloxyphosphine, an acid or an organic salt is used. In that case, the acid to be used is tetrazol, acetic acid or p-toluenesulfonic acid, and the organic salt to be used is tetrazol diisopropylamine salt, acetic acid diisopropylamine salt or p-toluenesulfonic acid diisopropylamine salt, preferably tetrazol or tetrazol diisopropylamine salt.

The reaction temperature is not particularly limited, but is normally from 0 to 80° C., preferably room temperature.

While the reaction time varies depending on the starting materials, the reagents and the temperature used, it is normally from 5 minutes to 30 hours; and in the case where the reaction is carried out at room temperature, it is preferably from 30 minutes to 10 hours.

After the reaction, the desired compound (3) of the present reaction is obtained, for example, by, after suitably neutralizing the reaction mixture, and removing any insoluble matter, if present, by filtration, addition of water and an immiscible organic solvent such as ethyl acetate, followed by washing with water, separating the organic layer containing the desired compound, drying with anhydrous magnesium sulfate or the like, and distilling off the solvent. The thus obtained desired compound can be further purified by ordinary methods such as recrystallization, reprecipitation or chromatography, if necessary.

(Step A-2)

The present step is a step, wherein compound (4) is produced by allowing compound (2) to react with tris-(1,2,4-triazolyl)phosphite in an inert solvent (preferably a halogenated hydrocarbon such as methylene chloride), and adding water thereto to cause H-phosphonation.

The reaction temperature is not particularly limited, but is normally from −20 to 100° C., preferably from 10 to 40° C.

While the reaction time varies depending on the starting materials, the reagents and the temperature used, it is normally from 5 minutes to 30 hours; and in the case where the reaction is carried out at room temperature, it is preferably 30 minutes.

After the reaction, the desired compound (4) of the present reaction is obtained, for example, by, after suitably neutralizing the reaction mixture, and removing any insoluble matter, if present, by filtration, addition of water and an immiscible organic solvent such as ethyl acetate, followed by washing with water, separating the organic layer containing the desired compound, drying with anhydrous magnesium sulfate or the like, and distilling off the solvent. The thus obtained desired compound can be further purified by ordinary methods such as recrystallization, reprecipitation or chromatography, if necessary.

(Step A-3)

The present step is a step, wherein compound (5) is produced by allowing compound (2) to react with a bis(1,2,4-triazolyl)arylphosphate, bis(1,2,4-triazolyl)benzylphosphate, bis(1,2,4-triazolyl)-2-cyanoethylphosphate, bis(1,2,4-triazolyl)(2,2,2-trichloroethyl)phosphate or bis(1,2,4-triazolyl)(2-propenyl)phosphate in an inert solvent (preferably a halogenated hydrocarbon such as methylene chloride), and adding water thereto to make a phosphodiester.

The bis(1,2,4-triazolyl)arylphosphate to be used can be, for example, bis(1,2,4-triazolyl)phenylphosphate, bis(1,2,4-triazolyl)(2-chlorophenyl)phosphate, bis(1,2,4-triazolyl)(4-chlorophenyl)phosphate, bis(1,2,4-triazolyl)(2-nitrophenyl) phosphate or bis(1,2,4-triazolyl)(4-nitrophenyl)phosphate, and is preferably bis(1,2,4-triazolyl)(2-chlorophenyl)phosphate or bis(1,2,4-triazolyl)(4-chlorophenyl)phosphate.

The reaction temperature is not particularly limited, but is normally from −20 to 100° C., preferably from 10 to 40° C.

While the reaction time varies depending on the starting materials, the reagents and the temperature used, it is normally from 5 minutes to 30 hours; and in the case where the reaction is carried out at room temperature, it is preferably 30 minutes.

After the reaction, the desired compound (5) of the present reaction is obtained, for example, by, after suitably neutralizing the reaction mixture, and removing any insoluble matter, if present, by filtration, addition of water and an immiscible organic solvent such as ethyl acetate, followed by washing with water, separating the organic layer containing the desired compound, drying with anhydrous magnesium sulfate or the like, and distilling off the solvent. The thus obtained desired compound can be further purified by ordinary methods such as recrystallization, reprecipitation or chromatography, if necessary.

(Step B-1)

The present step is a step, wherein compound (7) is produced by allowing compound (6) to react with a protecting reagent in the presence of a basic catalyst in an inert solvent.

The solvent to be used can preferably be an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or diethylene glycol dimethyl ether; a ketone such as acetone, methyl ethyl ketone, methyl isobutyl ketone, isophorone or cyclohexanone; a nitro compound such as nitroethane or nitrobenzene; a nitrile such as acetonitrile or isobutyronitrile; an amide such as formamide, dimethylformamide (DMF), dimethylacetamide or hexamethylphosphortriamide; a sulfoxide such as dimethyl sulfoxide or sulfolane; an aliphatic tertiary amine such as trimethylamine, triethylamine or N-methylmorpholine; or an aromatic amine such as pyridine or picoline; and is more preferably a halogenated hydrocarbon (particularly methylene chloride) or an aromatic amine (particularly pyridine).

The protecting reagent to be used is not particularly limited so long as it is adapted for the following nucleic acid synthesis and can be removed under acidic or neutral conditions, and can preferably be a tri-arylmethyl halide such as trityl chloride, mono-methoxytrityl chloride or dimethoxytrityl chloride; or a triarylmethanol ether such as dimethoxytrityl-O-triflate.

In the case of using a tri-arylmethyl halide as the protecting reagent, a base is normally used. In that case, the base to be used can be a heterocyclic amine such as pyridine, dimethylaminopyridine or pyrrolidinopyridine; or an aliphatic tertiary amine such as trimethylamine or triethylamine; and is preferably pyridine, dimethylaminopyridine or pyrrolidinopyridine.

In the case of using a liquid base as the solvent, since the base itself functions as a deoxidizer, it is not necessary to add a further base.

The reaction temperature varies depending on the starting materials, the reagents and the solvent used, and is normally from 0 to 150° C., preferably from 20 to 100° C. While the reaction time varies depending on the starting materials, the solvent and the reaction temperature used, it is normally from 1 to 100 hours, preferably from 2 to 24 hours.

After the reaction, the desired compound (7) of the present reaction is obtained, for example, by concentrating the reaction mixture, adding water and an immiscible organic solvent such as ethyl acetate, followed by washing with water, separating the organic layer containing the desired compound, drying with anhydrous magnesium sulfate or the like, and distilling off the solvent.

The resulting compound can be further purified by ordinary methods, for example, recrystallization or silica gel column chromatography, if necessary.

(Step B-2)

The present step is a step, wherein compound (8) is produced by allowing compound (7) prepared in Step B-1 to react with a mono-substituted chloro(alkoxy)phosphine, di-substituted alkoxyphosphine, mono-substituted chloro(benzyloxy)phosphine or di-substituted benzyloxyphosphine, which is normally used for amidite formation, in an inert solvent.

The present step is carried out similarly to Step (A-1).

(Step B-3)

The present step is a step, wherein compound (9) is produced by allowing compound (7) prepared in Step B-1 to react with tris-(1,2,4-triazolyl)phosphite in an inert solvent (preferably a halogenated hydrocarbon such as methylene chloride), followed by adding water to carry out H-phosphonation.

The present step is carried out similarly to Step (A-2).

(Step B-4)

The present step is a step, wherein compound (8) is produced by allowing compound (7) prepared in Step B-1 to react with a bis(1,2,4-triazolyl)arylphosphate, bis(1,2,4-triazolyl)benzylphosphate, bis(1,2,4-triazolyl)-2-cyanoethylphosphate, bis(1,2,4-triazolyl) (2,2,2-trichloroethyl)phosphate, or bis(1,2,4-triazolyl) (2-propenyl)phosphate in an inert solvent (preferably a halogenated hydrocarbon such as methylene chloride), followed by adding water to make a phosphodiester.

The present step is carried out similarly to Step A-3.

(Step C-1)

The present step is a step, wherein compound (12) is produced by allowing compound (11) to react with a mono-substituted chloro(alkoxy)phosphine, di-substituted alkoxyphosphine, mono-substituted chloro(benzyloxy)phosphine, or di-substituted benzyloxyphosphine normally used for amidite formation, in an inert solvent.

Compound (11) is a compound wherein a nucleoside has been reacted with an alkyl halide such as methyl iodide or an alkenyl halide such as allyl bromide in the presence of sodium hydride, according to the method described in PCT/US94/10131, to obtain the 3'-substituted compound, and then the 5'-hydroxyl group, and amino group of the base portion, have been protected by protecting groups. For example, 3'-O-allyladenosine (catalogue No.: RP-3101) can be purchased from ChemGene Industries, and 5'-O-dimethoxytrityl-3'-O-allyl-N-benzoyladenosine can be obtained therefrom by protection using publicly known methods.

The present step is carried out similarly to Step A-1.

Amongst compounds (12), 5'-O-dimethoxytrityl-3'-O-methyl-N-benzoyladenosine-2'-O-(2-cyanoethyl N,N-diisopropylphosphoramidite) (catalogue No.: ANP-2901), for example, can be purchased from ChemGene Industries.

(Step D-1)

The present step is a step, wherein compound (14) is produced by allowing compound (13) to react with a mono-substituted chloro(alkoxy)phosphine, di-substituted alkoxyphosphine, mono-substituted chloro(benzyloxy)phosphine, or di-substituted benzyloxyphosphine normally used for amidite formation, in an inert solvent.

Compound (13) is the same compound as compound (20) described in Process F of Japanese Patent Application (Kokai) No. 2002-249497, or the compound described in Japanese Patent Application (Kokai) No. Hei 10-195098 in which $Y_1$ is a protecting group and $Y_2$ is a hydrogen atom.

The present step is carried out similarly to Step (A-1).

(Step E-1)

The present step is a step, wherein compound (16) is produced by allowing compound (15) to react with a protecting reagent in the presence of a basic catalyst in an inert solvent.

The present step is carried out similarly to Step (B-1).

(Step E-2)

The present step is a step, wherein compound (17) is produced by allowing compound (16) prepared in Step E-1 to react with a dicarboxylic anhydride in an inert solvent.

The solvent to be used is not particularly limited so long as it does not inhibit the reaction and dissolves the starting material to a certain extent, and can be, for example, an aromatic hydrocarbon such as benzene, toluene or xylene; a halogenated hydrocarbon such as methylene chloride or chloroform; an ether such as ether, tetrahydrofuran, dioxane or dimethoxyethane; an amide such as dimethylformamide, dimethylacetamide or hexamethylphosphortriamide; a sulfoxide such as dimethyl sulfoxide; a ketone such as acetone or methyl ethyl ketone; a heterocyclic amine such as pyridine; or a nitrile such as acetonitrile; and is preferably a halogenated hydrocarbon such as methylene chloride.

The deoxidizer to be used can be a pyridine such as pyridine, dimethylaminopyridine or pyrrolidinopyridine, and is preferably dimethylaminopyridine.

The dicarboxylic anhydride to be used is not limited so long as it is the anhydride of an α,ω-alkyl dicarboxylic acid having from 3 to 16 carbon atoms, and can preferably be succinic anhydride.

While the reaction temperature and the reaction time vary depending on the acid anhydride and deoxidizer used, in the case where succinic anhydride is used, and dimethylaminopyridine is used as the deoxidizer, the reaction is carried out at room temperature for 30 minutes.

After the reaction, the desired compound is collected from the reaction mixture according to ordinary methods. For example, after suitably neutralizing the reaction mixture and removing any insoluble matter, if present, by filtration, water and an immiscible organic solvent such as ethyl acetate are added, followed by washing with water, separating the organic layer containing the desired compound, drying the extract with anhydrous magnesium sulfate or the like, and distilling off the solvent to obtain the desired compound. The resulting desired compound can be further purified by ordinary methods, for example, recrystallization, reprecipitation or chromatography if necessary.

(Step E-3)

The present step is a step, wherein active ester (18) is formed by reaction of the carboxyl group of compound (17) having a free carboxyl group with an ester-forming reagent in an inert solvent, and then reaction with a phenol which may be substituted.

The solvent to be used is not particularly limited so long as it does not inhibit the reaction, and it can be an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, ethyl acetate, propyl acetate, butyl acetate or diethyl carbonate; a ketone such as acetone, methyl ethyl ketone, methyl isobutyl ketone, isophorone or cyclohexanone; a nitro compound such as nitroethane or nitrobenzene; a nitrile such as acetonitrile or isobutyronitrile; an amide such as formamide, dimethylformamide (DMF), dimethylacetamide or hexamethylphosphortriamide; or a sulfoxide such as dimethyl sulfoxide or sulfolane; and is preferably a halogenated hydrocarbon (particularly methylene chloride) or an amide (particularly dimethylformamide).

The phenol to be used is not particularly limited so long as it can be used as an active ester, and it can be 4-nitrophenol, 2,4-dinitrophenol, 2,4,5-trichlorophenol, 2,3,4,5,6-pentachlorophenol or 2,3,5,6-tetrafluorophenol, and is preferably pentachlorophenol.

The ester-forming reagent to be used can be, for example, an N-hydroxy compound such as N-hydroxysuccinimide, 1-hydroxybenzotriazole or N-hydroxy-5-norbornene-2,3-dicarboxyimide; a diimidazole compound such as 1,1'-oxalyldiimidazole or N,N'-carbonyldiimidazole; a disulfide compound such as 2,2'-dipyridyldisulfide; a succinic acid compound such as N,N'-disuccinimidylcarbonate; a phosphinic chloride compound such as N,N'-bis(2-oxo-3-oxazolidinyl)phosphinic chloride; an oxalate compound such as N,N'-disuccinimidyloxalate (DSO), N,N-diphthalimidyloxalate (DPO), N,N'-bis(norbornenylsuccinimidyl)oxalate (BNO), 1,1'-bis(benzotriazolyl)oxalate (BBTO), 1,1'-bis(6-chlorobenzotriazolyl)oxalate (BCTO) or 1,1'-bis(6-trifluoromethylbenzotriazolyl)oxalate (BTBO); or a carbodiimide such as dicyclohexylcarbodiimide (DCC); and is preferably a diimidazole compound or a carbodiimide (particularly DCC).

While the reaction temperature and the reaction time vary depending on the ester-forming reagent and the kind of the solvent used, the reaction is carried out at from 0° C. to 100° C. for from 5 to 50 hours and, particularly in the case where pentachlorophenol and DCC are used in DMF, the reaction is carried out at room temperature for 18 hours.

After the reaction, the desired compound is collected from the reaction mixture according to ordinary methods. For example, after suitably neutralizing the reaction mixture and removing any insoluble matter, if present, by filtration, water and an immiscible organic solvent such as ethyl acetate are added, followed by washing with water, separating the organic layer containing the desired compound, drying the extract with anhydrous magnesium sulfate or the like, and distilling off the solvent to obtain the desired compound. The resulting desired compound can be further purified by ordinary methods, for example, recrystallization, reprecipitation or chromatography if necessary.

(Step E-4)

The present step is a step, wherein high molecular weight derivative (20), which can be used as a carrier for oligonucleotide synthesis, is produced by allowing compound (18) having an activated carboxyl group obtained in Step E-3 to react with a high molecular weight substance (19), such as a control pore glass (CPG) bonded to an amino group, a hydroxyl group, a sulfhydryl group or the like through an alkylene group, in an inert solvent.

The high molecular weight substance (19) used in the present step is not particularly limited so long as it is used as a carrier, but it is necessary to examine the particle size of the carrier, the size of surface area by a three-dimensional network structure, the ratio of hydrophilic group positions, the chemical composition, strength against pressure, and the like.

The carrier to be used can be a polysaccharide derivative such as cellulose, dextran or agarose; a synthetic polymer such as polyacrylamide gel, polystyrene resin or polyethylene glycol; or an inorganic substance such as silica gel, porous glass or a metal oxide. Specifically, it can be a commercially available carrier such as aminopropyl-CPG, long chain aminoalkyl-CPG (these are manufactured by CPG Inc.), Cosmoseal $NH_2$, Cosmoseal Diol (these are manufactured by Nacalai Tesque), CPC-Silica Carrier Silane Coated, aminopropyl-CPG-550 Å, aminopropyl-CPG-1400 Å, polyethylene glycol 5000 monomethyl ether (these are manufactured by Furuka Inc.), p-alkoxybenzyl alcohol resin, aminomethyl resin, hydroxymethyl resin (these are manufactured by Kokusan Kagaku Inc.) and polyethylene glycol 14000 monomethyl ether (these are manufactured by Union Carbide Inc.), but it is not limited to these.

Further, the functional group bonded to the carrier can preferably be an amino group, a sulfhydryl group, or a hydroxyl group.

The solvent used in the present step is not particularly limited so long as it does not inhibit the reaction and dissolves the starting material to a certain extent, and it can preferably be an aromatic hydrocarbon such as benzene, toluene or xylene; a halogenated hydrocarbon such as methylene chloride, chloroform, carbon tetrachloride, dichloroethane, chlorobenzene or dichlorobenzene; an ester such as ethyl formate, ethyl acetate, propyl acetate, butyl acetate or diethyl carbonate; a ketone such as acetone, methyl ethyl ketone, methyl isobutyl ketone, isophorone or cyclohexanone; a nitro compound such as nitroethane or nitrobenzene; a nitrile such as acetonitrile or isobutyronitrile; an amide such as formamide, dimethylformamide (DMF), dimethylacetamide or hexamethylphosphortriamide; or a sulfoxide such as dimethyl sulfoxide or sulfolane; and is preferably a halogenated hydrocarbon (particularly methylene chloride), or an amide (particularly dimethylformamide).

The reaction temperature is normally from −20 to 150° C., preferably from 0 to 50° C. The reaction time varies depending on the starting materials, the solvent, and the reaction temperature used, but it is normally from 1 to 200 hours, preferably from 24 to 100 hours. After the reaction, the desired compound is collected from the reaction mixture according to ordinary methods. For example, the desired compound is obtained by recovering the high molecular weight carrier from the reaction mixture by filtration, washing with an organic solvent such as methylene chloride, and drying under reduced pressure.

(Step F-1)

The present step is a step, wherein 2-5A analog (1) is produced on a DNA automatic synthesizer by ordinary methods using the CPG (20) prepared in Step E-4, using the compounds (3), (8), (12) and (14) prepared in Step A-1, B-2, C-1 or D-1, and a commercially available phosphoramidite reagent (21).

The 2-5A analog having the desired nucleotide sequence can be synthesized according to a method described in the literature (Nucleic Acids Research, 12, 4539 (1984)), and the manual attached to the synthesizer, by a phosphoramidite method using a DNA synthesizer, for example, model 392 of Perkin Elmer Inc.

As the compound (21), for example, 5'-O-dimethoxytrityl-3'-O-(t-butyldimethylsilyl)-N-benzoyladenosine-2'-O-(2-cyanoethyl N,N-diisopropylphosphoramidite) can be purchased from ChemGene Inc. (catalogue No.: ANP-5681).

In the present step, the amidite reagent for the compounds (3), (8), (12), (14) and (21) is activated using an acid catalyst to form a phosphorous acid tri-ester bond, and it is oxidized to a phosphoric acid tri-ester using an appropriate oxidizing agent, or it is made into a thiophosphoric tri-ester using an appropriate thioating agent.

The acidic substance used as a catalyst in the condensation reaction of the present step can be an acidic substance such as a tetrazole, and is preferably tetrazole or ethylthiotetrazole. The oxidizing agent used in the oxidation reaction of the present step is not particularly limited so long as it is normally used in oxidation reactions, and is preferably an inorganic metal oxidizing agent such as a manganese oxide, i.e., potassium permanganate or manganese dioxide; a ruthenium oxide, i.e., ruthenium tetraoxide; a selenium compound, i.e., selenium dioxide; an iron compound, i.e., iron chloride; an osmium compound, i.e., osmium tetraoxide; a silver compound, i.e., silver oxide; a mercury compound, i.e., mercury acetate; a lead oxide compound, i.e., lead oxide or lead tetraoxide; a chromic acid compound, i.e., potassium chromate, a chromic acid-sulfuric acid complex, or a chromic acid-pyridine complex; or a cerium compound, i.e., cerium ammonium nitrate (CAN); an inorganic oxidizing agent such as a halogen molecule, i.e., a chlorine molecule, a bromine molecule or an iodine molecule; a periodic acid, i.e., sodium periodate; ozone; hydrogen peroxide; a nitrous acid compound, i.e., nitrous acid; a chlorous acid compound, i.e., potassium chlorite or sodium chlorite; or a persulfuric acid compound, i.e., potassium persulfate or sodium persulfate; or an organic oxidizing agent such as a reagent used in DMSO oxidation (a complex of dimethyl sulfoxide with dicyclohexylcarbodiimide, oxalyl chloride, acetic anhydride or phosphorus pentaoxide, or a complex of pyridine-sulfur trioxide) a peroxide such as t-butyl hydroperoxide; a stable cation such as triphenylmethyl cation; a succinic acid imide such as N-bromosuccinic acid imide; a hypochlorous acid compound such as t-butyl hypochlorite; an azodicarboxylic acid compound such as azodicarboxylic acid ester; a disulfide such as dimethyl disulfide, diphenyl disulfide, or dipyridyl disulfide and triphenylphosphine; a nitrous acid ester such as methyl nitrite; a carbon tetrahalide, e.g., carbon tetrabromide; or a quinone compound, e.g., 2,3-dichloro-5,6-dicyano-p-benzoquinone (DDQ); preferably iodine.

The solvent to be used is not particularly limited so long as it does not inhibit the reaction and dissolves the starting material to a certain extent, and it can preferably be an aromatic hydrocarbon such as benzene, toluene or xylene; a halogenated hydrocarbon such as methylene chloride or chloroform; an ether such as ether, tetrahydrofuran, dioxane or dimethoxyethane; an amide such as dimethylformamide, dimethylacetamide or hexamethylphosphortriamide; a sulfoxide such as dimethyl sulfoxide; an alcohol such as methanol, ethanol, n-propanol, isopropanol, n-butanol, isobutanol or isoamyl alcohol; a dilute acid such as aqueous sulfuric acid; a dilute base such as aqueous sodium hydroxide; water; a ketone such as acetone or methyl ethyl ketone; a heterocyclic amine such as pyridine; or a nitrile such as acetonitrile; preferably a heterocyclic amine (particularly pyridine), a nitrile (particularly acetonitrile), an ether (particularly tetrahydrofuran), or a halogenated hydrocarbon (particularly methylene chloride).

Further, in the case where the compound is thioated, if desired, the thioate derivative can be obtained according to a method described in the literature (Tetrahedron Letters, 32, 3005 (1991), J. Am Chem. Soc., 112, 1253 (1990)) using a reagent such as sulphur, tetraethyl thiuram disulfide (TETD, Applied Biosystems Inc., or Beaucage reagent (Millipore Inc.) for forming a thioate by reacting with a phosphite.

The reaction temperature is normally from 0 to 150° C., preferably from 10 to 60° C. The reaction time varies depending on the starting materials, the solvent and the reaction temperature used, but it is normally from 1 minute to 20 hours, preferably from 1 minute to 1 hour.

In the case where the H-phosphonic acid compound (4) or (9) obtained in Step A-2 or B-3 is condensed to form a phosphoric tri-ester bond in the present step, after it is condensed, for example, in the presence of a condensing agent such as pivaloyl chloride and a deoxidizer to form the H-phosphonic acid diester bond, the H-phosphonic acid bond can be converted to the phosphoric acid diester bond using an oxidizing agent.

The solvent used in the present step is not particularly limited so long as it does not inhibit the reaction, but anhydrous acetonitrile is preferably used. As the reagent used as the condensing agent, an acid chloride of a carboxylic acid or phosphoric acid is used, and pivaloyl chloride is preferably used.

The oxidizing agent for oxidizing the ODN having a H-phosphonic acid bond to a phosphodiester type ODN is not particularly limited so long as it is normally used for oxidation reactions, and can be a inorganic metal oxidizing agent such as a manganese oxide, e.g., potassium permanganate or manganese dioxide; a ruthenium oxide, e.g., ruthenium tetraoxide; a selenium compound, e.g., selenium dioxide; an iron compound, e.g., iron chloride; an osmium compound, e.g., osmium tetraoxide; a silver compound, e.g., silver oxide; a mercury compound, e.g., mercury acetate; a lead oxide compound, e.g., lead oxide or lead tetraoxide; a chromic acid compound, e.g., potassium chromate, a chromic acid-sulfuric acid complex or a chromic acid-pyridine complex; or a cerium compound, e.g., cerium ammonium nitrate (CAN); an inorganic oxidizing agent such as a halogen molecule, e.g., a chlorine molecule, a bromine molecule or an iodine molecule; a periodic acid, e.g., sodium periodate; ozone; hydrogen peroxide; a nitrous acid compound, e.g., nitrous acid; a chlorous acid compound e.g., potassium chlorite or sodium chlorite; or a persulfuric acid compound, e.g., potassium persulfate or sodium persulfate; or an organic oxidizing agent such as a reagent used in DMSO oxidation (a complex of dimethyl sulfoxide with dicyclohexylcarbodiimide, oxalyl chloride, acetic anhydride or phosphorous pentaoxide, or a complex of pyridine-sulfur trioxide); a peroxide such as t-butylhydroperoxide; a stable cation such as triphenylmethyl cation; a succinic acid imide such as N-bromosuccinic acid imide; a hypochlorous acid compound such as t-butyl hypochlorite; an azodicarboxylic acid compound such as methyl azodicarboxylate; a disulfide such as dimethyl disulfide, diphenyl disulfide or dipyridyl disulfide and triphenylphosphine; a nitrous acid ester such as methyl nitrite; a carbon tetrahalide, e.g., carbon tetrabromide; or a quinone compound, e.g., 2,3-dichloro-5,6-dicyano-p-benzoquinone (DDQ); preferably iodine molecule.

The deoxidizer to be used can be a heterocyclic amine such as pyridine or dimethylaminopyridine; or an aliphatic amine such as trimethylamine, triethylamine or diisopropylethylamine; and is preferably an aliphatic amine (particularly diisopropylethylamine). The reaction temperature is not particularly limited but it is normally from −50 to 50° C., preferably room temperature.

The reaction time varies depending on the starting materials, the reagent and the temperature used, but it is normally from 5 minutes to 30 hours, preferably in the case where the reaction is carried out at room temperature, it is 30 minutes.

The solvent in the reaction for forming a methoxyethylamino phosphate group is not particularly limited so long as it does not inhibit the reaction, but carbon tetrachloride that is normally used as a reagent is used at a solvent amount.

The reaction temperature is not particularly limited in a range of from −50 to 100° C., but in the case where the reaction is carried out at room temperature, the reaction time is from 1 to 10 hours.

Further, in the case where the phosphodiester compound (5) or (10) obtained in Step A-3 or B-4 is condensed to form the phosphate tri-ester bond in the present step, the solvent used in the present step is not particularly limited so long as it does not inhibit the reaction, but an aromatic amine such as pyridine is preferably used.

The condensing agent used in the condensation can be dicyclocarbodiimide (DCC), mesitylenesulfonic chloride (Ms-Cl), triisopropylbenzenesulfonic chloride, mesitylenesulfonic acid triazolide (MST), mesitylenesulfonic acid-3-nitrotriazolide (MSNT), triisopropylbenzenesulfonic acid tetrazolide (TPS-Te), triisopropylbenzenesulfonic acid nitroimidazolide (TPS-NI) or triisopropylbenzenesulfonic acid pyridyltetrazolide, and is preferably MSNT, TPS-Te and TPS-NI.

The reaction temperature is not particularly limited in a range of from −10 to 100° C., but the reaction is normally carried out at room temperature.

The reaction time varies depending on the solvent used and the reaction temperature, but in the case where pyridine is used as the reaction solvent, and the reaction is carried out at room temperature, it is 30 minutes.

Cleavage from CPG in the case where the 2-5 analog is bonded to CPG and removal of the protecting groups other than the substituent portion at the 5'-end described next can be carried out by a publicly known method (J. Am. Chem. Soc., 103, 3185, (1981)).

The resulting crude 2-5A analog can be confirmed by purification using a reverse phase chromatocolumn and analyzing the purity of the purified product by HPLC.

The chain length of the thus obtained oligonucleotide analog is normally from 2 to 50, preferably from 10 to 30 nucleoside units.

(Step G-1)

The present step is to prepare 2-5A analog (1) on a DNA automatic synthesizer by ordinary methods using CPG (22), using the compounds (3), (4), (5), (8), (9), (10), (12) or (14) prepared in Step A-1, A-2, A-3, B-2, B-3, B-4, C-1 or D-1 and (21).

CPG (22) is the same as the compound (24) described in Process G of Japanese Patent Application (Kokai) No. 2002-249497, and the present step is carried out similarly to Step F-1.

(Step H-1)

The present step is a step, wherein 2-5A analog (1) is produced on a DNA automatic synthesizer by ordinary methods using CPG (23), using the compounds (3), (4), (5), (8), (9), (10), (12) or (14) prepared in Step A-1, A-2, A-3, B-2, B-3, B-4, C-1 or D-1 and (21).

CPG (23) is the same as the compound (4) described in Japanese Patent Application (Kokai) No. Hei 7-53587, and the present step is carried out similarly to Step F-1.

Further, in the 2-5A analog (1), in the case where any one of $R^1$, $R^2$, $R^3$, $R^4$, $R^5$, $R^6$ and $R^7$ is a mercapto group, after the 2-5A analog (1) is synthesized and purified by Process F, G or H, a substituent can be introduced onto the mercapto group by reacting with a compound having a halide group, in the presence of a base in an inert solvent.

The halogen can be, for example, a fluorine atom, a chlorine atom, a bromine atom, or an iodine atom, and is preferably a chlorine atom, a bromine atom, or an iodine atom.

The compound having a halide group to be used is not particularly limited so long as it is a compound having a halide group which can be reacted with a thiophosphoric acid group, and can be, for example, an "alkyl halide which may be substituted" such as an ethyl halide, a propyl halide, a butyl halide, a 2-halo ethanol, a 3-halo propanol, or a 4-halo butanol; an "acyloxyalkyl halide" such as a 2-(stearoyloxy) ethyl halide, a 2-(myristoyloxy)ethyl halide, a 2-(decanoyloxy)ethyl halide, a 2-(benzoyloxy)ethyl halide, a 2-(pivaloyloxy)ethyl halide, a 2-(2,2-dimethyloctadecanoyloxy)ethyl halide, a 3-(stearoyloxy)propyl halide, a 3-(myristoyloxy) propyl halide, a 3-(decarioyloxy)propyl halide, a 3-(benzoyloxy)propyl halide, a 3-(pivaloyloxy)propyl halide, a 3-(2,2-dimethyloctadecanoyloxy)propyl halide, a 4-(stearoyloxy) butyl halide, a 4-(myristoyloxy)butyl halide, a 4-(decanoyloxy)butyl halide, a 4-(benzoyloxy)butyl halide, a 4-(pivaloyloxy)butyl halide, or a 4-(2,2-dimethyloctadecanoyloxy)butyl halide; an "alkylcarbamoyloxyalkyl halide" such as a 2-stearylcarbamoyloxyethyl halide; or one of the following compounds:

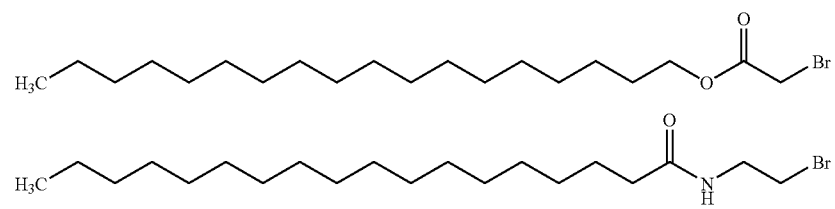

-continued

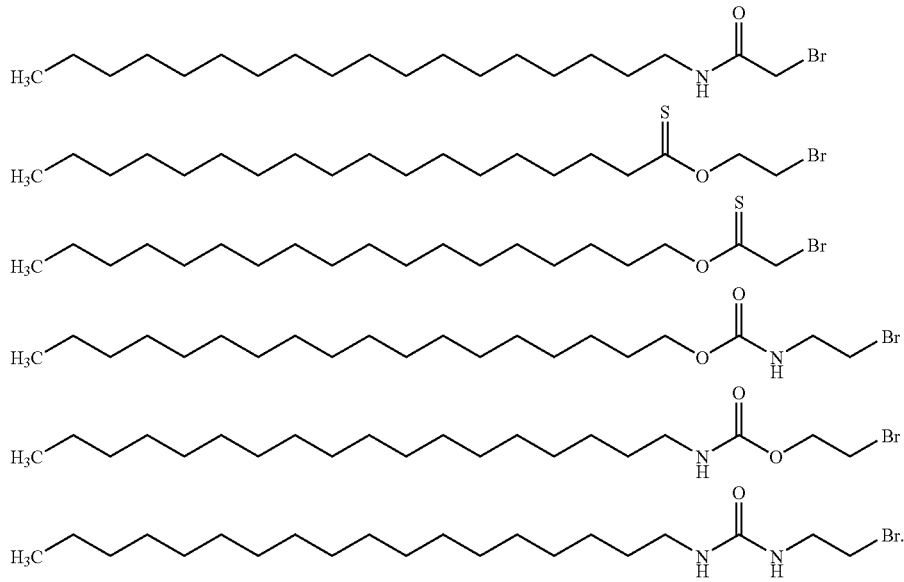

In the above compounds, a 2-stearoyloxyethyl halide and a 2-(2,2-dimethyloctadecanoyloxy)ethyl halide are preferred.

Of the compounds having these halide groups, compounds having an ester group (—OC(=O)— or —C(=O)O—), a carbamate group (—NHC(=O)O— or —OC(=O)NH—), an amide group (—NHC(=O)— or —C(=O)NH—), a thio ester group (—SC(=O)— or —C(=O)S—), a urea group (—NHC(=O)NH—), a thiocarboxylic acid ester group (—OC(=S)— or —C(=S)O—), or a thiocarboxylic acid amide group (—NHC(=S)— or —C(=S)NH—), can be prepared in the presence of a base or a condensing agent by condensation of an acid halide compound or a carboxylic acid compound with a compound having an alcohol group; condensation of a formic, acid ester halide compound with a compound having an amino group; condensation of an acid halide compound or a carboxylic acid compound with a compound having an amino group; condensation of an acid halide compound or a carboxylic acid compound with a compound having a thiol group; condensation of compounds having two kinds of amino group with phosgene; condensation of a thiocarboxylic acid compound with a compound having an alcohol group; or condensation of a thiocarboxylic acid compound with the compound having an amino group.

The base to be used can be a heterocyclic amine such as pyridine or dimethylaminopyridine; or an aliphatic amine such as trimethylamine, triethylamine or diisopropylamine; and is preferably a heterocyclic amine (particularly pyridine).

There is no particular limitation on the solvent to be used, provided that it does not inhibit the reaction and dissolves the starting material to a certain extent, and it can be water; an amide such as dimethylformamide, dimethylacetamide or hexamethylphosphortriamide; a sulfoxide such as dimethyl sulfoxide; a heterocyclic amine such as pyridine; a nitrile such as acetonitrile; or a mixture of these solvents; and is preferably dimethylformamide.

The reaction temperature is not particularly limited in a range of from −50 to 100° C., but the reaction is normally carried out at room temperature. The reaction time varies depending on the material, the reagent used, and the temperature, but it is normally from 10 hours to 100 hours.

The reaction speed can also be appropriately increased by adding an iodide salt such as tetrabutylammonium iodide.

Instead of using CPG(23) used in method H, a 2-5A antisense oligonucleotide can be synthesized by condensing a phosphoramidite serving as a linker, such as DMT-butanol-CED phosphoramidite (ChemGene) or Spacer phosphoramidite 18 (GlenResearch), to CPG to which is bonded an oligonucleotide having the desired antisense sequence that is protected with a protecting group, followed by carrying out the procedure of the present step. For example, in the case of "CPG to which is bonded an oligonucleotide protected with a protecting group", a modified oligonucleotide can be synthesized in which the oxygen atom at the 2' position of the sugar portion is bridged to a carbon atom at the 4' position with an alkylene group according to the method described in Japanese Patent Application (Kokai) No. Hei 10-304889 or Japanese Patent Application (Kokai) No. 2000-297097. In addition, a modified oligonucleotide having a 2'-O-methoxyethoxy group can be synthesized by referring to the literature (Teplove, M. et al., Nat. Struct. Biol. (1999), 6, 535; Zhang H. et al., Nature Biotech. (2000), 18, 862), and a modified oligonucleotide having a 3'-amino group can be synthesized by referring to the literature (Gryaznov, S. M. et al., Proc. Natl. Acad. Sci. USA 1995, 92, 5798; Tereshko, V. et al., J. Am. Chem. Soc. 1998, 120, 269).

The antitumor activity (cytocidal activity) of the present compounds can be investigated by adding the present compounds to cancer cells in a medium, and culturing the cells, followed by counting the number of viable cells using the MTT assay method (Tim Mosmann, J. Immunological Methods, 1983: 65, 55-63), the MTS assay method (Rotter, B. A., Thompson, B. K., Clarkin, S., Owen, T. C. Nat. Toxins 1993; 1(5): 303-7), the XTT assay method (Meshulam, T., Levitz, S. M., Christin, L., Diamond, R. D. J. Infect. Dis. 1995; 172(4): 1153-6), or Trypan blue staining.

Compounds of the invention will show anti-cancer activity against any type of malignant neoplasm and leukemia that express Rnase L, a target protein of this invention, including lung cancer, colorectal cancer, breast cancer, renal cancer, melanoma and glioma.

The antivirus activity of the present compounds can be investigated using an infected cell culture system such as HeLa cells, MDCK cells, MRC-5 cells or the like, by adding the present compounds to virus cells, such as of vaccinia virus, influenza virus or cytomegalovirus, in a medium either before or after infection, culturing for a predetermined amount of time, and then measuring the virus growth inhibition rate using the plaque assay method which measures virus infection titer (Kobayashi, N., Nagata, K. Virus Experimental Protocols, Medical View Publishing), or the ELISA method which measures the level of virus antigen (Okuno, Y., Tanaka, K., Baba, K., Maeda, A., Kunita, N., Ueda, J. Clin. Microbiol., Jun. 1, 1990; 28(6): 1308-13). The present compounds have antiviral activity to the aforesaid viruses and also to hepatitis C.

The administration forms of the 2-5A analogs of general formula (1) of the present invention can include, for example, oral administration by tablets, capsules, granules, powders or syrups, or parenteral administration by injection or suppositories. These preparations are prepared by known methods using pharmaceutically acceptable carriers such as additives such as excipients (which include, for example, organic excipients such as sugar derivatives, e.g., lactose, sucrose, glucose, mannitol and sorbitol; starch derivatives, e.g., corn starch, potato starch, α-starch and dextrin; cellulose derivatives, e.g., crystalline cellulose; gum arabic; dextran; and pullulan; and inorganic excipients such as silicate derivatives, e.g., light silicic anhydride, synthetic aluminum silicate, calcium silicate and magnesium aluminate meta-silicate; phosphates, e.g., calcium hydrogenphosphate; carbonates, e.g., calcium carbonate; and sulfates, e.g., calcium sulfate), lubricants (which can include, for example, stearic acid and its metal salts such as stearic acid, calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine; sodium salts of aliphatic acids; lauryl sulfates such as sodium lauryl sulfate and magnesium lauryl sulfate; silicic acids such as silicic anhydride; and the above starch derivatives), binders (which can include, for example, hydroxypropyl cellulose, hydroxypropylmethyl cellulose, polyvinylpyrrolidone, Macrogol, and compounds similar to the above excipients), disintegrating agents (which can include, for example, cellulose derivatives such as low substituted hydroxypropyl cellulose, carboxymethyl cellulose, carboxymethyl cellulose calcium and internally cross-linked carboxymethyl cellulose sodium; and chemically modified starches/celluloses such as carboxymethyl starch, carboxymethyl starch sodium and cross-linked polyvinylpyrrolidone), stabilizers (which can include paraoxybenzoates such as methyl paraben and propyl paraben; alcohols such as chlorobutanol, benzyl alcohol and phenylethyl alcohol; benzalkonium chloride; phenols such as phenol and cresol; thimerosal; dehydroacetic acid; and sorbic acid), flavoring agents (which can include, for example, sweeteners, acidifiers, perfumes or the like normally used), diluents, and the like.

While the amount of the 2-5A analog of the present invention used varies depending on the symptoms, the age, the administration method, and the like, it is desirable to administer to the patient, such as a mammal, e.g., a human, once to several times a day, and, in the case of oral administration, 0.01 mg/kg body weight (preferably 0.1 mg/kg body weight) per time as a lower limit and 1000 mg/kg body weight (preferably 100 mg/kg body weight) as an upper limit, and, in the case of intravenous administration, 0.001 mg/kg body weight (preferably 0.01 mg/kg body weight) per time as a lower limit and 100 mg/kg body weight (preferably 10 mg/kg body weight) as an upper limit corresponding to the symptoms of the patient.

Other modes of administration include topical administration (e.g., pulmonary, intratracheal and intranasal) and other parenteral administration modes including intraarterial, subcutaneous, intraperitoneal or intramuscular injection or infusion; or intracranial administration.

Further, the preparations may be used in combination with other antitumor agents, for example, nitrosourea type chemicals such as 5FU, AraC, ACNU or BCNU, cisplatin, daunomycin, adriamycin, mitomycin C, vincristine, and taxol.

In the following, the present invention will be explained in more detail by Examples, Reference examples and Test examples.

Example 1

Synthesis of Example 1 Compound (Exemplary Compound No. 4)

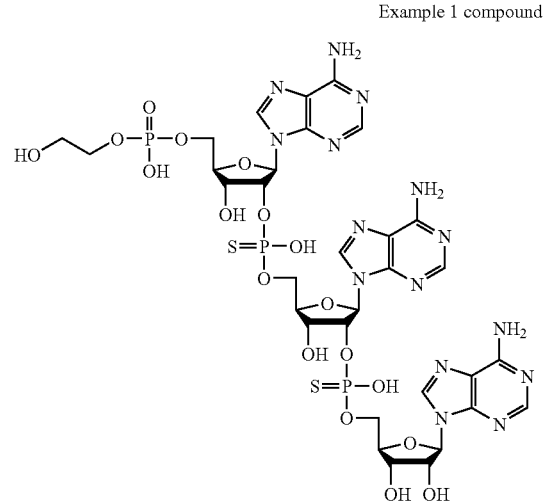

Example 1 compound

The ABI Model 392 DNA/RNA Synthesizer (Applied Biosystems) was used as the DNA synthesizer. The solvents, reagents, and phosphoramidite concentrations in each synthesis cycle were the same as in the case of general natural oligonucleotide synthesis, and the products of Applied Biosystems were used for those reagents and solvents other than the phosphoramidite and sulfurizing agent. The 5'-O-DMTr-riboadenosine analog, Bz-Adenosine-RNA-500 (Glen Research) (2.0 μmol), bound to a CPG support, was used as the starting substance. Synthesis was carried out using the DNA synthesizer based on one condensation cycle consisting of the following steps 1) to 4) using a synthesis program for ordinary synthesis of 1 μmol of RNA. 3'-tBDSilyl-ribo Adenosine (N-bz) phosphoramidite-(ChemGene) was used as the phosphoramidite in cycles 1 and 2, while the compound of Example 8a described in Japanese Patent Application (Kokai) No. Hei 11-246592 was used in cycle 3. For the oxidation or sulfurizing agent, xanthane hydride (Tokyo Kasei Kogyo) was used in cycles 1 and 2, while iodine was used in cycle 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Sulfurization (cycles 1 and 2): Xanthane hydride (0.02 M)/acetonitrile-pyridine (9:1 mixed solvent); 15 min.

Oxidation (cycle 3): Iodine/water/pyridine/tetrahydrofuran; 15 sec.

After synthesizing the protected 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 0-13% $CH_3CN$ (linear gradient, 30 min.); 40° C.; 10 ml/min; 254 nm), and the fractions that eluted at 20.9, 22.7, 25.4 and 28.0 minutes corresponding to the four diastereomers were collected. The present compound eluted in the vicinity of 10.55 minutes when analyzed by ion exchange HPLC (column (Tosoh DEAE-2SW (4.6×150 mm)); solution A (20% acetonitrile), solution B (20% acetonitrile and 67 mM phosphate buffer, 2 M NaCl); solution B 5→60% (15 min., linear gradient); 60° C.; 1 ml/min). (Yield: 457 nmol as UV measured value using the calculated $\epsilon=39400$ (260 nm) of the adenosine trimer)) $\lambda$max $(H_2O)=258.3$ nm, ESI-Mass (negative): 1080.1 $[M-H]^-$.

Example 2

Synthesis of Example 2 Compound (Exemplary Compound No. 1)

Example 2 compound

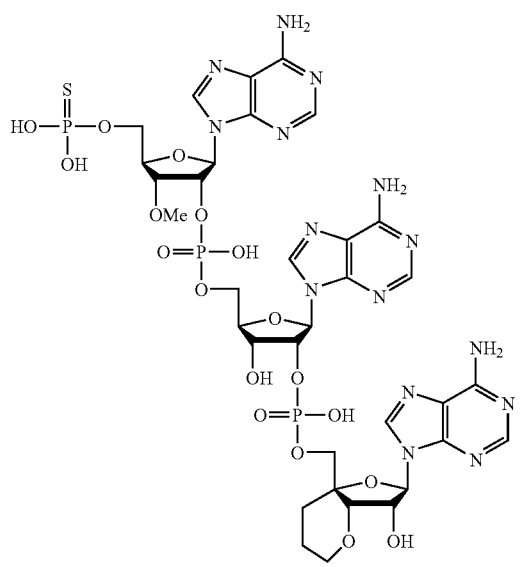

Synthesis was carried out using the compound of Example 17 described in Japanese Patent Application (Kokai) No. 2002-249497 (2.0 µmol) as the 5'-O-DMTr-riboadenosine analog bound to a CPG support with the DNA synthesizer based on one condensation cycle consisting of the following steps 1) to 4) using a synthesis program for ordinary synthesis of 1 µmol of RNA. 31-tBDSilyl-ribo Adenosine (N-bz) phosphoramidite (ChemGene) was used as the phosphoramidite in cycle 1, 5'-DMT-3'-(O-methyl) adenosine(bz)2'-phosphoramidite (ChemGene) was used in cycle 2, and Chemical Phosphorylation Reagent II (Glen Research) was used in cycle 3. For the oxidation or sulfurizing agent, iodine was used in cycles 1 and 2, while xanthane hydride (Tokyo Kasei Kogyo) was used in cycle 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 1 and 2):

Iodine/water/pyridine/tetrahydrofuran; 15 sec.

Sulfurization (cycle 3): Xanthane hydride (0.02 M)/acetonitrile-pyridine (9:1 mixed solvent); 15 min.

After synthesizing the 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethyl amine acetate (TEAA), pH 7; 0-15% $CH_3CN$ (linear gradient, 30 min.); 40° C.; 10 ml/min; 254 nm), and the fraction that eluted at 16.7 minutes was collected. The present compound eluted in the vicinity of 9.46 minutes when analyzed by reverse HPLC (column (Tosoh superODS (4.6×50 mm)); 0.1M aqueous triethylamine acetate (TEAA), pH7; 0-25% $CH_3CN$ (linear gradient, 14 min); 60° C.; 10 ml/min). (Yield: 445 nmol as UV measured value at 260 nm) $\lambda$max $(H_2O)=258.2$ nm, ESI-Mass (negative): 1074.15 $[M-H]^-$.

Example 3

Synthesis of Example 3 Compound (Exemplary Compound No. 5)

Example 3 compound

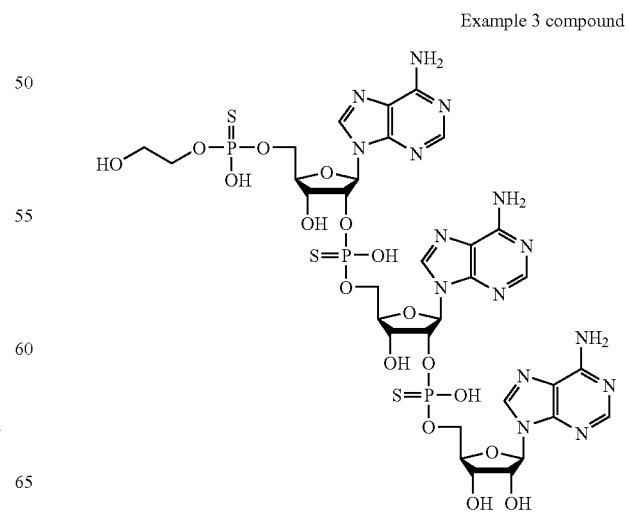

Synthesis was carried out using Bz-Adenosine-RNA 500 (Glen Research Co.) (2.0 μmol) as the 5'-O-DMTr-riboadenosine analog bound to a CPG support with the DNA synthesizer based on one condensation cycle consisting of the following steps 1) to 4) using a synthesis program for ordinary synthesis of 1 μmol of RNA. 3'-tBDSilyl-riboAdenosine (N-bz) phosphoramidite (ChemGene) was used as the phosphoramidite in cycles 1 and 2, and the compound of Example 8a described in Japanese Patent Application (Kokai) No. Hei 11-246592 was used in cycle 3. Xanthane hydride (Tokyo Kasei Kogyo) was used as the sulfurizing agent in cycles 1, 2 and 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 1, 2 and 3): Xanthane hydride (0.02 M)/acetonitrile-pyridine (9:1 mixed solvent); 15 min.

After synthesizing the 2-5A analog having the desired structure with the 5'-DMTr group still intact, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 60% $CH_3CN$ (isocratic); 40° C.; 10 ml/min; 254 nm), and the fractions that eluted at 9.5 and 11.8 minutes as diastereomers were collected. After the solvent was distilled off under reduced pressure, 80% aqueous acetic acid was added thereto, the mixture was left to stand for 30 minutes, and the DMTr group was removed. After the solvent was distilled off, a mixture of concentrated aqueous ammonia-ethanol (4:1) was added thereto, and the mixture was left to stand for 30 minutes. After the solvent was distilled off, the pH was adjusted to 2.0 by adding aqueous hydrochloric acid (2 N), followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 0-15% $CH_3CN$ (linear gradient, 30 min.); 40° C.; 10 ml/min; 254 nm), and the fractions that eluted at 16.5-19.1 minutes were collected. The present compound eluted in the vicinity of 8.8-9.8 minutes when analyzed by reverse phase HPLC (column (Tosoh superODS (4.6×50 mm)); 0.1M aqueous triethylamine acetate (TEAA), pH7; 0-25% $CH_3CN$ (linear gradient, 14 min); 60° C.; 1 ml/min). (Yield: 565 nmol as UV measured value at 260 nm) λmax ($H_2O$)=258.2 nm, ESI-Mass (negative): 1096.1 $[M-H]^-$.

Example 4

Synthesis of Example 4 Compound (Exemplary Compound No. 8)

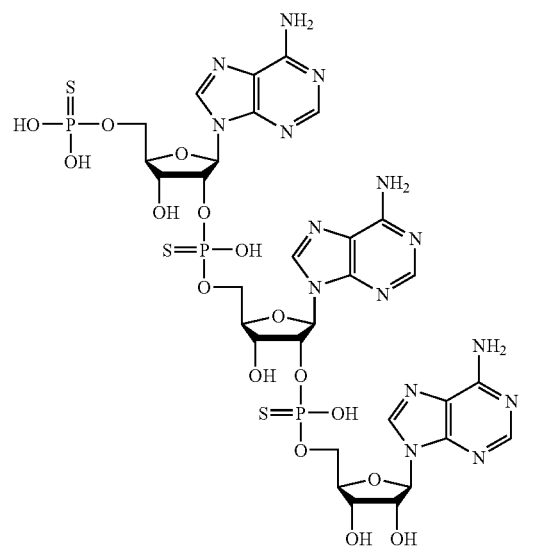

Example 4 compound

Synthesis was carried out using Bz-Adenosine-RNA 500 (Glen Research Co.) (2.0 mol) as the 5'-O-DMTr-riboadenosine analog bound to a CPG support with the DNA synthesizer based on one condensation cycle consisting of the following steps 1) to 4) using a synthesis program for ordinary synthesis of 1 μmol of RNA. 3'-tBDSilyl-ribo Adenosine (N-bz) phosphoramidite (ChemGene) was used as the phosphoramidite in cycles 1 and 2 and Chemical Phosphorylation Reagent II (Glen Research Co.) was used in cycle 3. Xanthane hydride (Tokyo Kasei Kogyo) was used as the sulfurizing agent in cycles 1, 2 and 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 1, 2 and 3): Xanthane hydride (0.02 M)/acetonitrile-pyridine (9:1 mixed solvent); 15 min.

After synthesizing the 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 6-25% CH₃CN (linear gradient, 30 min.); 40° C.; 10 ml/min; 254 nm), and the four fractions that eluted at 13.3, 13.7, 13.9 and 14.4 minutes corresponding to the four diastereomers were collected. The present compound eluted in the vicinity of 7.2-8.0 minutes when analyzed by reverse phase HPLC (column (Tosoh superODS (4.6×50 mm)); 0.1M aqueous triethylamine acetate (TEAA), pH 7; 0-20% CH₃CN (linear gradient, 10 min); 60° C.; 1 ml/min). (Yield: 252 nmol as UV measured value at 260 nm) λmax (H₂O)=258.0 nm, ESI-Mass (negative): 1052.1 [M-H]⁻.

30 nmol of Example 2 compound were dissolved in 30 μl of anhydrous DMF, and 1 μl of pivaloyloxymethyl chloride (Tokyo Kasei Kogyo), approximately 1 mg of tetrabutylammonium iodide (Tokyo Kasei Kogyo), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6× 50 mm); 0.1M aqueous triethylamine acetate (TEAA), pH 7; 5-42% CH₃CN (linear gradient, 10 min); 60° C.; 2 ml/min; 254 nm), and the fraction at 5.6 minutes was collected. When the present compound was analyzed by reverse phase HPLC (column (Tosoh superODS (4.6×50 mm)); 0.1M aqueous triethylamine acetate (TEAA), pH 7; 5-42% CH₃CN (linear gradient, 14 min); 60° C.; 1 ml/min), it eluted at 7.52 minutes. Yield: 4.8 nmol, λmax (H₂O)=258 nm, ESI-Mass (negative); 1188.2 [M-H]⁻.

Example 5

Synthesis of Example 5 Compound (Exemplary Compound No. 290)

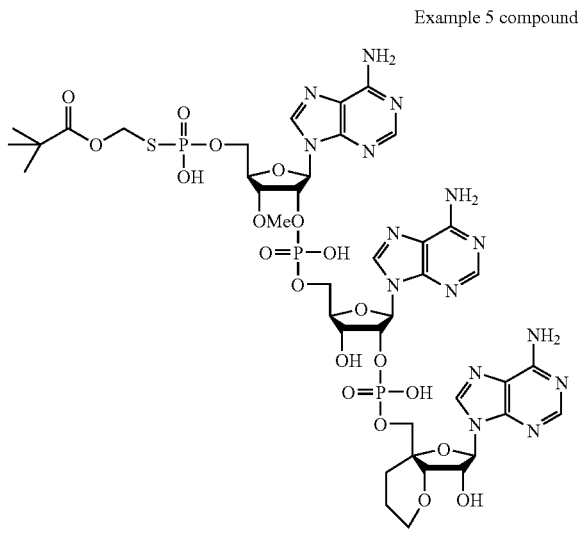

Example 5 compound (Exemplary Compound No. 290)

Example 6

Synthesis of Example 6 Compound (Exemplary Compound No. 334)

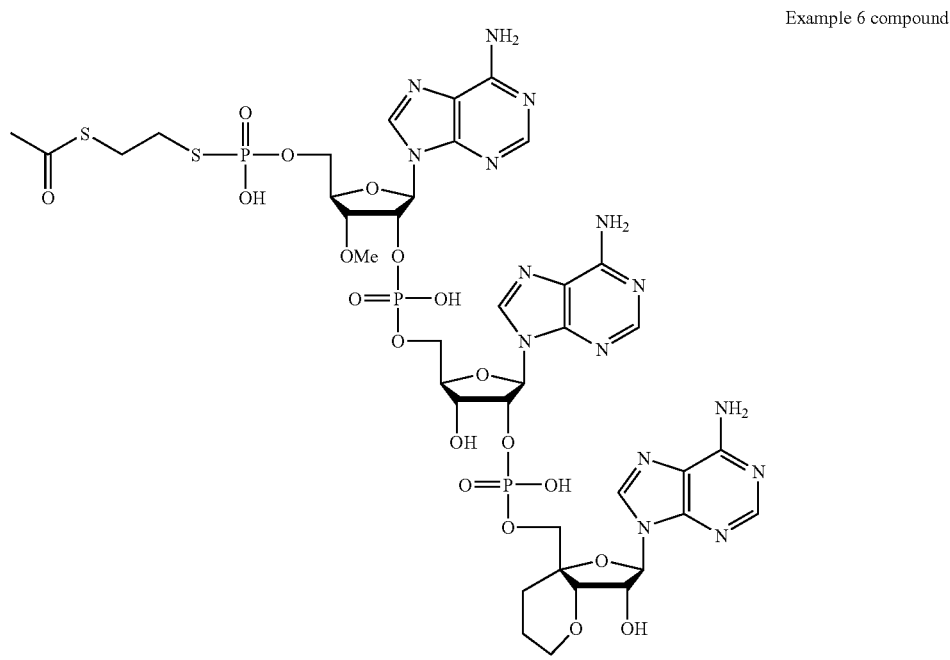

Example 6 compound (Exemplary Compound No. 334)

30 nmol of Example 2 compound were dissolved in 30 μl of anhydrous DMF, and 1 μl of thioacetic acid S-(2-bromoethyl) ester (Bauer, L. et al. J. Org. Chem. 1965, 30, 949-951), approximately 1 mg of tetrabutylammonium iodide (Tokyo Kasei Kogyo), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6×50 mm)); 0.1M aqueous triethylamine acetate (TEAA), pH 7; 5-43% CH$_3$CN (linear gradient, 10 min); 60° C.; 2 ml/min; 254 nm), and the fraction at 4.5 minutes was collected. When the present compound was analyzed by reverse phase HPLC (column (Tosoh superODS (4.6×50 mm)); 0.1M aqueous triethylamine acetate (TEAA), pH 7; 5-43% CH$_3$CN (linear gradient, 10 min); 60° C.; 1 ml/min), it eluted at 7.25 minutes. Yield: 14 nmol, λmax (H$_2$O)=258 nm, ESI-Mass (negative); 1176.2 [M-H]$^-$.

Example 7

Synthesis of Example 7 Compound (Exemplary Compound No. 953)

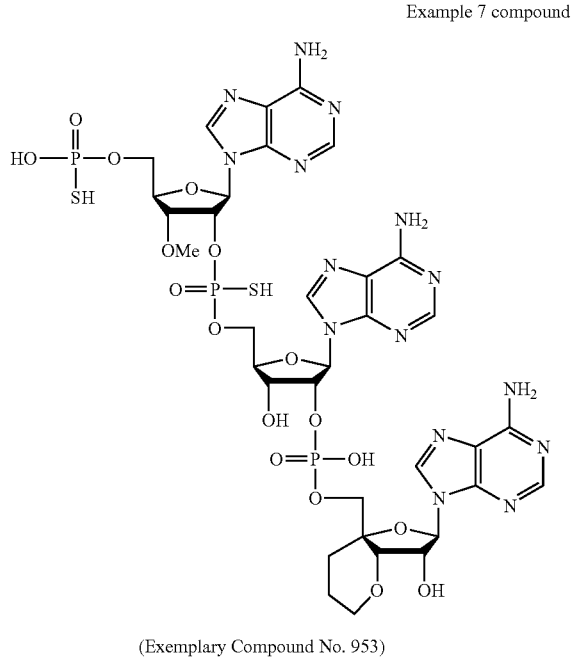

Example 7 compound (Exemplary Compound No. 953)

Synthesis was carried out using the compound of Example 17 described in Japanese Patent Application (Kokai) No. 2002-249497 (2.0 μmol) as the 5'-O-DMTr-riboadenosine analog bound to a CPG support with the DNA synthesizer based on one condensation cycle consisting of the following steps 1) to 4) using a synthesis program for ordinary synthesis of 1 μmol of RNA. 3'-tBDSilyl-ribo Adenosine (N-bz) phosphoramidite (ChemGene) was used as the phosphoramidite in cycle 1, 5'-DMT-3'-(O-methyl) adenosine(N-bz)2'-phosphoramidite (ChemGene) was used in cycle 2, and Chemical Phosphorylation Reagent II (Glen Research) was used in cycle 3. For the oxidation or sulfurizing agent, iodine was used in cycle 1, and xanthane hydride (Tokyo Kasei Kogyo) was used in cycles 2 and 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycle 1): Iodine/water/pyridine/tetrahydrofuran; 15 sec.

sulfurization (cycles 2 and 3): Xanthane hydride (0.02 M)/acetonitrile-pyridine (9:1 mixed solvent); 15 min.

After synthesizing the 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 9-25% CH$_3$CN (linear gradient, 20 min.); 40° C.; 10 ml/min; 254 nm), and the fractions that eluted at 12.1 and 13.0 minutes corresponding to the two diastereomers were collected. The present compound eluted in the vicinity of 8.66 and 8.98 minutes when analyzed by reverse phase HPLC (column (Tosoh superODS (4.6×50 mm)); 0.1M aqueous triethylamine acetate (TEAA), pH 7; 0-15% CH$_3$CN (linear gradient, 10 min); 60° C.; 1 ml/min). Yield: 768 nmol as UV measured value at 260 nm, λmax (H$_2$O) 258 nm, ESI-Mass (negative): 1090.2 [M-H]$^-$.

Example 8

Synthesis of Example 8 Compound (Exemplary Compound No. 954)

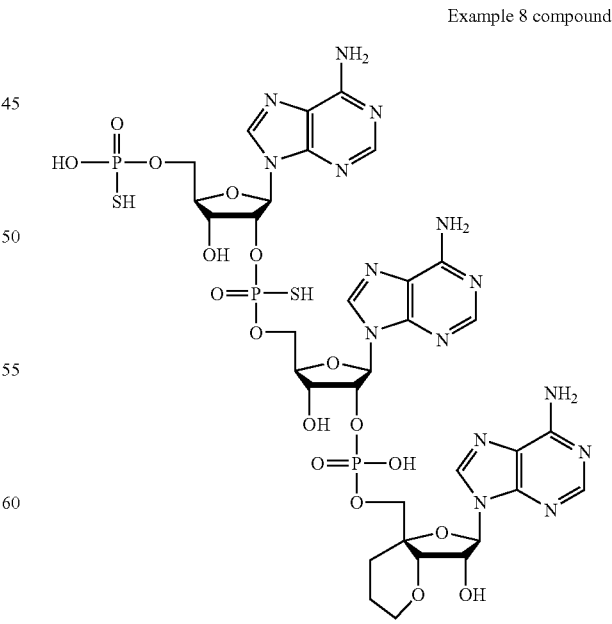

Example 8 compound (Exemplary Compound No. 954)

Synthesis was carried out using the compound of Example 17 described in Japanese Patent Application (Kokai) No. 2002-249497 (2.0 μmol) as the 5'-O-DMTr-riboadenosine analog bound to a CPG support with the DNA synthesizer based on one condensation cycle consisting of the following steps 1) to 4) using a synthesis program for ordinary synthesis of 1 μmol of RNA. 3'-tBDSilyl-ribo Adenosine (N-bz) phosphoramidite (ChemGene) was used as the phosphoramidite in cycles 1 and 2, and Chemical Phosphorylation Reagent II (Glen Research) was used in cycle 3. For the oxidation or sulfurizing agent, iodine was used in cycle 1, and xanthane hydride (Tokyo Kasei Kogyo) was used in cycles 2 and 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycle 1): Iodine/water/pyridine/tetrahydrofuran; 15 sec.

sulfurization (cycles 2 and 3): Xanthane hydride (0.02 M)/acetonitrile-pyridine (9:1 mixed solvent); 15 min.

After synthesizing the 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 9-25% $CH_3CN$ (linear gradient, 20 min.); 40° C.; 10 ml/min; 254 nm), and the fractions that eluted at 11.5 and 12.4 minutes corresponding to the two diastereomers were collected. The present compound eluted in the vicinity of 8.28 and 8.60 minutes when analyzed by reverse phase HPLC (column (Tosoh superODS (4.6×50 mm)); 0.1M aqueous triethylamine acetate (TEAA), pH 7; 0-15% $CH_3CN$ (linear gradient, 10 min); 60° C.; 1 ml/min). Yield: 718 nmol as UV measured value at 260 nm, λmax ($H_2O$)=258 nm, ESI-Mass (negative): 1076.1 [M-H]$^-$.

Example 9

Synthesis of Example 9 Compound (Exemplary Compound No. 955)

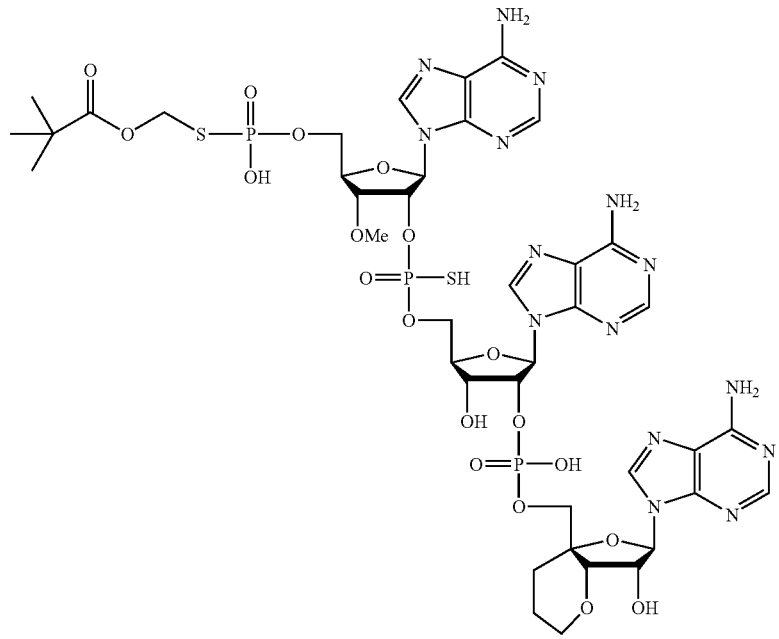

Example 9 compound (Exemplary Compound No. 955)

30 nmol of Example 7 compound were dissolved in 30 μl of anhydrous DMF, and 1 μl of pivaloyloxymethyl chloride (Tokyo Kasei Kogyo), approximately 1 mg of tetrabutylammonium iodide (Tokyo Kasei Kogyo), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6×

50 mm); 0.1M aqueous triethylamine acetate (TEAA), pH 7; 5-43% $CH_3CN$ (linear gradient, 10 min); 60° C.; 2 ml/min; 254 nm), and the fractions at 5.5 minutes and 5.6 minutes corresponding to two diastereomers were collected. When the present compound was analyzed by reverse phase HPLC (column (Tosoh superODS (4.6×50 mm)); 0.1M aqueous triethylamine acetate (TEAA), pH 7; 5-43% $CH_3CN$ (linear gradient, 10 min); 60° C.; 1 ml/min), it eluted at 7.42 and 7.56 minutes. Yield: 1.8 nmol in terms of UV measurement at 260 nm, λmax ($H_2O$)=258 nm, ESI-Mass (negative); 1204.2 [M-H]$^-$.

Example 10

Synthesis of Example 10 Compound (Exemplary Compound No. 956)

30 nmol of Example 8 compound were dissolved in 30 μl of anhydrous DMF, and 1 μl of pivaloyloxymethyl chloride (Tokyo Kasei Kogyo), approximately 1 mg of tetrabutylammonium iodide (Tokyo Kasei Kogyo), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6× 50 mm); 0.1M aqueous triethylamine acetate (TEAA), pH 7; 5-43% $CH_3CN$ (linear gradient, 10 min); 60° C.; 2 ml/min; 254 nm), and the fractions at 5.7 and 5.9 minutes corresponding to two diastereomers were collected. When the present compound was analyzed by reverse phase HPLC (column (Tosoh superODS (4.6×50 mm)); 0.1M aqueous triethy-

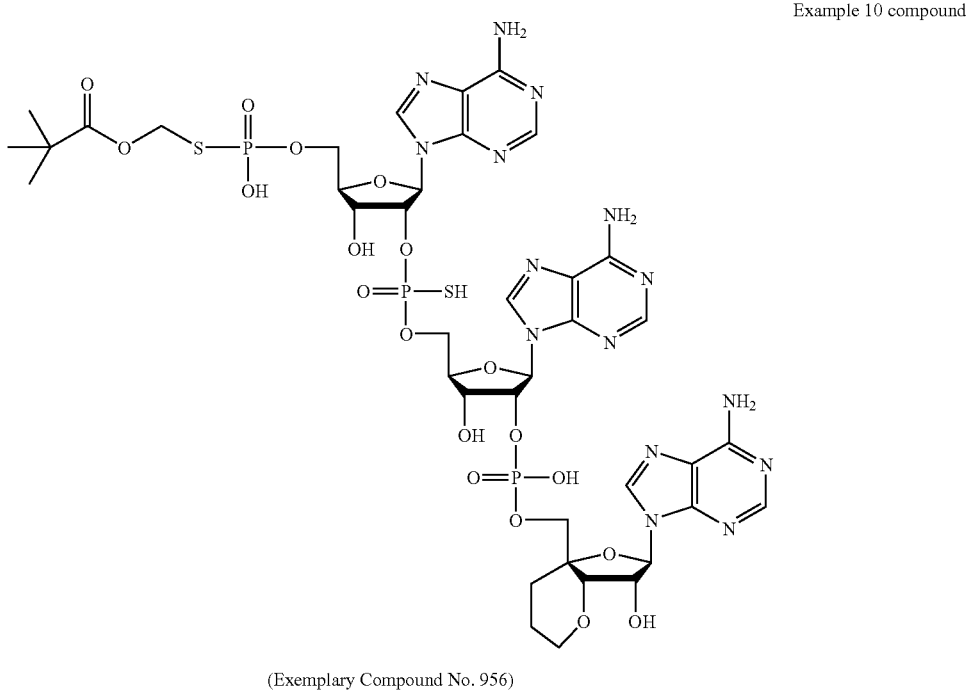

Example 10 compound (Exemplary Compound No. 956)

lamine acetate (TEAA), pH 7; 5-43% $CH_3CN$ (linear gradient, 10 min); 60° C.; 1 ml/min), it eluted at 7.68 and 7.85 minutes. Yield: 11 nmol in terms of UV measurement at 260 nm, λmax ($H_2O$)=258 nm, ESI-Mass (negative); 1191.20 [M-H]$^-$.

Example 11

Synthesis of Example 11 Compound (Exemplary Compound No. 957)

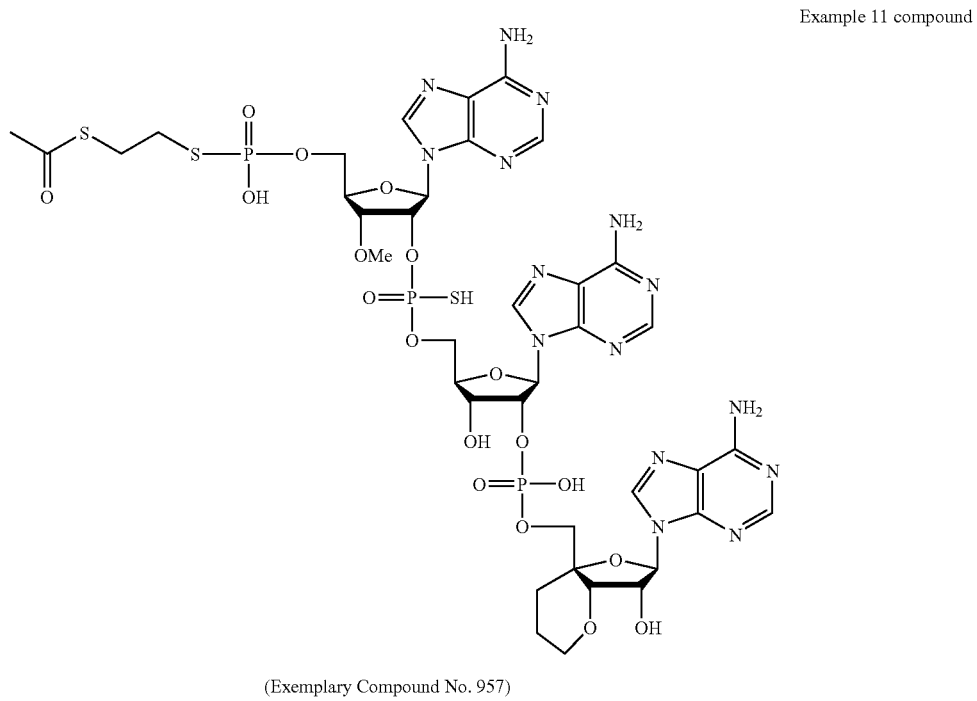

Example 11 compound (Exemplary Compound No. 957)

30 nmol of Example 7 compound were dissolved in 30 μl of anhydrous DMF, and 1 μl of thioacetic acid S-(2-bromoethyl) ester (Bauer, L. et al. J. Org. Chem. 1965, 30, 949-951), approximately 1 mg of tetrabutylammonium iodide (Tokyo Kasei Kogyo), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-43% $CH_3CN$ (linear gradient, 10 min); 60° C.; 2 ml/min; 254 nm), and the fractions at 4.7 and 4.8 minutes corresponding to two diastereomers were collected. When the present compound was analyzed by reverse phase HPLC (column (Tosoh superODS (4.6×50 mm)); 0.1M aqueous triethylamine acetate (TEAA), pH 7; 5-43% $CH_3CN$ (linear gradient, 10 min); 60° C.; 1 ml/min), it eluted at 6.57 and 6.75 minutes. Yield: 20 nmol in terms of UV measurement at 260 nm, λmax ($H_2O$)=258 nm, ESI-Mass (negative); 1192.1 [M-H]$^-$.

Example 12

Synthesis of Example 12 Compound (Exemplary Compound No. 958)

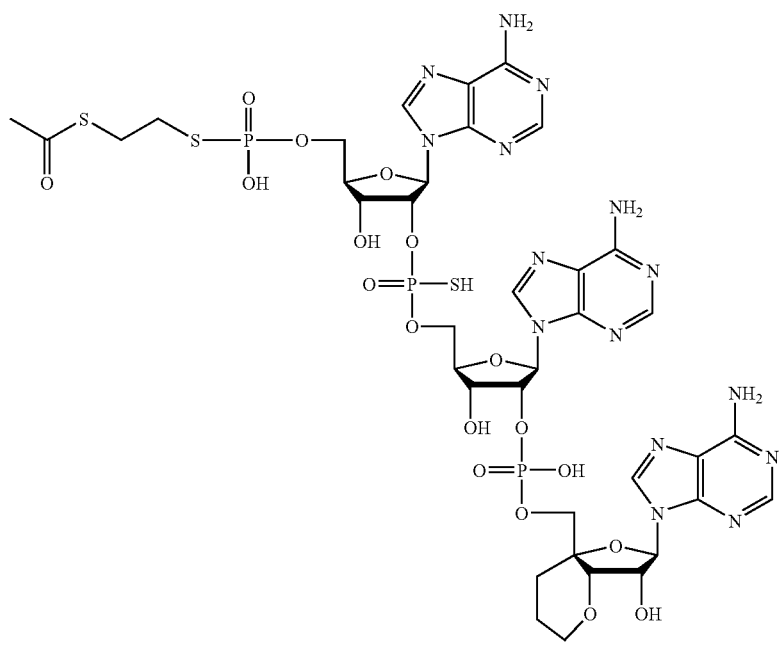

Example 12 compound (Exemplary Compound No. 958)

30 nmol of Example 8 compound were dissolved in 30 μl of anhydrous DMF, and 1 μl of thioacetic acid S-(2-bromoethyl) ester (Bauer, L. et al. J. Org. Chem. 1965, 30, 949-951), approximately 1 mg of tetrabutylammonium iodide (Tokyo Kasei Kogyo), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-43% $CH_3CN$ (linear gradient, 10 min); 60° C.; 2 ml/min; 254 nm), and the fractions at 4.9 and 5.1 minutes corresponding to two diastereomers were collected. When the present compound was analyzed by reverse phase HPLC (column (Tosoh superODS (4.6×50 mm)); 0.1M aqueous triethylamine acetate (TEAA), pH 7; 5-43% $CH_3CN$ (linear gradient, 10 min); 60° C.; 1 ml/min), it eluted at 6.83 and 7.04 minutes. Yield: 6.7 nmol in terms of UV measurement at 260 nm, λmax ($H_2O$)=258 nm, ESI-Mass (negative); 1178.1 [M-H]$^-$.

Example 13

Synthesis of Example 13 Compound (Exemplary Compound No. 964)

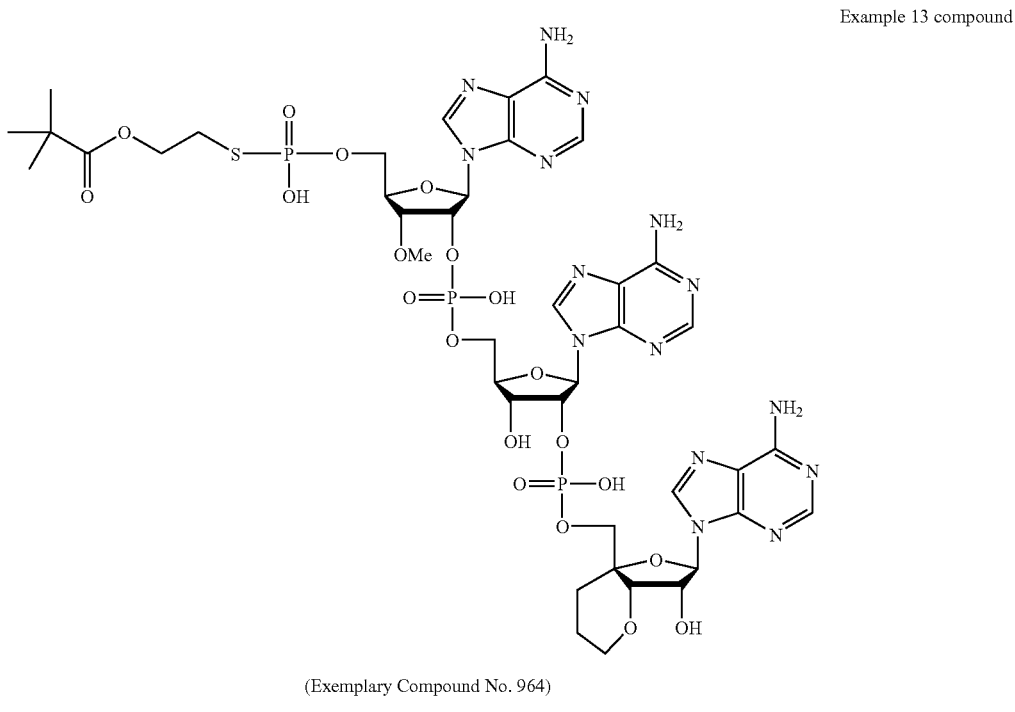

(Exemplary Compound No. 964)

30 nmol of Example 2 compound were dissolved in 30 µl of anhydrous DMF, and 1 µl of 2-(pivaloyloxy)ethyl bromide (Preparation process described in EP0395313), and 1 µl of triethylamine were added thereto, followed by reacting the mixture at room temperature overnight. After completion of the reaction, 100 µl of water were added, and the aqueous layer was washed three times with 50 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 60° C.; 5-80% $CH_3CN$ (linear gradient, 10 min); 60° C.; 2 ml/min; 254 nm), and the fraction at 4.3 minutes was collected. When the present compound was analyzed by reverse phase HPLC (column (Tosoh superODS (4.6×50 mm)); 0.1M aqueous triethylamine acetate (TEAA), pH 7; 5-80% $CH_3CN$ (linear gradient, 10 min); 60° C.; 1 ml/min), it eluted at 7.48 minutes. Yield: 19.1 nmol in terms of UV measurement at 260 nm, λmax ($H_2O$)=258.6 nm, FAB-Mass (negative); 1202 [M-H]$^-$.

Example 14

Synthesis of Example 14 compound (Exemplary Compound No. 965)

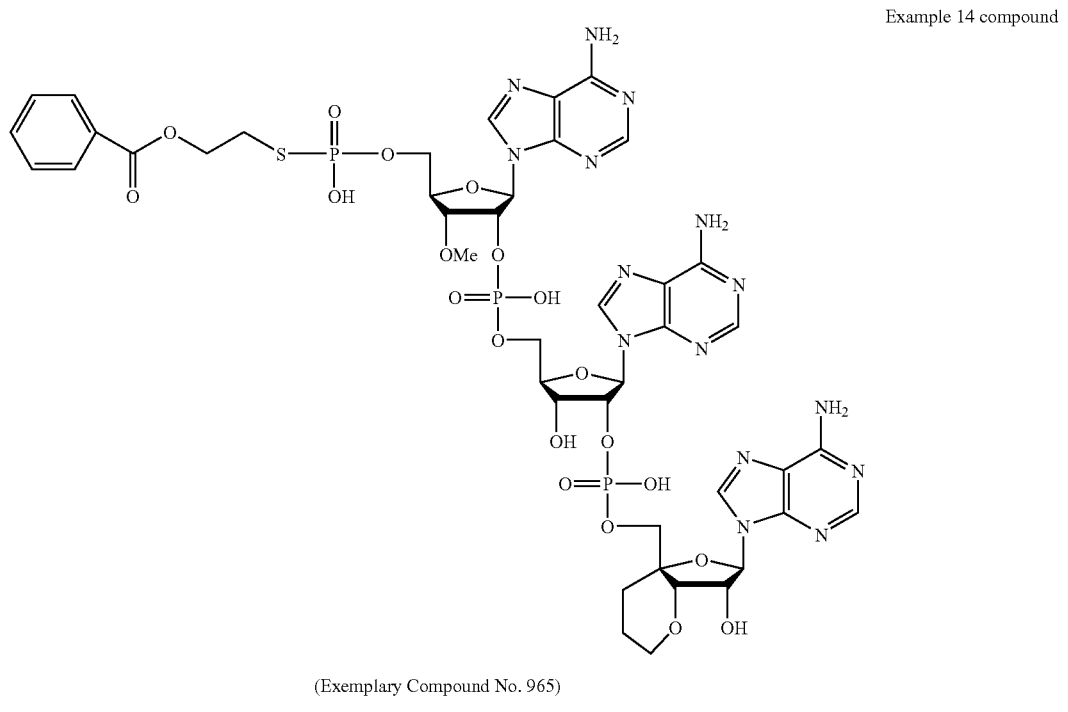

Example 14 compound (Exemplary Compound No. 965)

30 nmol of Example 2 compound were dissolved in 30 µl of anhydrous DMF, and 1 µl of 2-(benzoyloxy)ethyl bromide (Tokyo Kasei Kogyo), and 1 µl of triethylamine were added thereto, followed by reacting the mixture at room temperature overnight. After completion of the reaction, 100 µl of water were added, and the aqueous layer was washed three times with 50 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-80% $CH_3CN$ (linear gradient, 10 min); 60° C.; 2 ml/min; 254 nm), and the fraction at 7.0 minutes was collected. When the present compound was analyzed by reverse phase HPLC (column (Tosoh superODS (4.6×50 mm)); 0.1M aqueous triethylamine acetate (TEAA), pH 7; 5-80% $CH_3CN$ (linear gradient, 10 min); 60° C.; 1 ml/min), it eluted at 7.44 minutes. Yield: 19.7 nmol in terms of UV measurement at 260 nm, λmax ($H_2O$)=258.7 nm, FAB-Mass (negative); 1222 [M-H]$^-$.

Example 15

Synthesis of Example 15 Compound (Exemplary Compound No. 967)

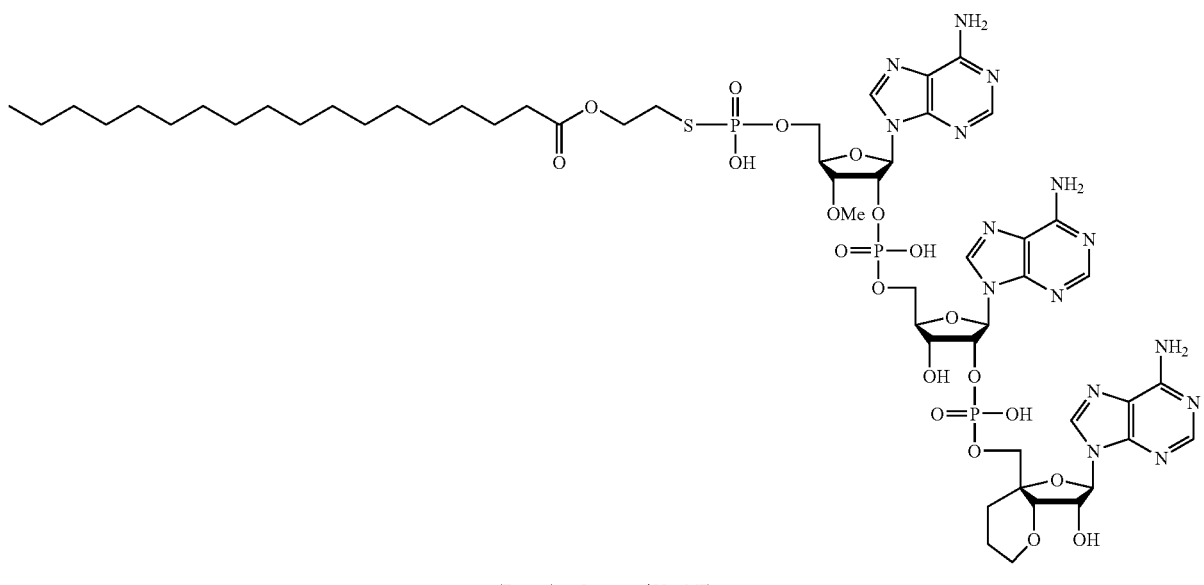

Example 15 compound (Exemplary Compound No. 967)

30 nmol of Example 2 compound were dissolved in 30 μl of anhydrous DMF, and 1 mg of 2-(stearoyloxy)ethyl bromide (Ackerman et al., J. Am. Chem. Soc., 78, 1956, 6025), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-80% $CH_3CN$ (linear gradient, 10 min); 60° C.; 2 ml/min; 254 nm), and the fraction at 8.2 minutes was collected. When the present compound was analyzed by reverse phase HPLC (column (Tosoh superODS (4.6×50 mm)); 0.1M aqueous triethylamine acetate (TEAA), pH 7; 5-80% $CH_3CN$ (linear gradient, 10 min); 60° C.; 1 ml/min), it eluted at 14.62 minutes. Yield: 14.9 nmol in terms of UV measurement at 260 nm, λmax ($H_2O$)=260.1 nm, FAB-Mass (negative); 1384 $[M-H]^-$.

Example 16

Synthesis of Example 16 Compound (Exemplary Compound No. 968)

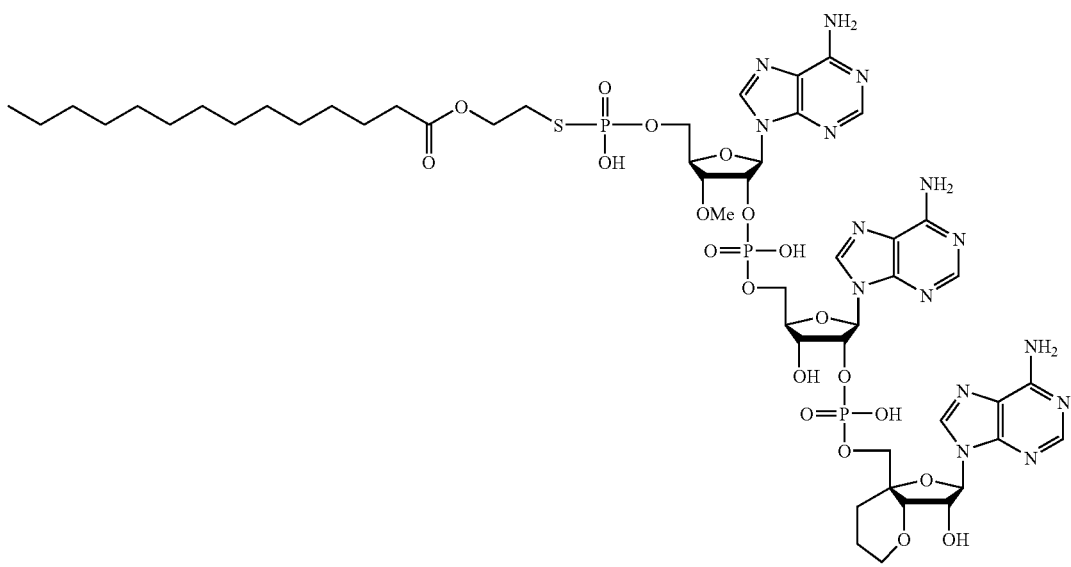

(Exemplary Compound No. 968)

Example 16 compound 30 nmol of Example 2 compound were dissolved in 30 μl of anhydrous DMF, and 1 mg of 2-(myristoyloxy)ethyl bromide (Ackerman et al., J. Am. Chem. Soc., 78, 1956, 6025), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-80% $CH_3CN$ (linear gradient, 10 min); 60° C.; 2 ml/min; 254 nm), and the fraction at 6.3 minutes was collected. When the present compound was analyzed by reverse phase HPLC (column (Tosoh superODS (4.6×50 mm)); 0.1M aqueous triethylamine acetate (TEAA), pH 7; 5-80% $CH_3CN$ (linear gradient, 10 min); 60° C.; 1 ml/min), it eluted at 12.57 minutes. Yield: 13.1 nmol in terms of UV measurement at 260 nm, λmax ($H_2O$)=259.7 nm, FAB-Mass (negative); 1328 [M-H]$^-$.

Example 17

Synthesis of Example 17 Compound (Exemplary Compound No. 969)

Example 17 compound

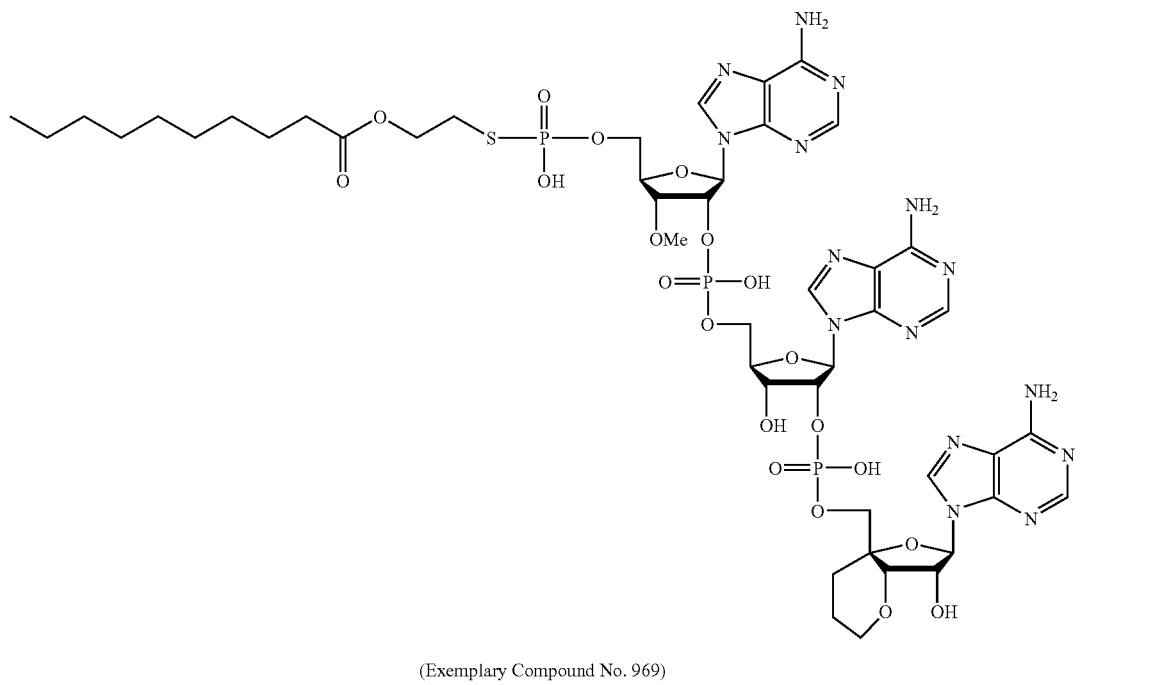

(Exemplary Compound No. 969)

30 nmol of Example 2 compound were dissolved in 30 μl of anhydrous DMF, and 1 mg of 2-(decanoyloxy)ethyl bromide (Devinsky, Ferdinand et al., Collect. Czech. Chem. Commun. 49, 12, 1984, 2819-2827), and 1 μl of triethylamine were added thereto, followed by reacting the mixture at room temperature overnight. After completion of the reaction, 100 μl of water were added, and the aqueous layer was washed three times with 50 μl of AcOEt. After the aqueous layer was evaporated, it was purified by reverse phase HPLC (Shimadzu Seisakusho LC-VP; column (Merck chromolith (4.6× 50 mm); 0.1M aqueous triethylamine acetate (TEA), pH 7; 5-80% $CH_3CN$ (linear gradient, 10 min); 60° C.; 2 ml/min; 254 nm), and the fraction at 4.3 minutes was collected. When the present compound was analyzed by reverse phase HPLC (column (Tosoh superODS (4.6×50 mm)); 0.1M aqueous triethylamine acetate (TEAA), pH 7; 5-80% $CH_3CN$ (linear gradient, 10 min); 60° C.; 1 ml/min), it eluted at 10.36 minutes. Yield: 19.8 nmol in terms of UV measurement at 260 nm, λmax ($H_2O$)=258.2 nm, FAB-Mass (negative); 1272 [M-H]$^-$.

Example 18

Synthesis of Example 18 Compound (Exemplary Compound No. 1074)

Example 18 compound

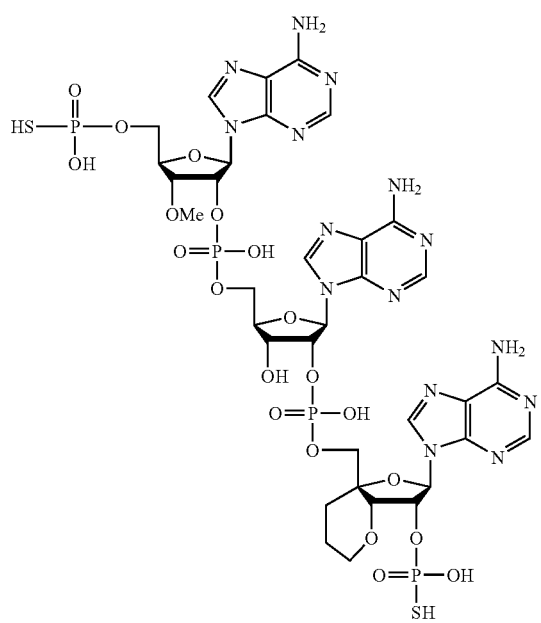

(Exemplary Compound No. 1074)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (2.0 μmol) was used as the solid phase carrier. The compound of Example 16 described in Japanese Patent Application (Kokai) No. 2002-249497 was used as the phosphoramidite in cycle 1, 3'-tBDSilyl-ribo Adenosine (N-bz) phosphoramidite (Chem-Gene) was used as the phosphoramidite in cycle 2, 5'-DMT-3'-(O-methyl) adenosine(N-bz)2'-phosphoramidite (Chem-Gene) was used in cycle 3, and the compound of Example 8a described in Japanese Patent Application (Kokai) No. Hei 11-246592 was used in cycle 4. For the oxidation or sulfurizing agent, xanthane hydride (Tokyo Kasei Kogyo) was used in cycle 1, and iodine was used in cycles 2, 3 and 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 2, 3 and 4):

Iodine/water/pyridine/tetrahydrofuran; 15 sec.

sulfurization (cycle 1): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure, and the pH was adjusted to 2.0 by adding aqueous hydrochloric acid (2 N) to the remaining residue, followed by reacting for 5 hours at 30° C. to remove the DMTr group and the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 5-17% $CH_3CN$ (linear gradient, 20 min.); 40° C.; 10 ml/min; 254 nm), and the fraction that eluted at 14.9 minutes was collected. The present compound eluted in the vicinity of 6.77 minutes when analyzed by reverse phase HPLC (column (Tosoh superODS (4.6×50 mm)); 0.1M aqueous triethylamine acetate (TEAA), pH 7; 0-15% $CH_3CN$ (linear gradient, 10 min); 60° C.; 1 ml/min). Yield: 1440 nmol as UV measured value at 260 nm, λmax ($H_2O$)=258.5 nm, ESI-Mass (negative): 1198.1 $[M-H]^-$.

Example 19

Synthesis of Example 19 Compound (Exemplary Compound No. 1075)

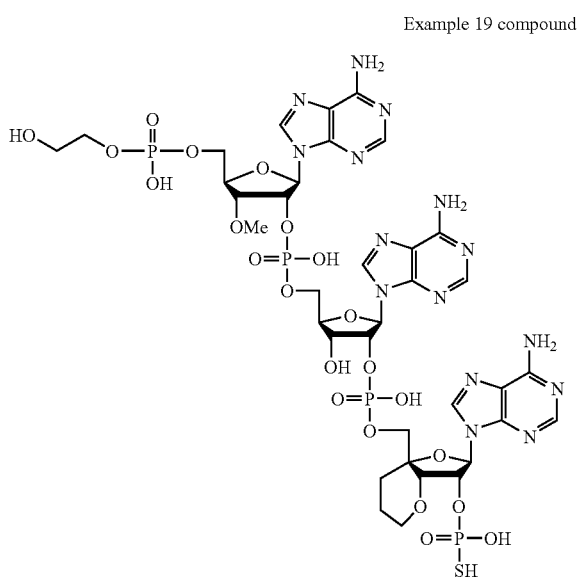

Example 19 compound (Exemplary Compound No. 1075)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (2.0 μmol) was used as the solid phase carrier. The compound of Example 16 described in Japanese Patent Application (Kokai) No. 2002-249497 was used as the phosphoramidite in cycle 1, 3'-tBDSilyl-ribo Adenosine (N-bz) phosphoramidite (Chem-Gene) was used as the phosphoramidite in cycle 2, 5'-DMT-3'-(O-methyl) adenosine(N-bz)2'-phosphoramidite (Chem-Gene) was used in cycle 3, and Chemical Phosphorylation Reagent II (Glen Research) was used in cycle 4. For the oxidation or sulfurizing agent, xanthane hydride (Tokyo Kasei Kogyo) was used in cycles 1 and 4, and iodine was used in cycles 2 and 3.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 2 and 3):

Iodine/water/pyridine/tetrahydrofuran; 15 sec.

sulfurization (cycles 1 and 4): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure, and the pH was adjusted to 2.0 by adding aqueous hydrochloric acid (2 N) to the remaining residue, followed by reacting for 5 hours at 30° C. to remove the DMTr group and the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate. (TEAA), pH 7; 5-17% CH$_3$CN (linear gradient, 20 min.); 40° C.; 10 ml/min; 254 nm), and the fraction that eluted at 15.5 minutes was collected. The present compound eluted in the vicinity of 8.63 minutes when analyzed by reverse phase HPLC (column (Tosoh superODS (4.6×50 mm)); 0.1M aqueous triethylamine acetate (TEAA), pH 7; 0-15% CH$_3$CN (linear gradient, 10 min); 60° C.; 1 ml/min). Yield: 1482 nmol as UV measured value at 260 nm, λmax (H$_2$O)=258.2 nm, ESI-Mass (negative): 1170.1 [M-H]$^-$.

Example 20

Synthesis of Example 20 Compound (Exemplary Compound No. 1937)

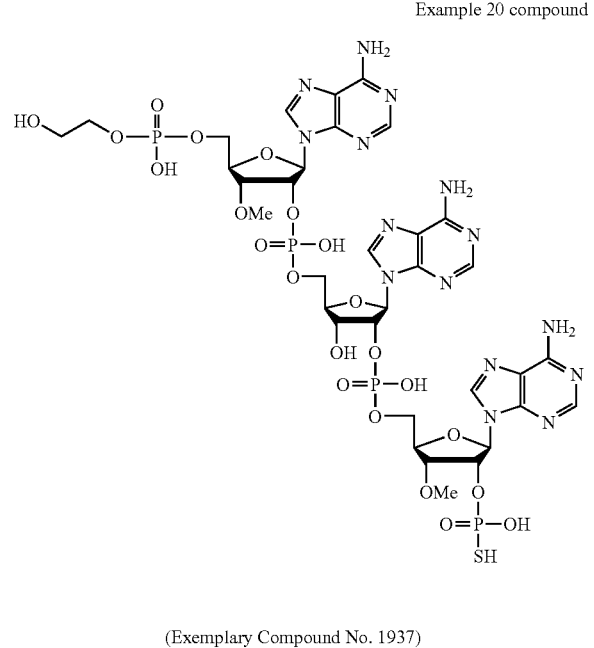

Example 20 compound (Exemplary Compound No. 1937)

Synthesis was carried out with the DNA synthesizer based on one condensation cycle consisting of the following steps 1) to 4) using a synthesis program for ordinary synthesis of 1 µmol of RNA. 31-Phosphate CPG (Glen Research) (1.0 µmol) was used as the solid phase carrier. 5'-DMT-3'-(O-methyl) adenosine(N-bz)2'-phosphoramidite (ChemGene) was used as the phosphoramidite in cycles 1 and 3, 3'-tBD-Silyl-ribo Adenosine (N-bz) phosphoramidite (ChemGene) was used as the phosphoramidite in cycle 2, and the compound of Example 8a described in Japanese Patent Application (Kokai) No. Hei 11-246592 was used in cycle 4. Iodine was used as the oxidizing agent.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation: Iodine/water/pyridine/tetrahydrofuran; 15 sec.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure, and the pH was adjusted to 2.0 by adding aqueous hydrochloric acid (2 N) to the remaining residue, followed by reacting for 5 hours at 30° C. to remove the DMTr group and the silyl group. After neutralizing with aqueous ammonia and distilling off the solvent, the product was purified by reverse phase HPLC (Shimadzu Seisakusho LC-VP; column (Merck chromolith (4.6×50 mm)); 0.1 M aqueous triethylamine acetate (TEAA), pH 7; 2.5-10% CH$_3$CN (linear gradient, 10 min.); 60° C.; 2 ml/min), and the fraction that eluted at 4.8 minutes was collected. The present compound eluted in the vicinity of 3.16 minutes when analyzed by reverse phase HPLC (column (((Merck chromolith (4.6×50 mm)); 0.1M aqueous triethylamine acetate (TEAA), pH 7; 5-10% CH$_3$CN (linear gradient, 10 min); 60° C.; 2 ml/min). Yield: 95 nmol as UV measured value at 260 nm, λmax (H$_2$O)=256.2 nm, ESI-Mass (negative): 1171.9 [M-H]$^-$.

Example 21

Synthesis of Example 21 Compound (Exemplary Compound No. 1099)

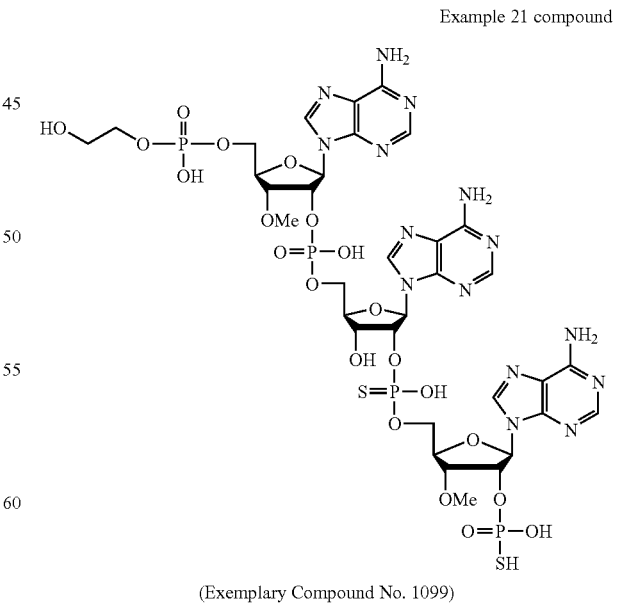

Example 21 compound (Exemplary Compound No. 1099)

Synthesis was carried out with the DNA synthesizer based on one condensation cycle consisting of the following steps 1)

to 4) using a synthesis program for ordinary synthesis of 1 μmol of RNA. 3'-Phosphate CPG (Glen Research) (1.0 μmol) was used as the solid phase carrier. 5'-DMT-3'-(O-methyl) adenosine(N-bz)2'-phosphoramidite (ChemGene) was used as the phosphoramidite in cycles 1 and 3, 3'-tBDSilyl-ribo Adenosine (N-bz) phosphoramidite (ChemGene) was used as the phosphoramidite in cycle 2, and the compound of Example 8a described in Japanese Patent Application (Kokai) No. Hei 11-246592 was used in cycle 4. For the oxidation or sulfurizing agent, xanthane hydride (Tokyo Kasei Kogyo) was used in cycles 1 and 2, and iodine was used in cycles 3 and 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 3 and 4):

Iodine/water/pyridine/tetrahydrofuran; 15 sec.

sulfurization (cycles 1 and 2): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure, and the pH was adjusted to 2.0 by adding aqueous hydrochloric acid (2 N) to the remaining residue, followed by reacting for 5 hours at 30° C. to remove the DMTr group and the silyl group. After neutralizing with aqueous ammonia and distilling off the solvent, the product was purified by reverse phase HPLC (Shimadzu Seisakusho LC-VP; column (Merck chromolith (4.6×50 mm)); 0.1 M aqueous triethyl amine acetate (TEAA), pH 7; 5-10% CH$_3$CN (linear gradient, 10 min.); 60° C.; 2 ml/min), and the fractions that eluted at 6.0 and 6.4 minutes were collected. The present compound eluted in the vicinity of 4.89 and 5.43 minutes when analyzed by reverse phase HPLC (column (((Merck chromolith (4.6×50 mm)); 0.1M aqueous triethylamine acetate (TEAA), pH 7; 5-10% CH$_3$CN (linear gradient, 10 min); 60° C.; 2 ml/min). Yield: 54 nmol as UV measured value at 260 nm, λmax (H$_2$O)=258.0 nm, ESI-Mass (negative): 1189 [M-H]$^-$.

Example 22

Synthesis of Example 22 Compound (Exemplary Compound No. 1110)

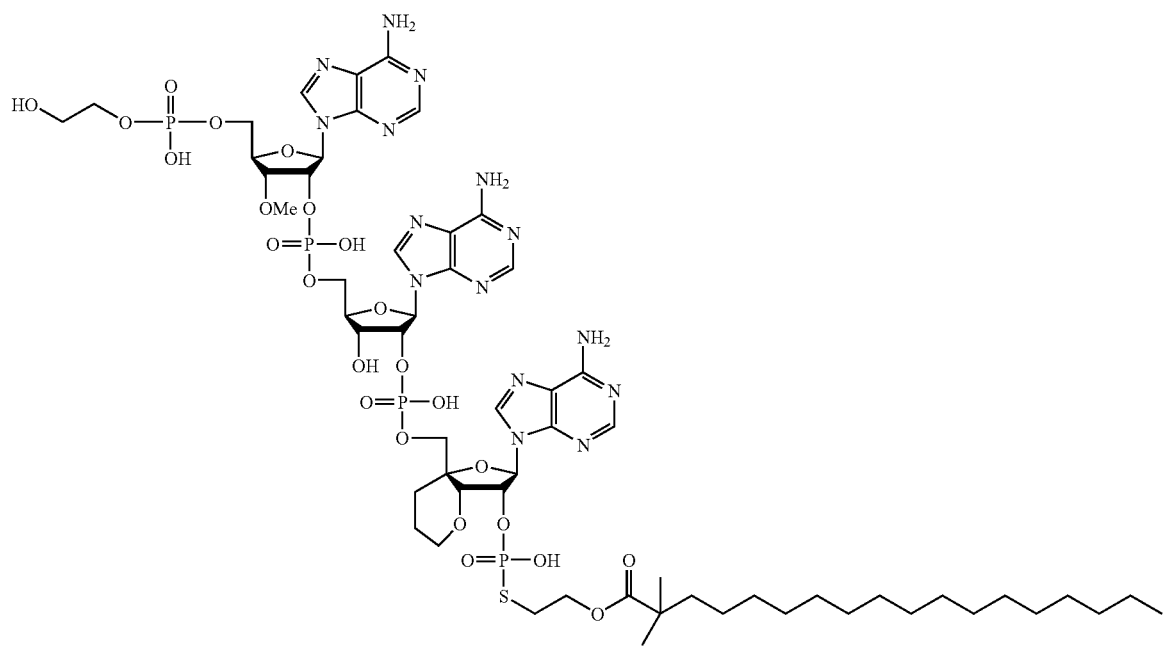

Example 22 compound (Exemplary Compound No. 1110)

500 mg (1.6 mmol) of 2,2-Dimethyl-octadecanoic acid (Roth, Bruce D. et al., J. Med. Chem. 1992, 35(9), 1609-17) were dissolved in anhydrous dichloromethane (10 ml), and 350 mg (1.8 mmol) of dicyclohexylcarbodiimide (DCC), and 140 μl (2 mmol) of 2-bromoethanol were added thereto, followed by stirring of the mixture at room temperature overnight. The reaction mixture was purified using a silica gel column (elution by hexane-ethyl acetate (7:1) solvent mixture) to obtain 230 mg of 2-(2,2-dimethyloctadecanoyloxy) ethyl bromide to be used below.

100 nmol of Example 19 compound were dissolved in 100 µl of anhydrous DMF, and 3 mg of 2-(2,2-dimethyloctadecanoyloxy)ethyl bromide, and 3 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6× 50 mm); 0.1M aqueous triethylamine acetate (TEAA), pH 7; 33-80% $CH_3CN$ (linear gradient, 10 min); 60° C.; 2 ml/min; 254 nm), and the fraction at 6.7 minutes was collected. When the present compound was analyzed by reverse phase HPLC (column (Tosoh superODS (4.6×50 mm)); 0.1M aqueous triethylamine acetate (TEAA), pH 7; 24-100% $CH_3CN$ (linear gradient, 10 min); 60° C.; 1 ml/min), it eluted at 9.65 minutes. Yield: 24.5 nmol in terms of UV measurement at 260 nm, λmax ($H_2O$)=259.3 nm, ESI-Mass (negative); 1537.3 [M-H]$^-$.

Example 23

Synthesis of Example 23 Compound (Exemplary Compound No. 1111)

100 nmol of Example 19 compound were dissolved in 100 µl of anhydrous DMF, and 3 mg of 2-(stearoyloxy)ethyl bromide (Ackerman et al., J. Am. Chem. Soc., 78, 1956, 6025), and 3 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 52-100% $CH_3CN$ (linear gradient, 10 min); 60° C.; 2 ml/min; 254 nm), and the fraction at 1.9 minutes was collected. When the present compound was analyzed by reverse phase HPLC (column (Tosoh superODS (4.6×50 mm)); 0.1M aqueous triethylamine acetate (TEAA), pH 7; 15-100% $CH_3CN$ (linear gradient, 10 min); 60° C.; 1 ml/min), it eluted at 10.06 minutes. Yield: 39.8 nmol in terms of UV measurement at 260 nm, λmax ($H_2O$)=258.2 nm, ESI-Mass (negative); 1508.4 [M-H]$^-$.

Example 23 compound

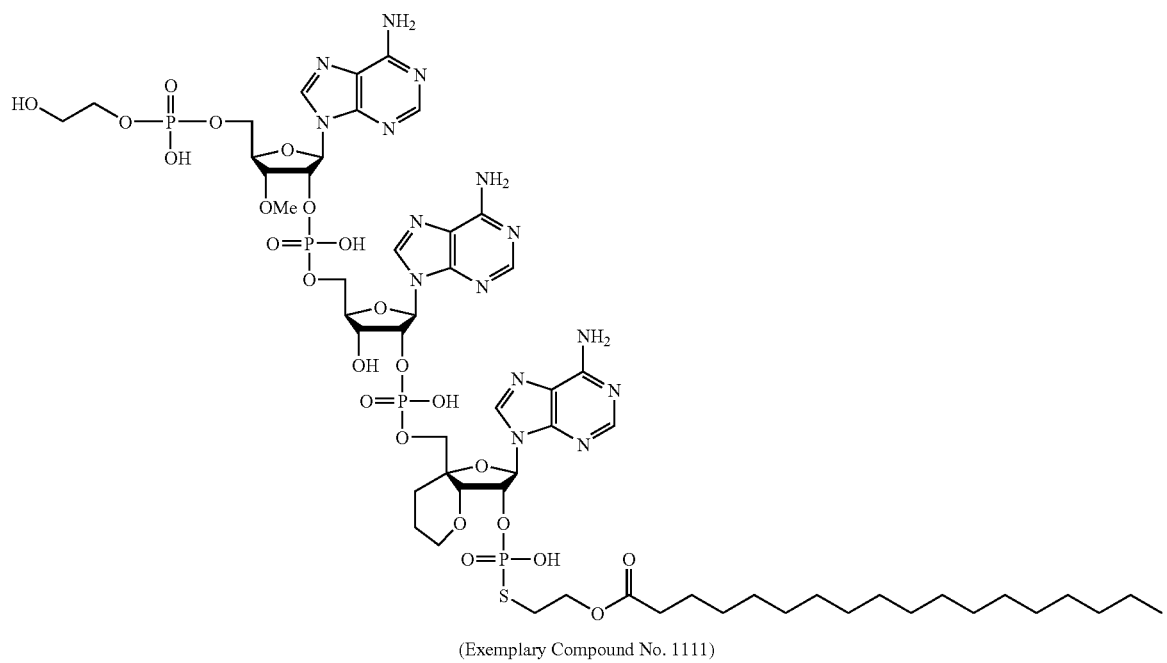

(Exemplary Compound No. 1111)

Example 24

Synthesis of Example 24 compound (Exemplary compound No. 1112)

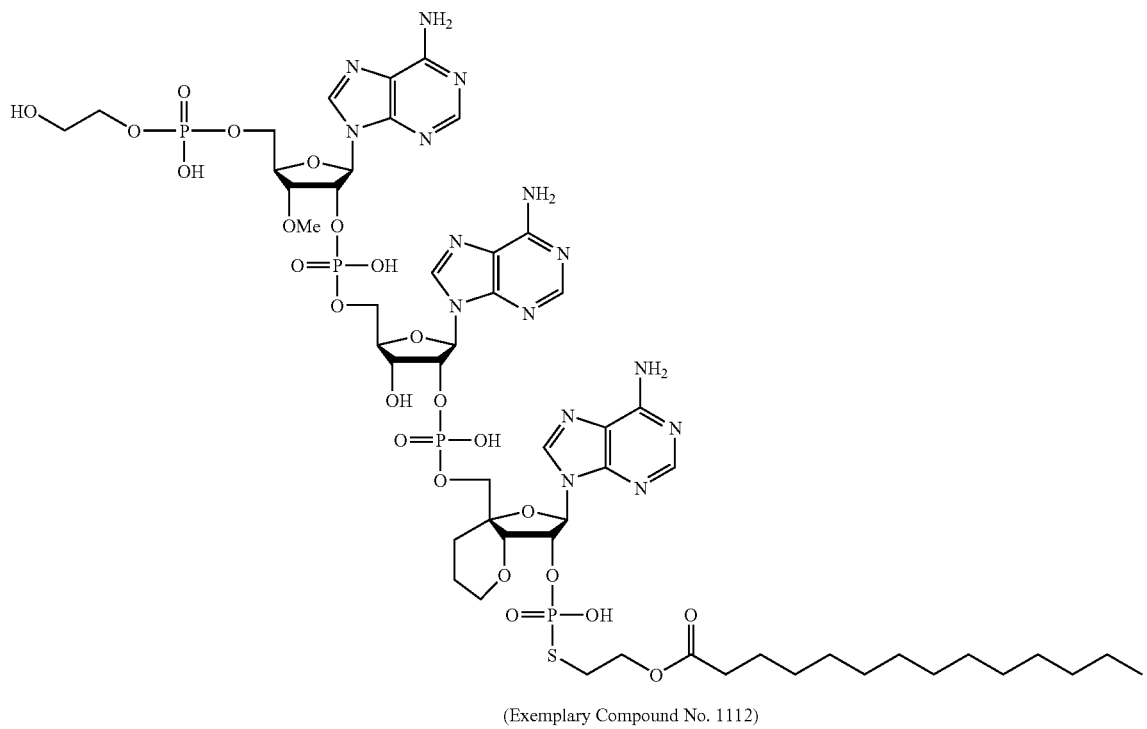

(Exemplary Compound No. 1112)

100 nmol of Example 19 compound were dissolved in 100 μl of anhydrous DMF, and 3 mg of 2-(myristoyloxy)ethyl bromide (Ackerman et al., J. Am. Chem. Soc., 78, 1956, 6025), and 3 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 33-100% $CH_3CN$ (linear gradient, 10 min); 60° C.; 2 ml/min; 254 nm), and the fraction at 4.1 minutes was collected. When the present compound was analyzed by reverse phase HPLC (column (Tosoh super-ODS (4.6×50 mm)); 0.1M aqueous triethylamine acetate (TEAA), pH 7; 15-100% $CH_3CN$ (linear gradient, 10 min); 60° C.; 1 ml/min), it eluted at 8.75 minutes. Yield: 54.3 nmol in terms of UV measurement at 260 nm, λmax ($H_2O$)=258.0 nm, ESI-Mass (negative); 1452.4 [M-H]⁻.

Example 25

Synthesis of Example 25 Compound (Exemplary Compound No. 1113)

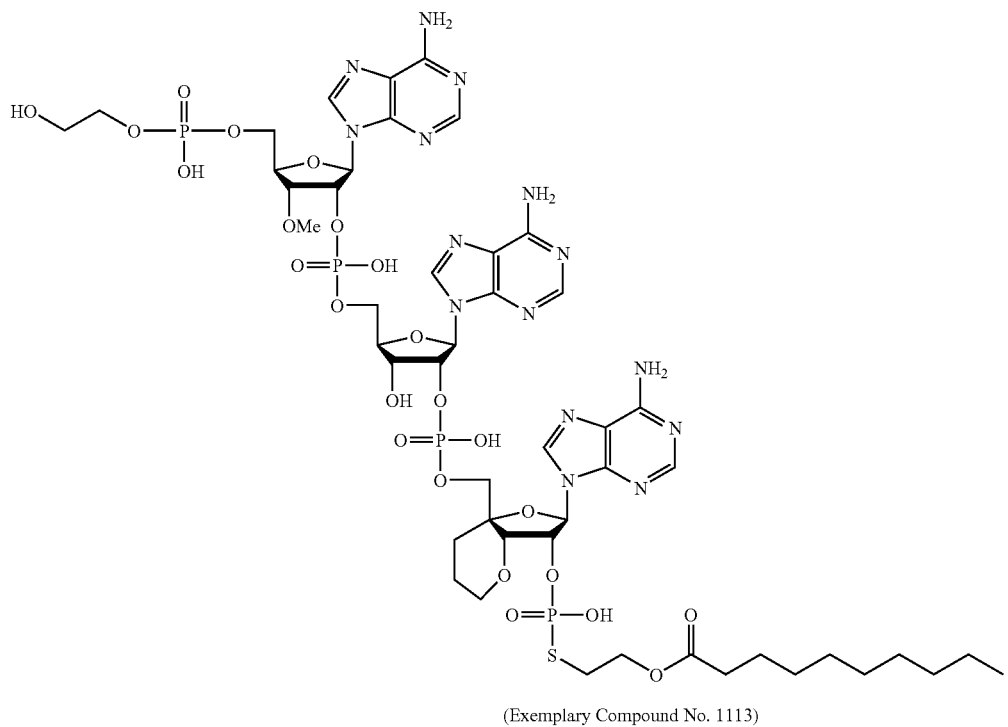

Example 25 compound (Exemplary Compound No. 1113)

100 nmol of Example 19 compound were dissolved in 100 μl of anhydrous DMF, and 3 mg of 2-(decanoyloxy)ethyl bromide (Devinsky, Ferdinand et al., Collect. Czech. Chem. Commun. 49, 12, 1984, 2819-2827), and 3 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6× 50 mm); 0.1M aqueous triethylamine acetate (TEAA), pH 7; 15-62% $CH_3CN$ (linear gradient, 10 min); 60° C.; 2 ml/min; 254 nm), and the fraction at 6.2 minutes was collected. When the present compound was analyzed by reverse phase HPLC (column (Tosoh superODS (4.6×50 mm)); 0.1M aqueous triethylamine acetate (TEAA), pH 7; 15-100% $CH_3CN$ (linear gradient, 10 min); 60° C.; 1 ml/min), it eluted at 7.29 minutes. Yield: 50.9 nmol in terms of UV measurement at 260 nm, λmax ($H_2O$)=258.4 nm, ESI-Mass (negative); 1396.3 [M-H]$^-$.

Example 26

Synthesis of Example 26 Compound (Exemplary Compound No. 1938)

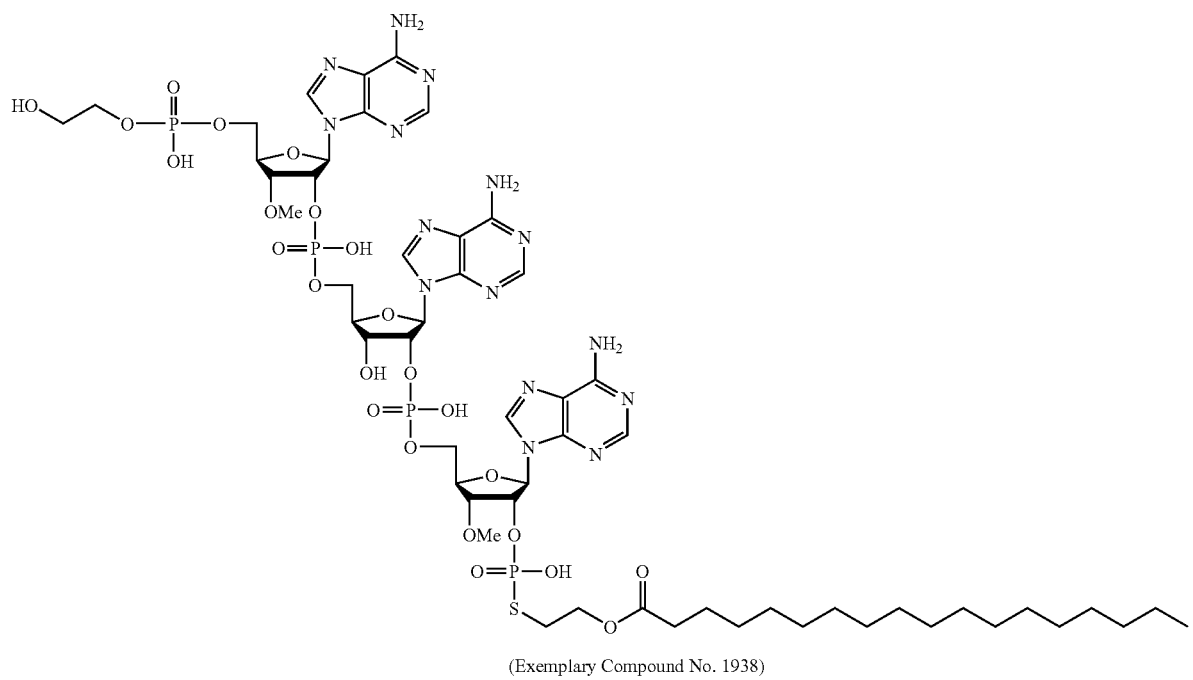

(Exemplary Compound No. 1938)

30 nmol of Example 20 compound were dissolved in 30 µl of anhydrous DMF, and 1 mg of 2-(stearoyloxy)ethyl bromide (Ackerman et al., J. Am. Chem. Soc., 78, 1956, 6025), and 1 µl of triethylamine were added thereto, followed by reacting the mixture at room temperature overnight. After completion of the reaction, 100 µl of water were added, and the aqueous layer was washed three times with 100 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 28-100% $CH_3CN$ (linear gradient, 10 min); 60° C.; 2 ml/min; 254 nm), and the fraction at 5.3 minutes was collected. When the present compound was analyzed by reverse phase HPLC (column Merck chromolith (4.6×50 mm)); 0.1M aqueous triethylamine acetate (TEAA), pH 7; 24-100% $CH_3CN$ (linear gradient, 10 min); 60° C.; 1 ml/min), it eluted at 7.51 minutes. Yield: 14.9 nmol in terms of UV measurement at 260 nm, λmax ($H_2O$)=258 nm, ESI-Mass (negative); 1483.2 $[M-H]^-$.

Synthesis of Example 27 Compound (Exemplary Compound No. 1183)

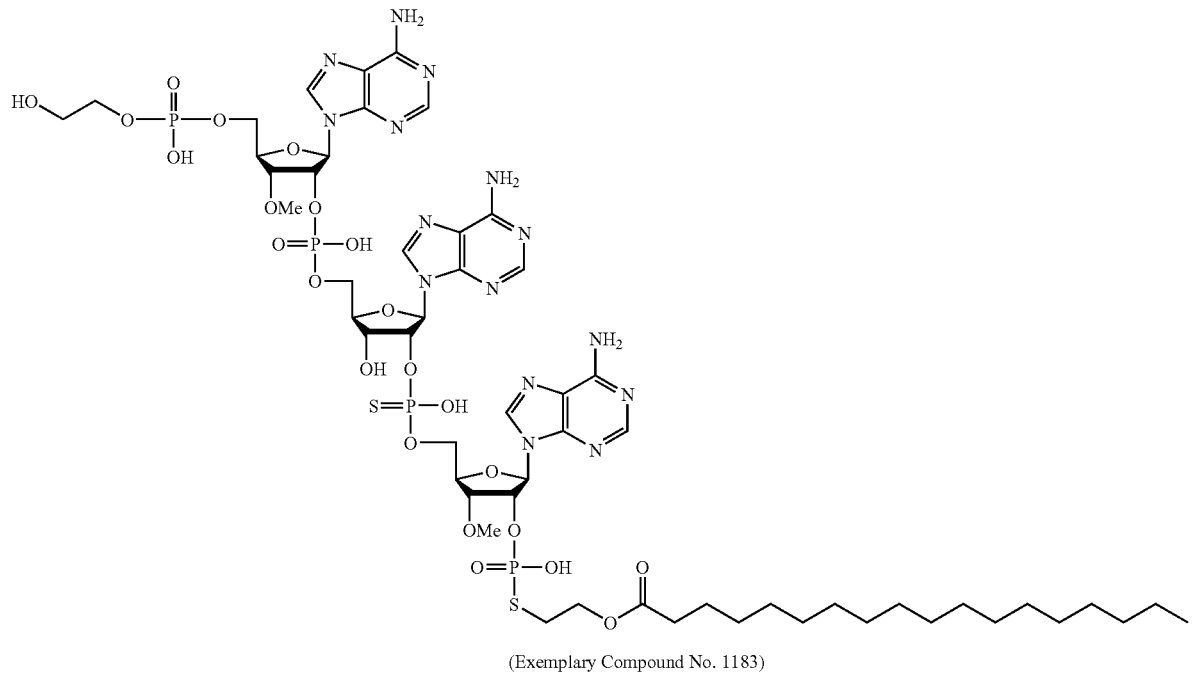

Example 27 compound (Exemplary Compound No. 1183)

30 nmol Example 21 compound were dissolved in 30 µl of anhydrous DMF, and 1 mg of 2-(stearoyloxy) ethyl bromide (Ackerman et al., J. Am. Chem. Soc., 78, 1956, 6025), and 1 µl of triethylamine were added thereto, followed by reacting the mixture at room temperature overnight. After completion of the reaction, 100 µl of water were added, and the aqueous layer was washed three times with 100 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEA), pH 7; 28-100% $CH_3CN$ (linear gradient, 10 min); 60° C.; 2 ml/min; 254 nm), and the fraction at 5.2 minutes was collected. When the present compound was analyzed by reverse phase HPLC (column Merck chromolith (4.6×50 mm); 0.1M aqueous triethylamine acetate (TEAA), pH 7; 24-100% $CH_3CN$ (linear gradient, 10 min); 60° C.; 1 ml/min), it eluted at 7.57 minutes. Yield: 16.8 nmol in terms of UV measurement at 260 nm, λmax ($H_2O$)=258 nm, ESI-Mass (negative); 1498.5 $[M-H]^-$.

Example 28

Synthesis of Example 28 Compound (Exemplary Compound No. 1219)

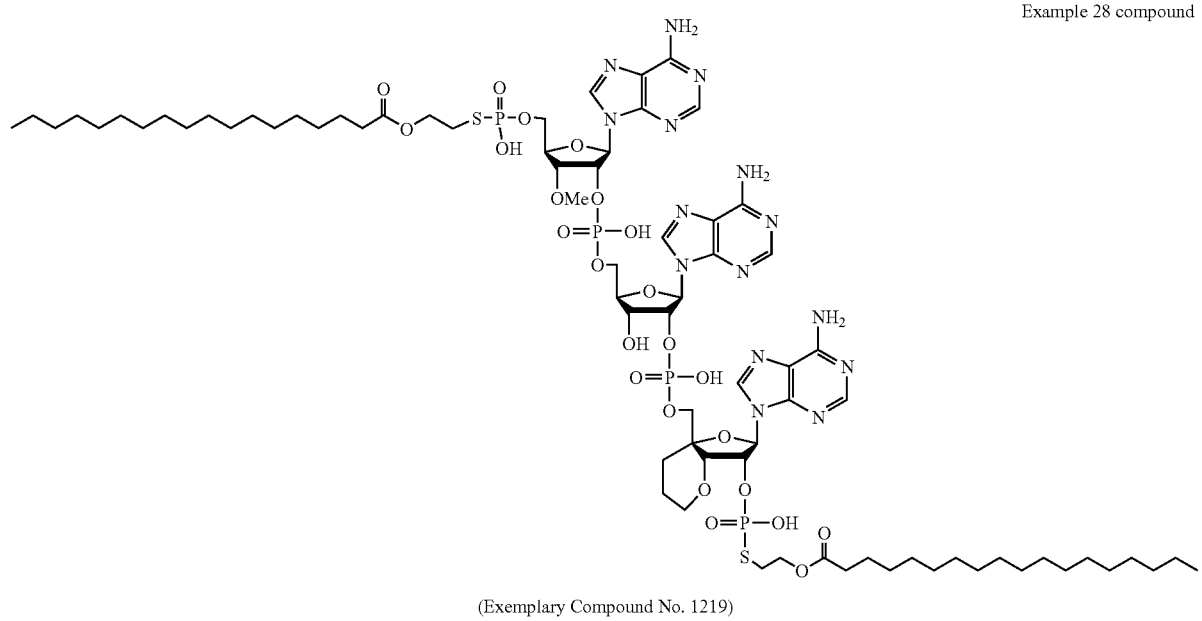

(Exemplary Compound No. 1219)

100 nmol of Example 18 compound were dissolved in 100 µl of anhydrous DMF, and 3 mg of 2-(stearoyloxy)ethyl bromide (Ackerman et al., J. Am. Chem. Soc., 78, 1956, 6025), and 3 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 72-100% $CH_3CN$ (linear gradient, 10 min); 60° C.; 2 ml/min; 254 nm), and the fraction at 3.3 minutes was collected. Yield: 8.6 nmol in terms of UV measurement at 260 nm, λmax ($H_2O$)=260.5 nm, ESI-Mass (negative); 1791.4 [M-H]$^-$.

Example 29

Synthesis of Example 29 Compound (Exemplary Compound No. 1220)

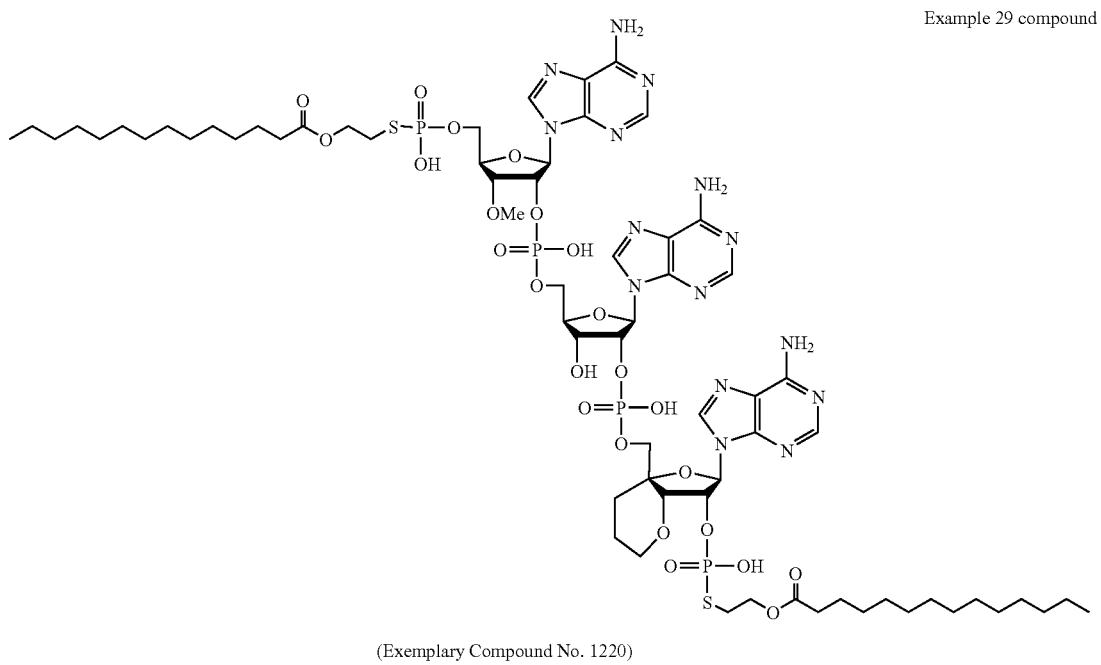

(Exemplary Compound No. 1220)

100 nmol of Example 18 compound were dissolved in 100 µl of anhydrous DMF, and 3 mg of 2-(myristoyloxy)ethyl bromide (Ackerman et al., J. Am. Chem. Soc., 78, 1956, 6025), and 3 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 52-100% $CH_3CN$ (linear gradient, 10 min); 60° C.; 2 ml/min; 254 nm), and the fraction at 3.7 minutes was collected. When the present compound was analyzed by reverse phase HPLC (column (Tosoh super-ODS (4.6×50 mm)); 0.1M aqueous triethylamine acetate (TEAA), pH 7; 15-100% $CH_3CN$ (linear gradient, 10 min); 60° C.; 1 ml/min), it eluted at 10.96 minutes. Yield: 41.6 nmol in terms of UV measurement at 260 nm, λmax ($H_2O$)=259.1 nm, ESI-Mass (negative); 1679.5 $[M-H]^-$.

Example 30

Synthesis of Example 30 Compound (Exemplary Compound No. 1221)

100 nmol of Example 18 compound were dissolved in 100 µl of anhydrous DMF, and 3 mg of 2-(decanoyloxy)ethyl bromide (Devinsky, Ferdinand et al., Collect. Czech. Chem. Commun. 49, 12, 1984, 2819-2827), and 3 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 34-100% $CH_3CN$ (linear gradient, 10 min); 60° C.; 2 ml/min; 254 nm), and the fraction at 4.5 minutes was collected. When the present compound was analyzed by reverse phase HPLC (column (Tosoh superODS (4.6×50 mm)); 0.1M aqueous triethylamine acetate (TEAA), pH 7; 15-100% $CH_3CN$ (linear gradient, 10 min); 60° C.; 1 ml/min), it eluted at 8.92 minutes. Yield: 46.6 nmol in terms of UV measurement at 260 nm, λmax ($H_2O$)=259.3 nm, ESI-Mass (negative); 1566$[M-H]^-$.

Example 30 compound

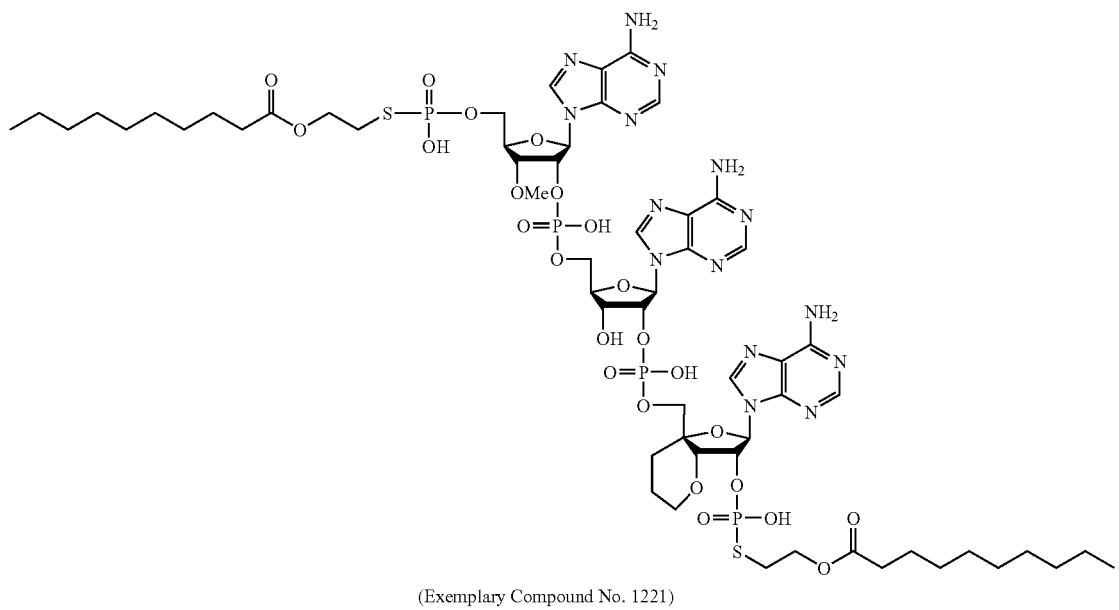

(Exemplary Compound No. 1221)

Example 31

Synthesis of Example 31 Compound (Exemplary Compound No. 1362)

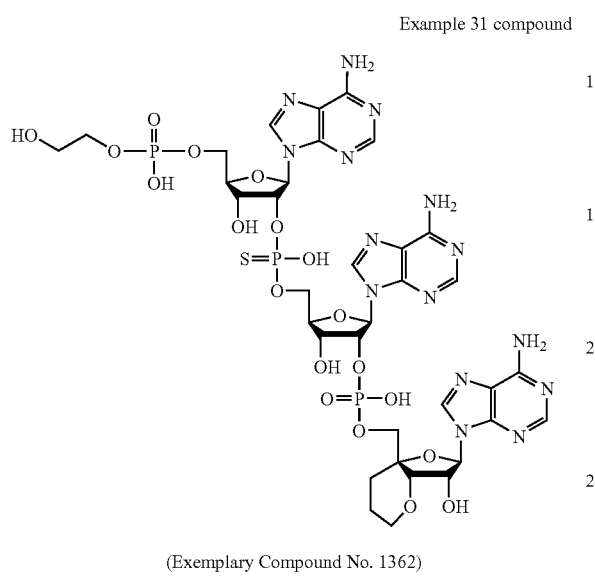

Example 31 compound (Exemplary Compound No. 1362)

Synthesis was carried out using the compound of Example 17 described in Japanese Patent Application (Kokai) No. 2002-249497 (2.0 μmol) as the 5'-O-DMTr-riboadenosine analog bound to a CPG support with the DNA synthesizer based on one condensation cycle consisting of the following steps 1) to 4) using a synthesis program for ordinary synthesis of 1 μmol of RNA. 3'-tBDSilyl-ribo Adenosine (N-bz) phosphoramidite (ChemGene) was used as the phosphoramidite in cycles 1 and 2, and the compound of Example 8a described in Japanese Patent Application (Kokai) No. Hei 11-246592 was used in cycle 3. For the oxidation or sulfurizing agent, iodine was used in cycles 1 and 3, and xanthane hydride (Tokyo Kasei Kogyo) was used in cycle 2.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 1 and 3):

Iodine/water/pyridine/tetrahydrofuran; 15 sec.

sulfurization (cycle 2): Xanthane hydride (0.02 M)/acetonitrile-pyridine (9:1 mixed solvent); 15 min.

After synthesizing the 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 9-25% $CH_3CN$ (linear gradient, 30 min.); 40° C.; 10 ml/min; 254 nm), and the fractions that eluted at 10.9 and 12.0 minutes corresponding to the two diastereomer were collected. The present compound eluted in the vicinity of 8.09 and 8.50 minutes when analyzed by reverse phase HPLC (column (Tosoh superODS (4.6×50 mm)); 0.1M aqueous triethylamine acetate (TEAA), pH 7; 0-15% $CH_3CN$ (linear gradient, 10 min); 60° C.; 1 ml/min). (Yield: 749 nmol as UV measured value at 260 nm) λmax ($H_2O$)=258 nm, ESI-Mass (negative): 1104.2 [M-H]⁻.

Example 32

Synthesis of Example 32 Compound (Exemplary Compound No. 1363)

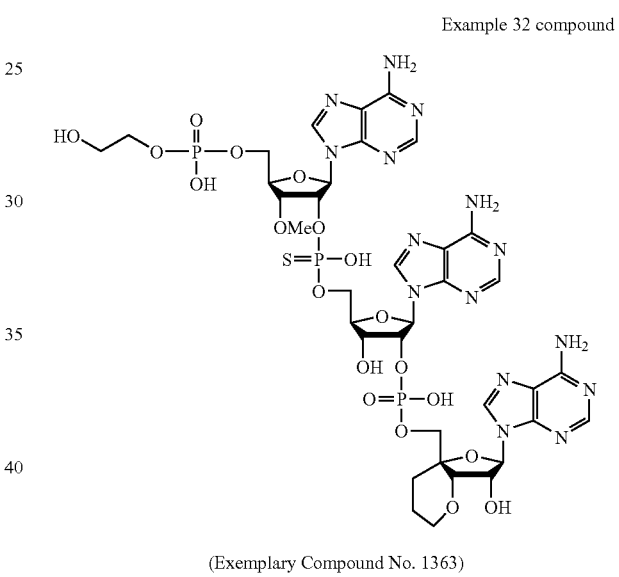

Example 32 compound (Exemplary Compound No. 1363)

Synthesis was carried out using the compound of Example 17 described in Japanese Patent Application (Kokai) No. 2002-249497 (2.0 μmol) as the 5'-0-DMTr-riboadenosine analog bound to a CPG support with the DNA synthesizer based on one condensation cycle consisting of the following steps 1) to 4) using a synthesis program for ordinary synthesis of 1 μmol of RNA. 3'-tBDSilyl-ribo Adenosine (N-bz) phosphoramidite (ChemGene) was used as the phosphoramidite in cycle 1, 51-DMT-3'-(O-methyl) adenosine(N-bz)2'-phosphoramidite (ChemGene) was used in cycle 2, and the compound of Example 8a described in Japanese Patent Application (Kokai) No. Hei 11-246592 was used in cycle 3. For the oxidation or sulfurizing agent, iodine was used in cycles 1 and 3, and xanthane hydride (Tokyo Kasei Kogyo) was used in cycle 2.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 1 and 3):

Iodine/water/pyridine/tetrahydrofuran; 15 sec.

sulfurization (cycle 2): Xanthane hydride (0.02 M)/acetonitrile-pyridine (9:1 mixed solvent); 15 min.

After synthesizing the 2-5A analog having the desired structure in the state in which the 5'-DMTr group has been removed, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the pH was adjusted to 2.0 by adding aqueous hydrochloric acid (2 N) to the remaining residue followed by reacting for 5 hours at 30° C. to remove the silyl group. After neutralizing with aqueous ammonia and distilling off the solvent, the product was purified by reverse phase HPLC (Shimadzu Seisakusho LC-VP; column (GL Science Inertsil Prep-ODS (20×250 mm)); 0.1 M aqueous triethylamine acetate (TEAA), pH 7; 9-25% $CH_3CN$ (linear gradient, 30 min.); 40° C.; 10 ml/min; 254 nm), and the fractions that eluted at 11.5 and 12.7 minutes corresponding to the two diastereomers were collected. The present compound eluted in the vicinity of 8.48 and 8.97 minutes when analyzed by reverse phase HPLC (column (Tosoh superODS (4.6×50 mm)); 0.1M aqueous triethylamine acetate (TEAA), pH 7; 0-15% $CH_3CN$ (linear gradient, 10 min); 60° C.; 1 ml/min). (Yield: 555 nmol as UV measured value at 260 nm) λmax ($H_2O$)=258 nm, ESI-Mass (negative): 1118.2 [M-H]$^-$.

Example 33

Synthesis of Example 33 Compound (Exemplary Compound No. 1369)

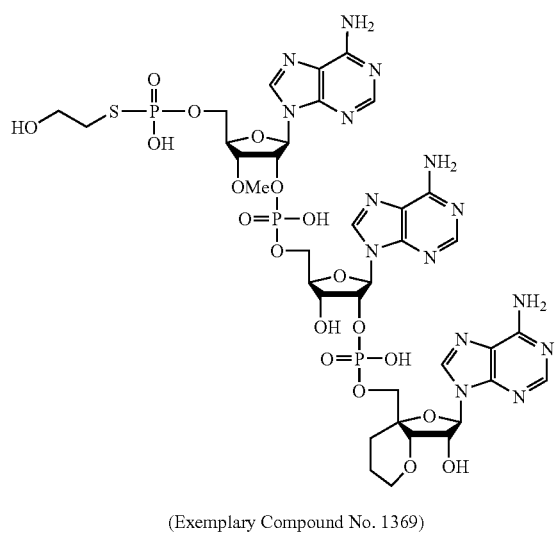

(Exemplary Compound No. 1369)

100 nmol of Example 2 compound were dissolved in 50 μl of anhydrous DMF, and 2 μl of 2-bromoethanol (Tokyo Kasei Kogyo), and 2 μl of triethylamine were added thereto, followed by reacting the mixture at room temperature overnight. After completion of the reaction, 200 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-25% $CH_3CN$ (linear gradient, 10 min); 60° C.; 2 ml/min; 254 nm), and the fraction at 6.4 minutes was collected. When the present compound was analyzed by reverse phase HPLC (column (Tosoh superODS (4.6×50 mm)); 0.1M aqueous triethylamine acetate (TEAA), pH 7; 0-15% $CH_3CN$ (linear gradient, 10 min); 60° C.; 1 ml/min), it eluted at 12.54 minutes. Yield: 20.3 nmol in terms of UV measurement at 260 nm, λmax ($H_2O$)=258.1 nm, ESI-Mass (negative); 1118.2[M-H]$^-$.

Example 34

Synthesis of Example 34 Compound (Exemplary Compound No. 1394)

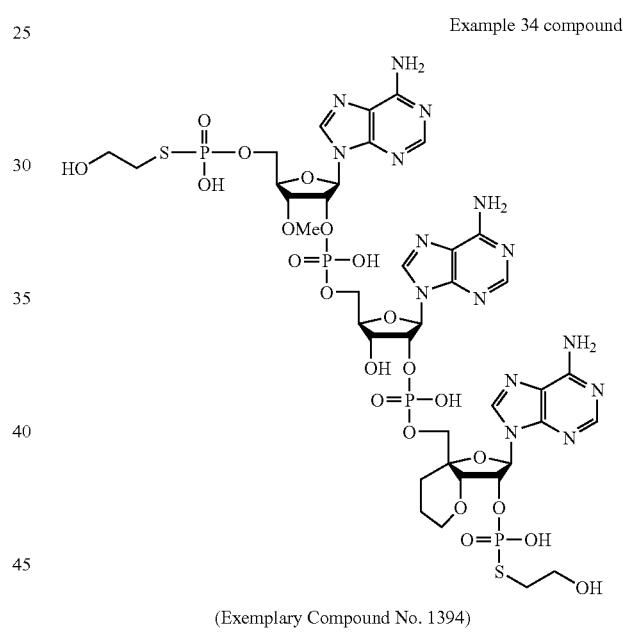

(Exemplary Compound No. 1394)

100 nmol of Example 19 compound were dissolved in 50 μl of anhydrous DMF, and 2 μl of 2-bromoethanol (Tokyo Kasei Kogyo), and 2 μl of triethylamine were added thereto, followed by reacting the mixture at room temperature overnight. After completion of the reaction, 200 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 5-25% $CH_3CN$ (linear gradient, 10 min); 60° C.; 2 ml/min; 254 nm), and the fraction at 6.0 minutes was collected. When the present compound was analyzed by reverse phase HPLC (column (Tosoh superODS (4.6×50 mm)); 0.1M aqueous triethylamine acetate (TEAA), pH 7; 0-15% $CH_3CN$ (linear gradient, 10 min); 60° C.; 1 ml/min), it eluted at 11.60 minutes. Yield: 48.2 nmol in terms of UV measurement at 260 nm, λmax (H$_2$O)=258.0 nm, ESI-Mass (negative); 1242.2 [M-H]$^-$.

Example 35

Synthesis of Example 35 Compound (Exemplary Compound No. 1645)

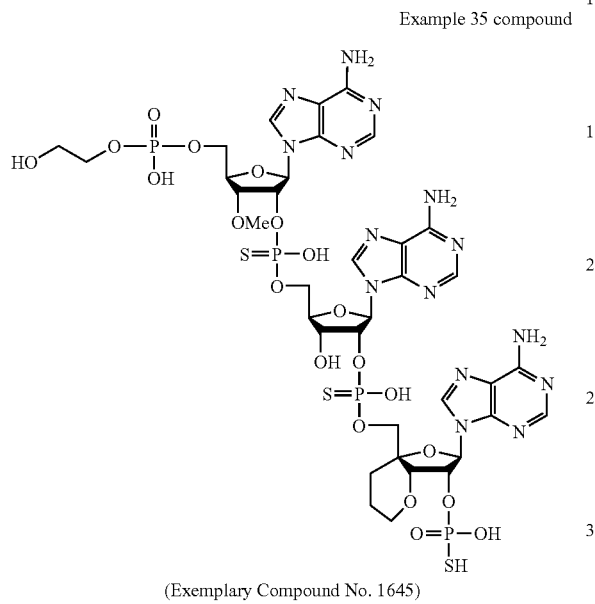

(Exemplary Compound No. 1645)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (0.5 μmol) was used as the solid phase carrier. The compound of Example 16 described in Japanese Patent Application (Kokai) No. 2002-249497 was used as the phosphoramidite in cycle 1, 3'-tBDSilyl-ribo Adenosine (N-bz) phosphoramidite (Chem-Gene) was used in cycle 2, 5'-DMT-3'-(O-methyl) adenosine (N-bz)2'-phosphoramidite (ChemGene) was used in cycle 3, and the compound of Example 8a described in Japanese Patent Application (Kokai) No. Hei 11-246592 was used in cycle 4. For the oxidation or sulfurizing agent, xanthane hydride (Tokyo Kasei Kogyo) was used in cycles 1, 2 and 3, and iodine was used in cycle 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycle 4): Iodine/water/pyridine/tetrahydrofuran; 15 sec.

sulfurization (cycles 1, 2 and 3): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the remaining residue was purified by reverse phase HPLC (Shimadzu Seisakusho LC-VP; column (Merck chromolith (4.6×50 mm)); 0.1 M aqueous triethylamine acetate (TEAA), pH 7; 24-100% CH$_3$CN (linear gradient, 10 min.); 60° C.; 2 ml/min), and the fractions that eluted at 4.8-5.2 minutes corresponding to the four diastereomers were collected.

After the solvent was evaporated under reduced pressure, 1 ml of aqueous hydrochloric acid (0.01N) was added to the remaining residue to accurately adjust the pH to 2.0, followed by reaction at 30° C. for 5 hours to remove the DMTr group and the silyl group. After neutralization with aqueous ammonia, the deprotected silanol and DMTrOH were removed by extraction with ethyl acetate to obtain the desired compound. When the present compound was analyzed by reverse phase HPLC (column (Merck chromolith (4.6×50 mm)); 0.1M aqueous triethylamine acetate (TEAA), pH 7; 5-25% CH$_3$CN (linear gradient, 8 min); 60° C.; 2 ml/min), it eluted at 4.72 and 5.06 minutes. Yield: 70 nmol (in terms of UV measurement at 260 nm), λmax (H$_2$O)=258 nm, ESI-Mass (negative); 1230.1 [M-H]$^-$.

Example 36

Synthesis of Example 36 Compound (Exemplary Compound No. 1646)

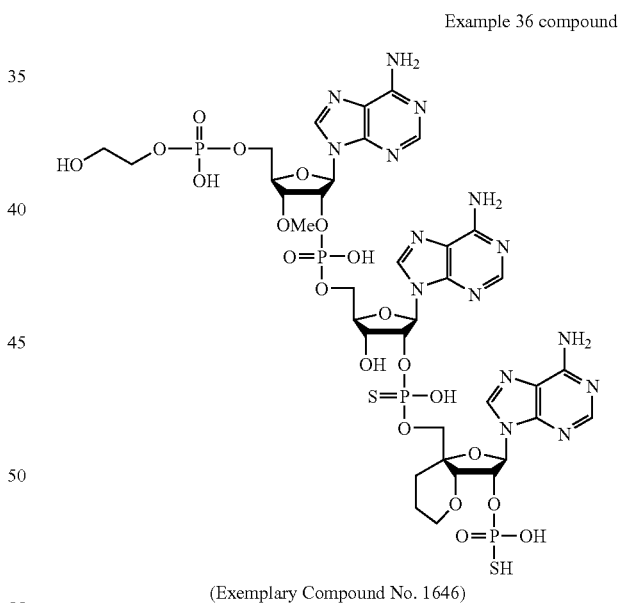

(Exemplary Compound No. 1646)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (0.5 μmol) was used as the solid phase carrier. The compound of Example 16 described in Japanese Patent Application (Kokai) No. 2002-249497 was used as the phosphoramidite in cycle 1, 3'-tBDSilyl-ribo Adenosine (N-bz) phosphoramidite (Chem-Gene) was used in cycle 2, 5'-DMT-3'-(O-methyl) adenosine (N-bz)2'-phosphoramidite (ChemGene) was used in cycle 3, and the compound of Example 8a described in Japanese Patent Application (Kokai) No. Hei 11-246592 was used in cycle 4. For the oxidation or sulfurizing agent, xanthane hydride (Tokyo Kasei Kogyo) was used in cycles 1 and 2, and iodine was used in cycles 3 and 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 3 and 4):

Iodine/water/pyridine/tetrahydrofuran; 15 sec.

sulfurization (cycles 1 and 2): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the remaining residue was purified by reverse phase HPLC (Shimadzu Seisakusho LC-VP; column (Merck chromolith (4.6×50 mm)); 0.1 M aqueous triethylamine acetate (TEAA), pH 7; 24-100% $CH_3CN$ (linear gradient, 10 min.); 60° C.; 2 ml/min), and the fractions that eluted at 4.7-5.0 minutes corresponding to the two diastereomers were collected.

After the solvent was evaporated under reduced pressure, 1 ml of aqueous hydrochloric acid (0.01N) was added to the remaining residue to accurately adjust the pH to 2.0, followed by reaction at 30° C. for 5 hours to remove the DMTr group and the silyl group. After neutralization with aqueous ammonia, the deprotected silanol and DMTrOH were removed by extraction with ethyl acetate to obtain the desired compound. When the present compound was analyzed by reverse phase HPLC (column (Merck chromolith (4.6×50 mm)); 0.1M aqueous triethylamine acetate (TEAA), pH 7; 5-20% $CH_3CN$ (linear gradient, 8 min); 60° C.; 2 ml/min), it eluted at 4.12 and 4.44 minutes. Yield: 95 nmol (in terms of UV measurement at 260 nm), λmax ($H_2O$)=258 nm, ESI-Mass (negative); 1214.2 $[M-H]^-$.

Example 37

Synthesis of Example 37 Compound (Exemplary Compound No. 1648)

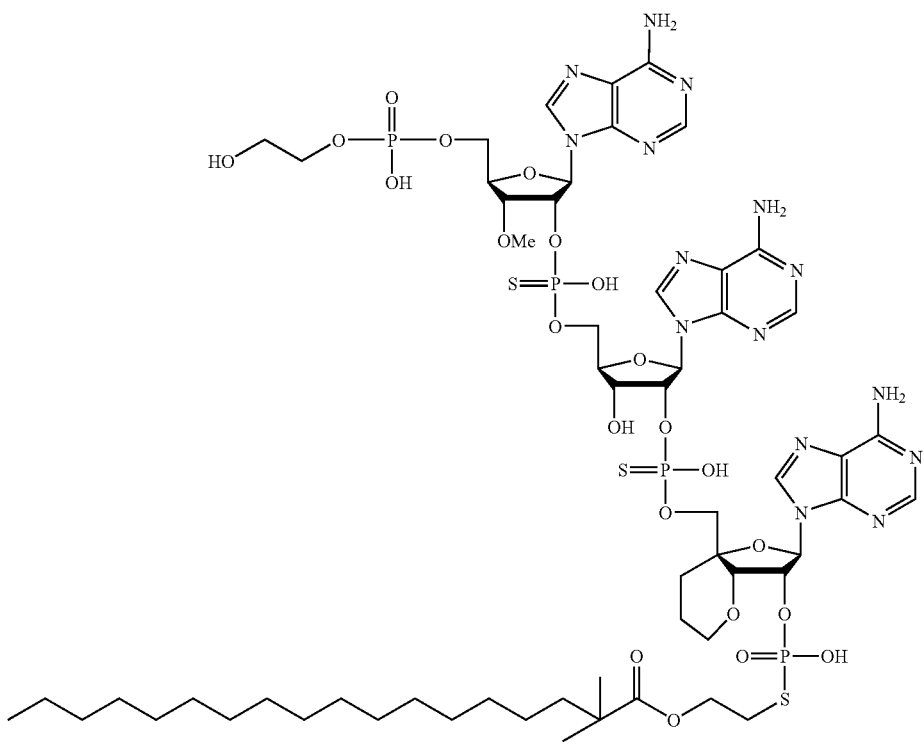

Example 37 compound (Exemplary Compound No. 1648)

40 nmol of Example 35 compound were dissolved in 40 μl of anhydrous DMF, and 1 mg of 2-(2,2-dimethyloctadecanoyloxy)ethyl bromides described in Example 22, and 1 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm)); 0.1M aqueous triethylamine acetate (TEAA), pH 7; 24-100% $CH_3CN$ (linear gradient, 8 min); 60° C.; 2 ml/min), and the fraction at 6.4 minutes was collected. Yield: 12.6 nmol in terms of UV measurement at 260 nm, λmax (H$_2$O)=258 nm, ESI-Mass (negative); 1568.3 [M-H]$^-$.

Example 38

Synthesis of Example 38 Compound (Exemplary Compound No. 1649)

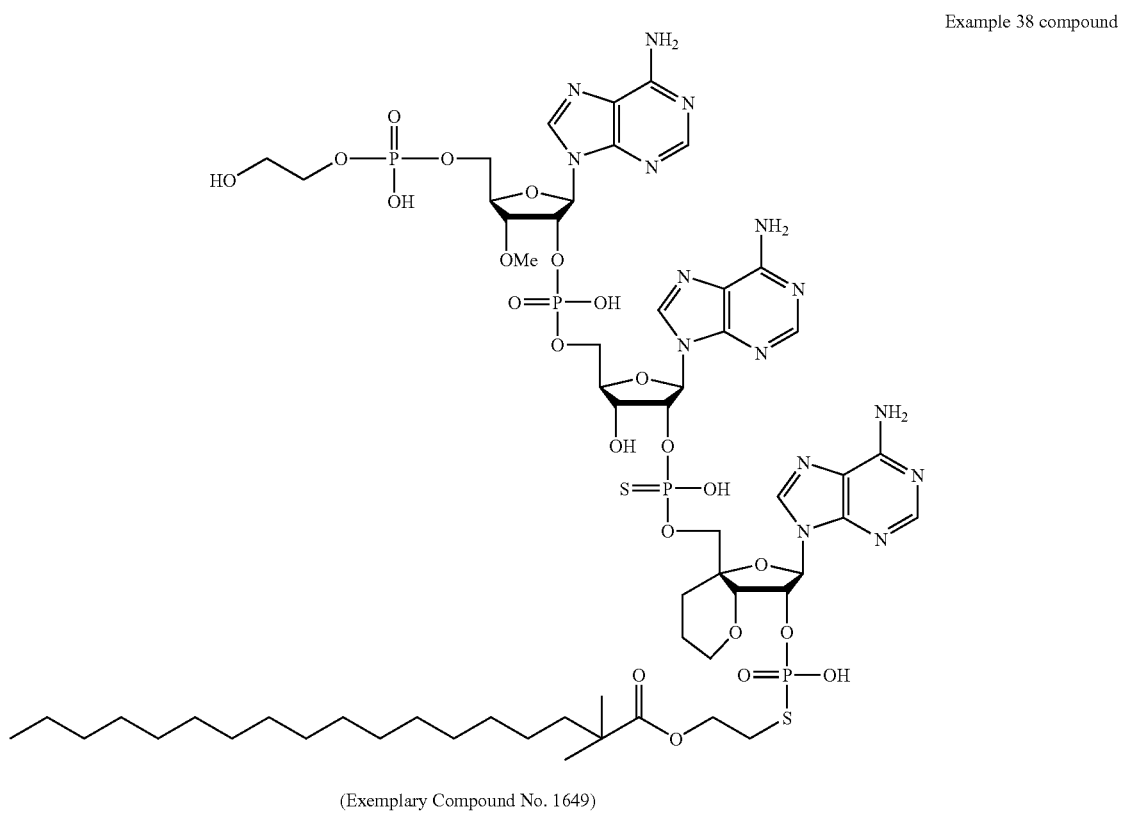

Example 38 compound (Exemplary Compound No. 1649)

40 nmol of Example 36 compound were dissolved in 40 μl of anhydrous DMF, and 1 mg of 2-(2,2-dimethyloctade-canoyloxy)ethyl bromide described in Example 22, and 1 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% CH$_3$CN (linear gradient, 8 min); 60° C.; 2 ml/min), and the fraction at 6.4 minutes was collected. Yield: 21.8 nmol in terms of UV measurement at 260 nm, λmax (H$_2$O)=258 nm, ESI-Mass (negative); 1552.3 [M-H]$^-$.

Example 39

Synthesis of Example 39 Compound (Exemplary Compound No. 1651)

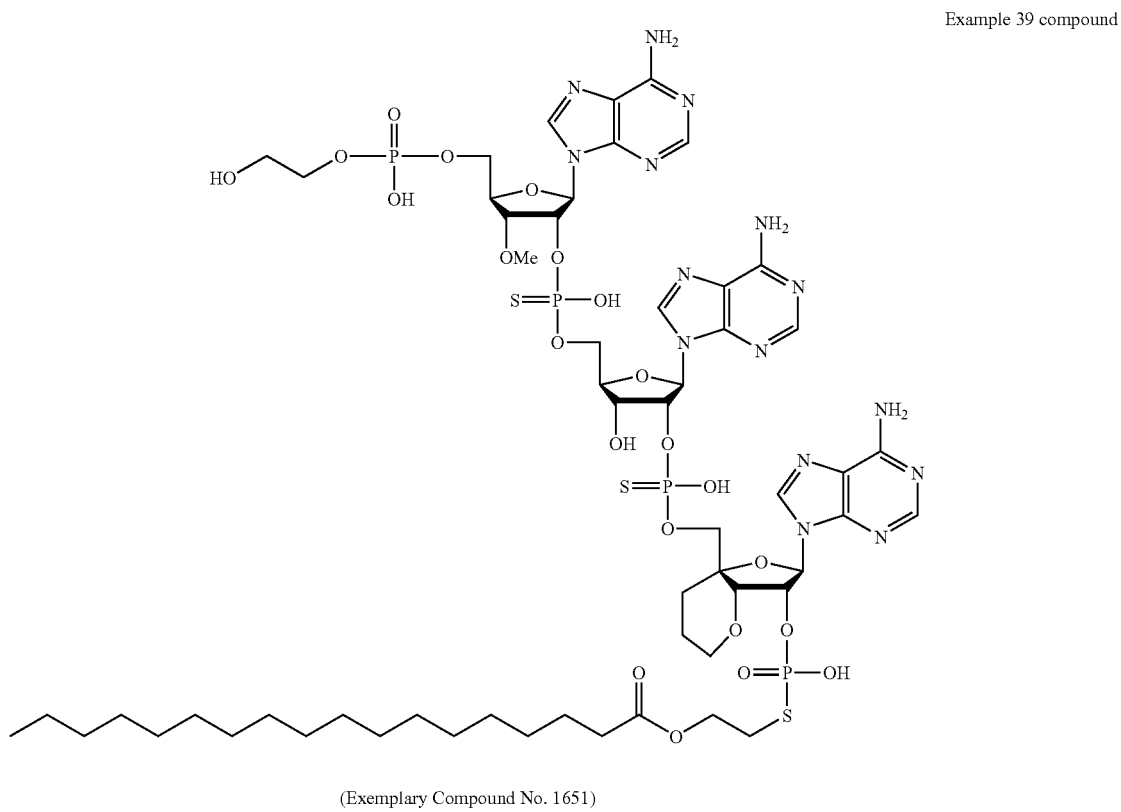

Example 39 compound (Exemplary Compound No. 1651)

40 nmol of Example 35 compound were dissolved in 40 μl of anhydrous DMF, and 1 mg of 2-(stearoyloxy)ethyl bromide (Ackerman et al., J. Am. Chem. Soc., 78, 1956, 6025), and 1 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% $CH_3CN$ (linear gradient, 8 min); 60° C.; 2 ml/min), and the fraction at 6.7 minutes was collected. Yield: 11.4 nmol in terms of UV measurement at 260 nm, λmax ($H_2O$)=258 nm, ESI-Mass (negative); 1540.3 $[M-H]^-$.

Example 40

Synthesis of Example 40 Compound (Exemplary Compound No. 1652)

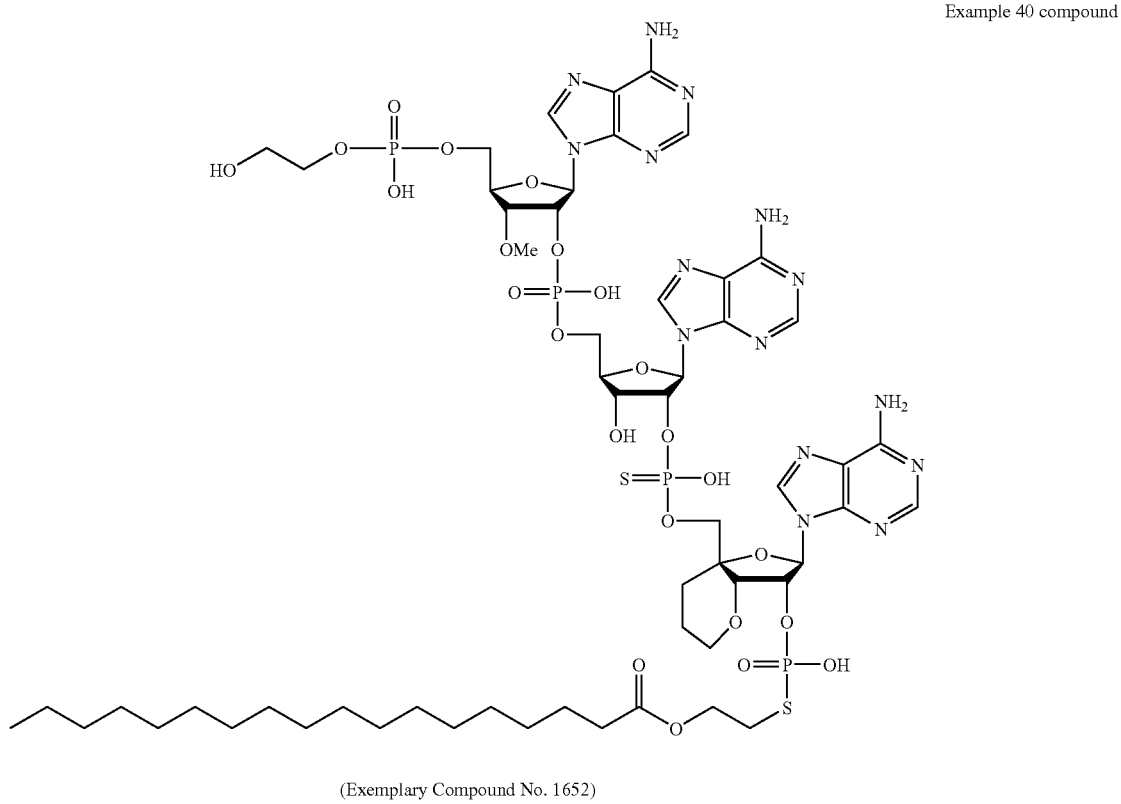

(Exemplary Compound No. 1652)

40 nmol of Example 36 compound were dissolved in 40 μl of anhydrous DMF, and 1 mg of 2-(stearoyloxy)ethyl bromide (Ackerman et al., J. Am. Chem. Soc., 78, 1956, 6025), and 1 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% $CH_3CN$ (linear gradient, 8 min); 60° C.; 2 ml/min), and the fraction at 7.0 minutes was collected. Yield: 23.1 nmol in terms of UV measurement at 260 nm, λmax ($H_2O$)=258 nm, ESI-Mass (negative); 1524.3 $[M-H]^-$.

Example 41

Synthesis of Example 41 Compound (Exemplary Compound No. 1663)

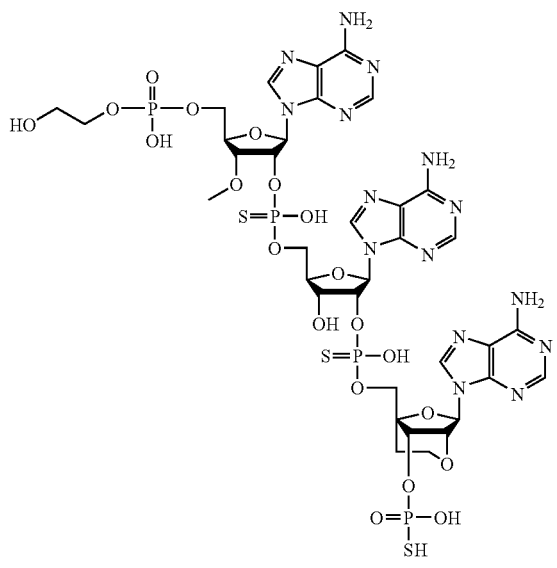

(Exemplary Compound No. 1663)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (0.5 μmol) was used as the solid phase carrier. The compound of Example 14 described in Japanese Patent No. 3420984 was used as the phosphoramidite in cycle 1, 3'-tBDSilyl-ribo Adenosine (N-bz) phosphoramidite (ChemGene) was used in cycle 2, 5'-DMT-3'-(O-methyl) adenosine(N-bz)2'-phosphoramidite (ChemGene) was used in cycle 3, and the compound of Example 8a described in Patent Application (Kokai) No. Hei 11-246592 was used in cycle 4. For the oxidation or sulfurizing agent, xanthane hydride (Tokyo Kasei Kogyo) was used in cycles 1, 2 and 3, and iodine was used in cycle 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycle 4): Iodine/water/pyridine/tetrahydrofuran; 15 sec.

sulfurization (cycles 1, 2 and 3): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure, and the pH was accurately adjusted to 2.0 by adding 1 ml of aqueous hydrochloric acid (0.01 N) to the remaining residue, followed by reacting for 5 hours at 30° C. to remove the DMTr group and the silyl group. After neutralizing with aqueous ammonia, the deprotected silanol and the DMTrOH were removed by extraction with ethyl acetate to obtain the desired compound. The product eluted at 3.75, 4.12, 4.53 and 4.76 minutes when analyzed by reverse phase HPLC (column (Merck chromolith (4.6×50 mm)); 0.1 M aqueous triethylamine acetate (TEAA), pH 7; 5-20% $CH_3CN$ (linear gradient, 10 min.); 60° C.; 2 ml/min). Yield: 111 nmol (in terms of UV measurement at 260 nm), λmax ($H_2O$)=258 nm, ESI-Mass (negative); 1216.1 [M-H]⁻.

Example 42

Synthesis of Example 42 Compound (Exemplary Compound No. 1664)

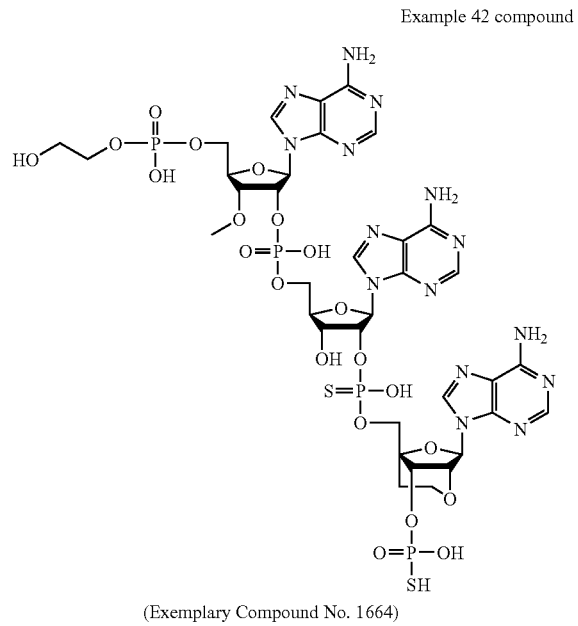

(Exemplary Compound No. 1664)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (0.5 μmol) was used as the solid phase carrier. The compound of Example 14 described in Japanese Patent No. 3420984 was used as the phosphoramidite in cycle 1, 3'-tBDSilyl-ribo Adenosine (N-bz) phosphoramidite (ChemGene) was used in cycle 2, 5'-DMT-3'-(O-methyl) adenosine(N-bz)2'-phosphoramidite (ChemGene) was used in cycle 3, and the compound of Example 8a described in Patent Application (Kokai) No. Hei 11-246592 was used in cycle 4. For the oxidation or sulfurizing agent, xanthane hydride (Tokyo Kasei Kogyo) was used in cycles 1 and 2, and iodine was used in cycles 3 and 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycles 3 and 4):

Iodine/water/pyridine/tetrahydrofuran; 15 sec.

sulfurization (cycles 1 and 2): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the remaining residue was purified by reverse phase HPLC (Shimadzu Seisakusho LC-VP; column (Merck chromolith (4.6×50 mm)); 0.1 M aqueous triethylamine acetate (TEAA), pH 7; 24-100% CH$_3$CN (linear gradient, 10 min); 60° C.; 2 ml/min), it eluted at 2.40 and 3.01 minutes. Yield: 127 nmol (in terms of UV measurement at 260 nm), λmax (H$_2$O)=258 nm, ESI-Mass (negative); 1200.15 [M-H]$^-$.

Example 43

Synthesis of Example 43 Compound (Exemplary Compound No. 1666)

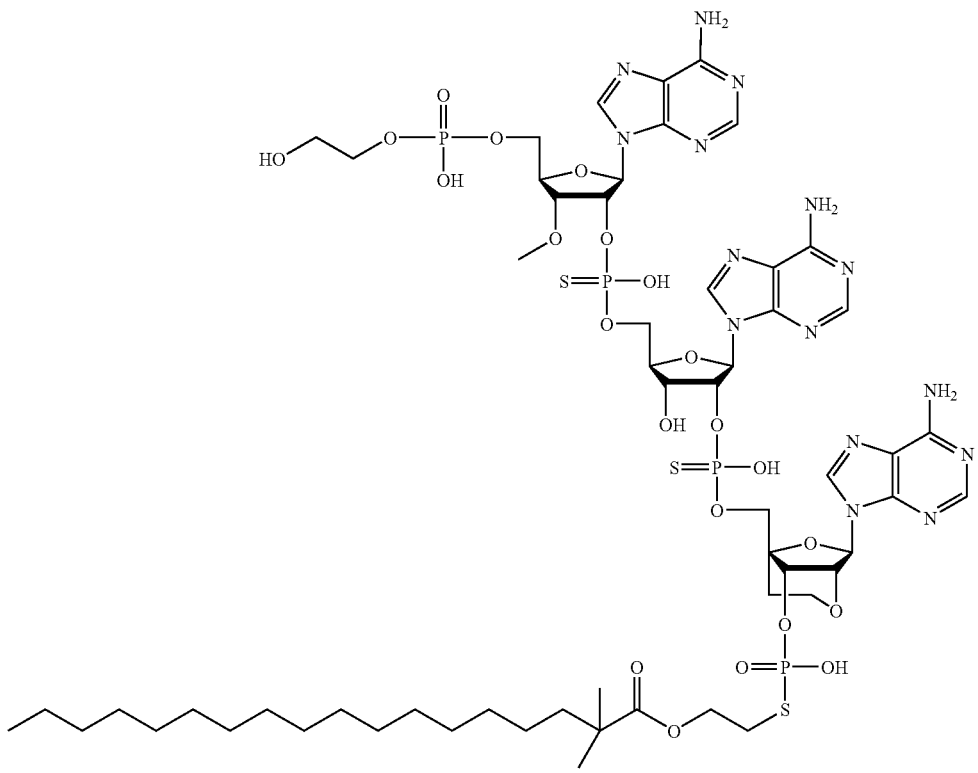

Example 43 compound (Exemplary Compound No. 1666)

ear gradient, 10 min.); 60° C.; 2 ml/min), and the fractions that eluted at 4.6-4.9 minutes corresponding to the two diastereomers were collected.

After the solvent was distilled off under reduced pressure, 1 ml of aqueous hydrochloric acid (0.01N) was added to the remaining residue to accurately adjust the pH to 2.0, followed by reaction at 30° C. for 5 hours to remove the DMTr group and the silyl group. After neutralization with aqueous ammonia, the deprotected silanol and DMTrOH were removed by extraction with ethyl acetate to obtain the desired compound. When the present compound was analyzed by reverse phase HPLC (column (Merck chromolith (4.6×50 mm)); 0.1M aqueous triethylamine acetate (TEAA), pH 7; 5-20% CH$_3$CN 40 nmol of Example 41 compound were dissolved in 40 μl of anhydrous DMF, and 1 mg of 2-(2,2-dimethyloctadecanoyloxy)ethyl bromide described in Example 22, and 1 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% CH$_3$CN (linear gradient, 8 min); 60° C.; 2 ml/min), and the fraction at 6.9 minutes was collected. Yield: 9.5 nmol in terms of UV measurement at 260 nm, λmax (H$_2$O)=258 nm, ESI-Mass (negative); 1554.3 [M-H]$^-$.

Example 44

Synthesis of Example 44 Compound (Exemplary Compound No. 1667)

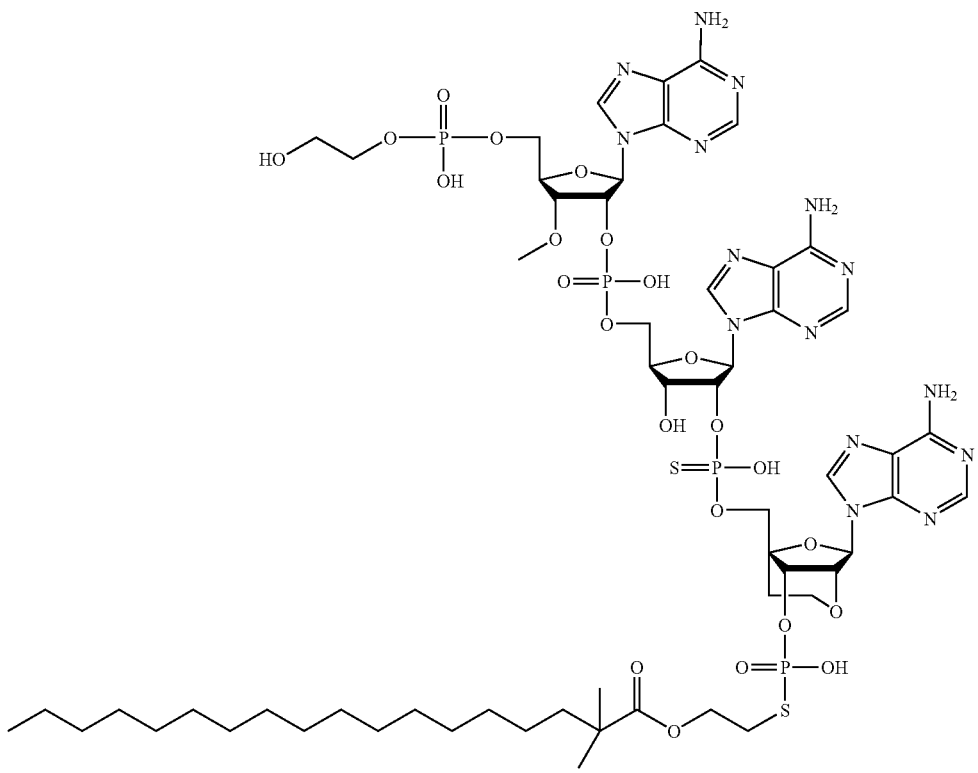

Example 44 compound (Exemplary Compound No. 1667)

40 nmol of Example 42 compound were dissolved in 40 μl of anhydrous DMF, and 1 mg of 2-(2,2-dimethyloctadecanoyloxy)ethyl bromide described in Example 22, and 1 μl of triethylamine were added thereto, followed by reacting the mixture at room temperature overnight. After completion of the reaction, 300 μl of water were added, and the aqueous layer was washed three times with 200 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% $CH_3CN$ (linear gradient, 8 min); 60° C.; 2 ml/min), and the fraction at 6.9 minutes was collected. Yield: 4.6 nmol in terms of UV measurement at 260 nm, λmax ($H_2O$)=258 nm, ESI-Mass (negative); 1538.3 $[M-H]^-$.

Example 45

Synthesis of Example 45 Compound (Exemplary Compound No. 1669)

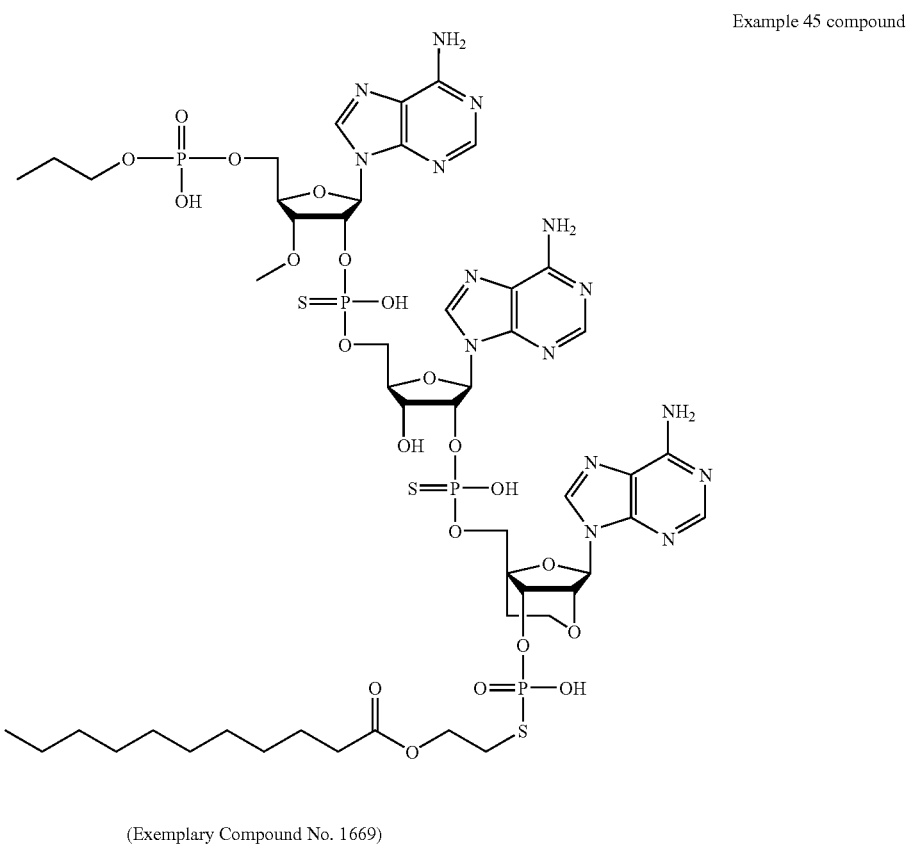

Example 45 compound (Exemplary Compound No. 1669)

80 nmol of Example 41 compound were dissolved in 100 μl of anhydrous DMF, and 1 mg of 2-(stearoyloxy)ethyl bromide (Ackerman et al., J. Am. Chem. Soc., 78, 1956, 6025), and 1 μl of pyridine were added thereto, followed by reacting the mixture at room temperature overnight. After completion of the reaction, 500 μl of water were added, and the aqueous layer was washed three times with 500 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% $CH_3CN$ (linear gradient, 8 min); 60° C.; 2 ml/min), and the fraction at 6.6 minutes was collected. Yield: 40.4 nmol in terms of UV measurement at 260 nm, λmax ($H_2O$)=258 nm, ESI-Mass (negative); 1526.3 $[M-H]^-$.

Example 46

Synthesis of Example 46 Compound (Exemplary Compound No. 1670)

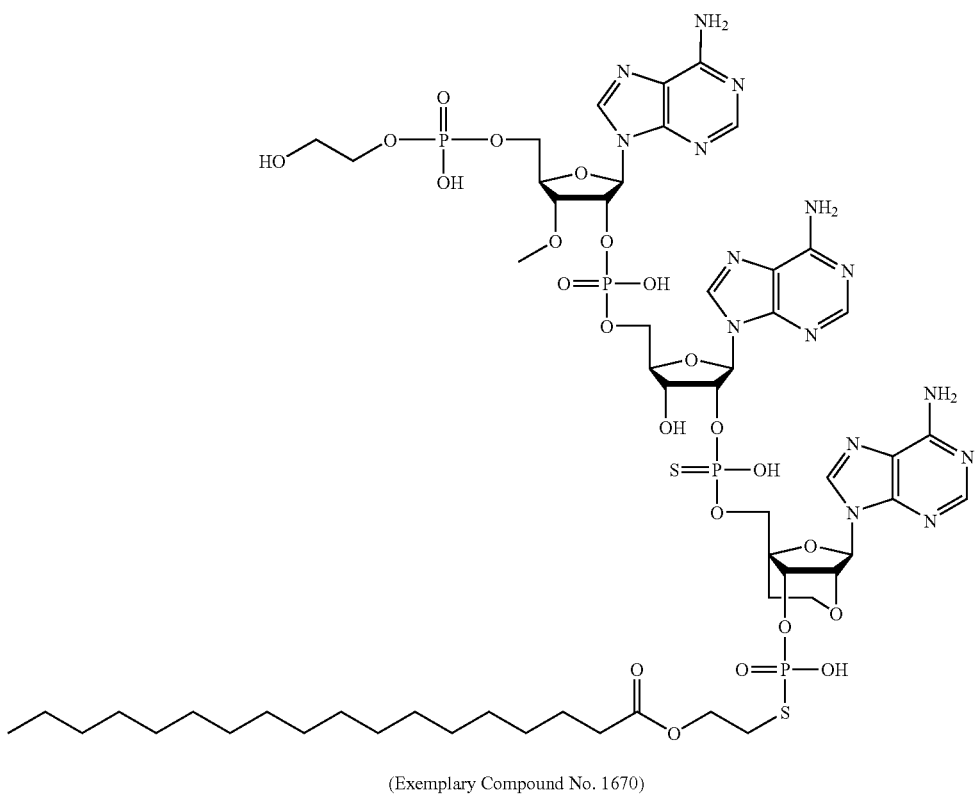

(Exemplary Compound No. 1670)

80 nmol of Example 42 compound were dissolved in 100 μl of anhydrous DMF, and 1 mg of 2-(stearoyloxy)ethyl bromide (Ackerman et al., J. Am. Chem. Soc., 78, 1956, 6025), and 1 μl of pyridine were added thereto, followed by reacting the mixture at room temperature overnight. After completion of the reaction, 500 μl of water were added, and the aqueous layer was washed three times with 500 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% CH$_3$CN (linear gradient, 8 min); 60° C.; 2 ml/min), and the fraction at 6.6 minutes was collected. Yield: 41.9 nmol in terms of UV measurement at 260 nm, λmax (H$_2$O)=259 nm, ESI-Mass (negative); 1510.29 [M-H]$^-$.

Example 47

Synthesis of Example 47 Compound (Exemplary Compound No. 1690)

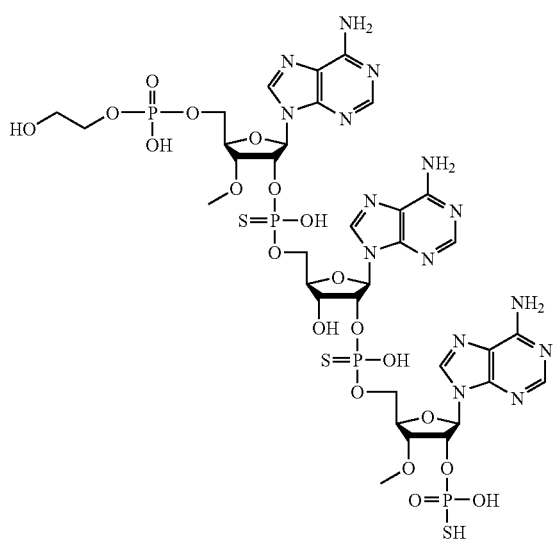

(Exemplary Compound No. 1690)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (0.5 μmol) was used as the solid phase carrier. 5'-DMT-3'-(O-methyl) Adenosine(N-bz)2'-phosphoramidite (ChemGene) was used as the phosphoramidite in cycles 1 and 3, 3'-tBDSilyl-riboAdenosine (N-bz) phosphoramidite (ChemGene) was used in cycle 2, and the compound of Example 8a described in Patent Application (Kokai) No. Hei 11-246592 was used in cycle 4. For the oxidation or sulfurizing agent, xanthane hydride (Tokyo Kasei Kogyo) was used in cycles 1, 2 and 3, and iodine was used in cycle 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycle 4): Iodine/water/pyridine/tetrahydrofuran; 15 sec.

sulfurization (cycles 1, 2 and 3): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the remaining residue was purified by reverse phase HPLC (Shimadzu Seisakusho LC-VP; column ((Merck chromolith (4.6×50 mm)); 0.1 M aqueous triethylamine acetate (TEAA), pH 7; 24-100% CH$_3$CN (linear gradient, 10 min.); 60° C.; 2 ml/min), and the fractions that eluted at 4.7-5.1 minutes corresponding to the two diastereomers were collected.

After the solvent was evaporated under reduced pressure, 1 ml of aqueous hydrochloric acid (0.01N) was added to the remaining residue to accurately adjust the pH to 2.0, followed by reaction at 30° C. for 5 hours to remove the DMTr group and the silyl group. After neutralization with aqueous ammonia, the deprotected silanol and DMTrOH were removed by extraction with ethyl acetate to obtain the desired compound. When the present compound was analyzed by reverse phase HPLC (column (Merck chromolith (4.6×50 mm)); 0.1M aqueous triethylamine acetate (TEAA), pH 7; 5-20% CH$_3$CN (linear gradient, 10 min); 60° C.; 2 ml/min), it eluted at 3.67, 4.01, 4.15 and 4.55 minutes. Yield: 140 nmol (in terms of UV measurement at 260 nm), λmax (H$_2$O) 258 nm, ESI-Mass (negative); 1204.1 [M-H]$^-$.

Example 48

Synthesis of Example 48 Compound (Exemplary Compound No. 1691)

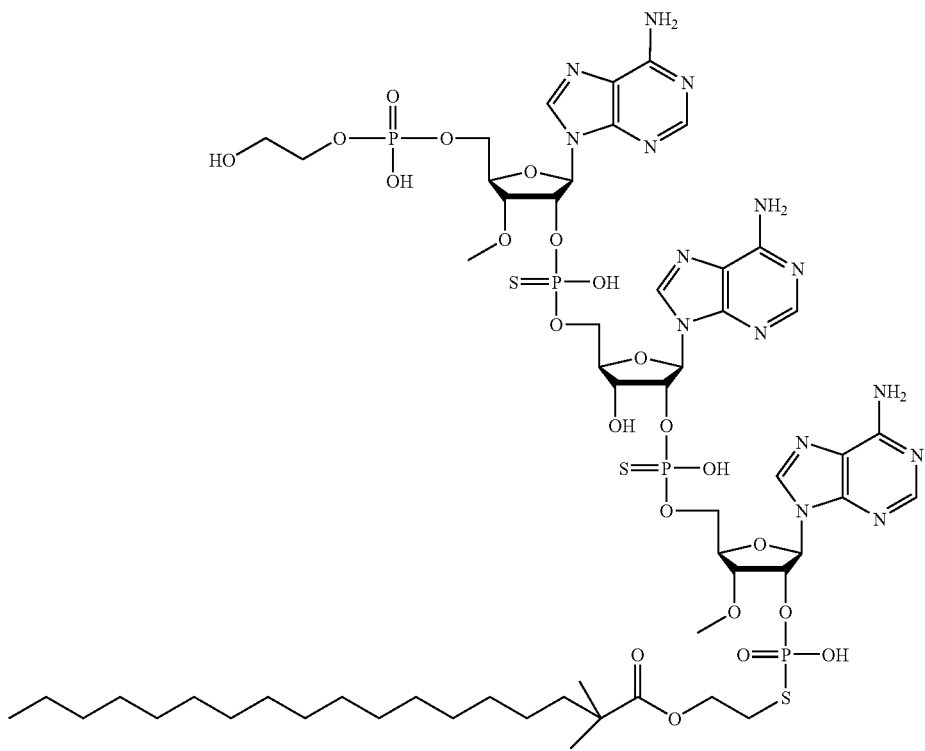

(Exemplary Compound No. 1691)

40 nmol of Example 47 compound were dissolved in 40 μl of anhydrous DMF, and 1 mg of 2-(2,2-dimethyloctadecanoyloxy)ethyl bromide described in Example 22, and 1 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% CH$_3$CN (linear gradient, 8 min); 60° C.; 2 ml/min), and the fraction at 7.0 minutes was collected. Yield: 2.5 nmol in terms of UV measurement at 260 nm, λmax (H$_2$O)=258 nm, ESI-Mass (negative); 1542.3 [M-H]$^-$.

Example 49

Synthesis of Example 49 Compound (Exemplary Compound No. 1692)

minutes was collected. Yield: 29.6 nmol in terms of UV measurement at 260 nm, λmax (H$_2$O)=258 nm, ESI-Mass (negative); 1514.3 [M-H]$^-$.

Example 50

Synthesis of Example 50 Compound (Exemplary Compound No. 1929) HOC$_2$H$_4$O—P(=O) (OH)—K$^{2-1}$—P(=O)(OH)—K$^{1-1}$—P(=O)(OH)—K$^{2-1}$—P(=O)(OH)—L$_1$—P(=O)(OH)—L$_1$-p-G$^e$-p-A$^e$-p-G$^e$-p-A$^e$-p-C$^e$-p-C''-p-C''-p-T''-p-G''-p-A''-p-A''-p-C''-p-A''-p-G''-p-T''-p-G$^e$-p-A$^e$-p-T$^e$-p-C$^e$-hp A 2-5A analog having the desired sequence was synthesized by coupling various phosphoramidites in order based on one condensation cycle consisting of the following steps 1) to 4) using a DNA synthesizer, a synthesis program for ordinary synthesis of 1 µmol of RNA, and 1 µmol of the compound Example 49 compound

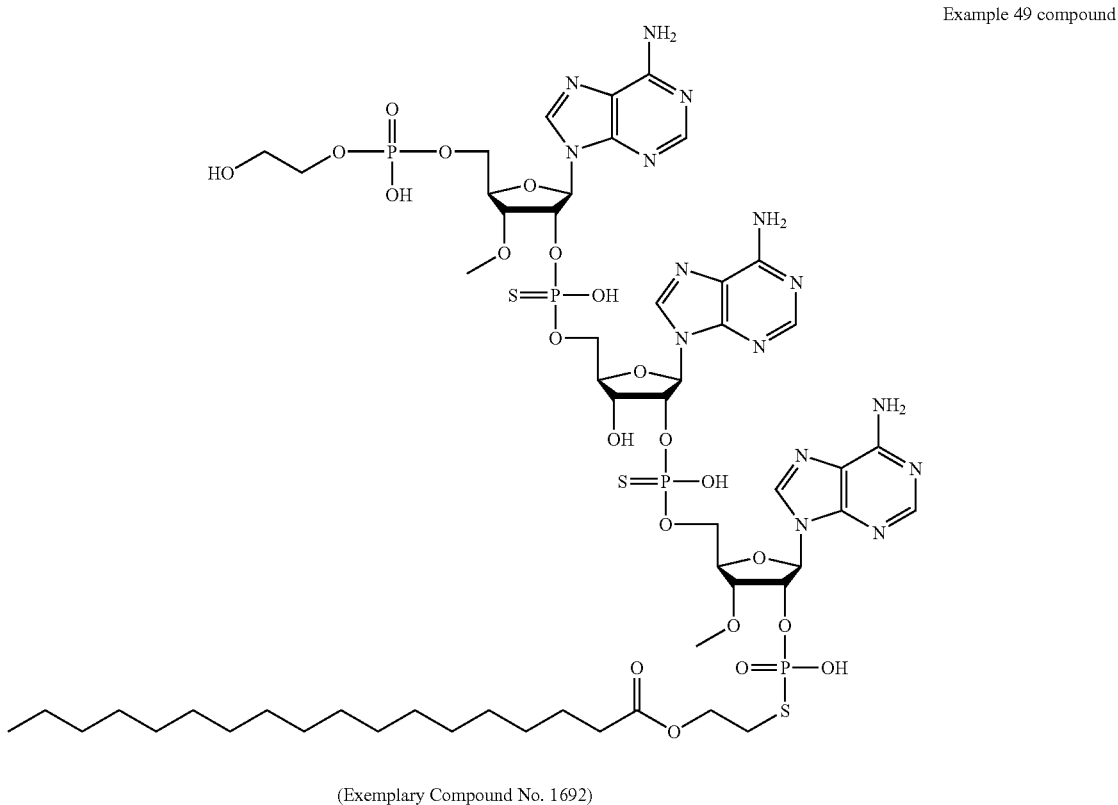

(Exemplary Compound No. 1692)

40 nmol of Example 47 compound were dissolved in 40 µl of anhydrous DMF, and 1 mg of 2-(stearoyloxy)ethyl bromide (Ackerman et al., J. Am. Chem. Soc., 78, 1956, 6025), and 1 µl of triethylamine were added thereto, followed by reacting the mixture at room temperature overnight. After completion of the reaction, 300 µl of water were added, and the aqueous layer was washed three times with 200 µl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH7; 24-100% CH$_3$CN (linear gradient, 8 min); 60° C.; 2 ml/min), and the fraction at 6.8 described in Example 12b of Patent Application (Kokai) No. Hei 7-87982 as the solid phase support.

Condensation Cycle:

1) Detritylation: Trichloroacetic acid/dichloromethane; 85 sec.

2) Coupling: Phosphoramidite (25 eq), acetonitrile/tetrazole; 10 to 20 min.

3) Capping: 1-methylimidazole/tetrahydrofuran, acetic anhydride/pyridine/tetrahydrofuran; 15 sec.

4) Oxidation: Iodine/water/pyridine/tetrahydrofuran; 15 sec.

As the phosphoramidites used to synthesize the antisense oligonucleotide portion, adenine ($dA^{bz}$) phosphoramidite, guanine ($dG^{ibu}$) phosphoramidite, cytosine ($dC^{bz}$) phosphoramidite, and thymine (T) phosphoramidite (Applied Biosystems) were used for the sequences equivalent to natural type nucleotides, while the compounds of Examples 14, 27, 22 and 9 described in Japanese Patent No. 3420984 were used for the sequences equivalent to non-natural type nucleotides ($A^e$, $G^e$, $C^e$, $T^e$). DMT-butanol-CED phosphoramidite (ChemGene) was used for the phosphoramidite equivalent to $L_1$, and 5'-DMT-3'-(O-methyl)adenosine(N-bz)2'-phosphoramidite (ChemGene), 3'-tBDsilyl-riboadenosine(N-bz) phosphoramidite (ChemGene), 5'-DMT-3'-(O-methyl)adenosine(N-bz)2'-phosphoramidite (ChemGene), and the phosphoramidite of Example 8a described in Patent Application (Kokai) No. Hei 11-246592, were coupled in order.

After synthesizing the protected 2-5A analog having the desired structure in the state in which the 5'-DMTr group has been removed, together with cleaving the oligomer from the support, the cyanoethyl group serving as the protecting group on the phosphorus atom and the protecting group on the nucleic acid base were removed by treating with a mixture of concentrated aqueous ammonia and ethanol (3:1). The solvent was then distilled off under reduced pressure, and 1 ml of triethylamine trihydrofluoride was added to the residue followed by stirring at room temperature. After 24 hours, 200 µl of $H_2O$ were added, followed by the addition of 10 ml of 1-butanol, allowing to stand for 1 hour at –20° C., and centrifuging to obtain a pellet-like precipitate. After gently washing this pellet with EtOH, it was dissolved in 150 µl of $H_2O$ and then subjected to electrophoresis on 15% denatured acrylamide gel (1× TBE solution (7 M urea, 0.89 M Tris, boric acid, EDTA solution (pH 8.3, Takara Shuzo), 600 V, 60 minutes). The band that absorbed UV in the gel was cut out and eluted from the gel with 1 ml of an elution buffer (0.5 M ammonium acetate, 10 mM magnesium acetate, 1 mM EDTA (pH 8.0), 0.1% SDS). The remaining gel was filtered off, 4 ml of EtOH were added to the filtrate, which was then allowed to stand for 1 hour at –20° C. followed by centrifugation to obtain a pellet-like precipitate. This was then purified by reverse phase HPLC (Shimadzu Seisakusho LC-VP; column (Merck Chromolith (4.6×50 mm)); 0.1 M aqueous triethyl amine acetate (TEAA), pH 7; 9-25% $CH_3CN$ (linear gradient, 8 min.); 60° C.; 2 ml/min), and the fraction that eluted at 4.02 minutes was collected. The yield was 16.0 nmol (as UV measured value at 260 nm), and λmax ($H_2O$)=259 nm.

Example 51

Synthesis of Example 51 Compound (Exemplary Compound No. 1930) $HOC_2H_4O$—$P(=O)(OH)$—$K^{2-1}$—$P(=O)(OH)$—$K^{1-1}$—$P(=O)(OH)$—$K^{2-1}$—$P(=O)(OH)$—$L_1$—$P(=O)(OH)$—$L_1$-p-$T^e$-p-$C^e$-p-$T^e$-p-$T^e$-p-$G^e$-p-$G''$-p-$T''$-p-$T''$-p-$G''$-p-$T''$-p-$A''$-p-$A''$-p-$G''$-p-$A''$p-$G''$-p-$A^e$-p-$G^e$-p-$A^e$-p-$G^e$-p-$A^e$-hp The title compound was obtained according to a similar method to Example 50. The present compound was purified by reverse phase HPLC (Shimadzu Seisakusho LC-VP; column (Merck chromolith (4.6×50 mm); 0.1M aqueous triethylamine acetate (TEAA), pH 7; 9-25% $CH_3CN$ (linear gradient, 8 min); 60° C.; 2 ml/min), and the fraction at 3.61 minutes was collected. Yield: 15.8 nmol (in terms of UV measurement at 260 mm), λmax ($H_2O$)=257 nm.

Example 52

Synthesis of Example 52 Compound (Exemplary compound No. 1931) $HOC_2H_4O$—$P(=O)(OH)$—$K^{2-1}$—$P(=O)(OH)$—$K^{1-1}$—$P(=O)(OH)$—$K^{2-1}$—$P(=O)(OH)$—$L_1$—$P(=O)(OH)$—$L_1$-p-$T^e$-p-$T^e$-p-$C^e$-p-$A^e$-p-$G^e$-p-$G''$-p-$C''$-p-$C''$-p-$T''$-p-$C''$-p-$C''$-p-$A''$-p-$T''$-p-$A''$-p-$T''$-p-$G^e$-p-$G^e$-p-$A^e$-p-$A^e$-p-$T^e$-hp The title compound was obtained according to a similar method to Example 50. The present compound was purified by reverse phase HPLC (Shimadzu Seisakusho LC-VP; column (Merck chromolith (4.6×50 mm); 0.1M aqueous triethylamine acetate (TEAA), pH 7; 9-25% $CH_3CN$ (linear gradient, 8 min); 60° C.; 2 ml/min), and the fraction at 3.66 minutes was collected. Yield: 7.8 nmol (in terms of UV measurement at 260 nm), λmax ($H_2O$)=259 nm.

Example 53

Synthesis of Example 53 Compound (Exemplary Compound No. 1932) $HOC_2H_4O$—$P(=O)(OH)$—$K^{2-1}$—$P(=O)(OH)$—$K^{1-1}$—$P(=O)(OH)$—$K^{2-1}$—$P(=O)(OH)$—$L_1$-$P(=O)(OH)$—$L_1$-p-$G^e$-p-$T^e$-p-$T^e$-p-$C^e$-p-$T^e$-p-$C''$-p-$G''$-p-$C''$-p-$T''$-p-$G''$-p-$G''$-p-$T''$-p-$G''$-p-$A''$-p-$G''$-p-$T^e$-p-$T^e$-p-$T^e$-p-$C^e$-p-$A^e$-hp The title compound was obtained according to a similar method to Example 50. The present compound was purified by reverse phase HPLC (Shimadzu Seisakusho LC-VP; column (Merck chromolith (4.6×50 mm); 0.1M aqueous triethylamine acetate (TEAA), pH 7; 8-12% $CH_3CN$ (linear gradient, 10 min); 60° C.; 2 ml/min), and the fraction at 8.0-10.0 minutes was collected. When the present compound was analyzed by reverse phase HPLC (column (Tosoh superODS (4.6×50 mm)); 0.1M aqueous triethylamine acetate (TEAA), pH 7; 5-29% $CH_3CN$ (linear gradient, 10 min); 60° C.; 1 ml/min), it eluted at 7.54 minutes. Yield: 37.6 nmol (in terms of UV measurement at 260 nm), λmax ($H_2O$)=258.9 nm.

Example 54

Synthesis of Example 54 Compound (Exemplary Compound No. 1933) $HOC_2H_4O$—$P(=O)(OH)$—$K^{2-1}$—$P(=O)(OH)$—$K^{1-1}$—$P(=O)(OH)$—$K^{2-1}$—$P(=O)(OH)$—$L_1$—$P(=O)(OH)$—$L_1$-p-$G^e$-p-$A^e$-p-$T^e$-p-$G^e$-p-$G^e$-p-$A''$-p-$A''$-p-$A''$p-$T''$-p-$C''$-p-$T''$-p-$C''$-p-$T''$-p-$G''$-p-$C''$-p-$C^e$-p-$G^e$-p-$C^e$-p-$A^e$-$T^e$-hp The title compound was obtained according to a similar method to Example 50. The present compound was purified by reverse phase HPLC (Shimadzu Seisakusho LC-VP; column (Merck chromolith (4.6×50 mm); 0.1M aqueous triethylamine acetate (TEAA), pH 7; 9-25% $CH_3CN$ (linear gradient, 8 min); 60° C.; 2 ml/min), and the fraction at 3.74 minutes was collected. Yield: 131 nmol (in terms of UV measurement at 260 nm), λmax ($H_2O$)=262 nm.

181

Example 55

Synthesis of Example 55 Compound (Exemplary Compound No. 1934) HOC$_2$H$_4$O—P(=O)(OH)—K$^{2-1}$—P(=O)(OH)—K$^{1-1}$—P(=O)(OH)—K$^{2-1}$—P(=O)(OH)—L$_1$—P(=O)(OH)—L$_1$-p-A$^e$-p-T$^e$-p-G$^e$-p-G$^e$-p-C$^e$-p-A''-p-C''-p-C''-p-T''-p-C''-p-T''-p-T''-p-G''-p-T''-p-G''-p-G$^e$-p-A$^e$-p-C$^e$-p-C$^e$-p-A$^e$-hp The title compound was obtained according to a similar method to Example 50. The present compound was purified by reverse phase HPLC (Shimadzu Seisakusho LC-VP; column (Merck chromolith (4.6×50 mm); 0.1M aqueous triethylamine acetate (TEAA), pH 7; 9-25% CH$_3$CN (linear gradient, 8 min); 60° C.; 2 ml/min), and the fraction at 3.83 minutes was collected. Yield: 5.5 nmol (in terms of UV measurement at 260 nm), λmax (H$_2$O)=261 nm.

Example 56

Synthesis of Example 56 Compound (Exemplary Compound No. 1935) HOC$_2$H$_4$O—P(=O)(OH)—K$^{2-1}$—P(=O)(OH)—K$^{1-1}$—P(=O)(OH)—K$^{2-1}$—P(=O)(OH)—L$_1$—P(=O)(OH)—L$_1$-p-C$^e$-p-A$^e$-p-G$^e$-p-C$^e$-p-C$^e$-p-A''-p-T''-p-G''-p-G''-p-T''-p-C''-p-C''-p-C''-p-C''-p-C''-p-C$^e$-p-C$^e$-p-C$^e$-p-A$^e$-p-A$^e$-hp The title compound was obtained according to a similar method to Example 50. The present compound was purified by reverse phase HPLC (Shimadzu Seisakusho LC-VP; column (Merck chromolith (4.6×50 mm); 0.1M aqueous triethylamine acetate (TEAA), pH 7; 9-25% CH$_3$CN (linear gradient, 8 min); 60° C.; 2 ml/min), and the fraction at 3.25 minutes was collected. Yield: 55 nmol (in terms of UV measurement at 260 nm), λmax (H$_2$O)=266 nm.

Example 57

Synthesis of Example 57 Compound (Exemplary Compound No. 1936) HOC$_2$H$_4$O—P(=O)(OH)—K$^{2-1}$—P(=O)(OH)—K$^{1-1}$—P(=O)(OH)—K$^{2-1}$—P(=O)(OH)-L$_2$-p-G$^e$-p-T$^e$-p-T$^e$-p-C$^e$-p-T$^e$-p-C''-p-G''-p-C''-p-T''-p-G''-p-G''-p-T''-p-G''-p-A''-p-G''-p-T$^e$-p-T$^e$-p-T$^e$-p-C$^e$-p-A$^e$-hp The title compound was obtained according to a similar method to Example 50. Here, Spacer phosphoramidite 18 (Glen Research Inc.) was used as the phosphoramidite corresponding to L$_2$. The present compound was purified by reverse phase HPLC (Shimadzu Seisakusho LC-VP; column (Merck chromolith (4.6×50 mm); 0.1M aqueous triethylamine acetate (TEAA), pH 7; 8-12% CH$_3$CN (linear gradient, 10 min); 60° C.; 2 ml/min), and the fraction at 8.0-10.0 minutes was collected. When the present compound was analyzed by reverse phase HPLC (column (Tosoh superODS (4.6×50 mm)); 0.1M aqueous triethylamine acetate (TEAA), pH 7; 5-29% CH$_3$CN (linear gradient, 10 min); 60° C.; 1 ml/min), it eluted at 7.52 minutes. Yield: 59.5 nmol (in terms of UV measurement at 260 nm), λmax (H$_2$O)=258.6 nm.

182

Example 58

Synthesis of Example 58 Compound (Exemplary Compound No. 1103)

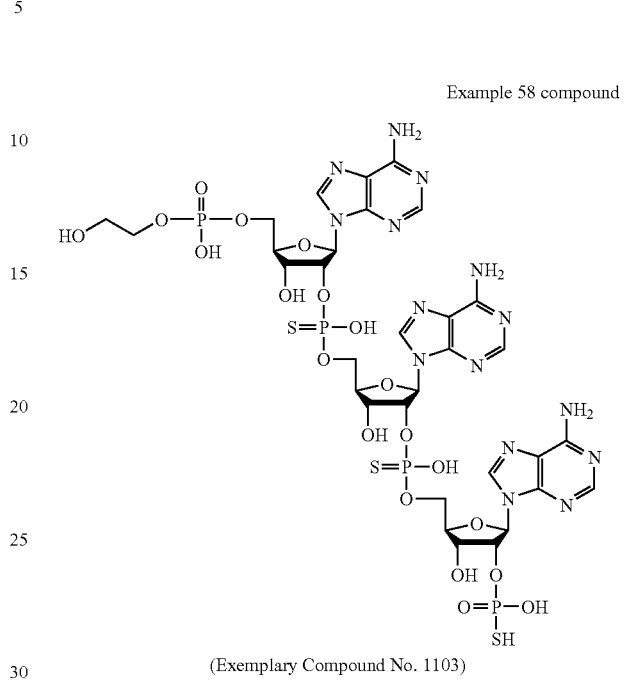

Example 58 compound (Exemplary Compound No. 1103)

Synthesis was carried out with the DNA synthesizer based on one condensation cycle consisting of the following steps 1) to 4) using a synthesis program for ordinary synthesis of 1 μmol of RNA. 3'-Phosphate CPG (Glen Research) (0.2 mol) was used as the solid phase carrier. 3'-tBDSilyl-ribo Adenosine (N-bz) phosphoramidite (ChemGene) was used as the phosphoramidite in cycles 1, 2 and 3, and the compound of Example 8a described in Patent Application (Kokai) No. Hei 11-246592 was used in cycle 4. For the oxidation or sulfurizing agent, xanthane hydride (Tokyo Kasei Kogyo) was used in cycles 1, 2 and 3, and iodine was used in cycle 4.

Condensation Cycle:

1) Detritylation: Trichloroacetic acid/dichloromethane; 85 sec.

2) Coupling: Phosphoramidite (about 25 eq)/acetonitrile, tetrazole/acetonitrile; 10 to 20 min.

3) Capping: 1-methylimidazole/tetrahydrofuran, acetic anhydride/pyridine/tetrahydrofuran; 15 sec.

4) Oxidation (cycle 4): Iodine/water/pyridine/tetrahydrofuran; 15 sec.

sulfurization (cycles 1, 2 and 3): Xanthane hydride (0.02 M)/acetonitrile-pyridine (9:1 mixed solvent); 15 min.

After synthesizing the 2-5A analog having the desired structure in the state in which the 5'-DMTr group is retained, together with cleaving the oligomer from the support, the cyanoethyl group serving as the protecting group on the phosphorus atom and the benzoyl group on the adenine base were removed by treating with a mixture of concentrated aqueous ammonia and ethanol (3:1). The solvent was then distilled off under reduced pressure and the remaining residue was purified by reverse phase HPLC (Shimadzu Seisakusho LC-VP; column ((Merck chromolith (4.6×50 mm)); 0.1 M aqueous triethylamine acetate (TEAA), pH 7; 24-100% $CH_3CN$ (linear gradient, 8 min.); 60° C.; 2 ml/min), and the fractions that eluted at 6.0-6.7 minutes corresponding to the four diastereomers were collected.

After the solvent was evaporated under reduced pressure, 1 ml of aqueous hydrochloric acid (0.01N) was added to the remaining residue to accurately adjust the pH to 2.0, followed by reaction at 30° C. for 5 hours to remove the DMTr group and the silyl group. After neutralization with aqueous ammonia, the deprotected silanol and DMTrOH were removed by extraction with ethyl acetate. When the remaining aqueous solution was analyzed by reverse phase HPLC (column (((Merck chromolith (4.6×50 mm)); 0.1M aqueous triethylamine acetate (TEAA), pH7; 0-20% $CH_3CN$ (linear gradient, 8 min); 60° C.; 2 ml/min), the fractions that eluted at 4.6 and 5.4 minutes were collected to obtain the desired compound. Yield: 38 nmol (in terms of UV measurement at 260 nm), λmax ($H_2O$)=259 nm Example 59

Synthesis of Example 59 Compound (Exemplary Compound No. 1195)

layer was washed three times with 500 μl of AcOEt. After the aqueous layer was evaporated, it was purified by reverse phase HPLC (Shimadzu Seisakusho LC-VP; column (Merck chromolith (4.6×50 mm); 0.1M aqueous triethylamine acetate (TEAA), pH 7; 24-100% $CH_3CN$ (linear gradient, 8 min); 60° C.; 2 ml/min), and the fraction at 6.8 minutes was collected. Yield: 8.9 nmol in terms of UV measurement at 260 nm, λmax ($H_2O$)=259 nm.

Test Example 1

Measurement of Cytotoxic Activity of 2-5A Analogs (MTT Assay)

Human lung cancer cell line A549 cells were plated at a density of 800 cells/200 μl in a 96-well plate using RPMI1640 (Gibco BRL) (containing 10% Fetal Bovine Serum (Hyclone)) for the medium followed by culturing overnight in 5% $CO_2$ at 37° C. Each 2-5A analog was added to each well so that the final concentration became 10 μM, followed by culturing for 72 hours (3 days). After culturing for 72 hours (3 days), MTT (3-[4,5-dimethylthiazol-2-yl]-2,5-diphenyltetrazolium bromide) was added in 50 μl aliquots to each well at a MTT/RPMI1640 concentration of 5 mg/ml, followed by additionally culturing for 4 hours. After 4 hours, the medium

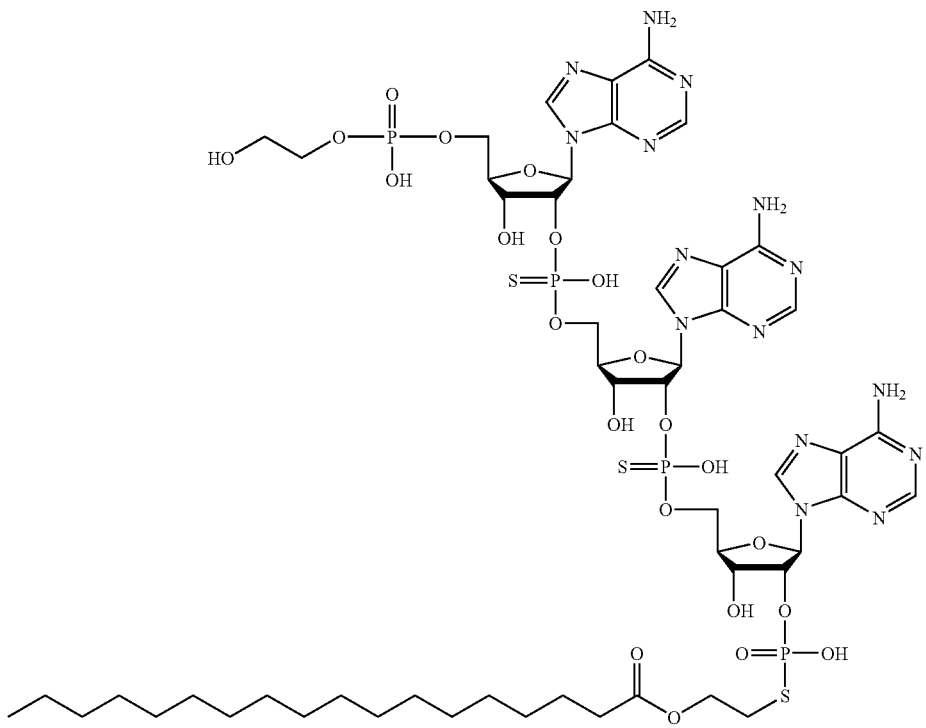

Example 59 compound (Exemplary Compound No. 1195)

40 nmol of Example 58 compound were dissolved in 100 μl of anhydrous DMF, and 1 mg of 2-(stearoyloxy)ethyl bromide (Ackerman et al., J. Am. Chem. Soc., 78, 1956, 6025), and 1 μl of pyridine were added thereto, followed by reacting the mixture at room temperature overnight. After completion of the reaction, 500 μl of water were added, and the aqueous was removed and 150 μl of dimethyl sulfoxide were added to each well. After shaking for 5 minutes, UV absorbance at 540 nm was measured to determine the relative ratio of the number of viable cells of the compound dose group to the number of viable cells of an untreated cell group at 72 hours after addition of the test compound.

The cytotoxic activity during addition of the subject compounds (10 μM) with respect to A549 cells is shown in the graph. In this graph, the natural type 2-5A indicates a 3 mer, 2',5'-oligoadenylate with a 5'-monophosphate group having the structure shown below (Imai, J. and Torrence, P. F., J. Org. Chem., 1985, 50(9), 1418-1426).

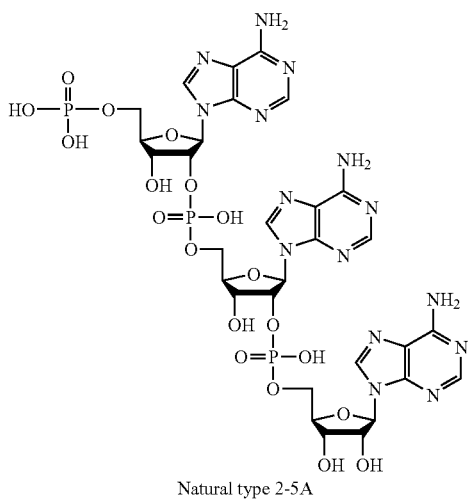

Natural type 2-5A

As is clear from FIG. 1, during addition to the medium at a concentration of 10 μM, in contrast to natural type 2-5A not demonstrating any cytotoxic effects against human lung cancer cell line A549 cells, the subject compounds demonstrated superior cytotoxic activity.

Test Example 2

Measurement of Cytotoxic Activity of 2-5A Analogs (MTT Assay)

Human lung cancer cell line A549 cells were plated at a density of 800 cells/200 μl in a 96-well plate using RPMI1640 (Gibco BRL) (containing 10% Fetal Bovine Serum (Hyclone)) for the medium followed by culturing overnight in 5% $CO_2$ at 37° C. Each 2-5A analog was added to each well so that the final concentration became 0.001-10 μM, followed by culturing for 72 hours (3 days) (n=3 or 4). After culturing for 72 hours (3 days), MTT (3-[4,5-dimethylthiazol-2-yl]-2,5-diphenyltetrazolium bromide) was added in 50 μl aliquots to each well at a MTT/RPMI1640 concentration of 5 mg/ml, followed by additionally culturing for 4 hours. After 4 hours, the medium was removed and 150 μl of dimethyl sulfoxide were added to each well. After shaking for 5 minutes, UV absorbance at 540 nm, was measured to determine the relative ratio of the number of viable cells of the compound dose group to the number of viable cells of an untreated cell group followed by calculation of the $IC_{50}$ concentration that inhibits cell growth by 50%.

The table shows the 50% growth inhibitory concentrations of the subject compounds with respect to A549 cells.

TABLE

50% Growth inhibitory concentrations of the subject compounds with respect to A549 cells

|  | Experiment 1 | Experiment 2 | Experiment 3 | Experiment 4 |
|---|---|---|---|---|
| Example 2 | 1.53 | 0.91 | | |
| Example 4 | 0.48 | 0.61 | 0.38 | |
| Example 5 | 0.40 | 0.32 | | |
| Example 8 | 2.23 | | | |
| Example 9 | 1.39 | | | |
| Example 13 | | 2.54 | | |
| Example 14 | | 2.34 | | |
| Example 15 | | 0.061 | 0.073 | |
| Example 16 | | 0.09 | | |
| Example 17 | | 0.35 | | |
| Example 19 | | | 13 | |
| Example 22 | | | 0.33 | |
| Example 23 | | | 0.13 | 0.091 |
| Example 24 | | | 0.30 | |
| Example 25 | | | 0.91 | |
| Example 26 | | | | 0.15 |
| Example 27 | | | | 0.36 |
| Example 28 | | | 0.13 | |
| Example 29 | | | 0.14 | |
| Example 30 | | | 0.43 | |
| Example 33 | | | 2.15 | |
| Example 34 | | | 6.60 | |

As is clear from the above table, in contrast to natural type 2-5A not demonstrating any cytotoxic effects against human lung cancer cell line A549 cells even at 10 μM, the subject compounds demonstrated superior cytocidal activity.

The compounds of the present invention have stability and excellent activity (particularly antitumor activity), and are useful as pharmaceutical drugs (particularly antitumor agents). The compounds of the present invention can be administered to a mammal, such as a human, to treat a tumor or a viral disease.

What is claimed is:
1. A 2',5'-oligoadenylate analog represented by the formula (1):

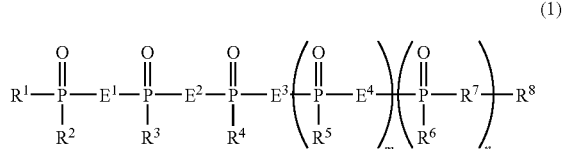

wherein m represents an integer of 0; n represents an integer of 0 or 1; $R^1$ represents an alkoxy group having from 1 to 6 carbon atoms substituted by a hydroxyl group, an unprotected mercapto group, an alkylthio group having from 1 to 4 carbon atoms substituted by a hydroxyl group, or a group of a formula $X_1-X_2-X_3-S-$; $R^2$, $R^3$, $R^4$, $R^5$ and $R^6$ independently represent an unprotected hydroxyl group, an unprotected mercapto group, an alkylthio group having from 1 to 4 carbon atoms substituted by a hydroxyl group, or a group of formula $X_1-X_2-X_3-S-$; $R^7$ represents an oxygen atom a sulfur atom, $-NH-$, a $-O(CH_2CH_2O)q-$ group, wherein g represents an integer of 2 to 6, or an oxyalkyleneoxy group having from 1 to 6 carbon atoms; $R^8$ represents a hydrogen atom, or a 5'-phosphorylated oligonucleotide analog which has one hydroxyl group removed from the 5'-phosphoric acid group; $E^1$ represents $K^2$; $E^2$ represents $K^1$; $E^3$ represents $K^2$ or $K^3$ and $E^4$ represents $K^1$, $K^2$ or $K^3$, wherein $K^1$, $K^2$ and $K^3$ represent, respectively,

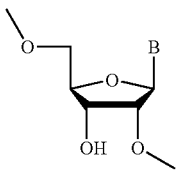

K¹

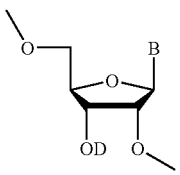

K²

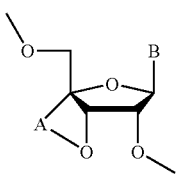

K³ wherein B represents an adeninyl group, A represents an alkylene group having from 1 to 4 carbon atoms, D represents an unsubstituted alkyl group having from 1 to 6 carbon atoms, or an unsubstituted alkenyl group having from 2 to 6 carbon atoms; $X_1$ represents an unsubstituted alkyl group having from 1 to 24 carbon atoms, or a phenyl group; $X_2$ represents a —C(=O)O—, —OC(=O)— or a —C(=O)S— group; and $X_3$ represents an unsubstituted alkylene group having from 1 to 6 carbon atoms, or a pharmacologically acceptable salt thereof.

2. The 2',5'-oligoadenylate analog or pharmacologically acceptable salt thereof according to claim 1, wherein $R^1$ is an alkoxy group having from 1 to 4 carbon atoms substituted by a hydroxyl group, an unprotected mercapto group, or an alkylthio group having from 1 to 4 carbon atoms substituted by a hydroxyl group, or a group of the formula $X_1$—$X_2$—$X_3$—

S—; $X_1$ is an unsubstituted alkyl group having from 10 to 24 carbon atoms; and $X_3$ is an unsubstituted alkylene group having from 1 to 4 carbon atoms.

3. The 2',5'-oligoadenylate analog or pharmacologically acceptable salt thereof according to claim 1 or claim 2, wherein $R^7$ represents an oxygen atom, a —O(CH$_2$CH$_2$O)q- group, wherein q represents an integer of 2 to 6, or an oxyalkyleneoxy group having from 1 to 6 carbon atoms.

4. The 2',5'-oligoadenylate analog or pharmacologically acceptable salt thereof according to claim 1, wherein D is a methyl group or a 2-propenyl group.

5. The 2',5'-oligoadenylate analog or pharmacologically acceptable salt thereof according to claim 1, wherein $E^3$ is $K^3$, and A is a methylene, ethylene, or propylene group.

6. The 2',5'-oligoadenylate analog according to claim 1, which is

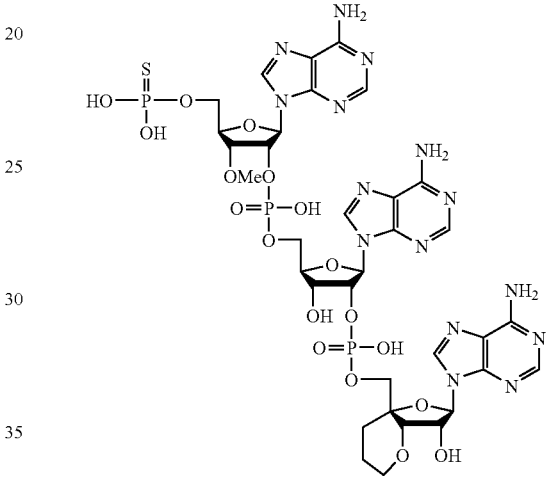

or pharmacologically acceptable salt thereof.

7. The 2',5'-oligoadenylate analog according to claim 1, which is

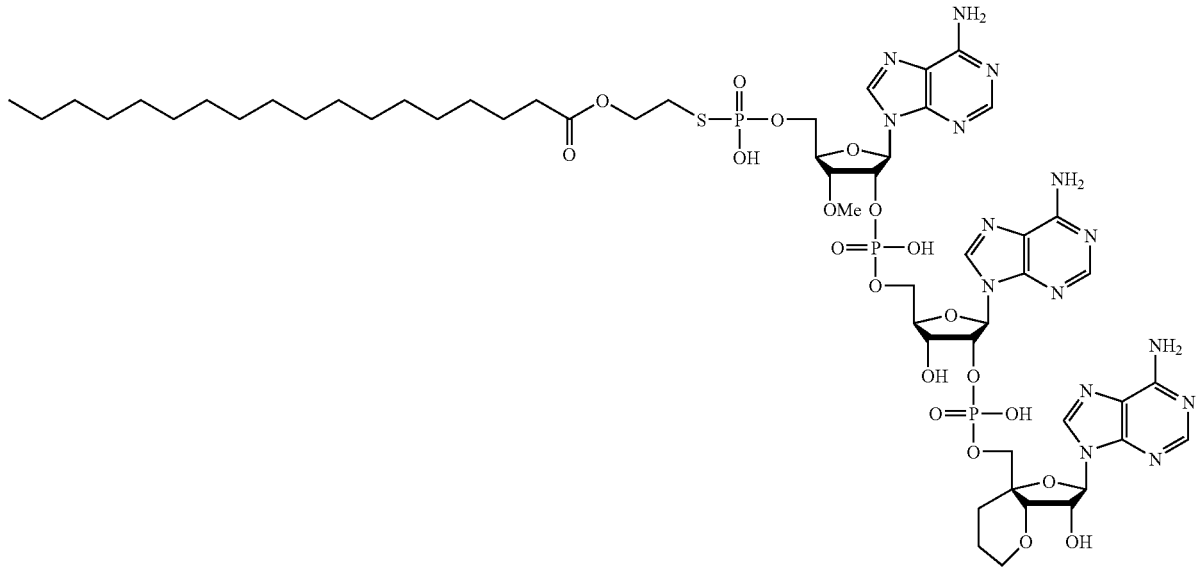

or pharmacologically acceptable salt thereof.

8. The 2',5'-oligoadenylate analog or pharmacologically acceptable salt thereof according to claim 1, wherein $R^1$ is an alkoxy group having from 1 to 4 carbon atoms substituted by a hydroxyl group, an unprotected mercapto group, an alkylthio group having from 1 to 4 carbon atoms substituted by a hydroxyl group, or a group of formula: $X_1$—$X_2$—$X_3$—S—; $X_2$ is a —C(—O)O— or —C(=O)S— group; $X_3$ is an unsubstituted alkylene group having from 1 to 4 carbon atoms; $R^7$ represents an oxygen atom, a —O(CH$_2$CH$_2$O)q- group, wherein q represents an integer of 2 to 6, or an oxyalkyleneoxy group having from 1 to 6 carbon atoms; D is a methyl group or a 2-propenyl group; $E^3$ is $K^3$; and A is a methylene, ethylene group or propylene group; and B is 6-aminopurin-9-yl or 6-amino-8-bromopurin-9-yl.

9. The 2',5'-oligoadenylate analog according to claim 1, which is

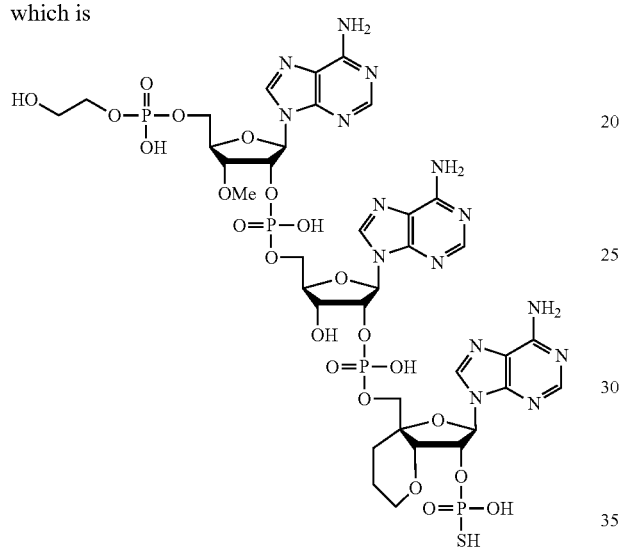

or a pharmacologically acceptable salt thereof.

10. The 2',5'-oligoadenylate analog according to claim 1, which is

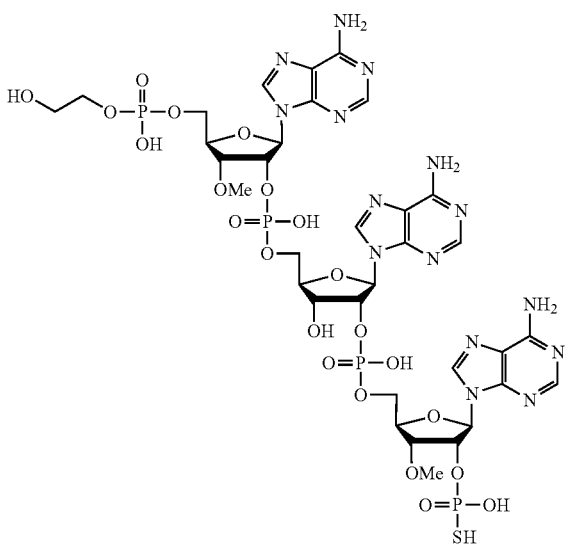

or a pharmacologically acceptable salt thereof.

11. The 2',5'-oligoadenylate analog according to claim 1, which is

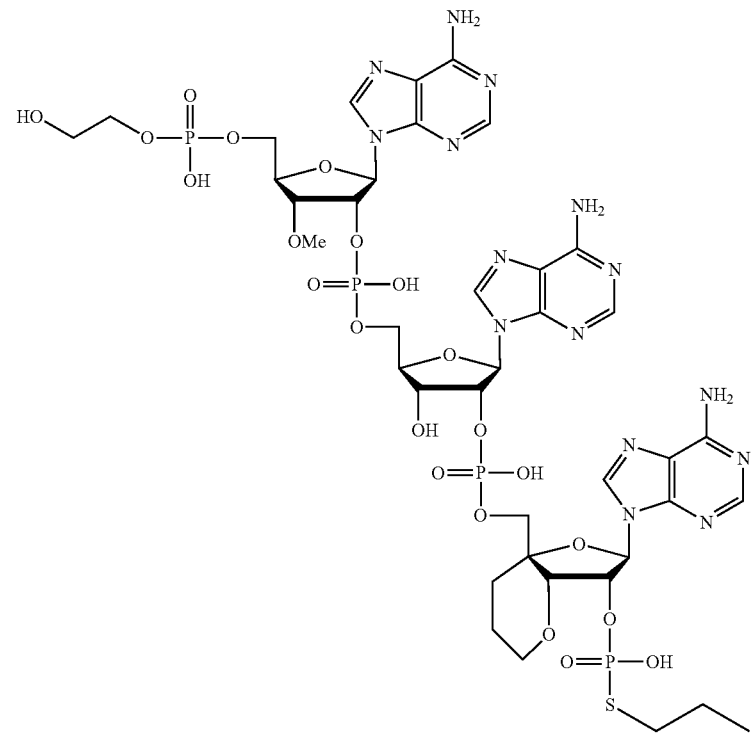

-continued
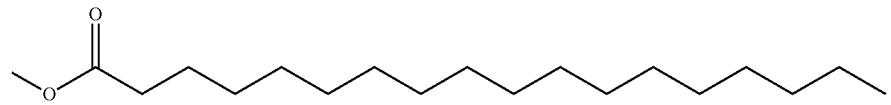
or a pharmacologically acceptable salt thereof.
12. The 2',5'-oligoadenylate analog according to claim 1, which is
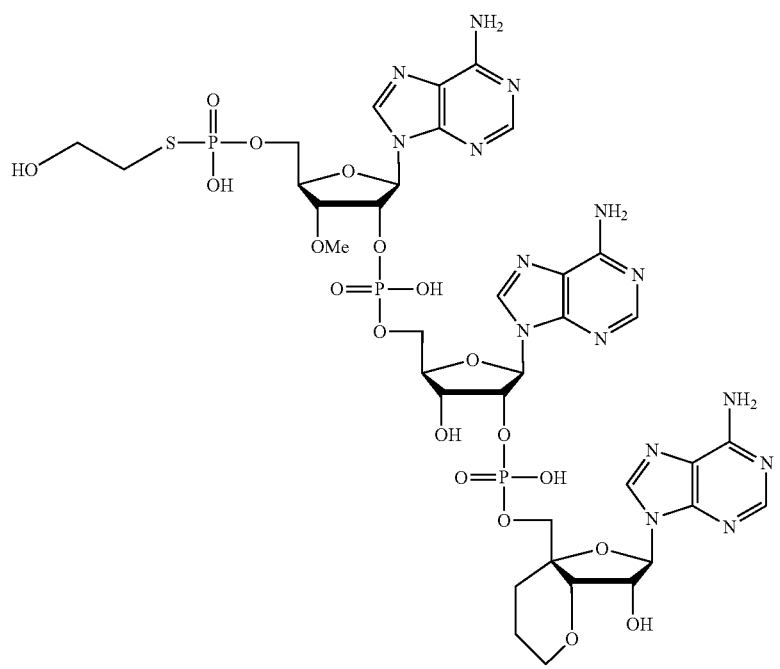
or a pharmacologically acceptable salt thereof.

13. The 2',5'-oligoadenylate analog according to claim 1, which is
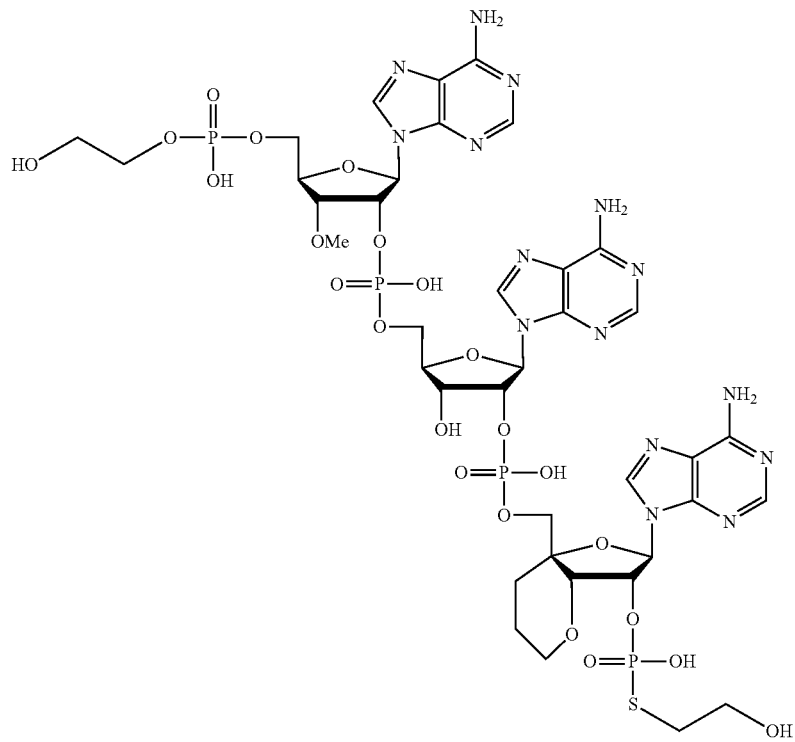
or a pharmacologically acceptable salt thereof.
14. The 2',5'-oligoadenylate analog according to claim 1, which is
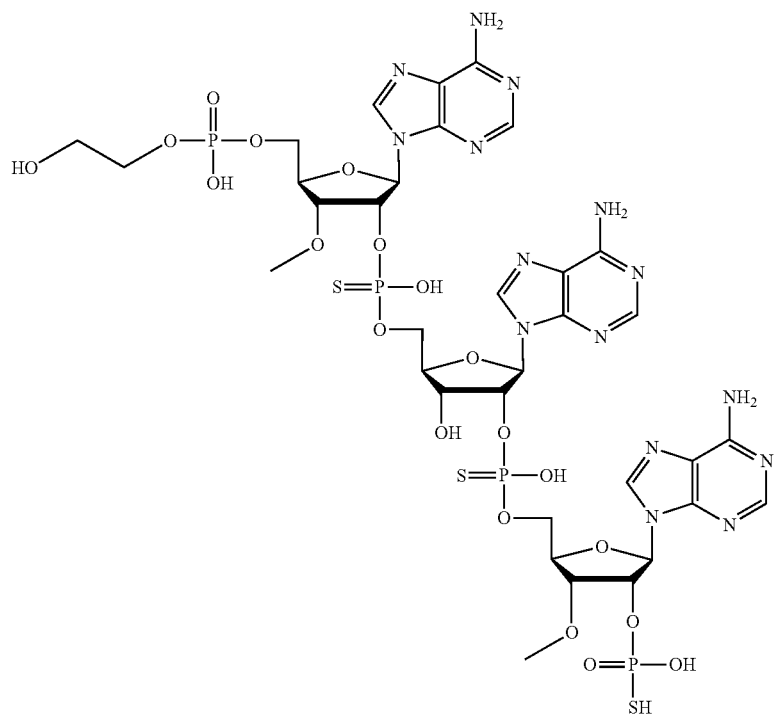
or a pharmacologically acceptable salt thereof.

15. A pharmaceutical composition comprising a pharmaceutically effective amount of the 2',5'-oligoadenylate analog according to claim 1 or a pharmacologically acceptable salt thereof in combination with a pharmaceutically acceptable carrier.

16. A method for treating lung cancer comprising administering to a human in need thereof a pharmaceutically effective amount of the 2',5'-oligoadenylate analog according to claim 1 or a pharmaceutically acceptable salt thereof.

17. The method according to claim 16, wherein the 2',5'-oligoadenylate analog is selected from the group consisting of

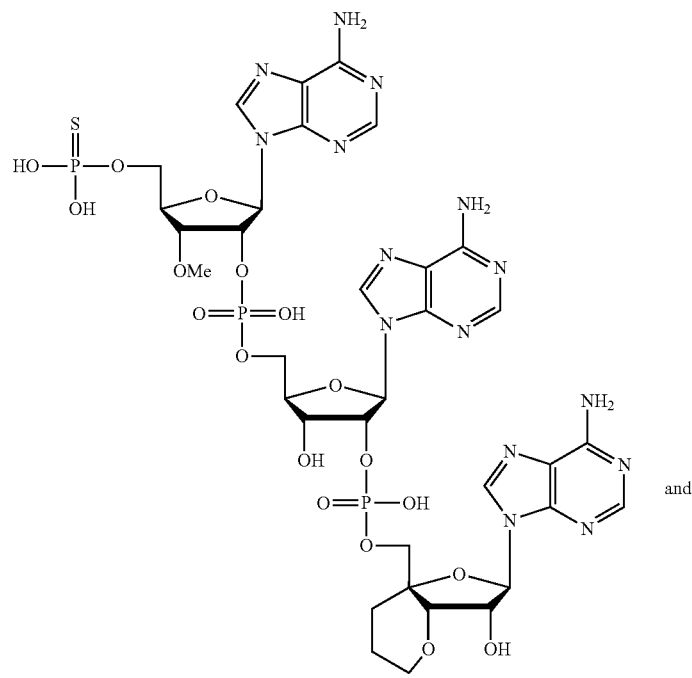

and

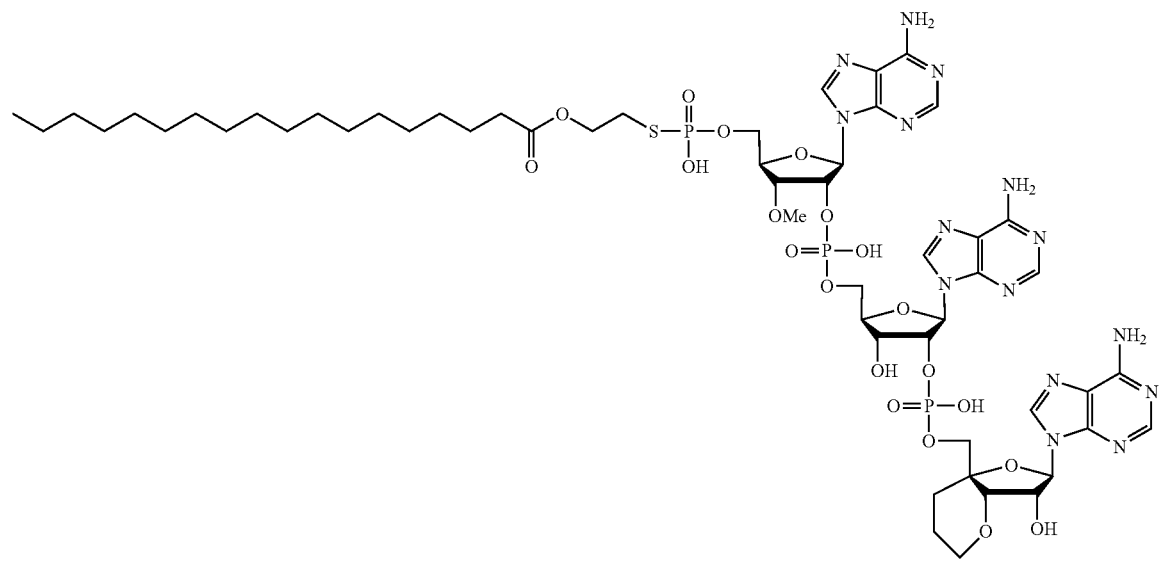

or a pharmacologically acceptable salt thereof.

18. The method according to claim 16, wherein the 2',5'-oligoadenylate analog is selected from the group consisting of
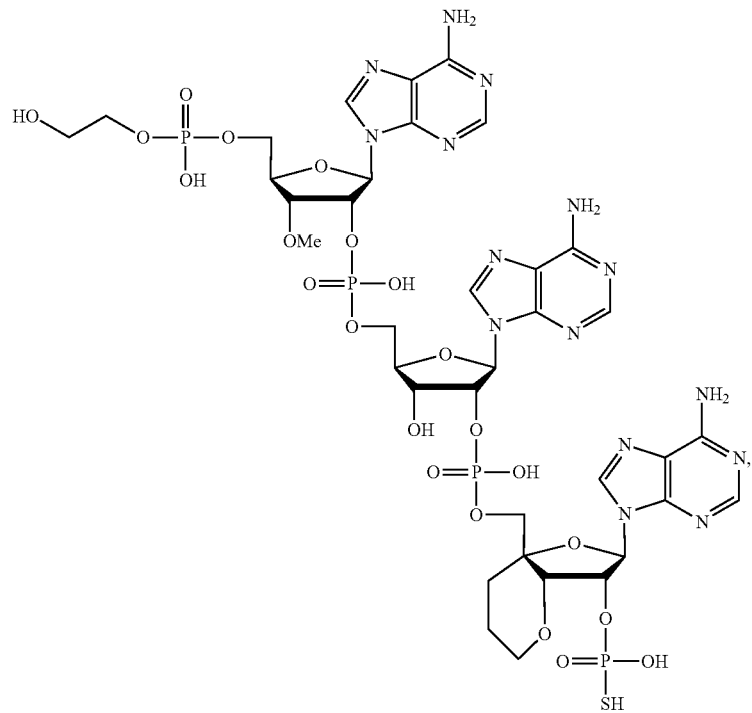
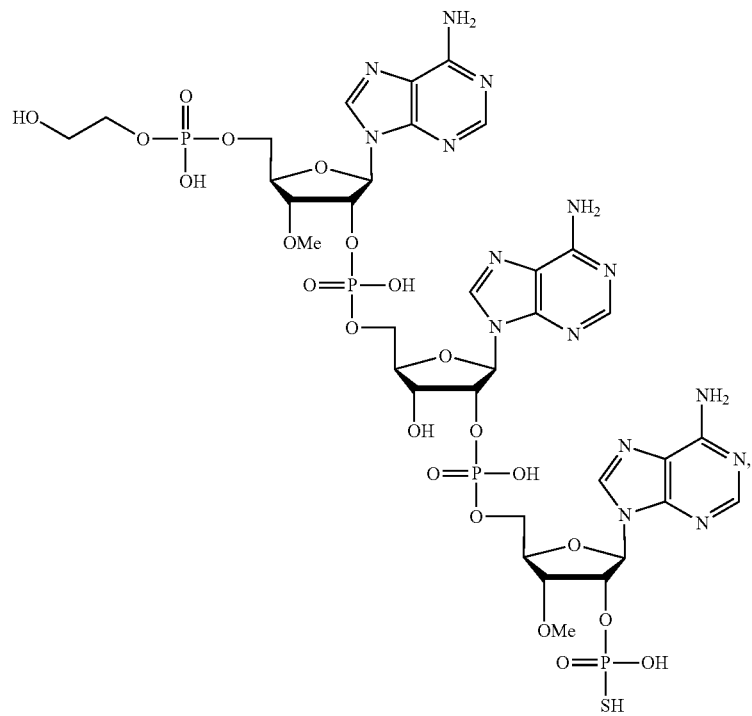

-continued
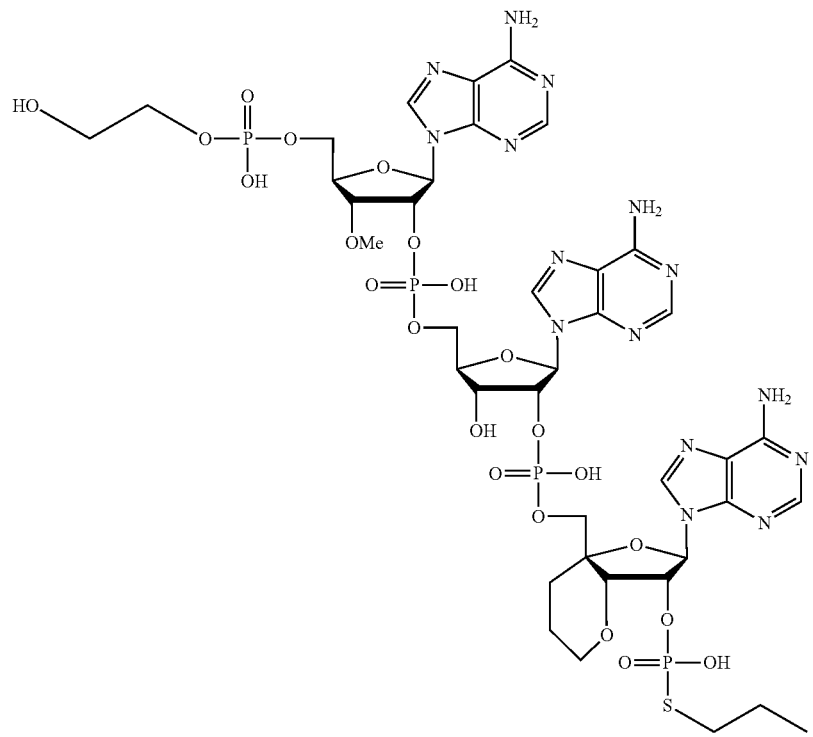
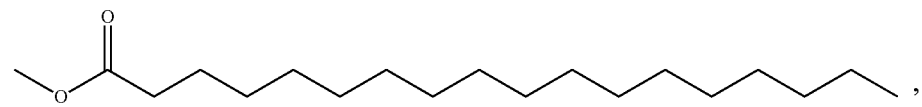
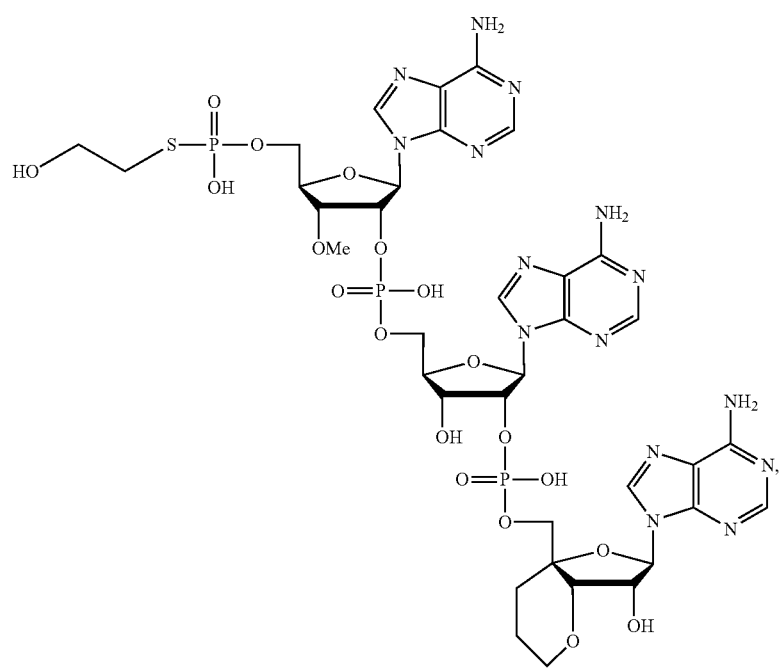

-continued
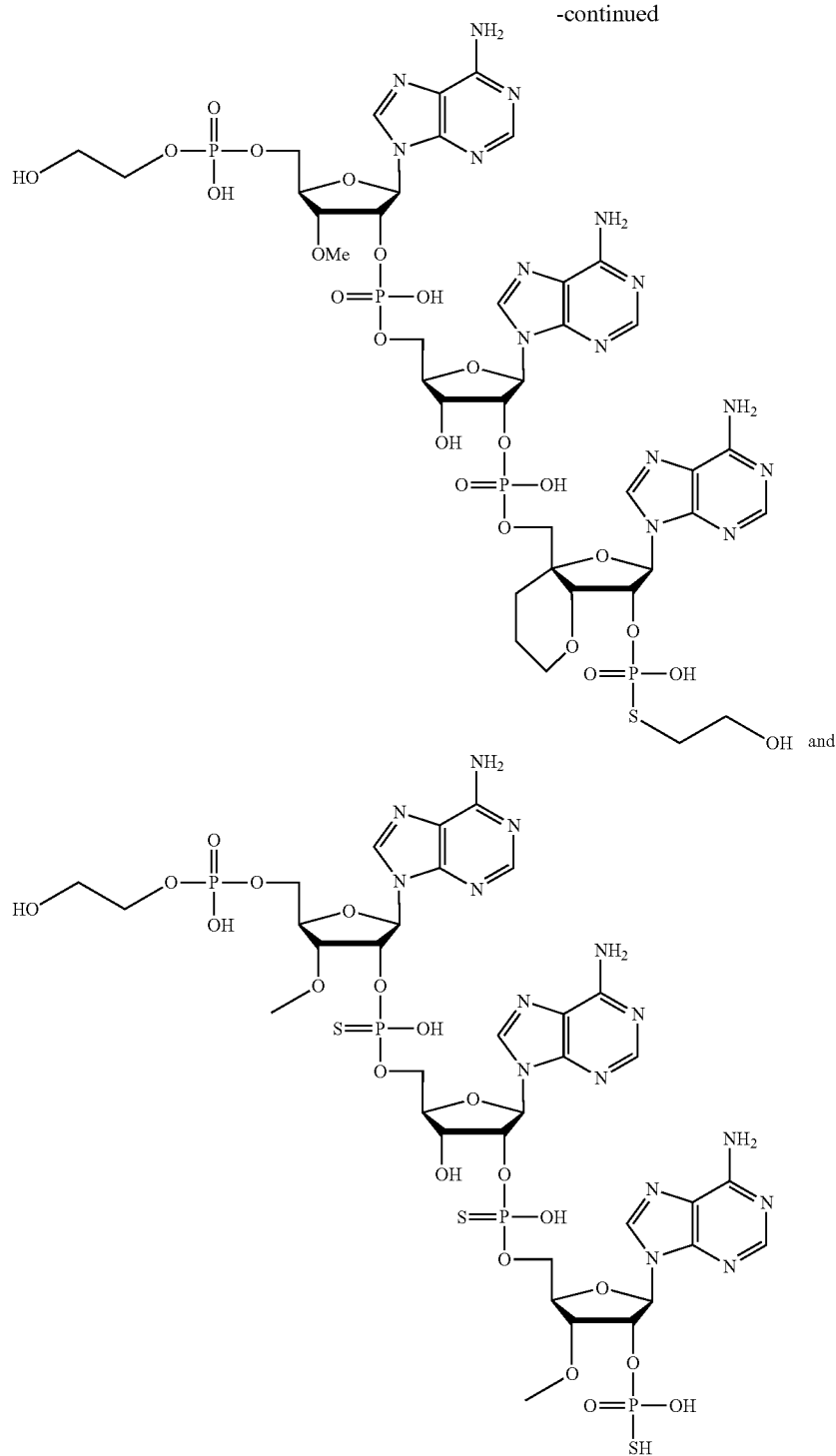
or a pharmacologically acceptable salt thereof.
* * * * *

UNITED STATES PATENT AND TRADEMARK OFFICE
CERTIFICATE OF CORRECTION

PATENT NO. : 7,651,999 B2
APPLICATION NO. : 11/131412
DATED : January 26, 2010
INVENTOR(S) : Koizumi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1235 days.

Signed and Sealed this

Twenty-third Day of November, 2010

David J. Kappos
*Director of the United States Patent and Trademark Office*